United States Patent [19]

Takase et al.

[11] Patent Number: 5,801,180

[45] Date of Patent: Sep. 1, 1998

[54] QUINAZOLINE DERIVATIVES

[75] Inventors: Yasutaka Takase; Nobuhisa Watanabe, both of Ibaraki; Makoto Matsui, Aichi; Hironori Ikuta, Ibaraki; Teiji Kimura, Ibaraki; Takao Saeki, Ibaraki; Hideyuki Adachi, Ibaraki; Tadakazu Tokumura, Ibaraki; Hisatoshi Mochida, Aichi; Yasunori Akita, Chiba; Shigeru Souda, Ibaraki, all of Japan

[73] Assignee: Eisai Co., Ltd., Japan

[21] Appl. No.: 904,260

[22] Filed: Jul. 31, 1997

Related U.S. Application Data

[62] Division of Ser. No. 408,867, Mar. 23, 1995, Pat. No. 5,693,652, which is a division of Ser. No. 196,110, Feb. 18, 1994, Pat. No. 5,576,322.

[30] Foreign Application Priority Data

Sep. 30, 1991 [JP] Japan ..................... 3-320853

[51] Int. Cl.$^6$ .................. A61K 31/505; C07D 239/94
[52] U.S. Cl. .................. 514/259; 544/284; 544/293
[58] Field of Search ............... 544/293, 284; 514/259

[56] References Cited

U.S. PATENT DOCUMENTS

| | | | |
|---|---|---|---|
| 3,511,836 | 5/1970 | Hess | 514/259 |
| 3,560,619 | 2/1971 | Harrison et al. | 514/259 |
| 3,635,979 | 1/1972 | Hess | 514/259 |
| 3,655,901 | 4/1972 | Jensen et al. | 548/310.4 |
| 3,686,411 | 8/1972 | Frick et al. | 548/310.4 |
| 4,880,804 | 11/1989 | Carini et al. | 514/234.5 |
| 4,925,853 | 5/1990 | Smith et al. | 548/304.4 |
| 5,064,833 | 11/1991 | Ife et al. | 514/260 |
| 5,210,091 | 5/1993 | Axelsson et al. | 514/322 |
| 5,411,963 | 5/1995 | Dreikorn et al. | 514/259 |
| 5,576,322 | 11/1996 | Takase et al. | 514/260 |

FOREIGN PATENT DOCUMENTS

| | | |
|---|---|---|
| 0 253 310 | 1/1988 | European Pat. Off. . |
| 0 291 969 | 11/1988 | European Pat. Off. . |
| 1015937 | 1/1966 | United Kingdom ........ 548/310.4 |
| 1 015 937 | 1/1996 | United Kingdom ........ 548/310.4 |

OTHER PUBLICATIONS

CA 63 (1965) 10519b, vol. 63.
CA 64 (1966) 14187e, vol. 64.

*Primary Examiner*—Johann Richter
*Assistant Examiner*—Laura L. Stockton
*Attorney, Agent, or Firm*—Nixon & Vanderhye

[57] ABSTRACT

The present invention provides a nitrogenous heterocyclic compound represented by the following general formula (1) or a pharmacologically acceptable salt thereof which is useful for various ischemic heart diseases and the like:

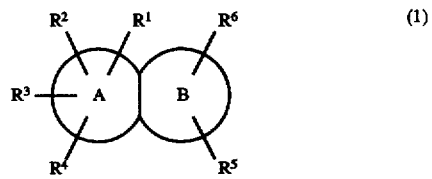

(1)

[in formula (1), ring A represents a benzene ring, a pyridine ring or a cyclohexane ring; ring B represents a pyridine ring, a pyrimidine ring or an imidazole ring, $R^1$, $R^2$, $R^3$ and $R^4$ represent each a hydrogen atom, a halogen atom or a group such as a lower alkoxy group; $R^5$ represents a group represented by the formula —$NR^{11}R^{12}$ (wherein $R^{11}$ and $R^{12}$ represent each a hydrogen atom or a group such as a lower alkyl group) or the like; and $R^6$ represents a group represented by the formula

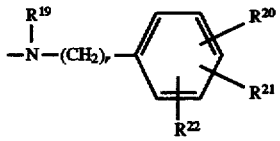

(wherein $R^{19}$ represents a hydrogen atom, a lower alkyl group or the like; $R^{20}$, $R^{21}$ and $R^{22}$ represent each a hydrogen atom, a halogen atom, a hydroxyl group or the like; and r represents 0 or an integer of 1 to 8)].

7 Claims, No Drawings

QUINAZOLINE DERIVATIVES

This application is a division of application Ser. No. 08/408,867, filed Mar. 23, 1995 now U.S. Pat. No. 5,693,652, which is a division of Ser. No. 08/196,110 filed Feb. 18, 1994 now U.S. Pat. No. 5,576,322.

[FIELD OF THE INVENTION]

The present invention relates to a nitrogeous heterocyclic compound having an excellent activity as a drug.

[BACKGROUND OF THE INVENTION AND PRIOR ART]

Angina pectoris which is one of ischemic heart diseases has been known as a disease which often attacks the aged. Although nitric and nitrous acid compounds, calcium antagonists and β-blocker have been used as therapeutic agents therefor, the effect of such a therapeutic agent is far insufficient to treat angina pectoris or to prevent the evolution thereof into myocardial infarction. Recently, the age of a patient with angina pectoris has lowered and the symptom thereof has become complicated owing to change in the style of living, stress increased by the complication of society and so forth, so that a new type of more excellent drug has been desired eagerly.

It is believed that cyclic GMP (hereinafter abbreviated to "cGMP") which is one of cyclic nucleotides and is known as an intracellular second messenger participates in the action of the nitric and nitrous acid compounds among the above drugs which are now used. The relaxing effect of cGMP on the smooth muscle of vessel and bronchus is well known. Although the mechanism of action of these drugs are not always apparent, it is generally presumed that the activity of this cGMP results from the acceleration of the synthesis of cGMP which is caused by the activation of guanylate cyclase. However, the above-mentioned drugs exhibit a low bioavailability and a relatively short time of action. Further, it is reported that the drug resistance is induced, which is a problem in a clinical field.

Under these circumstances, the present inventors have started studies to develop a new type of more excellent drug.

That is, the present inventors have paid their attention to cGMP phosphodiesterase (hereinafter abbreviated to "cGMP-PDE")-inhibiting activity and have made extensive studies on compounds having such an activity for many years. As a result of the studies, they have found that a nitrogenous heterocyclic compound which will be described below has such an activity to be efficacious for various ischemic heart diseases and have accomplished the present invention.

Although quinazoline derivatives useful as drugs are included in, e.g., Publication of International Patent Application by Japanese No. 502462/1990, they are different from the compounds of the present invention in respect of both structure and activity.

[DISCLOSURE OF THE INVENTION]

The present invention provides a nitrogenous heterocyclic compound represented by the following general formula (1) or a pharmacologically acceptable salt thereof:

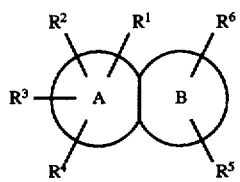

[in formula (1), ring A represents a benzene ring, a pyridine ring or a cyclohexane ring; ring B represents a pyridine ring, a pyrimidine ring or an imidazole ring.

Provided that the ring A and the ring B are combined sharing two atoms and the atoms shared may be either a carbon atom or a nitrogen atom.

In the case where the ring A is a pyridine ring and that except the case where the ring B shares the nitrogen atom of this pyridine ring to combine therewith, the ring A is represented by

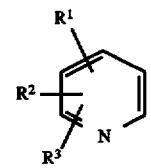

$R^1$, $R^2$, $R^3$ and $R^4$, each of which may be the same or different from one another, represent each a hydrogen atom, a halogen atom, a lower alkyl group which may be substituted with a halogen atom, a cycloalkyl group which may be substituted, a lower alkoxy group, a hydroxyalkyl group, a nitro group, a cyano group, an acylamino group, a carboxyl group which may be protected, a group represented by the formula

(wherein $R^7$ represents a lower alkyl group, and n represents 0 or an integer of 1 to 2), or a group represented by the formula

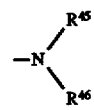

(wherein $R^{45}$ and $R^{46}$, each of which may be the same or different from each other, represent each a hydrogen atom or a lower alkyl group; or $R^{45}$ and $R^{46}$ can form a ring which may contain another nitrogen atom or oxygen atom together with the nitrogen atom to which they are bonded with the proviso that this ring may be substituted); or, two of $R^1$, $R^2$, $R^3$ and $R^4$ may together form methylenedioxy, ethylenedioxy or a phenyl ring.

$R^5$ represents a hydrogen atom, a halogen atom, a hydroxyl group, a hydrazino group, a lower alkyl group, a cycloalkyl group which may be substituted, a lower alkoxy group, a lower alkenyl group, a carboxyalkyl group which may be protected, a carboxyalkenyl group which may be protected, a hydroxyalkyl group, a carboxyl group which may be protected, a group represented by the formula

(wherein $R^8$ represents a lower alkyl group, and m represents 0 or an integer of 1 to 2), a group represented by the formula —O—$R^9$ (wherein $R^9$ represents a hydroxyalkyl group which may be protected, a carboxyalkyl group which may be protected or a benzyl group which may be substituted), a group represented by the formula

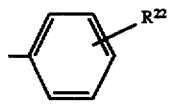

(wherein $R^{23}$ represents a hydroxyl group, a lower alkyl group, a lower alkoxy group, a hydroxyalkyl group or a hydroxyalkyloxy group), a heteroaryl group which may be substituted, a 1,3-benzdioxolyl group which may be substituted, a 1,4-benzdioxyl group which may be substituted, a 1,3-benzdioxolylalkyl group which may be substituted, a 1,4-benzdioxylalkyl group which may be substituted, a group represented by the formula —C($R^{24}$)=X [wherein X represents an oxygen atom, a sulfur atom or a group represented by the formula =N—$R^{10}$ (wherein $R^{10}$ represents a hydroxyl group, a cyano group or a carboxyalkyloxy group which may be protected); and $R^{24}$ represents a hydrogen atom or a lower alkyl group], or a group represented by the formula —$NR^{11}R^{12}$ (wherein $R^{11}$ and $R^{12}$, each of which may be the same or different from each other, represent each a hydrogen atom, a lower alkyl group, a hydroxyalkyl group, an aminoalkyl group, a carboxyalkyl group which may-be protected, an alkylcarbamoyl group, a carboxyalkylcarbamoyl group which may be protected, a heteroarylalkyl group which may be substituted, a 1,3-benzoxolylalkyl group or a 1,4-benzdioxylalkyl group; or, further, $R^{11}$ and $R^{12}$ can form a ring which may contain another nitrogen atom or oxygen atom together with a nitrogen atom to which they are bonded with the proviso that this ring may be substituted).

$R^6$ represents a hydrogen atom, a halogen atom, a hydroxyl group, an amino group, a lower alkyl group, a lower alkoxy group, a lower alkenyl group, a 1,3-benzdioxolylalkyloxy group, a 1,4-benzdioxylalkyloxy group, a phenylalkyloxy group which may be substituted, a group represented by the formula

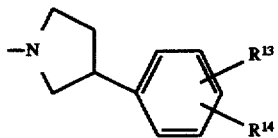

(wherein $R^{13}$ and $R^{14}$, each of which may be the same or different from each other, represent each a hydrogen atom, a lower alkyl group or a lower alkoxy group; or, further, $R^{13}$ and $R^{14}$ may together form methylenedioxy or ethylenedioxy), a group represented by the formula

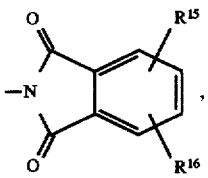

a group represented by the formula

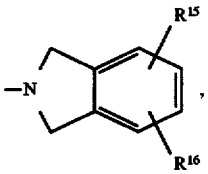

a group represented by the formula

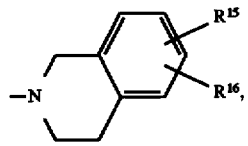

a group represented by the formula

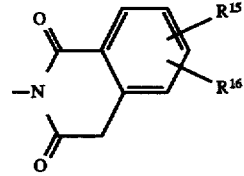

(in these formulas, $R^{15}$ and $R^{16}$, each of which may be the same or different from each other, represent each a hydrogen atom, a lower alkyl group or a lower alkoxy group; or, further, $R^{15}$ and $R^{16}$ may together form methylenedioxy or ethylenedioxy), a piperidne-4-spiro-2'-dioxan-1-yl group, a group represented by the formula

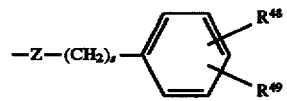

(wherein $R^{48}$ and $R^{49}$, each of which may be the same or different from each other, represent each a hydrogen atom, a lower alkyl group or a lower alkoxy group; or, further, $R^{48}$ and $R^{49}$ may together form methylenedioxy or ethylenedioxy; and Z represents a sulfur atom or an oxygen atom), a group represented by the formula

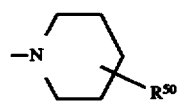

(wherein $R^{50}$ represents a hydroxyl group, a halogen atom, a lower alkyl group, a lower alkoxy group, a carboxyl group which may be protected, a cyano group, a hydroxyalkyl group or a carboxyalkyl group), a group represented by the formula

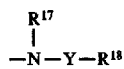

[wherein $R^{17}$ represents a hydrogen atom, a lower alkyl group, an acyl group, a lower alkoxyalkyl group, a carboxyalkyl group which may be protected or a hydroxyalkyl group; Y represents a group represented by the formula —$(CH_2)_q$— (wherein q is 0 or an integer of 1 to 8), or a group represented by the formula

further, in the group represented by the formula —$(CH_2)_q$—, when q is an integer of 1 to 8, each carbon atom may have 1 to 2 substituent(s); and $R^{18}$ represents a hydrogen atom, a hydroxyl group, a carboxyl group which may be protected, a cyano group, an acyl group, a heteroaryl group which may be substituted or a cycloalkyl group which may be substituted], or a group represented by the formula

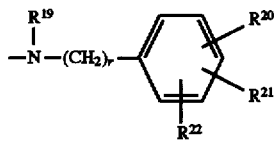

(wherein $R^{19}$ represents a hydrogen atom, a lower alkyl group, a lower alkoxyalkyl group, an acyl group, a carboxyalkyl group which may be protected or a hydroxyalkyl group; $R^{20}$, $R^{21}$ and $R^{22}$, each of which may be the same or different from one another, represent each a hydrogen atom, a halogen atom, a hydroxyl group, an amino group, a nitro group, a lower alkyl group, a lower alkoxy group, a lower alkoxyalkyl group, a lower alkenyl group, an acyl group, an acylamino group, an alkylsulfonylamino group, a hydroxyiminoalkyl group, an alkyloxycarbonylamino group, an alkyloxycarbonyloxy group or a heteroaryl group which may be substituted; or, further, two of $R^{20}$, $R^{21}$ and $R^{22}$ may together form a saturated or unsaturated ring which may contain a nitrogen atom, a sulfur atom or an oxygen atom; and r represents 0 or an integer of 1 to 8)].

The quinazoline derivative represented by the following formula (I) or the pharmacologically acceptable salt thereof can be cited as one of the preferred embodiments of the nitrogenous heterocyclic compound represented by the formula (1) described above or the pharmacologically acceptable salt thereof:

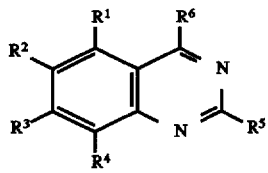

[in formula (I), $R^1$, $R^2$, $R^3$ and $R^4$, each of which may be the same or different from one another, represent each a hydrogen atom, a halogen atom, a lower alkyl group, a lower alkoxy group, a hydroxyalkyl group, a cyano group, an acylamino group, a carboxyl group which may be protected or a group represented by the formula

(wherein $R^7$ represents a lower alkyl group; and n represents 0 or an integer of 1 to 2), or two of $R^1$, $R^2$, $R^3$ and $R^4$ may together form methylenedioxy, ethylenedioxy or a phenyl ring.

$R^5$ represents a hydrogen atom, a halogen atom, a hydroxyl group, a hydrazino group, a lower alkyl group, a lower alkoxy group, a lower alkenyl group, a carboxyalkyl group which may be protected, a carboxyalkenyl group which may be protected, a hydroxyalkyl group, a carboxyl group which may be protected, a group represented by the formula

(wherein $R^8$ represents a lower alkyl group, and m represents 0 or an integer of 1 to 2), a group represented by the formula —O—$R^9$ (wherein $R^9$ represents a hydroxyalkyl group which may be protected, a carboxyalkyl group which may be protected or a benzyl group), a group represented by the formula

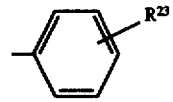

(wherein $R^{23}$ represents a hydroxyl group, a lower alkyl group, a lower alkoxy group, a hydroxyalkyl group or a hydroxyalkyloxy group), a heteroaryl group which may be substituted, a 1,3-benzdioxolyl group which may be substituted, a 1,4-benzdioxyl group which may be substituted, a 1,3-benzdioxolylalkyl group which may be substituted, a 1,4-benzdioxylalkyl group which may be substituted, a group represented by the formula —C($R^{24}$)=X [wherein X represents an oxygen atom or a group represented by the formula =N—$R^{10}$ (wherein $R^{10}$ represents a hydroxyl group or a carboxyalkyloxy group which may be protected); and $R^{24}$ represents a hydrogen atom or a lower alkyl group], or a group represented by the formula —$NR^{11}R^{12}$ (wherein $R^{11}$ and $R^{12}$ each of which may be the same or different from each other, represent each a hydrogen atom, a lower alkyl group, a hydroxyalkyl group, an aminoalkyl group, a carboxyalkyl group which may be protected, an alkylcarbamoyl group, a 1,3-benzoxolylalkyl group or a 1,4-benzdioxylalkyl group; or, further, $R^{11}$ and $R^{12}$ can form a ring which may contain another nitrogen atom or oxygen atom together with a nitrogen atom to which they are bonded with the proviso that this ring may be substituted).

$R^6$ represents a hydrogen atom, a halogen atom, a hydroxyl group, an amino group, a lower alkyl group, a lower alkoxy group, a 1,3-benzdioxolylalkyloxy group, a 1,4-benzdioxylalkyloxy group, a phenylalkyloxy group which may be substituted, a group represented by the formula

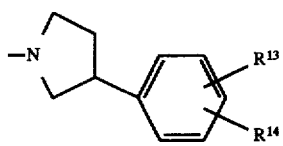

(wherein $R^{13}$ and $R^4$, each of which may be the same or different from each other, represent each a hydrogen atom, a lower alkyl group or a lower alkoxy group; or, further, $R^{13}$ and $R^{14}$ may together form methylenedioxy or ethylenedioxy), a group represented by the formula

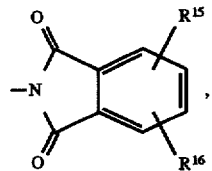

a group represented by the formula

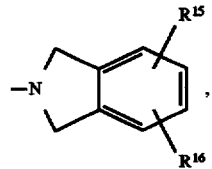

a group represented by the formula

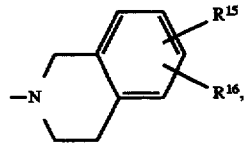

a group represented by the formula

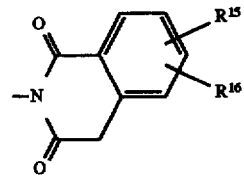

(in these formulas, $R^{15}$ and $R^{16}$ represent each a hydrogen atom, a lower alkyl group or a lower alkoxy group; or, further, $R^{15}$ and $R^{16}$ may together form methylenedioxy or ethylenedioxy), a piperidne-4-spiro-2'-dioxan-1-yl group or a group represented by the formula

[wherein $R^{17}$ represents a hydrogen atom, a lower alkyl group, an acyl group, a lower alkoxyalkyl group, a carboxyalkyl group which may be protected or a hydroxyalkyl group; Y represents a group represented by the formula $-(CH_2)_q-$ (wherein q is 0 or an integer of 1 to 8), or a group represented by the formula

further, in the group represented by the formula $-(CH_2)_q-$, when q is an integer of 1 to 8, each carbon atom may have 1 to 2 substituent(s); and $R^{18}$ represents a hydrogen atom, a hydroxyl group, a carboxyl group which may be protected, a cyano group, an acyl group, a heteroaryl group which may be substituted or a group represented by the formula

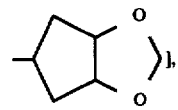

or a group represented by the formula

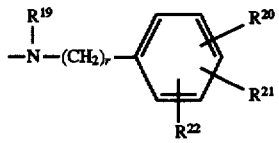

(wherein $R^{19}$ represents a hydrogen atom, a lower alkyl group, a lower alkoxyalkyl group, an acyl group, a carboxyalkyl group which may be protected or a hydroxyalkyl group; $R^{20}$, $R^{21}$ and $R^{22}$, each of which may be the same or different from one another, represent each a hydrogen atom, a halogen atom, a hydroxyl group, an amino group, a nitro group, a lower alkyl group, a lower alkoxy group, a lower alkoxyalkyl group, a lower alkenyl group, an acyl group, an acylamino group, an alkylsulfonylamino group, a hydroxyiminoalkyl group, an alkyloxycarbonylamino group, an alkyloxycarbonyloxy group or a heteroaryl group which may be substituted; or, two of $R^{20}$, $R^{21}$ and $R^{22}$ may together form a saturated or unsaturated ring which may contain a nitrogen atom, a sulfur atom or an oxygen atom; and r represents 0 or an integer of 1 to 8)].

The present invention also provides a preventive or therapeutic agent for diseases for which phosphodiesterase-inhibiting action is efficacious, especially for which cyclic-GMP phosphodiesterase-inhibiting action is efficacious, which contains a nitrogenous heterocyclic compound or a pharmacologically acceptable salt thereof described above as the active ingredient.

As diseases described above, ischemic heart diseases, concretely angina pectoris, hypertension, heart failure and asthma, are cited.

Furthermore, the present invention provides a drug composition comprising a nitrogenous heterocyclic compound and/or a pharmacologically acceptable salt thereof described above and a pharmacologically acceptable filler.

The present invention provides a use of a nitrogenous heterocyclic compound or a pharmacologically acceptable salt thereof to prepare a therapeutic agent for diseases for which phosphodiesterase-inhibiting action is efficacious, and a treating method for a disease which comprises administering a therapeutic effective amount of a nitrogenous heterocyclic compound and/or a pharmacologically acceptable salt thereof to a patient suffering from a disease for which phosphodiesterase-inhibiting action is efficacious.

The lower alkyl group defined with respect to $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{45}$, $R^{46}$, $R^{48}$, $R^{49}$ and $R^{50}$ in the above definition of the compound (1) according to the present invention is a straight-chain or branched alkyl group having 1 to 8 carbon atoms and examples thereof include methyl group, ethyl group, propyl group, isopropyl group, butyl group, isobutyl group, sec-butyl group, tert-butyl group, pentyl group (amyl group), neopentyl group, tert-pentyl group, 2-methylbutyl group, 3-methylbutyl group, 1,2-dimethylpropyl group, hexyl group, isohexyl group, 1-methylpentyl group, 2-methylpentyl group, 3-methylpentyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group and octyl group. Among these groups, methyl group, ethyl group, propyl group and isopropyl group are cited as preferable ones. Among these groups, methyl group and ethyl group are cited as still preferable ones.

In these lower alkyl groups, a carbon atom at its terminal may be represented by a sulfonic acid group (—$SO_3H$) or a group represented by the formula —$ONO_2$. Furthermore, the sulfonic acid group may form a salt such as groups represented by the formulas —$SO_3Na$ and —$SO_3K$.

The lower alkyl group which may be substituted with a halogen atom used in the definition of $R^1$, $R^2$, $R^3$ and $R^4$ refers to a lower alkyl group described above in which one or two or more hydrogen atoms may be replaced by halogen atom(s).

The lower alkoxy group defined with respect to $R^1$, $R^2$, $R^3$, $R^4$, $R^5$, $R^6$, $R^{13}$, $R^{14}$, $R^{15}$, $R^{16}$, $R^{20}$, $R^{21}$, $R^{22}$, $R^{23}$, $R^{48}$, $R^{49}$ and $R^{50}$ is a straight-chain or branched alkoxy group having 1 to 8 carbon atoms and examples thereof include methoxy group, ethoxy group, n-propoxy group, isopropoxy group, n-butoxy group, isobutoxy group, sec-butoxy group, tert-butoxy group, 2-methylbutoxy group, 2,3-dimethylbutoxy group and hexyloxy group. Among these groups, methoxy group and ethoxy group are cited as preferable ones.

The lower alkenyl group defined with respect to $R^5$, $R^6$, $R^{20}$, $R^{21}$ and $R^{22}$ is one derived from the above-mentioned lower alkyl group and examples thereof include ethylene group, propylene group, butylene group and isobutylene group.

The hydroxyalkyl group defined with respect to $R^1$, $R^2$, $R^3$, $R^4$, $R^5$, $R^{11}$, $R^{12}$, $R^{17}$, $R^{19}$, $R^{23}$ and $R^{50}$ is one derived from the above-mentioned lower alkyl group.

The hydroxyalkyl group which may be protected used in the definition of $R^9$ refers to a hydroxyalkyl group wherein the hydroxyl group is protected with, for example, nitro group, a lower alkyl group as described above such as methyl group and ethyl group, an acyl group such as acetyl group, propionyl group, butyroyl group, pivaloyl group and nicotinoyl group or other group which may have a c-GMP PDE-inhibitory activity. The nitrogenous heterocyclic compound thus protected according to the present invention exhibits an effect as a drug after being deprotected the protective group in vivo or as such.

The acyl group defined with respect to $R^{17}$, $R^{18}$, $R^{19}$, $R^{20}$, $R^{21}$ and $R^{22}$ is one derived from an aliphatic one, an aromatic one or a heterocycle and examples thereof include lower alkanoyl groups such as formyl group, acetyl group, propionyl group, butyryl group, valeryl group, isovaleryl group and pivaloyl group; aroyl groups such as benzoyl group, toluoyl group and naphthoyl group; and heteroaroyl groups such as furoyl group, nicotinoyl group and isonicotinoyl group. Among these groups, formyl group, acetyl group and benzoyl group are cited as preferable ones.

The carboxyl-protective group defined with respect to $R^1$, $R^2$, $R^3$, $R^4$, $R^5$, $R^{18}$ and $R^{50}$ includes lower alkyl groups such as methyl group, ethyl group and t-butyl group; lower alkyl groups substituted with a phenyl group which may have a substituent, such as p-methoxybenzyl group, p-nitrobenzyl group, 3,4-dimethoxybenzyl group, diphenylmethyl group, trityl group and phenethyl group; halogenated lower alkyl groups such as 2,2,2-trichloroethyl group and 2-iodoethyl group; lower alkanoyloxy lower alkyl groups such as pivaloyloxymethyl group, acetoxymethyl group, propionyloxymethyl group, butyryloxymethyl group, valeryloxymethyl group, 1-acetoxyethyl group, 2-acetoxyethyl group, 1-pivaloyloxyethyl group and 2-pivaloyloxyethyl group; higher alkanoyloxy lower alkyl groups such as palmitoyloxyethyl group, heptadecanoyloxymethyl group and 1-palmitoyloxyethyl group; lower alkoxy-carbonyloxy lower alkyl groups such as methoxycarbonyloxymethyl group, 1-butoxycarbonyloxyethyl group and 1-(isopropoxycarbonyloxy)ethyl group; carboxy lower alkyl groups such as carboxymethyl group and 2-carboxyethyl group; heterocyclic groups such as 3-phthalidyl group; benzoyloxy lower alkyl groups which may have a substituent, such as 4-glycyloxybenzoyloxymethyl group and 4-[N-(t-butoxycarbonyl)glycyloxy]benzoyloxymethyl group; (substituted dioxolene) lower alkyl groups such as (5-methyl-2-oxo-1,3-dioxolen-4-yl)methyl group; cycloalkyl-substituted lower alkanoyloxy lower alkyl groups such as 1-cyclohexylacetyloxyethyl group; and cycloalkyloxycarbonyloxy lower alkyl groups such as 1-cyclohexyloxycarbonyloxyethyl group.

Further, the protected carboxyl group also includes various acid amides groups. That is, the protected carboxyl group may be any one, so far as it can be deprotected in vivo to give a carboxyl group. The nitrogenous heterocyclic compound thus protected according to the present invention exhibits an effect as a drug after being deprotected the protective group in vivo or as such.

Although the cycloalkyl group which may be substituted used in the definition of $R^1$, $R^2$, $R^3$, $R^4$, $R^5$ and $R^{18}$ refers to one having 3 to 8 carbon atoms, those having 3 to 6 carbon atoms are preferable.

The heteroaryl group constituting the heteroaryl group which may be substituted defined with respect to $R^5$, $R^{18}$, $R^{20}$, $R^{21}$ and $R^{22}$ is a 5- to 7-membered monocyclic group or a condensed heterocyclic group each containing one to two oxygen atom(s), nitrogen atom(s) or sulfur atom(s) as the heteroatom(s) and examples thereof include furyl group, pyridyl group, thienyl group, imidazolyl group, quinazolyl group and benzimidazolyl group.

The heteroaryl group constituting the heteroarylalkyl group which may be substituted defined with respect to $R^{11}$ and $R^{12}$ refers to any of the heteroaryl groups described above. Further, the alkyl group constituting the heteroaryl group refers to any of the lower alkyl groups described above.

"$R^{11(45)}$ and $R^{12(46)}$ and the nitrogen atom to which both groups are bonded may together form a ring which may contain another nitrogen atom or an oxygen atom" described in the definition of $R^{11}$ and $R^{12}$, and $R^{45}$ and $R^{46}$ refers to piperidino group, piperazino group and morpholino group as specific examples. Further, the substituent with which the ring may be substituted includes hydroxyl group; halogen atoms such as chlorine atom, fluorine atom, bromine atom and iodine atom; lower alkyl groups such as methyl, ethyl and t-butyl; lower alkoxy groups such as methoxy, ethoxy and t-butoxy; cyano groups; carboxyl groups which may be protected; hydroxyalkyl groups; carboxyalkyl groups; heteroaryl groups such as tetrazolyl group; and so on. The ring may have one to two substituents described above.

The substituent constituting the "heteroaryl group which may be substituted" contained in the definition of $R^5$, $R^{18}$, $R^{20}$, $R^{21}$ and $R^{22}$, the "phenylalkyloxy group which may be substituted" contained in the definition of $R^6$, the "1,3-benzdioxolyl group which may be substituted, 1,4-benzdioxyl group which may be substituted, 1,3-benzdioxolylalkyl group which may be substituted or 1,4-benzdioxylalkyl group which may be substituted" contained in the definition of $R^5$, the "benzyl group which may be substituted" defined with respect to $R^5$ and the "heteroarylalkyl group which may be substituted" defined with respect to $R^{11}$ and $R^{12}$ includes, for example, hydroxyl group; nitro group; halogen atoms such as chlorine atom, fluorine atom, bromine atom and iodine atom; lower alkyl groups such as methyl, ethyl and t-butyl; lower alkoxy groups such as methoxy, ethoxy and t-butoxy; carboxyl groups which may be protected; hydroxyalkyl groups; carboxyalkyl groups; tetrazolyl group; and so on.

Further, the substituent constituting the "group represented by the formula $-(CH_2)_q-$, wherein each carbon may have one to two substituents when q is an integer of 1 to 8" contained in the definition of Y includes the same substituents as those described above.

Although the acylamino group defined with respect to $R^1$, $R^2$, $R^3$, $R^4$, $R^{20}$, $R^{21}$ and $R^{22}$ refers to an amino group wherein an acyl group(s) as described above is(are) bonded to the nitrogen atom of the amino group, i.e., monoacylamino group or diacylamino group, the monoacylamino group is preferred.

The halogen atom defined with respect to $R^1$, $R^2$, $R^3$, $R^4$, $R^5$, $R^6$, $R^{20}$, $R^{21}$, $R^{22}$ and $R^{50}$ includes fluorine atom, chlorine atom, bromine atom and iodine atom.

The carboxylalkyl group which may be protected defined with respect to $R^5$, $R^9$, $R^{10}$, $R^{11}$, $R^{12}$, $R^{17}$ and $R^{19}$ is a carboxyalkyl group wherein the carboxyl group may be protected with the carboxyl-protective group described above. Further, the carboxy group(s) in this carboxyalkyl group may be bonded to any and one to two carbon atom(s) of the lower alkyl group as described above.

The carboxyalkenyl group which may be protected defined with respect to $R^5$ refers to a carboxyalkenyl group wherein the carboxyl group is protected with the carboxyl-protective group described above. Further, the carboxy group(s) in this carboxyalkenyl group may be bonded to any and one to two carbon atom(s) of the lower alkyl group as described above.

The lower alkoxyalkyl group defined with respect to $R^{17}$, $R^{19}$, $R^{20}$, $R^{21}$ and $R^{22}$ is one derived from the above-mentioned lower alkyl group and examples thereof include methoxymethyl group, methoxyethyl group, methoxybutyl group and ethoxyethyl group.

The aminoalkyl group defined with respect to $R^{11}$ and $R^{12}$ refers to a lower alkyl group as described above wherein an amino group is bonded to any of the carbon atoms constituting the lower alkyl group.

The alkylcarbamoyl group defined with respect to $R^{11}$ and $R^{12}$ refers to one derived from the above-mentioned lower alkyl group.

The carboxyalkylcarbamoyl group which may be protected used in the definition of $R^{11}$ and $R^{12}$ refers to any of the alkylcarbamoyl groups described above which has a carboxyl group, which may be protected, bonded to any carbon atom of the alkyl.

The alkylsulfonylamino group defined with respect to $R^{20}$, $R^{21}$ and $R^{22}$ refers to one derived from the above-mentioned lower alkyl group.

The hydroxyiminoalkyl group defined with respect to $R^{20}$, $R^{21}$ and $R^{22}$ is a lower alkyl group as described above wherein a hydroxyimino group is bonded to any of the carbon atoms constituting the lower alkyl group.

Although the alkyloxycarbonylamino group defined with respect to $R^{20}$, $R^{21}$ and $R^{22}$ is an amino group wherein the nitrogen atom of the amino group is mono- or disubstituted with an alkyloxycarbonyl derived from the above-mentioned lower alkyl group, the mono-substituted alkyloxycarbonylamino group is preferable.

The alkyloxycarbonyloxy group defined with respect to $R^{20}$, $R^{21}$ and $R^{22}$ refers to a group wherein an alkyloxycarbonyl derived from the above-mentioned lower alkyl group is bonded to an oxygen atom.

The hydroxyalkyloxy group defined with respect to $R^{23}$ refers to one derived from the hydroxyalkyl group described above.

In the compounds of the present invention, a ring part of a bicyclic skeleton wherein the ring A and ring B are combined or a three or more ring skeleton when two of the substituents on the ring A together form a ring, is formed. Among these, desirable examples are as follows:

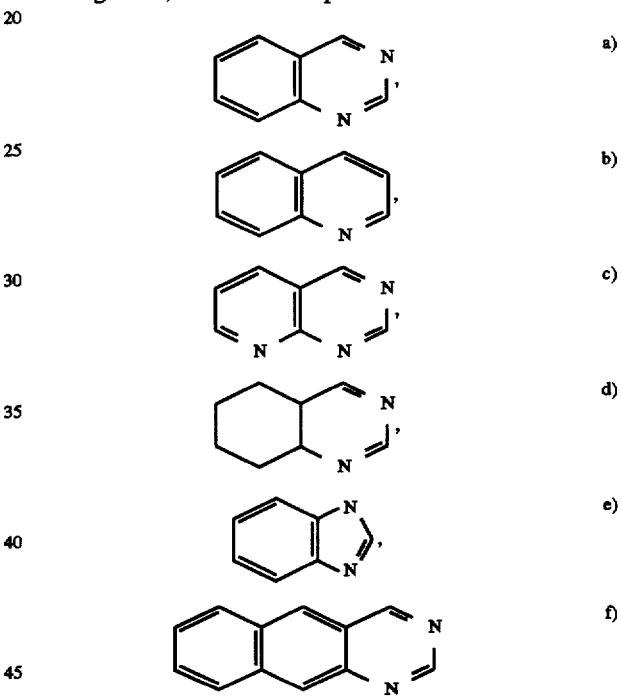

Among these, a), b), c) and e) are cited as more desirable ones and a), b) and c) are cited as more desirable ones. Most desirable one is a).

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of the present invention also includes these metal salts.

Although the compound of the present invention may be present as various isomers including geometrical isomers, i.e., cis-isomer and trans-isomer, and optical isomers, i.e., d-isomer and l-isomer depending upon the kinds and combination of the substituents, it is needless to say that the compounds of the present invention includes all of the isomers.

Preferable specific examples of the compound of the present invention will now be described in order to facilitate the understanding of the present invention, though it is needless to say that the compounds of the present invention are not limited to these examples.

The most desirable specific examples of the compound include compounds represented by the following general formula (A) and pharmacologically acceptable salts thereof:

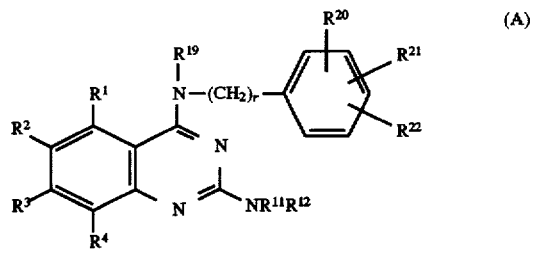

[in general formula (A), $R^1$, $R^2$, $R^3$, $R^4$, $R^{11}$, $R^{12}$, $R^{19}$, $R^{20}$, $R^{21}$, $R^{22}$ and r are the same as those in general formula (1)].

As $R^1$, $R^2$, $R^3$ and $R^4$, each of which may be the same or different from one another, hydrogen atom, a halogen atom and cyano group are preferable and, among them, hydrogen atom, cyano group and chlorine atom are still preferable.

To enter into details with respect to the combination of $R^1$, $R^2$, $R^3$ and $R^4$, it is desirable that one of $R^1$, $R^2$, $R^3$ and $R^4$ is cyano group or chlorine atom and the others are hydrogen atoms and, among them, it is most desirable that $R^2$ is cyano group or chlorine atom and $R^1$, $R^3$ and $R^4$ are hydrogen atoms.

As $R^{11}$ and $R^{12}$, each of which may be the same or different from each other, hydrogen atom, a lower alkyl group and a carboxyalkyl group which may be protected are preferable and, among these, hydrogen atom, methyl group and 3-carboxypropyl group are preferable.

Further, it is most desirable that $R^{11}$ and $R^{12}$, together with the nitrogen atom to which they are bonded, form a ring which may be substituted, and among them, a piperidine ring is most desirable. It is still preferable that this ring is substituted with a lower alkyl group, a lower alkoxy group, a carboxyl group which may be protected, a hydroxyl group, a halogen atom, a hydroxyalkyl group or a carboxyalkyl group, and among them, a carboxyl group which may be protected is most preferable.

$R^{19}$ is preferably a hydrogen atom or a lower alkyl group such as methyl group and ethyl group, particularly preferably a hydrogen atom.

r is desirably 0, 1 or 2, most desirably 1.

As $R^{20}$, $R^{21}$ and $R^{22}$, a hydrogen atom, a lower alkyl group, a lower alkoxy group and a halogen atom are preferable, or it is preferable that two of $R^{20}$, $R^{21}$ and $R^{22}$ together form methylenedioxy or ethylenedioxy.

[Preparation process]

Representative processes for the preparation of the compound according to the present invention will now be described below.

Though compounds having a quinazoline skelton are mainly described in the following explanation, the following explanation can be applied for compounds having a skelton other than the quinazoline skelton.

Preparation process 1

When $R^5$ is a hydrogen atom, a halogen atom or a group selected from among those which are directly bonded to the quinazoline skeleton through a carbon atom in the general formula (I), a compound represented by the general formula (I) can also be prepared by the following process:

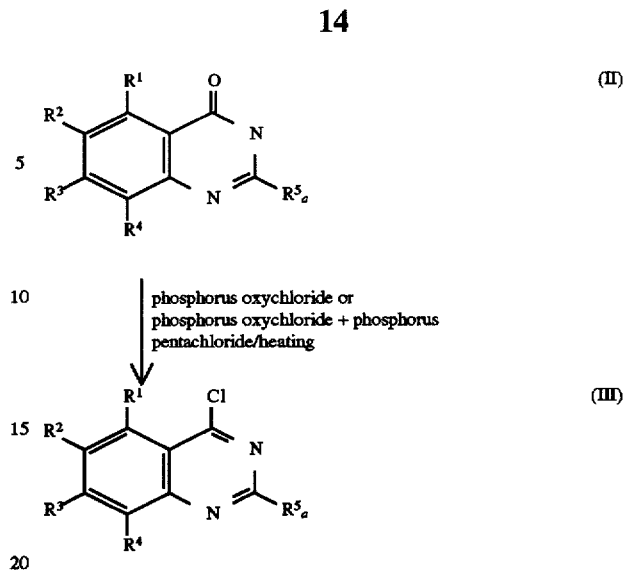

(in a series of formulas, $R^5_a$ is a hydrogen atom, a halogen atom or a group selected from among those which are directly bonded to the quinazoline skeleton through a carbon atom in $R^5$ described above; and $R^1$, $R^2$, $R^3$ and $R^4$ are each as defined above.

That is, this process is one for preparing a quinazoline derivative represented by the general formula (III) by reacting a quinazoline derivative represented by the general formula (II) with phosphorus oxychloride or by reacting it with phosphorus oxychloride in the presence of phosphorus pentachloride under heating.

Preparation process 2

When $R^5$ is a group selected from among a hydrogen atom, a halogen atom, a group represented by the formula

(wherein $R^8$ and m are each as defined above), a group represented by the formula —O—$R^9$ (wherein $R^9$ is as defined above), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxolylalkyl group which may be substituted and a 1,4-benzodioxylalkyl group which may be substituted); and $R^6$ is a group selected from among those defined above with respect to $R^6$ except a hydrogen atom, halogen atoms and lower alkyl groups in the general formula (I), a compound represented by the general formula (I) can be prepared by the following process:

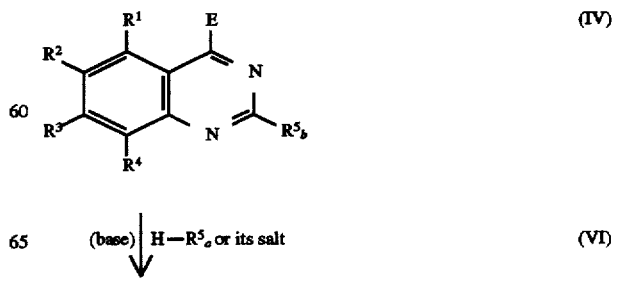

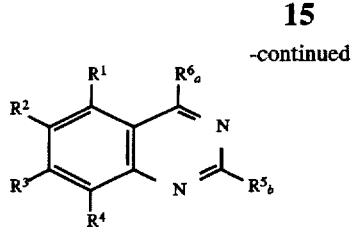 (V)

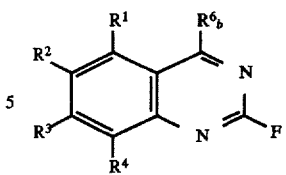 (VII)

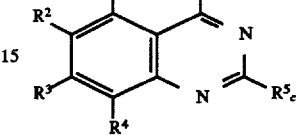 H—R⁵_c or its salt (IX)

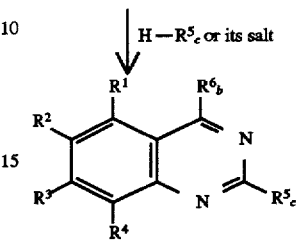 (VIII)

[in a series of formulas, $R^1$, $R^2$, $R^3$ and $R^4$ are each as defined above; $R^5_b$ represents a group selected from among a hydrogen atom, a halogen atom, a group represented by the formula

(wherein $R^8$ and m are each as defined above), a group represented by the formula —O—$R^9$ (wherein $R^9$ is as defined above), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxolylalkyl group which may be substituted and a 1,4-benzodioxylalkyl group which may be substituted); $R^6_a$ represents a group selected from among those defined above with respect to $R^6$ except a hydrogen atom, halogen atoms and lower alkyl groups; and E represents an eliminable group].

That is, this process is one for preparing an objective compound (V) by condensing a quinazoline derivative represented by the general formula (IV) with a compound represented by the general formula (VI).

The eliminable group represented by E in the formula includes halogen atoms and alkoxy groups.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropyl alcohol, tetrahydrofuran, dimethylformamide and dimethyl sulfoxide. This process can be conducted even in the absence of any solvent in some cases.

The reaction temperature preferably ranges from –20° to 300° C.

Preparation process 3

When $R^5$ is a group selected from among those defined above with respect to $R^5$ except a hydrogen atom, halogen atoms and groups which are directly bonded to the quinazoline skeleton through a carbon atom; and $R^6$ is a group selected from among those defined above with respect to $R^6$ except halogen atoms in the general formula (I), a compound represented by the general formula (I) can be prepared by the following process:

(in a series of formulas, $R^1$, $R^2$, $R^3$ and $R^4$ are each as defined above; $R^5_c$ is a group selected from among those defined above with respect to $R^5$ except a hydrogen atom, halogen atoms and groups which are directly bonded to the quinazoline skeleton through a carbon atom;

$R^6_b$ is a group selected from among those defined above with respect to $R^6$ except halogen atoms; and F represents an eliminable group).

That is, this process is one for preparing an objective compound (VIII) by condensing a compound represented by the general formula (VII) with a compound represented by the general formula (IX).

The eliminable group represented by F in the formula includes, for example, halogen atoms, alkylthio groups and so forth.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropanol, tetrahydrofuran, dimethylformamide and dimethyl sulfoxide.

The reaction temperature preferably ranges from 0° to 300° C.

Preparation process 4

When $R^5$ is a group represented by the formula

(wherein $R^{24}$ is a hydrogen atom or a lower alkyl group in the general formula (I), a compound represented by the general formula (I) can also be prepared by the following process:

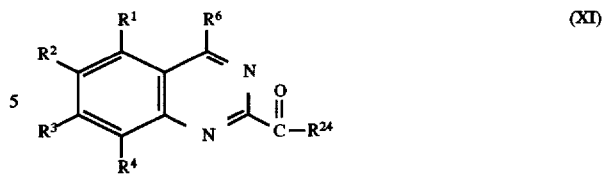

(XI)

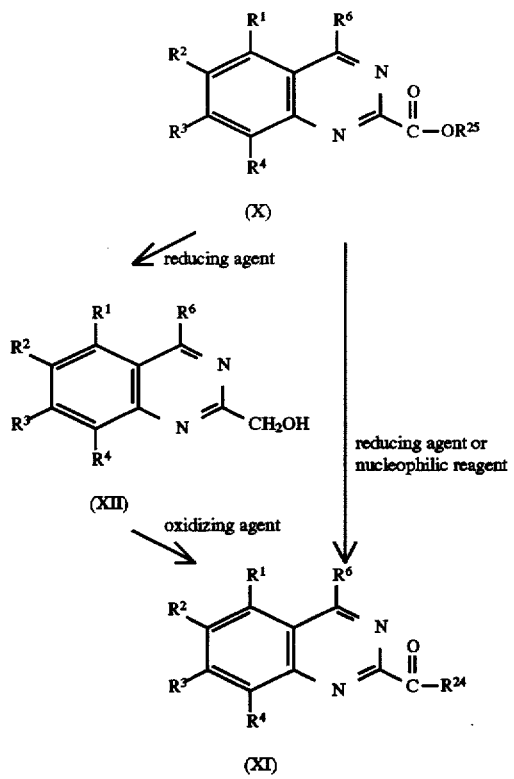

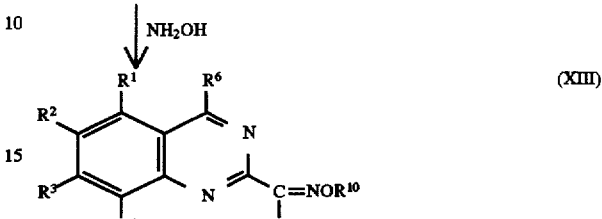

(XIII)

(in a series of formulas, $R^1$, $R^2$, $R^3$, $R^4$, $R^5$, $R^6$, $R^{10}$ and $R^{24}$ are each as defined above).

That is, this process is one for preparing a compound represented by the formula (XIII) by reacting a compound represented by the general formula (XI) with hydroxyamine.

As the reaction solvent, every solvent which is inert to the reaction can be used.

The reaction temperature ranges form 0° C. to the refluxing temperature of the solvent.

Preparation process 6

When $R^5$ is a group represented by the formula

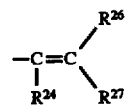

(wherein $R^{24}$ is as defined above; $R^{26}$ represents a hydrogen atom or a lower alkyl group; and $R^{27}$ represents a hydrogen atom, a lower alkyl group, a carboxyl group which may be protected or a carboxyalkyl group which may be protected) in the general formula (I), a compound represented by the formula (I) can also be prepared by the following process:

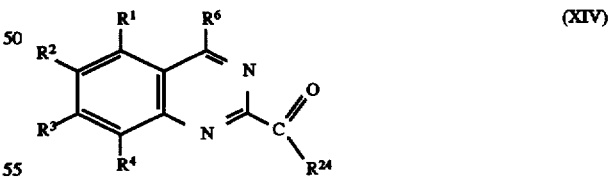

(XIV)

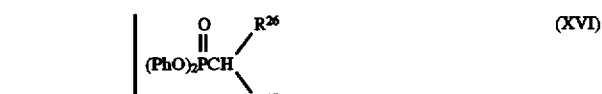

(XVI)

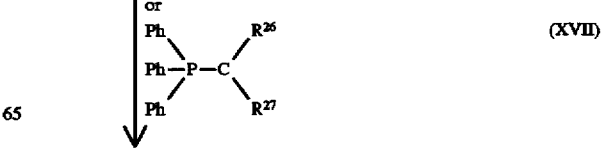

(XVII)

(in a series of formulas, $R^1$, $R^2$, $R^3$, $R^4$ and $R^6$ are each as defined above; and $R^{24}$ and $R^{25}$, each of which may be the same or different from each other, represent each a hydrogen atom or a lower alkyl group).

That is, this process is one for preparing an objective compound (XI) by reacting a compound represented by the general formula (X) with an ordinary reducing agent or an ordinary nucleophilic reagent, either directly or through the oxidation of an alcohol (XII).

The reducing agent includes lithium aluminum hydride, sodium borohydride, diisobutylaluminum hydride and so forth.

The nucleophilic reagent includes lower alkyl metals such as methyllithium, methylmagnesium bromide and so forth.

The oxidizing agent to be used when the reaction is conducted through the alcohol (XII) includes potassium bichromate/sulfuric acid, dimethyl sulfoxide/oxalyl chloride and so forth.

As the reaction solvent, every solvent which is inert to the reaction can be used.

The reaction temperature ranges from 0° C. to the refluxing temperature of the solvent.

Preparation process 5

When $R^5$ is a group represented by the formula

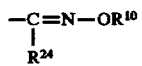

(wherein $R^{10}$ and $R^{24}$ are each as defined above) in the general formula (I), a compound represented by the general formula (I) can also be prepared by the following process:

-continued

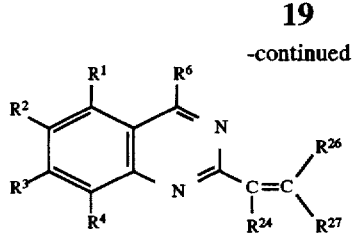
(XV)

(in a series of formulas, $R^1$, $R^2$, $R^3$, $R^4$, $R^6$, $R^{24}$, $R^{26}$ and $R^{27}$ are each as defined above; and Ph represents a phenyl group).

That is, this process is one for preparing a compound represented by the general formula (XV) by reacting a compound represented by the general formula (XIV) with a compound represented by the general formula (XVI) or the general formula (XVII) through the Wittig reaction.

As the reaction solvent, every solvent which is inert to the reaction can be used.

The reaction temperature ranges from 0° C. to the refluxing temperature of the solvent.

Preparation process 7

When $R^5$ is a group represented by the formula

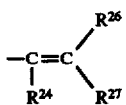

(wherein $R^{24}$, $R^{26}$ and $R^{27}$ are each as defined above) in the general formula (I), a compound represented by the formula (I) can also be prepared by the following process:

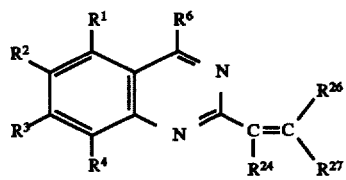
(XV)

↓ Pd—C or Pt

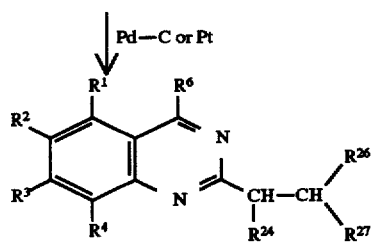
(XVIII)

(in a series of formulas, $R^1$, $R^2$, $R^3$, $R^4$, $R^6$, $R^{24}$, $R^{26}$ and $R^{27}$ are each as defined above).

That is, this process is one for preparing an objective compound (XVIII) by reducing the compound represented by the general formula (XV) prepared in the Preparation process 6.

The reduction can be conducted by conventional means, for example, catalytic reduction using palladium/carbon or platinum catalyst.

As the reaction solvent, every solvent which is inert to the reaction is used.

Preparation process 8

When $R^6$ is a group represented by the formula

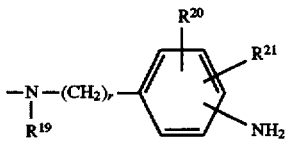

(wherein $R^{19}$, $R^{20}$, $R^{21}$ and r are each as defined above) in the general formula (I), a compound represented by the general formula (I) can also be prepared by the following process:

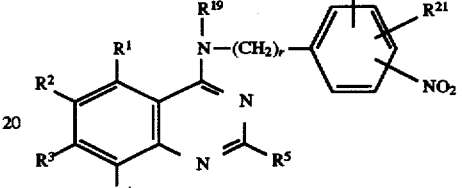
(XIX)

↓

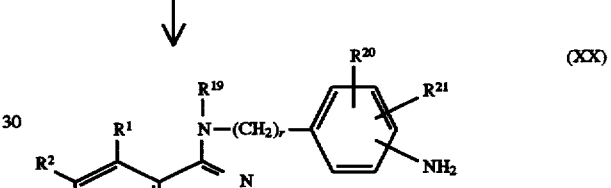
(XX)

(in a series of formulas, $R^1$, $R^2$, $R^3$, $R^4$, $R^5$, $R^{19}$, $R^{20}$, $R^{21}$ and r are each as defined above).

That is, this process is one for preparing an objective compound (XX) by reducing a compound represented by the general formula (XIX).

The reduction is conducted by conventional means, e.g., catalytic reduction using palladium/carbon or platinum catalyst or reduction with iron or tin.

As the reaction solvent, every solvent which is inert to the reaction can be used.

Preparation process 9

When $R^5$ is a group represented by the formula —O—$R^{9'}$ (wherein $R^{9'}$ is a carboxyl group which may be protected) in the general formula (I), a compound represented by the formula (I) can be prepared by the following process:

(The first step)

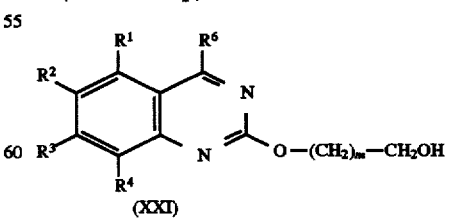
(XXI)

↓ Oxidation

-continued

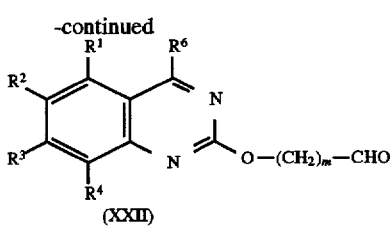

(in a series of formulas, $R^1$, $R^2$, $R^3$, $R^4$ and $R^6$ are each as defined above; and m represents 0 or an integer of 1 to 2).

That is, this process is one for preparing a compound represented by the general formula (XXII) by oxidizing a compound represented by the general formula (XXI) by conventional means.

As the oxidizing agent, everyone can be used so far as it is conventionally used and examples thereof include chrominum (VI), dimethyl sulfoxide and oxalyl chloride.

As the reaction solvent, every solvent which is inert to the reaction can be used.

The reaction temperature ranges from 0° C. to the refluxing temperature of the solvent.

(The second step)

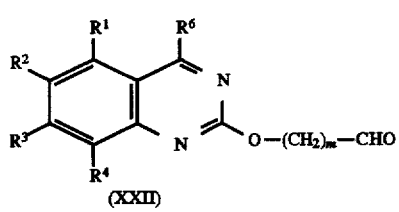

+

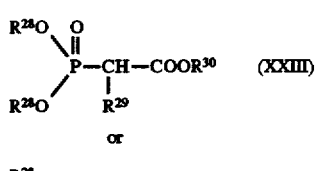

or

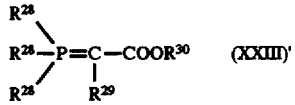

↓ Wittig reaction

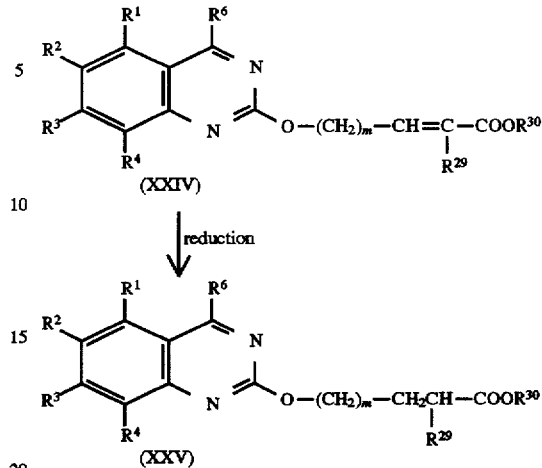

(in a series of formulas, $R^1$, $R^2$, $R^3$, $R^4$, $R^6$ and m are each as defined above; and $R^{28}$, $R^{29}$ and $R^{30}$, each of which may be the same or different from one another, represent each a hydrogen atom or a lower alkyl group).

That is, this process is one for preparing a compound represented by the general formula (XXIV) by reacting the compound (XXII) prepared in the first step with the Wittig reagents (XXIII) or (XXIII)'.

As the reaction solvent, everyone which is inert to the reaction can be used.

The reaction temperature ranges from 0° C. to the refluxing temperature of the solvent.

(The third step)

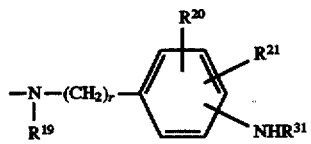

↓ reduction (in a series of formulas, $R^1$, $R^2$, $R^3$, $R^4$, $R^6$, $R^{29}$, $R^{30}$ and m are each as defined above).

That is, this process is one for preparing the objective compound (XXV) by reducing the compound (XXIV) prepared in the second step.

The reduction may be conducted by conventional means, and examples thereof include catalytic reduction using palladium/carbon or platinum catalyst.

Preparation process 10

When $R^6$ is a group represented by the formula $$-N-(CH_2)_r-\underset{R^{19}}{\underset{|}{}}\phantom{x}\text{(aryl with } R^{20}, R^{21}, NHR^{31}\text{)}$$

(wherein $R^{19}$, $R^{20}$, $R^{21}$ and r are each as defined above; and $R^{31}$ represents an acyl group, a lower alkylsulfonyl group or a lower alkyloxycarbonyl group) in the general formula (I), a compound represented by the general formula (I) can also be prepared by the following process:

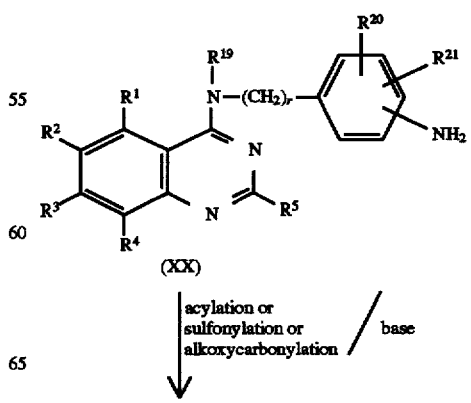

↓ acylation or sulfonylation or alkoxycarbonylation / base

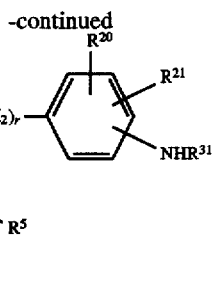

(XXVI)

(in a series of formulas, $R^1$, $R^2$, $R^3$, $R^4$, $R^5$, $R^{19}$, $R^{20}$, $R^{21}$, $R^{31}$ and r are each as defined above).

That is, this process is one for preparing an objective compound (XXVI) by subjecting the compound represented by the general formula (XX) prepared in the Preparative process 8 to the conventional acylation, sulfonylation or alkoxycarbonylation in the presence of a base.

As the acylating agent, every acylating agent which is conventionally used, for example, activated derivatives of carboxylic acids such as acid chloride, acid anhydride and mixed acid anhydride; and condensing agents such as dicyclohexylcarbodiimide is used.

As the sulfonylating agent, every sulfonylating agent which is conventionally used can be used and examples thereof include a lower alkylsulfonyl chloride and a lower alkylsulfonic anhydride.

The alkoxycarbonylating agent includes every alkoxycarbonylating agent which is conventionally used, for example, a lower alkyloxycarbonyl chloride and a lower alkyl pyrocarbonate.

As the base, every base can be used and examples thereof include organic bases such as pyridine and triethylamine; and inorganic bases such as sodium carbonate, potassium carbonate, sodium hydroxide and sodium hydride.

Preparation process 11

When the ring A is selected from any of a benzene ring, a pyridine ring and a cyclohexane ring, the ring B is selected from among a pyridine ring, a pyrimidine ring and an imidazole ring, $R^5$ represents a group selected from among those defined above with respect to $R^5$ except groups which are directly bonded to the ring portion through a carbon atom; and $R^6$ represents a group selected from among those defined above with respect to $R^5$ except groups which are directly bonded to the ring portion through a carbon atom in the general formula (1), the compound represented by the general formula (1) can also be prepared by the following process. The case in which the ring portion forms a quinazoline skeleton is shown below as the representative of the above:

(The first step)

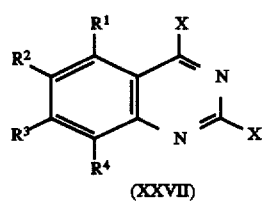

(XXVII)

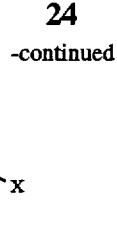

(XXVIII)

(in a series of formulas, $R^1$, $R^2$, $R^3$ and $R^4$ are each as defined above; $R^5_a$ represents a group selected from among those defined above with respect to $R^5$ except groups which are directly bonded to the ring portion through a carbon atom; and X represents a halogen atom).

That is, the first step is a condensation reaction according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^5_a$ is bonded to the ring portion through a nitrogen atom, it is preferred that the reaction is proceeded by heating under reflux in the presence of a tertiary amine such as triethylamine while removing HCl generated. While in the case where $R^5_a$ is bonded to the ring portion through an oxygen atom or a sulfur atom, it is preferred that the reaction is proceeded by heating under reflux in the presence of an alkali such as sodium hydroxide and sodium carbonate.

(The second step)

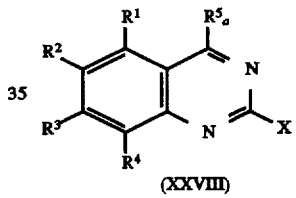

(XXVIII)

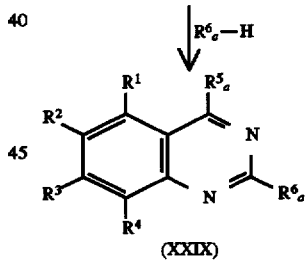

(XXIX)

(in a series of formulas, $R^1$, $R^2$, $R^3$, $R^4$, $R^5_a$ and X are each as defined above; $R^6_a$ represents a group selected from among those defined above with respect to $R^6$ except groups which are directly bonded to the ring portion through a carbon atom).

The second step is a reaction wherein the compound (XXVIII) obtained in the first step is condensed with a compound represented by the formula $R^6_a$—H according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^6_a$ is bonded to the ring portion through a nitrogen atom, it is preferred that the reaction is proceeded by heating under reflux in the presence of an organic base such as triethylamine, pyridine and ethyldiisopropylamine, an inorganic base such as sodium carbonate, potassium carbonate, sodium hydrogencarbonate, sodium hydride and sodium hydroxide or an alkoxide such as sodium methoxide and potassium t-butoxide. While in the case where $R^6_a$ is bonded to the ring portion through an oxygen atom or a sulfur atom, it is preferred that the reaction is proceeded by heating under reflux in the presence of an alkali such as sodium hydroxide and sodium carbonate.

Preparation process 12

When the compound represented by the general formula (1) is a compound represented by the following general formula (XXXII):

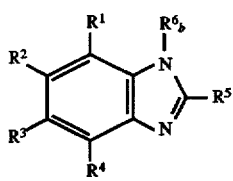

the compound can also be prepared by the following process.

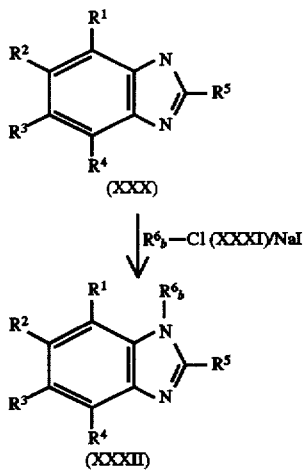

(in a series of formulas, $R^1$, $R^2$, $R^3$, $R^4$ and $R^5$ are each as defined above; and $R^6_b$ represents a group selected from among groups which are directly bonded to the ring portion through a carbon atom in those defined above with respect to $R^6$).

That is, this process is one for preparing an objective compound by reacting, for example, piperonyl chloride (XXXI) with a benzimidazole derivative represented by the general formula (XXX) in the presence of an alkali by a conventional process.

Sodium iodide is preferred as alkali.

Although every solvent which is inert to the reaction can be used as the reaction solvent, polar solvents such as dimethylforamide can be cited as preferable ones.

The reaction temperature is preferably about 60° to 100° C., particularly preferably about 70° to 80° C.

Preparation process 13

The compound of the present invention can also be prepared by the following process:

(The first step)

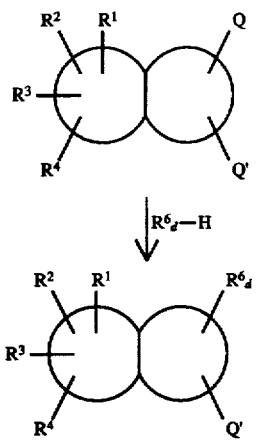

(in a series of formulas, $R^1$, $R^2$, $R^3$ and $R^4$ are each as defined above; $R^6_d$ represents a group selected from among those defined above with respect to $R^6$ except groups which are directly bonded to the ring portion through a carbon atom;

and Q and Q' represent halogen atoms).

The first step is a condensation reaction according to a conventional process.

In the case where $R^6_d$ is bonded to the ring portion through a nitrogen atom, it is preferred that the reaction is proceeded by heating under reflux in the presence of an organic base such as triethylamine, pyridine and diisopropylethylamine, an inorganic base such as sodium carbonate, potassium carbonate, sodium hydrogencarbonate, sodium hydroxide and sodium hydride or an alkoxide such as sodium methoxide and potassium t-butoxide. While in the case where $R^6_d$ is bonded to the ring portion through an oxygen atom or a sulfur atom, it is preferred that the reaction is proceeded by heating under reflux in the presence of an inorganic base such as sodium hydroxide and sodium carbonate.

Every solvent which is inert to the reaction can be used as the reaction solvent, and examples thereof include alcohol solvents such as ethanol and isopropyl alcohol, ether solvents such as tetrahydrofuran, dimethylformamide and dimethylsulfoxide. Further, in the present process, the reaction can be proceeded in the absence of a reaction solvent in some cases.

(The second step)

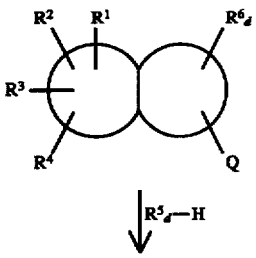

-continued

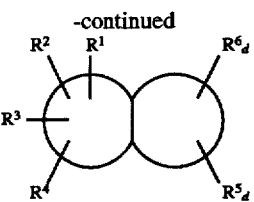

(in a series of formulas, $R^1$, $R^2$, $R^3$, $R^4$, $R^6d$ and Q are each as defined above; and $R^5_d$ represents a group selected from among those defined above with respect to $R^5$ except groups which are directly bonded to the ring portion through a carbon atom).

That is, the second step is a process for preparing an objective compound in which the compound obtained in the first step is condensed with a compound represented by the general formula $R^5_d$—H.

In the present process, the reaction can be proceeded in the presence of a base at need.

As the base, organic bases such as triethylamine, pyridine and diisopropylethylamine, inorganic bases such as sodium carbonate, potassium carbonate, sodium hydrogencarbonate, sodium hydroxide and sodium hydride and alkoxides such as sodium methoxide and potassium t-butoxide can be cited.

Every solvent which inert to the reaction can be used as the reaction solvent, and examples thereof include alcohol solvents such as ethanol and isopropanol, ether solvents such as tetrahydrofuran, dimethylformamide and dimethylsulfoxide.

The reaction temperature is preferably 0° C. to 300° C.

In the case where $R^5_d$ is a group which is bonded to the ring portion through a nitrogen atom, it is preferred that the reaction is proceeded by heating under reflux in the presence of a tertiary amine such as triethylamine. While in the case where $R^5_d$ is a group which is bonded to the ring portion through an oxygen atom or a sulfur atom, it is preferred that the reaction is proceeded by heating under reflux in the presence of an alkali such as sodium hydroxide and sodium carbonate.

The compounds thus obtained in the preparation processes 1 to 13 described above can form salts thereof by a conventional process, for example, by adding sodium hydroxide, potassium hydroxide or methanesulfonic chloride.

Next, the preparation processes for the raw compounds used in the preparation processes will be shown.

Preparation process A

Among the starting materials used in the preparation process 13, the compound in which the ring portion is a quinazoline ring and Q and Q' are chlorine atoms can also be prepared by the following process:

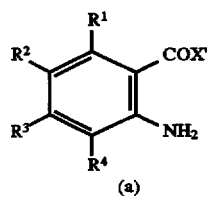

(a)

↓ (the first step)

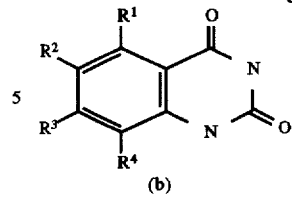

(b)

↓ (the second step)

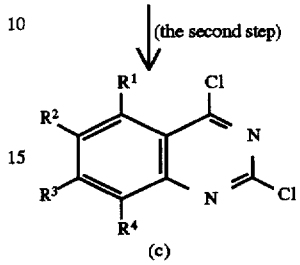

(c)

(in a series of formulas, $R^1$, $R^2$, $R^3$ and $R^4$ are each as defined above; and X' represents any group among a hydroxyl group, an alkoxy group and an amino group).

That is, this process is one for preparing the objective compound (c) by cyclizing the compound (a) by a conventional process to obtain the compound (b) and then chlorinating it by a conventional process.

The first step is a cyclization reaction. It is a step in which urea is reacted with the compound (a) to obtain the compound (b). In this case, the reaction temperature is preferably about 170° to 190° C., and although every solvent can be used as long as it is inert to the reaction, preferable examples thereof include N-methylpyrrolidone and the like. In this step, the reaction can also be proceeded in the absence of the solvent.

Further, the compound (b) can also be obtained by cyclizing with carbonyldiimidazole or by cyclizing under an acidic or basic condition after converting to urethane with a chloroformic ester when X' is an amino group.

The second step is a chlorination reaction. This step can be carried out by a conventional manner, and examples thereof include a process in which the compound (b) is heated under reflux with phosphorus pentachloride and phosphorus oxychloride, or phosphorus oxychloride while stirring to chlorinate.

Preparation process B

The starting material (II) used in the preparation process 1 can be prepared by the following process:

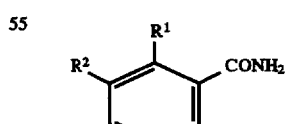

(d)

(the first step) | acylating agent such as acid chloride/base

↓

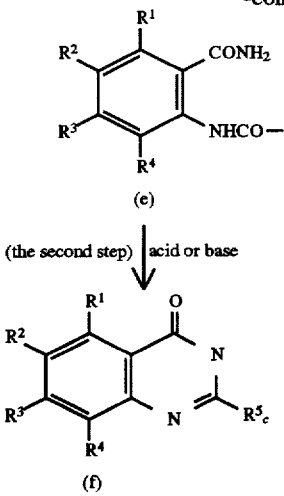

(e)

(the second step) ↓ acid or base

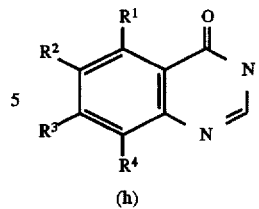

(f)

(in a series of formulas, $R^1$, $R^2$, $R^3$ and $R^4$ are each as defined above; and $R^5_c$ represents a halogen atom or a group selected from among groups which are directly bonded to the ring portion through a carbon atom in those defined with respect to above $R^5$).

That is, the above process is a reaction in which an amide product is obtained by a conventional process in the first step and a cyclization is carried out in the presence of an acid or a base in the second step.

The amide product (e) can be obtained by a conventional process, and it can be obtained, for example, by reacting the compound (d) with an acylating agent such as an acid chloride represented by $R^5_c$—CDCl in the presence of a base.

Tertiary amines such as triethylamine and organic bases such as pyridine are preferably cited as the base.

Specific examples of the acylating agent include acid chlorides such as benzoyl chloride, acetyl chloride, ethyloxalyl chloride and benzyloxyacetyl chloride.

The reaction temperature is preferably about 0° C. to 30° C.

In the second step, the compound (e) obtained in the first step is heated under reflux in the presence of an acid or a base to obtain the compound (f).

The acid includes acetic anhydride and the like.

The base includes sodium hydroxide and the like.

Preparation process C

The starting material (II) can also be prepared by the following process when $R^5_a$ is a hydrogen atom in the preparation process 1:

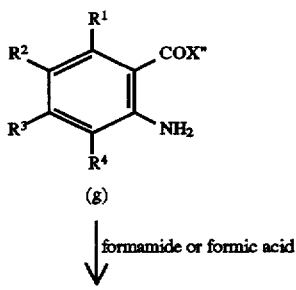

(g)

↓ formamide or formic acid (h)

(in a series of formulas, $R^1$, $R^2$, $R^3$ and $R^4$ are each as defined above; and X" represents a hydroxyl group or a lower alkoxy group).

That is, the above process is a cyclization reaction by a conventional process.

The objective compound (h) can be synthesized, for example, by condensing the raw compound (g) with formamide by heating under reflux, or by heating it together with formic acid.

[Effect of the Invention]

Experimental Examples will now be described to illustrate the effect of the compound of the present invention.

EXPERIMENTAL EXAMPLES

Enzyme inhibiting action with the use of cGMP-PDE prepared from the swine aorta

1. Method of experiment

The enzymatic activity of the cGMP-PDE prepared from the swine aorta was determined according to the method of Thompson et al. [1]. The enzymatic activity thereof was determined in the presence of 1 mM EGTA by the use of 1 μM cGMP as a substrate. The compound of the present invention was dissolved in DMSO, added to the reaction liquid and examined for the inhibitory activity. The final concentration of DMSO in the reaction liquid was adjusted to 4% or below. (1) Thompson, W. J. and Strada, S. J., Cyclic Nucleotide Phosphodiesterase (PDE), in Methods of Enzymatic Analysis, vol 4, p.127–234, 1984.

Preparation of cGMP-PDE

The swine aorta was sliced, followed by the addition of 10 times by volume as much Buffer A (20 mM Tris/HCl, 2 mM Mg acetate, 1 mM Dithiothreitol, 5 mM EDTA, 1400 TIU/liter aprotinin, 10 mg/liter leupeptin, 1 mM benzamidine, 0.2 mM PMSF, pH 7.5). The obtained mixture was homogenized and the homogenate was centrifuged at 100000×g for one hour. The obtained supernatant was supplied a DEAE-Toyopearl 650S (Tosoh, Tokyo, Japan) column. After the column was washed with Buffer B (50 mM Tris/HCl, 0.1 mM EGTA, 2 mM Mg acetate, 1 mM Dithiothreitol, 0.2 mM PMSF, pH 7.5), gradient elution with 0.05 to 0.4M NaCl was conducted. Thus, CaM-independent cGMP-PDE fractions were obtained.

2. Results of experiment

The results of experiment of the compounds of the present invention are given in Tables 1 to 6B.

TABLE 1

| Ex. No. | $IC_{50}(\mu M)$ |
|---|---|
| 7 | 1.0 |
| 19 | 0.39 |
| 22 | 0.36 |
| 25 | 0.78 |
| 33 | 0.37 |
| 38 | 0.42 |
| 40 | 0.65 |
| 41 | 0.35 |

TABLE 1-continued

| Ex. No. | IC$_{50}$(µM) |
|---|---|
| 42 | 0.19 |
| 45 | 0.41 |
| 46 | 0.24 |
| 49 | 0.041 |
| 50 | 0.032 |
| 51 | 0.069 |
| 52 | 0.069 |
| 53 | 0.12 |
| 54 | 0.47 |
| 55 | 0.030 |
| 57 | 0.038 |
| 58 | 0.042 |
| 59 | 0.27 |
| 60 | 0.18 |
| 61 | 0.42 |

TABLE 2

| Ex. No. | IC$_{50}$(µM) |
|---|---|
| 64 | 0.38 |
| 65 | 0.093 |
| 67 | 0.14 |
| 68 | 0.62 |
| 69 | 0.19 |
| 70 | 0.84 |
| 71 | 0.81 |
| 72 | 0.73 |
| 73 | 0.94 |
| 74 | 0.35 |
| 78 | 0.50 |
| 81 | 0.44 |
| 82 | 0.55 |
| 83 | 0.024 |
| 84 | 0.22 |
| 86 | 0.96 |
| 87 | 0.68 |
| 89 | 0.16 |
| 91 | 0.036 |
| 92 | 0.094 |
| 93 | 0.032 |
| 95 | 0.20 |
| 97 | 0.79 |

TABLE 3

| Ex. No. | IC$_{50}$(µM) |
|---|---|
| 98 | 0.062 |
| 104 | 0.010 |
| 105 | 0.18 |
| 107 | 0.0040 |
| 114 | 0.0030 |
| 112 | 0.0020 |
| 115 | 0.0020 |
| 120 | 0.0010 |
| 121 | 0.65 |
| 122 | 0.0050 |
| 123 | 0.031 |
| 124 | 0.0080 |
| 125 | 0.0090 |
| 126 | 0.0010 |
| 127 | 0.11 |
| 128 | 0.30 |
| 133 | 0.77 |
| 134 | 0.0050 |
| 136 | 0.93 |
| 137 | 0.38 |
| 138 | 0.81 |
| 139 | 0.021 |
| 140 | 0.68 |

TABLE 4

| Ex. No. | IC$_{50}$(µM) |
|---|---|
| 146 | 0.015 |
| 150 | 0.0072 |
| 151 | 0.081 |
| 152 | 0.11 |
| 164 | 0.0080 |
| 165 | 0.016 |
| 166 | 0.026 |
| 167 | 0.56 |
| 168 | 0.011 |
| 169 | 0.011 |
| 170 | 0.029 |
| 171 | 0.00040 |
| 172 | 0.095 |
| 174 | 0.0040 |
| 175 | 0.0060 |
| 176 | 0.0030 |
| 177 | 0.012 |
| 178 | 0.011 |
| 179 | 0.0020 |
| 180 | 0.0090 |
| 181 | 0.0050 |
| 182 | 0.0080 |
| 183 | 0.00040 |

TABLE 5

| Ex. No. | IC$_{50}$(µM) |
|---|---|
| 184 | 0.0060 |
| 185 | 0.010 |
| 187 | 0.12 |
| 188 | 0.029 |
| 189 | 0.016 |
| 190 | 0.0050 |
| 191 | 0.019 |
| 192 | 0.020 |
| 193 | 0.00080 |
| 194 | 0.0040 |
| 197 | 0.066 |
| 200 | 0.064 |
| 201 | 0.049 |
| 202 | 0.0020 |
| 203 | 0.028 |
| 204 | 0.0040 |
| 206 | 0.029 |
| 208 | 0.00019 |
| 213 | 0.023 |
| 214 | 0.0090 |
| 216 | 0.017 |
| 220 | 0.00024 |
| 222 | 0.0065 |

TABLE 6A

| Ex. No. | IC$_{50}$(µM) |
|---|---|
| 227 | 0.0026 |
| 228 | 0.00052 |
| 230 | 0.0058 |
| 231 | 0.41 |
| 232 | 0.044 |
| 233 | 0.013 |
| 234 | 0.0060 |
| 235 | 0.0020 |
| 236 | 0.0060 |
| 237 | 0.014 |
| 238 | 0.0050 |
| 239 | 0.0080 |
| 240 | 0.0040 |
| 241 | 0.18 |
| 243 | 0.00015 |

TABLE 6A-continued

| Ex. No. | IC$_{50}$(μM) |
| --- | --- |
| 244 | 0.0090 |
| 245 | 0.10 |

TABLE 6B

| Ex. No. | IC$_{50}$(μM) |
| --- | --- |
| 255 | 0.032 |
| 256 | 0.0021 |
| 260 | 0.00016 |
| 262 | 0.88 |
| 266 | 0.11 |
| 278 | 0.25 |
| 280 | 0.25 |
| 376 | 0.021 |

It became apparent from the above experimental examples that the compounds of the present invention exhibit PDE, particularly cGMP-PDE, inhibiting action. That is, it became obvious that the compounds of the present invention exhibit the effect to increase the concentration of cGMP in vivo by revealing the cGMP-PDE inhibiting action. Accordingly, the nitrogenous heterocyclic compounds which are the compounds of the present invention are effective in the prevention and medical treatment of diseases for which cGMP-PDE inhibiting actions is efficacious. Examples of these diseases include ischemic heart disease such as angina pectoris, myocardial infarction and chronic and acute cardiac failures, lung hypertension which may accompany with cor pulmonale, other hypertensions attributable to all causes, peripheral circulatory disturbance, brain circulatory diturbance, brain function diturbance and allergic diseases such as bronchial asthma, atopic dermatitis and allergic rhinitis.

Those inhibiting a calmodulin-depending type PDE are also included in the compound group of the present invention. There is high possibility that the diseases for which this action is efficacious are the same as the diseases for which cGMP-PDE inhibitoy action described above is efficacious, and, also from this point, it can be said that the compounds of the present invention can be used for prevention and medical treatment of the diseases described above.

Further, the compounds of the present invention are lowly toxic and therefore are extremely safe. Therefore, the present invention is valuable also from this standpoint.

When the compounds of the present invention are used as drugs for these diseases, they may be each administered orally or parenterally. The dose varies depending upon the extent of symptom; age, sex, weight and sensitivity of a patient; the method of administration; the timing and interval of administration, the properties, dispensing and kind of medical preparation; and the kind of an active ingredient and is not particularly limited.

In orally administration, the dose thereof per adult a day is generally about 1 to 1000 mg, preferably about 5 to 500 mg, still preferably 10 to 100 mg, which may be generally administered in 1 to 3 portions a day.

In the case of an injection, the dose thereof is generally 1 μg/kg to 3,000 μg/kg, preferably about 3 μg/kg to 1,000 μg/kg.

In the preparation of a solid preparation for oral administration, a filler and, if necessary, a binder, disintegrator, lubricant, color and/or corrigent is(are) added to the active ingredient and then there is shaped into a tablet, a coated tablet, granule, powder or a capsule by a conventional manner.

Examples of the filler to be used include lactose, corn starch, sucrose, glucose, sorbitol, crystalline cellulose and silicon dioxide; those of the binder to be used include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant to be used include magnesium stearate, talc, polyethylene glycol, silica and hardened vegetable oil; those of the color to be used include those authorized as pharmaceutical additives; and those of the corrigent to be used include cocoa powder, mentha herb, aromatic acid, mentha oil, borneol and powdered cinnamon bark. Of course, the tablet and granule may be suitably coated with sugar, gelatin or the like, if necessary.

In the preparation of an injection, a pH modifier, buffer, suspending agent, solubilizing agent, stabilizer, tonicity agent and/or preservative is(are) added to the active ingredient at need and then there is formulated into an injection for intravenous, subcutaneous or intramuscular administration by a conventional manner. It is also necessary that the injection is freeze-dried according to a conventional method.

Examples of the suspending agent include methylcellulose, Polysorbate 80, hydroxyethylcellulose, acacia, tragacanth powder, sodium carboxymethylcellulose and polyoxyethylene sorbitan monolaurate.

Examples of the solubilizing agent include polyoxyethylene hardened castor oil, Polysorbate 80, nicotinamide, polyoxyethylene sorbitan monolaurate, Macrogol and ethyl ester of castor oil fatty acid.

[Example]

Examples of the present invention will now be described, though it is needless to say that the present invention is not limited to them. In advance of Examples, preparative example of the raw compound for compounds according to the present invention will be described. In the Examples, Me represents a methyl group, Et an ethyl group, Bzl a benzyl group and Ac an acetyl group.

Preparative Example 1

2-Ethoxycarbonyl-6-chloroquinazolin-4(3H)-one

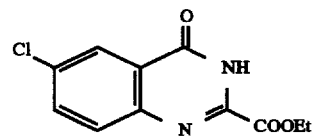

2.50 g (0.0147 mol) of 2-amino-5-chlorobenzamide was dissolved in 15 ml of pyridine. 2.0 ml of ethyloxalyl chloride was dropped into the obtained solution under stirring at room temperature. The obtained mixture was stirred for several hours and distilled under a reduced pressure to remove the solvent. The obtained residue was used as such in the subsequent reaction.

The residue was dissolved in 50 ml of acetic acid, followed by the addition of 5 ml of acetic anhydride. The obtained mixture was heated under reflux for 24 hours. The solvent was distilled away under a reduced pressure and ethanol was added to the obtained crystalline residue. The obtained mixture was filtered to recover the crystal. The crystal was washed with ethanol and ether and air-dried to give 2.78 g of the title compound as a pale-yellow crystal.
yield (%); 75 m.p. (°C.); 239–240

Mass; 253 (M+H)⁺

NMR δ(DMSO-d₆); 1.36 (3H, t, J=7.2 Hz), 4.39 (2H, q, J=7.2 Hz), 7.86 (1H, d, J=8.8 Hz), 7.92 (1H, dd, J=8.8 Hz, 2.4 Hz), 8.11 (1H, d, J=2.4 Hz), 12.85 (1H, brs)

Example 1

4-Chloro-6-cyanoquinazoline

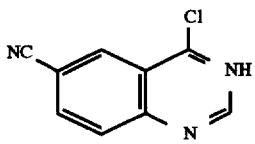

A mixture comprising 2 g of 4-hydroxy-6-carbamoylquinazoline, 30 ml of thionyl chloride and 60 ml of phosphorus oxychloride was heated under reflux for 20 hours. The reaction mixture was concentrated under a reduced pressure and the obtained residue was dissolved in 100 ml of ethyl acetate. The obtained solution was washed with water (150 ml), dried over magnesium sulfate and concentrated under a reduced pressure. The obtained residue was introduced into a silica gel column, followed by eluting with ethyl acetate and acetone to give 800 mg of the title compound.

molecular formula; C₃H₄N₃Cl (189.5)

yield (%); 40 m.p. (°C.); >290

Mass; 190 (M+1)⁺

NMR δ(DMSO-d₆); 7.79 (1H, d, J=8.8 Hz), 8.16 (1H, dd, J=8.8 Hz, 2.0 Hz), 8.26 (1H, s), 8.49 (1H, d, J=2.0 Hz)

Example 2

2,4-Dichloro-6-cyanoquinazoline

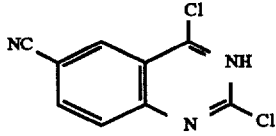

12 g of 2,4-dihydroxy-6-carbamoylquinazoline and 48.8 g of phosphorus pentachloride were suspended in a mixture comprising 200 ml of phosphorus oxychloride and 70 ml of thionyl chloride and the obtained suspension was heated under reflux for 24 hours. The reaction mixture was concentrated under a reduced pressure and the obtained crystalline residue was washed with 100 ml of ethyl acetate and 100 ml of n-hexane to give 6.8 g of the title compound.

molecular formula; C₃H₃Cl₂N₃ yield (%); 52 m.p. (°C.); 161–163

Mass; 224 (M+1)⁺

NMR δ(CDCl₃); 7.94 (1H, d, J=8.0 Hz), 8.00 (1H, dd, J=8.0 Hz, 2.0 Hz), 8.49 ((1H, d, J=2.0 Hz)

Example 3

2-Ethoxycarbonyl-4,6-dichloroquinazoline

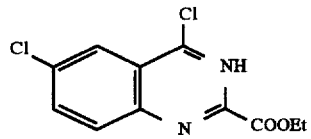

2.68 g (0.0106 mol) of 2-ethoxycarbonyl-6-chloroquinazolin-4(3H)-one obtained in Preparative Example 1 was suspended in 40 ml of phosphorus oxychloride. The suspension was heated under reflux for one hour and distilled under a reduced pressure to remove the solvent. The residue was dissolved in ethyl acetate and the obtained solution was washed with a saturated aqueous solution of sodium hydrogencarbonate. The organic layer was recovered, dried over anhydrous magnesium sulfate and filtered. The filtrate was distilled under a reduced pressure to remove the solvent, giving 2.82 g of the title compound as a pale-yellow crystal.

yield (%); 98 m.p. (°C.); 129–130

Mass; 271 (M+1)⁺

NMR δ(CDCl₃);

1.50 (3H, t, J=7.2 Hz), 4.60 (2H, q, J=7.2 Hz), 7.99 (1H, dd, J=8.8 Hz, 2.4 Hz), 8.25 (1H, d, J=8.8 Hz), 8.34 (1H, d, J=2.4 Hz)

Example 4

4-(3,4-Methylenedioxybenzyl)amino-6,7,8-trimethoxyquinazoline

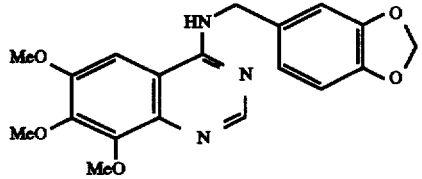

21.2 g (0.083 mol) of 4-chloro-6,7,8-trimethoxyquinazoline, 17.0 g (0.112 mol) of piperonylamine and 13.5 g (0.127 mol) of sodium carbonate were mixed with 400 ml of isopropyl alcohol. The obtained mixture was heated under reflux for 24 hours and distilled under a reduced pressure to remove the solvent. The residue was purified by silica gel column chromatography (ethyl acetate) and recrystallized from ethyl acetate to give 21.3 g of the title compound as a pale-yellow needle.

molecular formula; C₁₉H₁₉N₃O₅ yield (%); 69 m.p. (°C.); 197–198

Mass; 370 (M+H)⁺

NMR δ(CDCl₃); 3.94 (3H, s), 4.03 (3H, s), 4.12 (3H, s), 4.76 (2H, d, J=8.0 Hz), 5.55 (1H, brs), 5.97 (2H, s), 6.64 (1H, s), 6.80 (1H, d, J=8.0 Hz), 6.87 (1H, d, J=8.0 Hz), 6.91 (1H, s), 8.66 (1H, s)

Examples 5 to 48

The following compounds were prepared in a similar manner to that of Example 4.

Example 5

4-(3,4-Methylenedioxyphenyl)amino-6,7,8-trimethoxyquinazoline

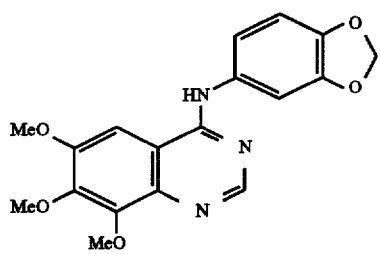

molecular formula; $C_{18}H_{17}N_3O_5$
yield (%); 58
m.p. (°C.); 254~255 (dec.)
Mass; 356 (M+H)$^+$
NMR δ(CDCl$_3$); 4.02 (3H, s), 4.05 (3H, s), 4.13 (3H, s), 5.99 (2H, s), 6.83 (1H, d, J=7.6 Hz), 7.02 (1H, d, J=7.6 Hz), 7.32 (1H, s), 7.33 (1H, s), 8.49 (1H, brs), 8.63 (1H, s)

Example 6

4-Benzylamino-6,7,8-trimethoxyquinazoline

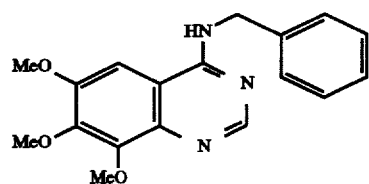

molecular formula; $C_{18}H_{19}N_3O_3$
yield (%); 91
m.p. (°C.); 180~181
Mass; 326 (M+H)$^+$
NMR δ(CDCl$_3$); 3.94 (3H, s), 4.03 (3H, s), 4.13 (3H, s), 4.87 (2H, d, J=5.2 Hz), 5.62 (1H, brs), 6.65 (1H, s), 7.4 (5H, m), 8.67 (1H, s)

Example 7

4-(4-Methoxybenzyl)amino-6,7,8-trimethoxyquinazoline

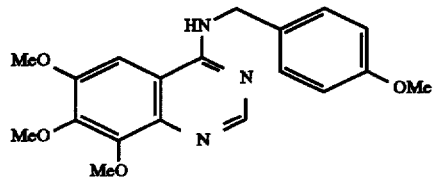

molecular formula; $C_{19}H_{21}N_3O_4$
yield (%); 97
m.p. (°C.); 174~175
Mass; 356 (M+H)$^+$
NMR δ(CDCl$_3$); 3.82 (3H, s), 3.93 (3H, s), 4.03 (3H, s), 4.13 (3H, s), 4.79 (2H, d, J=4.8 Hz), 5.53 (1H, brs), 6.63 (1H, s), 6.92 (2H, d, J=8.4 Hz), 7.35 (2H, d, J=8.4 Hz), 8.67 (1H, s)

Example 8

4-(3-Methoxybenzyl)amino-6,7,8-trimethoxyquinazoline

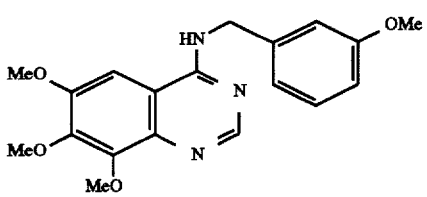

molecular formula; $C_{19}H_{21}N_3O_4$
yield (%); 89
m.p. (°C.); 142~143
Mass; 356 (M+H)$^+$
NMR δ(CDCl$_3$); 3.80 (3H, s), 3.96 (3H, s), 4.03 (3H, s), 4.12 (3H, s), 4.85 (2H, d, J=4.8 Hz), 5.96 (1H, brs), 6.76 (1H, s), 6.86 (1H, d, J=8.0 Hz), 6.99 (1H, d, J=8.0 Hz), 7.02 (1H, s), 7.29 (1H, t, J=8.0 Hz), 8.65 (1H, s)

Example 9

4-(4-Nitrobenzyl)amino-6,7,8-trimethoxyquinazoline

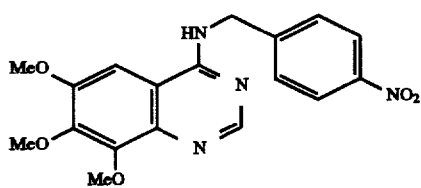

molecular formula; $C_{18}H_{18}N_4O_5$
yield (%); 28
m.p. (°C.); 210~212
Mass; 371 (M+H)$^+$
NMR δ(CDCl$_3$); 3.97 (3H, s), 4.05 (3H, s), 4.13 (3H, s), 5.01 (2H, d, J=5.6 Hz), 5.96 (1H, brs), 6.76 (1H, s), 7.54 (2H, d, J=8.8 Hz), 8.17 (2H, d, J=8.8 Hz), 8.62 (1H, s)

Example 10

4-(3-Nitrobenzyl)amino-6,7,8-trimethoxyquinazoline

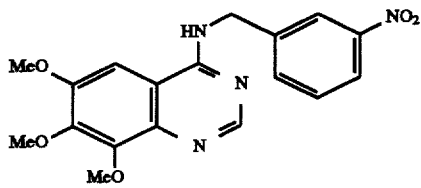

molecular formula; $C_{18}H_{18}N_4O_5$
yield (%); 30
m.p. (°C.); 159~160
Mass; 371 (M+H)$^+$
NMR δ(CDCl$_3$); 3.97 (3H, s), 4.04 (3H, s), 4.12 (3H, s), 4.99 (2H, d, J=5.6 Hz), 6.06 (1H, brs), 6.79 (1H, s), 7.51 (1H, t, J=8.0 Hz), 7.76 (1H, d, J=8.0 Hz), 8.12 (1H, d, J=8.0 Hz), 8.22 (1H, s), 8.63 (1H, s)

Example 11

4-(4-Chlorobenzyl)amino-6,7,8-trimethoxyquinazoline

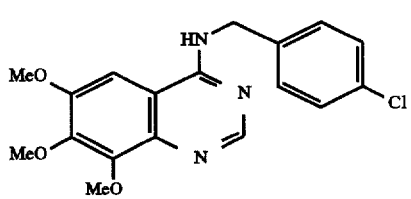

molecular formula; $C_{18}H_{18}N_3O_3Cl$
yield (%); 61
m.p. (°C.); 181~182
Mass; 360 (M+H)$^+$
NMR δ(CDCl$_3$); 3.94 (3H, s), 4.03 (3H, s), 4.12 (3H, s), 4.85 (2H, d, J=5.6 Hz), 5.76 (1H, brs), 6.70 (1H, s), 7.32 (4H, brs), 8.64 (1H, s)

Example 12

4-(3-Chlorobenzyl)amino-6,7,8-trimethoxyquinazoline

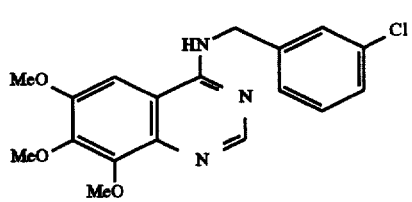

molecular formula; $C_{18}H_{18}N_3O_3Cl$
yield (%); 85
m.p. (°C.); 161~162
Mass; 360 (M+H)$^+$
NMR δ(CDCl$_3$); 3.97 (3H, s), 4.04 (3H, s), 4.13 (3H, s), 4.87 (2H, d, J=5.2 Hz), 5.66 (1H, brs), 6.68 (1H, s), 7.29 (3H, s), 7.39 (1H, s), 8.65 (1H, s)

Example 13

4-Furfurylamino-6,7,8-trimethoxyquinazoline

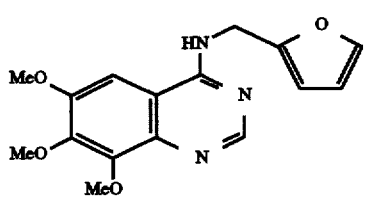

molecular formula; $C_{16}H_{17}N_3O_4$
yield (%); 81
m.p. (°C.); 198~199
Mass; 316 (M+H)$^+$
NMR δ(CDCl$_3$); 3.97 (3H, s), 4.03 (3H, s), 4.12 (3H, s), 4.87 (2H, d, J=5.2 Hz), 5.67 (1H, brs), 6.37 (2H, m), 6.68 (1H, s), 7.42 (1H, s), 8.67 (1H, s)

Example 14

4-(4-Picolyl)amino-6,7,8-trimethoxyquinazoline

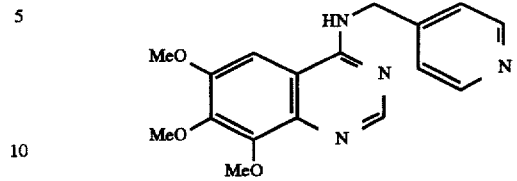

molecular formula; $C_{17}H_{18}N_4O_3$
yield (%); 76
m.p. (°C.); 166~168
Mass; 327 (M+H)$^+$
NMR δ(CDCl$_3$); 3.97 (3H, s), 4.05 (3H, s), 4.12 (3H, s), 4.92 (2H, d, J=6.0 Hz), 6.06 (1H, brs), 6.80 (1H, s), 7.28 (2H, d, J=6.0 Hz), 8.55 (2H, d, J=6.0 Hz), 8.62 (1H, s)

Example 15

4-(4-Ethylbenzyl)amino-6,7,8-trimethoxyquinazoline

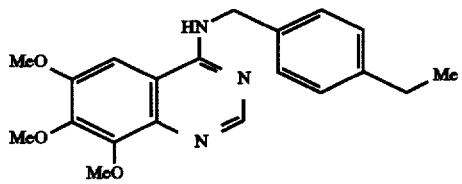

molecular formula; $C_{20}H_{23}N_3O_3$
yield (%); 88
m.p. (°C.); 195~196
Mass; 354 (M+H)$^+$
NMR δ(CDCl$_3$); 1.25 (3H, t, J=7.6 Hz), 2.67 (2H, q, J=7.6 Hz), 3.94 (3H, s), 4.03 (3H, s), 4.13 (3H, s), 4.83 (2H, d, J=4.8 Hz), 5.56 (1H, brs), 6.63 (1H, s), 7.23 (2H, d, J=8.0 Hz), 7.35 (2H, d, J=8.0 Hz), 8.67 (1H, s)

Example 16

4-Indan-5ylmethyl)amino-6,7,8-trimethoxyquinazoline

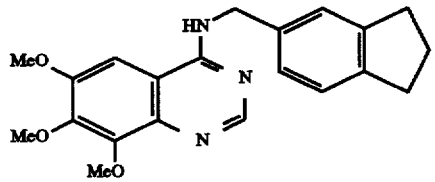

molecular formula; $C_{21}H_{23}N_3O_3$
yield (%); 61
m.p. (°C.); 198~199
Mass; 366 (M+H)$^+$
NMR δ(CDCl$_3$); 2.11 (2H, quintet, J=7.2 Hz), 2.93 (4H, t, J=7.2 Hz), 3.94 (3H, s), 4.04 (3H, s), 4.14 (3H, s), 4.83 (2H, d, J=4.4 Hz), 5.55 (1H, brs), 6.64 (1H, s), 7.2~7.3 (3H, m), 8.68 (1H, s)

Example 17

4-(4-Carboxybenzyl)amino-6,7,8-trimethoxyquinazoline

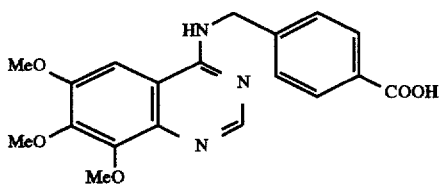

molecular formula; $C_{19}H_{19}N_3O_5$
yield (%); 86
m.p. (°C.); 227~228 (dec.)
Mass; 370 (M+H)$^+$
NMR δ(DMSO-d$_6$); 3.89 (3H, s), 3.92 (3H, s), 3.98 (3H, s), 4.86 (2H, d, J=5.6 Hz), 7.46 (2H, d, J=8.0 Hz), 7.54 (1H, s), 7.90 (2H, d, J=8.0 Hz), 8.35 (1H, s), 8.67 (1H, brs)

Example 18

4-(3-Hydroxymethylbenzyl)amino-6,7,8-trimethoxyquinazoline

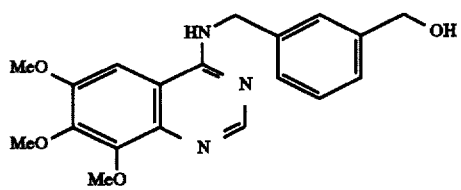

molecular formula; $C_{19}H_{21}N_3O_4$
yield (%); 86
m.p. (°C.); amorphous
Mass; 356 (M+H)$^+$
NMR δ(CDCl$_3$); 3.93 (3H, s), 4.03 (3H, s), 4.12 (3H, s), 4.70 (2H, s), 4.86 (2H, d, J=5.2 Hz), 5.82 (1H, brs), 6.72 (1H, s), 7.3~7.4 (4H, m), 8.63 (1H, s)

Example 19

4-(3,4-Dichlorobenzyl)amino-6,7,8-trimethoxyquinazoline

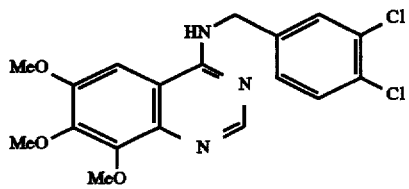

molecular formula; $C_{18}H_{17}N_3O_3Cl_2$
yield (%); 85
m.p. (°C.); 205~206
Mass; 394 (M+H)$^+$
NMR δ(CDCl$_3$); 3.97 (3H, s), 4.04 (3H, s), 4.12 (3H, s), 4.84 (2H, d, J=5.6 Hz), 5.88 (1H, brs), 6.74 (1H, s), 7.24 (1H, d, J=8.4 Hz), 7.40 (1H, d, J=8.4 Hz), 7.47 (1H, s), 8.63 (1H, s)

Example 20

4-(3-Chloro-4-methoxybenzyl)amino-6,7,8-trimethoxyquinazoline

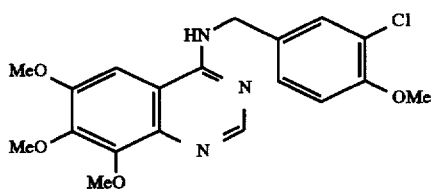

molecular formula; $C_{19}H_{20}N_3O_4Cl$
yield (%); 83
m.p. (°C.); 164~165
Mass; 390 (M+H)$^+$
NMR δ(CDCl$_3$); 3.90 (3H, s), 3.97 (3H, s), 4.04 (3H, s), 4.13 (3H, s), 4.80 (2H, d, J=5.2 Hz), 5.90 (1H, brs), 6.75 (1H, s), 6.91 (1H, d, J=8.8 Hz), 7.30 (1H, dd, J=8.8 Hz, 2.0 Hz), 7.43 (1H, d, J=2.0 Hz), 8.65 (1H, s)

Example 21

4-(3,4-Difluorobenzyl)amino-6,7,8-trimethoxyquinazoline

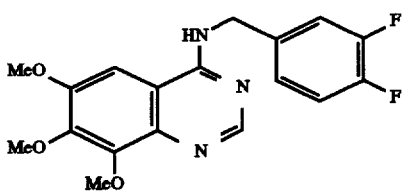

molecular formula; $C_{18}H_{17}N_3O_3F_2$
yield (%); 96
m.p. (°C.); 175~177
Mass; 362 (M+H)$^+$
NMR δ(CDCl$_3$); 3.97 (3H, s), 4.04 (3H, s), 4.13 (3H, s), 4.85 (2H, d, J=5.2 Hz), 5.73 (1H, brs), 6.69 (1H, s), 7.1~7.3 (3H, m), 8.64 (1H, s)

Example 22

4-(3-Fluoro-4-methoxybenzyl)amino-6,7,8-trimethoxyquinazoline

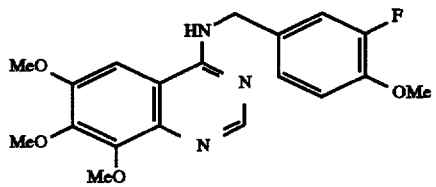

molecular formula; $C_{19}H_{20}N_3O_4F$
yield (%); 82
m.p. (°C.); 171~172
Mass; 374 (M+H)$^+$
NMR δ(CDCl$_3$); 3.89 (3H, s), 3.98 (3H, s), 4.04 (3H, s), 4.12 (3H, s), 4.81 (2H, d, J=5.6 Hz), 6.27 (1H, brs), 6.86 (1H, s), 6.94 (1H, m), 7.14~7.19 (2H, m), 8.64 (1H, s)

Example 23

4-(3,4-Dimethoxybenzyl)amino-6,7,8-trimethoxyquinazoline

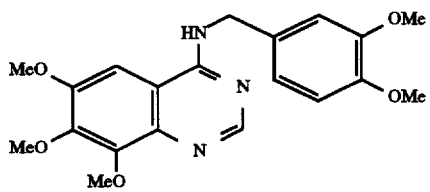

molecular formula; $C_{20}H_{23}N_3O_5$
yield (%); 32
m.p. (°C.); 171~172
Mass; 386 (M+H)$^+$
NMR δ(CDCl$_3$); 3.87 (3H, s), 3.89 (3H, s), 3.94 (3H, s), 4.03 (3H, s), 4.13 (3H, s), 4.79 (2H, d, J=5.2 Hz), 5.67 (1H, brs), 6.69 (1H, s), 6.86 (1H, d, J=8.8 Hz), 6.96 (1H, s), 6.98 (1H, d, J=8.8 Hz), 8.67 (1H, s)

Example 24

4-(4-Hydroxy-3-methoxybenzyl)amino-6,7,8-trimethoxyquinazoline

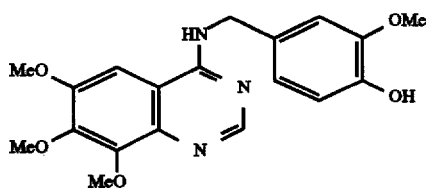

molecular formula; $C_{19}H_{21}N_3O_5$
yield (%); 16
m.p. (°C.); 201~202 (dec.)
Mass; 372 (M+H)$^+$
NMR δ(CDCl$_3$); 3.88 (3H, s), 3.96 (3H, s), 4.03 (3H, s), 4.12 (3H, s), 4.78 (2H, d, J=5.2 Hz), 6.00 (1H, brs), 6.77 (1H, s), 6.91 (1H, s), 6.92 (1H, s), 6.97 (1H, s), 8.65 (1H, s)

Example 25

4-(4-Ethylenedioxybenzyl)amino-6,7,8-trimethoxyquinazoline

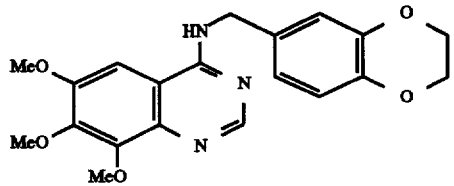

molecular formula; $C_{20}H_{21}N_3O_5$
yield (%); 92
m.p. (°C.); 217~219
Mass; 384 (M+H)$^+$
NMR δ(CDCl$_3$); 3.95 (3H, s), 4.03 (3H, s), 4.13 (3H, s), 4.26 (4H, s), 4.75 (2H, d, J=5.2 Hz), 5.54 (1H, brs), 6.64 (1H, s), 6.87 (1H, d, J=8.0 Hz), 6.90 (1H, d, J=8.0 Hz), 6.94 (1H, s), 8.66 (1H, s)

Example 26

4-(3-Allyl-4-methoxymethoxybenzyl)amino-6,7,8-trimethoxyquinazoline

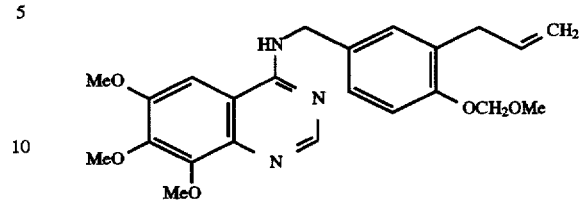

molecular formula; $C_{23}H_{27}N_3O_5$
yield (%); 49
m.p. (°C.); 120~121
Mass; 426 (M+H)$^+$
NMR δ(CDCl$_3$); 3.41 (2H, d, J=6.8 Hz), 3.48 (3H, s), 3.94 (3H, s), 4.03 (3H, s), 4.12 (3H, s), 4.77 (2H, d, J=5.2 Hz), 5.06 (2H, m), 5.21 (2H, s), 5.78 (1H, brs), 5.98 (1H, m), 6.71 (1H, s), 7.07 (1H, d, J=8.4 Hz), 7.23 (1H, s), 7.24 (1H, d, J=8.4 Hz), 8.65 (1H, s)

Example 27

4-(Benzimidazol-5-ylmethyl)amino-6,7,8-trimethoxyquinazoline

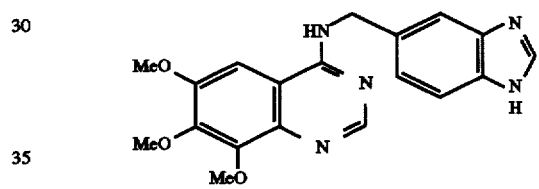

molecular formula; $C_{19}H_{19}N_5O_3$
yield (%); 52
m.p. (°C.); 235~240 (dec.)
Mass; 366 (M+H)$^+$
NMR δ(DMSO-d$_6$); 3.93 (3H, s), 3.95 (3H, s), 3.98 (3H, s), 4.97 (2H, d, J=6.0 Hz), 7.30 (1H, dd, J=8.4 Hz, 1.6 Hz), 7.57 (1H, d, J=8.4 Hz), 7.63 (1H, d, J=1.6 Hz), 7.83 (1H, s), 8.31 (1H, s), 8.36 (1H, brs), 8.52 (1H, s), 9.76 (1H, brs)

Example 28

4-(4-Benzyloxy-3-nitrobenzyl)amino-6,7,8-trimethoxyquinazoline

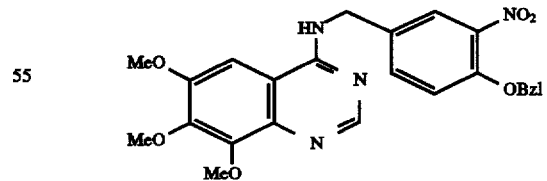

molecular formula; $C_{25}H_{24}N_4O_6$
yield (%); 81
m.p. (°C.); 181~182
Mass; 477 (M+H)$^+$
NMR δ(CDCl$_3$); 3.98 (3H, s), 4.03 (3H, s), 4.10 (3H, s), 4.85 (2H, d, J=5.2 Hz), 5.21 (2H, s), 6.54 (1H, brs), 6.93

(1H, s), 7.06 (1H, d, J=8.4 Hz), 7.30~7.45 (5H, m), 7.60 (1H, dd, J=8.4 Hz, 2.4 Hz), 7.87 (1H, d, J=2.4 Hz), 8.61 (1H, s)

Example 29

4-(4-Chloro-3-nitrobenzyl)amino-6,7,8-trimethoxyquinazoline

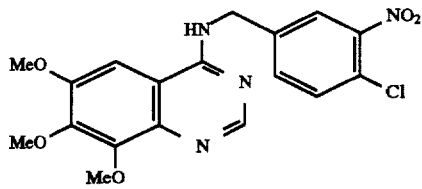

molecular formula; C<sub>18</sub>H<sub>17</sub>N<sub>4</sub>O<sub>5</sub>Cl yield (%); 88 m.p. (°C.); 218~219 (dec.)

Mass; 405 (M+H)<sup>+</sup>

NMR δ(CDCl<sub>3</sub>); 3.98 (3H, s), 4.04 (3H, s), 4.13 (3H, s), 4.93 (2H, d, J=6.0 Hz), 5.98 (1H, brs), 6.75 (1H, s), 7.50 (1H, d, J=8.4 Hz), 7.58 (1H, dd, J=8.4 Hz, 2.0 Hz), 7.87 (1H, d, J=2.0 Hz), 8.61 (1H, s)

Example 30

4-(2-Propoxybenzyl)amino-6,7,8-trimethoxyquinazoline

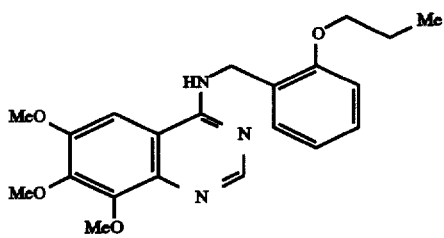

molecular formula; C<sub>21</sub>H<sub>25</sub>N<sub>3</sub>O<sub>4</sub> yield (%); 80 m.p. (°C.); 139~140

Mass; 384 (M+H)<sup>+</sup>

NMR δ(CDCl); 1.07 (3H, t, J=7.4 Hz), 1.85 (2H, m), 3.95 (3H, s), 4.02 (3H, s), 4.02 (2H, t, J=6.4 Hz), 4.10 (3H, s), 4.89 (2H, d, J=5.6 Hz), 6.72 (1H, s), 6.9 (2H, m), 7.28 (1H, m), 7.38 (1H, d, J=7.2 Hz), 8.64 (1H, s)

Example 31

4-(2,4,6-Trimethoxybenzyl)amino-6,7,8-trimethoxyquinazoline

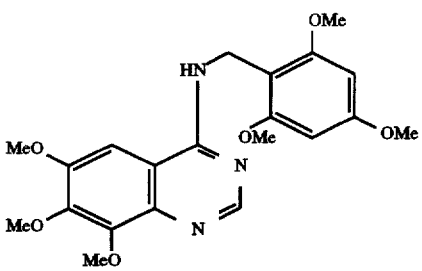

molecular formula; C<sub>21</sub>H<sub>25</sub>N<sub>3</sub>O<sub>6</sub> yield (%); 64 m.p. (°C.); 213~215

Mass; 416 (M+H)<sup>+</sup>

NMR δ(CDCl<sub>3</sub>); 3.85 (9H, s), 3.92 (3H, s), 4.01 (3H, s), 4.11 (3H, s), 4.79 (2H, d, J=4.4 Hz), 5.65 (1H, brs), 6.20 (2H, s), 6.60 (1H, s), 8.68 (1H, s)

Example 32

4-(3,4,5-Trimethoxybenzyl)amino-6,7,8-trimethoxyquinazoline

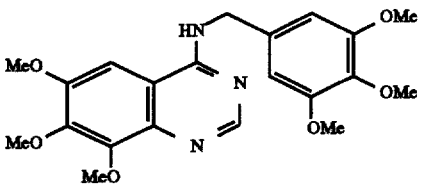

molecular formula; C<sub>21</sub>H<sub>25</sub>N<sub>3</sub>O<sub>6</sub> yield (%); 60 m.p. (°C.); 153~154

NMR δ(CDCl<sub>3</sub>); 3.85 (9H, s), 3.97 (3H, s), 4.03 (3H, s), 4.13 (3H, s), 4.80 (2H, d, J=5.6 Hz), 6.66 (2H, s), 6.80 (1H, s), 8.66 (1H, s)

Example 33

4-(2-Chloro-4,5-methylenedioxybenzyl)amino-6,7,8-trimethoxyquinazoline

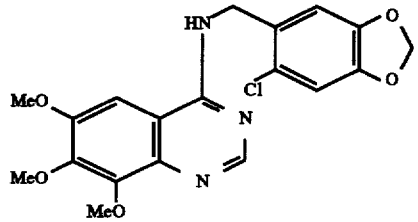

molecular formula; C<sub>19</sub>H<sub>18</sub>N<sub>3</sub>O<sub>5</sub>Cl yield (%); 76 m.p. (°C.); 220~221

Mass; 404 (M+H)<sup>+</sup>

NMR δ(CDCl<sub>3</sub>); 3.97 (3H, s), 4.02 (3H, s), 4.11 (3H, s), 4.86 (2H, d, J=6.0 Hz), 5.95 (2H, s), 6.70 (1H, brt, J=6.0 Hz), 6.86 (1H, s), 6.95 (1H, s), 6.98 (1H, s), 8.61 (1H, s)

Example 34

4-(45,-Methylenedioxy-2-nitrobenzyl)amino-6,7,8-trimethoxyquinazoline

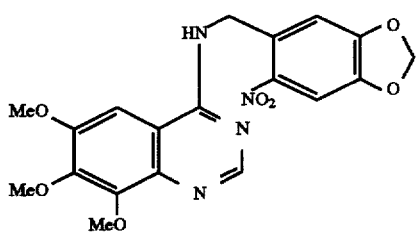

molecular formula; $C_{19}H_{18}N_4O_7$
yield (%); 15
m.p. (°C.); 182~183
Mass; 415 (M+H)$^+$
NMR δ(CDCl$_3$);
3.99 (3H, s), 4.02 (3H, s), 4.10 (3H, s), 5.08 (2H, d, J=6.4 Hz), 6.09 (2H, s), 6.82 (2H, s & brs), 7.27 (1H, s), 7.57 (1H, s), 8.61 (1H, s)

Example 35

4-[2-(4-Nitrophenyl)ethyl]amino-6,7,8-trimethoxyquinazoline

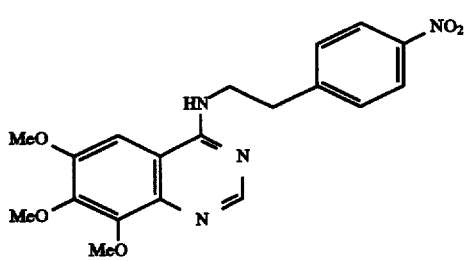

molecular formula; $C_{19}H_{20}N_4O_5$
yield (%); 58
m.p. (°C.); 152~153
Mass; 385 (M+H)$^+$
NMR δ(CDCl$_3$); 3.18 (2H, t, J=7.2 Hz), 3.92 (3H, s), 3.96 (3H, m), 4.04 (3H, s), 4.13 (3H, s), 5.57 (1H, brs), 6.58 (1H, s), 7.41 (2H, d, J=8.8 Hz), 8.17 (2H, d, J=8.8 Hz), 8.66 (1H, s)

Example 36

4-[9-(4-Methylenedioxyphenyl)ethyl]amino-6,7,8-trimethoxyquinazoline

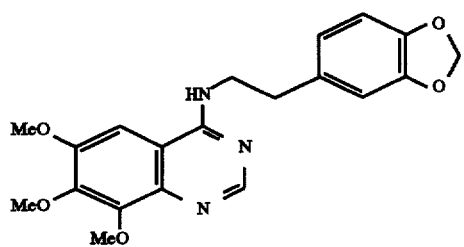

molecular formula; $C_{20}H_{21}N_3O_5$
yield (%); 68 m.p. (°C.); 193~194
Mass; 384 (M+H)$^+$
NMR δ(CDCl$_3$);
2.96 (2H, t, J=6.8 Hz), 3.87 (2H, m), 3.93 (3H, s), 4.03 (3H, s), 4.12 (3H, s), 5.43 (1H, brs), 5.95 (2H, s), 6.52 (1H, s), 6.71 (1H, d, J=8.0 Hz), 6.77 (1H, s), 6.78 (1H, d, J=8.0 Hz), 8.65 (1H, s)

Example 37

4-[2-(Imidazol-4-Yl)ethyl]amino-6,7,8-trimethoxyquinazoline

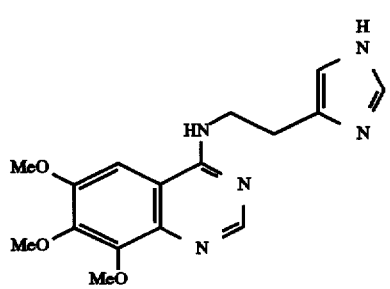

molecular formula; $C_{16}H_{19}N_5O_3$
yield (%); 77
m.p. (°C.); 164~166 (dec.)
Mass; 330 (M+H)$^+$
NMR δ(DMSO-d$_6$); 3.00 (2H, t, J=7.2 Hz), 3.81 (2H, m), 3.87 (3H, s), 3.92 (3H, s), 3.97 (3H, s), 7.25 (1H, s), 7.56 (1H, s), 8.39 (1H, s), 8.45 (1H, s), 8.50 (1H, brs)

Example 38

4-(α-Methyl-3,4-methylenedioxybenzyl)amino-6,7,8-trimethoxyquinazoline

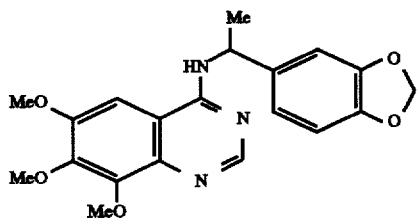

molecular formula; $C_{20}H_{21}N_3O_5$
yield (%); 67
m.p. (°C.); 200~201
Mass; 384 (M+H)$^+$
NMR δ(CDCl); 1.67 (2H, d, J=6.8 Hz), 3.99 (3H, s), 4.04 (3H, s), 4.13 (3H, s), 5.47 (1H, brs), 5.57 (1H, t, J=6.8 Hz), 5.97 (2H, s), 6.65 (1H, s), 6.81 (1H, d, J=7.6 Hz), 6.94 (1H, d, J=7.6 Hz), 6.95 (1H, s), 8.63 (1H, s)

Example 39

4-[1-Methyl-1-(4-methylenedioxyphenyl)ethyl]amino-6,7,8-trimethoxyquinazoline

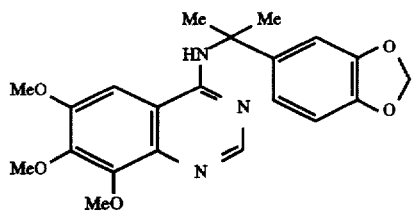

molecular formula; C₂₁H₂₃N₃O₅
yield (%); 4
m.p. (°C.); 191–192
Mass; 398 (M+H)⁺
NMR δ(CDCl₃); 1.90 (6H, s), 4.03 (3H, s), 4.03 (3H, s), 4.09 (3H, s), 5.93 (2H, s), 6.74 (1H, d, J=7.6 Hz), 6.82 (1H, s), 6.92 (2H, m), 8.46 (1H, s)

Example 40

4-[N-Ethyl-(3,4-methylenedioxyphenyl)amino]-6,7,8-trimethoxyquinazoline

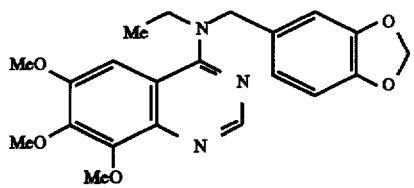

molecular formula; C₂₁H₂₃N₃O₅
yield (%); 73
m.p. (°C.); 100–101
Mass; 398 (M+H)⁺
NMR δ(CDCl₃); 1.37 (3H, t, J=7.0 Hz), 3.56 (3H, s), 3.67 (2H, q, J=7.0 Hz), 4.03 (3H, s), 4.11 (3H, s), 4.79 (2H, s), 5.98 (2H, s), 6.85 (1H, d, J=7.2 Hz), 6.93 (1H, s), 6.93 (1H, d, J=7.2 Hz), 6.97 (1H, s), 8.69 (1H, s)

Example 41

4-[N-(Ethoxycarbonylmethyl)-(3,4-methylenedioxybenzyl)amino]-6,7,8-trimethoxyquinazoline

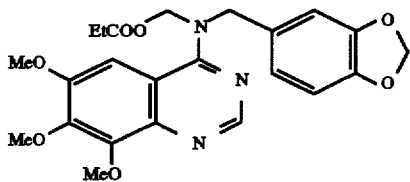

molecular formula; C₂₃H₂₅N₃O₇
yield (%); 41
m.p. (°C.); oily substance
Mass; 456 (M+H)⁺
NMR δ(CDCl₃); 1.29 (3H, t, J=7.2 Hz), 3.44 (3H, s), 4.02 (3H, s), 4.10 (3H, s), 4.20 (2H, s), 4.25 (2H, q, J=7.2 Hz), 4.98 (2H, s), 6.00 (2H, s), 6.88 (1H, d, J=8.0 Hz), 6.97 (1H, s), 7.01 (1H, d, J=8.0 Hz), 8.64 (1H, s)

Example 42

4-[N-(2-Methoxyethyl)-(3,4-methylenedioxybenzyl)-amino]-6,7,8-trimethoxyquinazoline

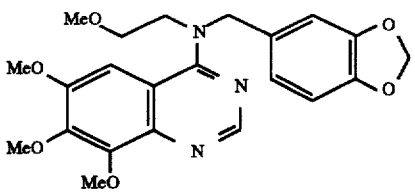

molecular formula; C₂₂H₂₅N₃O₆
yield (%); 21
m.p. (°C.); 87–88
Mass; 428 (M+H)⁺
NMR δ(CDCl₃); 3.36 (3H, s), 3.58 (3H, s), 3.80–3.85 (4H, m), 4.02 (3H, s), 4.10 (3H, s), 4.92 (2H, s), 5.97 (2H, s), 6.83 (1H, d, J=7.6 Hz), 6.92 (1H, d, J=7.6 Hz), 6.94 (1H, s), 7.19 (1H, s), 8.67 (1H, s)

Example 43

4-(6,7-Dimethoxy-1,2,3,4-tetrahydroisoquinolin-2-yl)-6,7,8-trimethoxyquinazoline

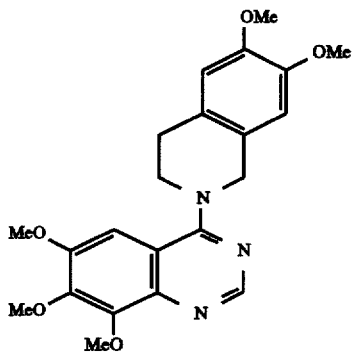

molecular formula; C₂₂H₂₅N₃O₅
yield (%); 79
m.p. (°C.); 157–158
Mass; 412 (M+H)⁺
NMR δ(CDCl₃); 3.11 (2H, t, J=5.8 Hz), 3.87 (3H, s), 3.89 (3H, s), 3.96 (2H, t, J=5.8 Hz), 3.99 (3H, s), 4.07 (3H, s), 4.14 (3H, s), 4.80 (2H, s), 6.67 (1H, s), 6.71 (1H, s), 7.03 (1H, s), 8.74 (1H, s)

Example 44

4-[4-(1-Hydroxyethyl)benzyl]amino-6-methoxyquinazoline

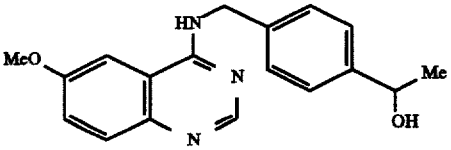

molecular formula; C₁₈H₁₉N₃O₂
yield (%); 46 m.p. (°C.); amorphous
Mass; 310 (M+H)⁺
NMR δ(CDCl₃); 1.47 (2H, d, J=6.4 Hz), 3.91 (3H, s), 4.87 (2H, d, J=5.2 Hz), 4.84~4.94 (1H, m), 7.34~7.42 (6H, m), 7.59 (1H, brs), 7.79 (1H, d, J=8.8 Hz), 8.52 (1H, s)

Example 45

4-(Benzimidazol-5-ylmethyl)amino-6-methoxyquinazoline

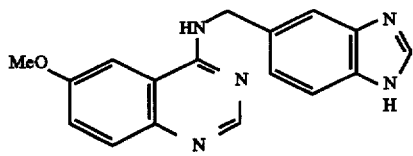

molecular formula; $C_{17}H_{15}N_5O$
yield (%); 18
m.p. (°C.); 254~255
Mass; 306 (M+1)⁺
NMR δ(DMSO-d₆); 3.88 (3H, s), 4.91 (2H, d, J=6.0 Hz), 7.24 (1H, d,
J=8.4 Hz), 7.40 (1H, dd, J=9.2 Hz, 2.8 Hz), 7.54 (1H, d, J=8.4 Hz), 7.56 (1H, s), 7.63 (1H, d, J=9.2 Hz), 7.73 (1H, d, J=2.8 Hz), 8.16 (1H, s), 8.37 (1H, s), 8.67 (1H, t, J=6.0 Hz), 12.33 (1H, brs)

Example 46

4-(3,4-Methylenedioxybenzyl)amino-6-methoxyquinazoline

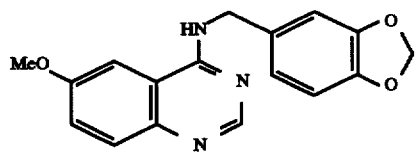

molecular formula; $C_{17}H_{15}N_3O_3$
yield (%); 86
m.p. (°C.); 207~208
Mass; 310 (M+H)⁺
NMR δ(CDCl₃); 3.89 (3H, s), 4.78 (2H, d, J=5.2 Hz), 5.70 (1H, brs), 5.97 (2H, s), 6.80 (1H, d, J=7.6 Hz), 6.9 (3H, m), 7.40 (1H, d, J=9.2 Hz), 7.80 (1H, d, J=9.2 Hz), 8.63 (1H, s)

Example 47

4-[9-(3,4-Methylenedioxyphenyl)pyrrolidino]-6-methoxyquinazoline

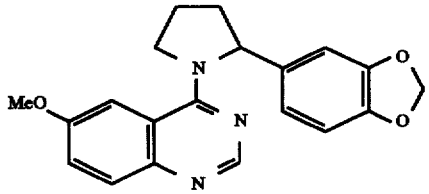

molecular formula; $C_{20}H_{19}N_3O_3$
yield (%); 85 m.p. (°C.); oily substance
Mass; 350 (M+1)⁺
NMR δ(CDCl₃); 1.95~2.10 (3H, m), 2.37 (1H, m), 3.58 (3H, s), 4.05~4.20 (2H, m), 5.58 (1H, m), 5.93 (1H, s), 5.94 (1H, s), 6.78 (1H, d, J=8.4 Hz), 6.84 (1H, s), 6.85 (1H, d, J=8.4 Hz), 7.30 (1H, d, J=10.0 Hz), 7.35 (1H, s), 7.74 (1H, d, J=10.0 Hz), 8.53 (1H, s)

Example 48

4-(4-Methoxy-3-nitrobenzyl)amino-6-methoxyquinazoline

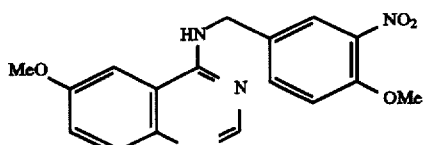

molecular formula; $C_{17}H_{16}N_4O_4$
yield (%); 22
m.p. (°C.); 205~206 (dec.)
Mass; 341 (M+1)⁺
NMR δ(CDCl₃); 3.93 (3H, s), 3.94 (3H, s), 4.91 (2H, d, J=6.0 Hz), 7.07 (1H, dd, J=8.4 Hz, 1.2 Hz), 7.21 (1H, d, J=1.2 Hz), 7.39 (1H, dd, J=9.2 Hz, 2.4 Hz), 7.53 (1H, d, J=2.4 Hz), 7.75 (1H, d, J=9.2 Hz), 7.82 (1H, d, J=8.4 Hz), 8.03 (1H, brs), 8.51 (1H, s)

Example 49

4-(3,4-Methylenedioxybenzyl)amino-6-methylthioquinazoline

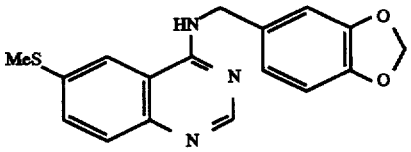

4.12 g (0.0196 mol) of 4-chloro-6-methylthioquinazoline, 3.70 g (0.0245 mol) of piperonylamine and 3.50 g (0.0330 mol) of sodium carbonate were mixed with 100 ml of isopropyl alcohol. The obtained mixture was heated under reflux for 24 hours and distilled under a reduced pressure to remove the solvent. The obtained residue was purified by silica gel column chromatography (ethyl acetate/n-hexane) and recrystallized from chloroform/n-hexane to give 5.32 g of the title compound as a pale-yellow crystal.

molecular formula; $C_{17}H_{15}O_2N_3S$
yield (%); 83
m.p. (°C.); 174~175
Mass; 326 (M+H)⁺
NMR δ(CDCl₃); 2.59 (3H, s), 4.79 (2H, d, J=5.6 Hz), 5.93 (2H, s), 6.77 (1H, d, J=8.0 Hz), 6.89 (1H, d, J=8.0 Hz), 6.94 (1H, s), 7.62 (1H, dd, J=8.8 Hz, 2.0 Hz), 7.75 (1H, d, J=8.8 Hz), 7.97 (1H, d, J=2.0 Hz), 8.10 (1H, brs), 8.56 (1H, s)

Examples 50 to 54

The following compounds were prepared in a similar manner to that of Example 49.

Example 50

4-(3,4-Dichlorobenzyl)amino-6-methylthioquinazoline

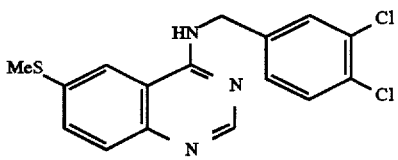

molecular formula; $C_{16}H_{13}N_3SCl_2$
yield (%); 85
m.p. (°C.); 184~185
Mass; 350 (M+H)$^+$
NMR δ(CDCl$_3$); 2.61 (3H, s), 4.83 (2H, d, J=5.6 Hz), 7.28 (1H, dd, J=8.4 Hz, 2.0 Hz), 7.40 (1H, d, J=8.4 Hz), 7.51 (1H, d, J=2.0 Hz), 7.64 (1H, dd, J=8.8 Hz, 2.0 Hz), 7.76 (1H, d, J=8.8 Hz), 7.97 (1H, d, J=2.0 Hz), 8.19 (1H, brs), 8.55 (1H, s)

Example 51

4-(3-Fluoro-4-methoxybenzyl)amino-6-methylthioquinazoline

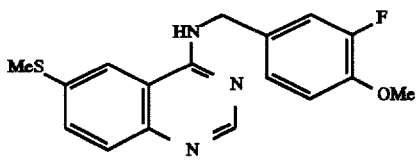

molecular formula; $C_{17}H_{16}N_3OSF$
yield (%); 89
m.p. (°C.); 168~169
Mass; 330 (M+H)$^+$
NMR δ(CDCl$_3$); 2.58 (3H, s), 3.90 (3H, s), 4.82 (2H, d, J=5.6 Hz), 6.29 (1H, brs), 6.95 (1H, m), 7.13~7.18 (2H, m), 7.54 (1H, s), 7.63 (1H, d, J=8.8 Hz), 7.79 (1H, d, J=8.8 Hz), 8.64 (1H, s)

Example 52

4-(Benzimidazol-5-ylmethyl)amino-6-methylthioquinazoline

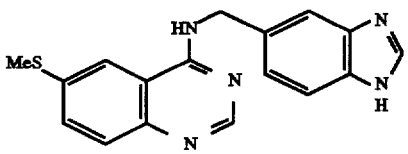

molecular formula; $C_{17}H_{15}N_5S$
yield (%); 48
m.p. (°C.); 271~275 (dec.)
Mass; 322 (M+H)$^+$
NMR δ(DMSO-d$_6$); 2.67 (3H, s), 5.06 (2H, d, J=5.6 Hz), 7.47 (1H, d, J=8.4 Hz), 7.68 (1H, d, J=8.8 Hz), 7.77 (2H, m), 7.87 (1H, d, J=8.8 Hz), 8.40 (1H, s), 8.77 (1H, s), 8.84 (1H, s), 10.68 (1H, brs)

Example 53

4-[N-(2-Methoxyethyl)-(3,4-methylenedioxybenzyl)amino]-6-methylthioquinazoline

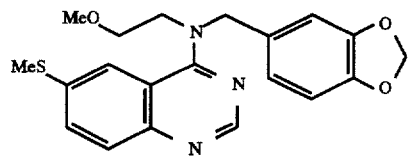

molecular formula; $C_{20}H_{21}N_3O_3S$
yield (%); 27
m.p. (°C.); 92~93
Mass; 384 (M+H)$^+$
NMR δ(CDCl$_3$); 2.16 (3H, s), 3.35 (3H, s), 3.82 (2H, t, J=5.0 Hz), 3.89 (2H, t, J=5.0 Hz), 5.01 (2H, s), 5.98 (2H, s), 6.84 (1H, d, J=8.4 Hz), 6.89 (1H, d, J=8.4 Hz), 6.90 (1H, s), 7.56 (1H, dd, J=8.8 Hz, 2.0 Hz), 7.66 (1H, d, J=2.0 Hz), 7.82 (1H, d, J=8. 8 Hz)

Example 54

4-[N-(2-Hydroxyethyl)-(3,4-methylenedioxybenzyl)amino]-6-methylthioquinazoline

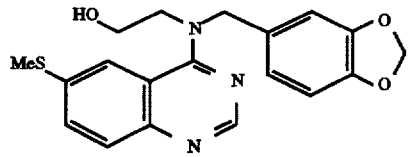

molecular formula; $C_{19}H_{19}N_3O_3S$
yield (%); 21
m.p. (°C.); 146~147 (dec.)
Mass; 370 (M+H)$^+$
NMR δ(CDCl$_3$); 2.00 (3H, s), 3.93 (2H, t, J=4.2 Hz), 4.01 (2H, t, J=4.2 Hz), 5.00 (2H, s), 6.01 (2H, s), 6.89 (3H, m), 7.57 (2H, m), 7.82 (1H, d, J=9.2 Hz), 8.55 (1H, s)

Example 55

4-(4-(Chloro-3-nitrobenzyl)amino-6-chloroquinazoline

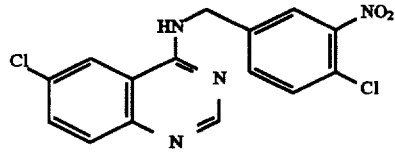

3.00 g (0.015 mol) of 4,6-dichloroquinazoline and 3.80 g (0.0170 mol) of 4-chloro-3-nitrobenzylamine hydrochloride were dissolved in a mixture comprising 100 ml of isopropyl alcohol and 15 ml of triethylamine. The obtained solution was heated under reflux for 24 hours and distilled under a reduced pressure to remove the solvent. The residue was purified by silica gel column chromatography (chloroform/ethyl acetate) and recrystallized from chloroform/n-hexane to give 4.85 g of the title compound as a pale-yellow crystal.
molecular formula; $C_{15}H_{10}N_4O_2Cl_2$ yield (%); 92
m.p. (°C.); 199–200
Mass; 349 (M+H)⁺
NMR δ(CDCl₃); 4.85 (2H, d, J=6.0 Hz), 7.49 (1H, d, J=8.4 Hz), 7.61 (1H, dd, J=8.4 Hz, 2.0 Hz), 7.66 (1H, dd, J=8.8 Hz, 2.0 Hz), 7.76 (1H, d, J=8.8 Hz), 7.96 (1H, d, J=2.0 Hz), 8.20 (1H, d, J=2.0 Hz), 8.23 (1H, brt, J=6.0 Hz), 8.58 (1H, s)

Example 56

4-(α-Ethoxycarbonyl-3,4-methylenedioxybenzyl)amino-6-chloroquinazoline

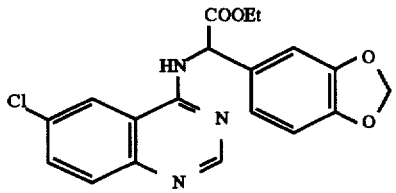

30 ml of 2-propanol, 1.07 g of triethylamine and 1.01 g of α-ethoxycarbonyl-3,4-methylenedioxybenzylamine were added to 704 mg of 4,6-dichloroquinazoline. The obtained mixture was refluxed for 4 hours, followed by the addition of water. The obtained mixture was extracted with chloroform thrice. The chloroform layers were combined, dried over magnesium sulfate and distilled under a reduced pressure to remove the solvent. The residue was recrystallized (from ethanol/ethyl acetate/hexane) to give 1.167 g of the title compound.

molecular formula; $C_{19}H_{16}N_3O_4Cl$
yield (%); 86
m.p. (°C.); 169–170
Mass m/e; 386 (M+1)
NMR δ(CDCl₃); 1.28 (3H, t, J=7.2 Hz), 4.27 (2H, m), 5.85 (1H, d, J=6.4 Hz), 5.98 (2H, s), 6.70 (1H, brs), 6.81 (1H, d, J=8.8 Hz), 6.99 (2H, m), 7.10 (1H, dd, J=8.8 Hz, 2.4 Hz), 7.83 (1H, d, J=2.4 Hz), 8.85 (1H, d, J=8.8 Hz), 8.63 (1H, s)

Examples 57 to 64

The following compounds were prepared in a similar manner to that of Example 56 or 57.

Example 57

4-(3,4-Methylenedioxyphenyl)amino-6-chloroquinazoline

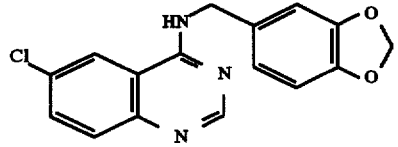

molecular formula; $C_{16}H_{12}N_3O_2Cl$
yield (%); 76
m.p. (°C.); 199–200
Mass; 314 (M+H)⁺
NMR δ(CDCl₃); 4.76 (2H, d, J=5.6 Hz), 5.82 (1H, brs), 5.98 (2H, s), 6.81 (1H, d, J=8.0 Hz), 6.87 (1H, d, J=8.0 Hz), 6.89 (1H, s), 7.67 (1H, s), 7.69 (1H, d, J=8.0 Hz), 7.81 (1H, d, J=8.0 Hz), 8.70 (1H, s)

Example 58

4-(3,4-Dichlorobenzyl)amino-6-chloroquinazoline

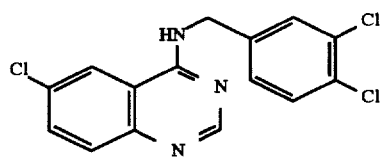

molecular formula; $C_{15}H_{10}N_3Cl_3$
yield (%); 72
m.p. (°C.); 215–216
Mass; 338 (M+H)⁺
NMR δ(CDCl₃); 4.85 (2H, d, J=5.6 Hz), 5.94 (1H, brs), 7.24 (1H, d, J=8.4 Hz), 7.43 (1H, d, J=8.4 Hz), 7.70 (1H, d, J=9.2 Hz), 7.72 (1H, s), 7.83 (1H, d, J=9.2 Hz), 8.68 (1H, s)

Example 59

4-(3,4-Dimethoxybenzyl)amino-6-chloroquinazoline

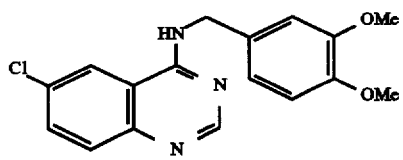

molecular formula; $C_{17}H_{16}N_3O_2Cl$
yield (%); 73
m.p. (°C.); 174–175
Mass; 330 (M+H)⁺
NMR δ(CDCl₃); 3.87 (6H, s), 4.78 (2H, d, J=5.2 Hz), 6.85 (1H, d, J=8.0 Hz), 6.96 (1H, d, J=8.0 Hz), 6.98 (1H, s), 7.34 (1H, brs), 7.65 (1H, dd, J=9.2 Hz, 2.0 Hz), 7.78 (1H, d, J=9.2 Hz), 8.08 (1H, d, J=2.0 Hz), 8.65 (1H, s)

Example 60

4-(Benzimidazol-5-ylmethyl)amino-6-chloroquinazoline

molecular formula; $C_{16}H_{12}N_5Cl$
yield (%); 76
m.p. (°C.); 243–244 (dec.)
Mass; 310 (M+H)⁺
NMR δ(DMSO-d₆); 4.89 (2H, d, J=5.6 Hz), 7.27 (1H, d, J=8.4 Hz) 7.55 (1H, d, J=8.4 Hz), 7.59 (1H, s), 7.72 (1H, d, J=8.8 Hz), 7.80 (1H, dd, J=8.8 Hz, 2.4 Hz), 8.25 (1H, s), 8.50 (1H, s), 8.53 (1H, d, J=2.4 Hz), 9.07 (1H, brt, J=5.6 Hz)

Example 61

4-(2-Methoxy-2,3-dihydrobenzofuran-5-yl)
methylamino-6-chloroquinazoline

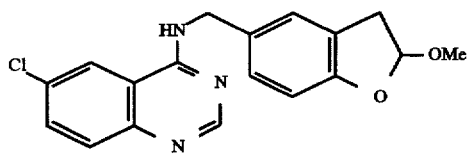

molecular formula; $C_{18}H_{16}N_3O_2Cl$ (341.798)

yield (%); 53 m.p. (°C.); 178~179

Mass; 342 (MH)$^+$

NMR δ(DMSO-d$_6$); 2.88 (1H, dd, J=2.0 Hz, 17.0 Hz), 3.28~3.34 (1H, m), 4.68 (1H, d, J=5.7 Hz), 5.68 (1H, dd, J=2.0 Hz, 6.6 Hz), 6.79 (1H, d, J=8.2 Hz), 7.14 (1H, d, J=8.2 Hz), 7.24 (1H, s), 7.70 (1H, d, J=9.0 Hz), 7.79 (1H, dd, J=2.2 Hz, 9.0 Hz), 8.46 (1H, d, J=2.2 Hz), 8.48 (1H, s), 8.82 (1H, t, J=5.7 Hz)

Example 62

4-(9-Methylbenzimidazol-5-ylmethyl)amino-6-chloroquinazoline

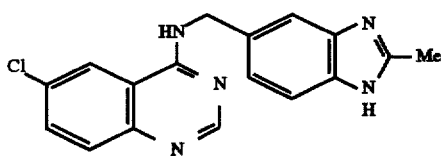

molecular formula; $C_{17}H_{14}N_5Cl$ yield (%); 17 m.p. (°C.); 273~274 (dec.)

Mass; 324 (M+H)$^+$

NMR δ(DMSO-d$_6$); 2.71 (3H, s), 4.94 (2H, d, J=5.6 Hz), 7.48 (1H, d, J=8.4 Hz), 7.63 (1H, d, J=8.4 Hz), 7.70 (1H, s), 7.77 (1H, d, J=8.8 Hz), 7.86 (1H, dd, J=8.8 Hz, 2.0 Hz), 8.58 (1H, s), 8.65 (1H, d, J=2.0 Hz), 9.65 (1H, brs)

Example 63

4-[1-Methyl-1-(3,4-methylenelenedioxyphenyl)ethyl]amino-6-chloroquinazoline

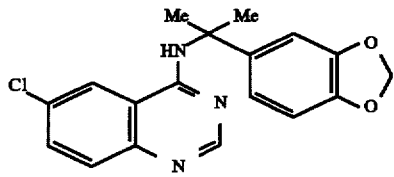

molecular formula; $C_{18}H_{16}N_3O_2Cl$ yield (%); 32 m.p. (°C.); 175~176

Mass; 342 (M+H)$^+$

NMR δ(CDCl$_3$); 1.92 (6H, s), 5.95 (2H, s), 6.14 (1H, brs), 6.76 (1H, d, J=7.6 Hz), 6.92 (1H, d, J=7.6 Hz), 6.93 (1H, s), 7.67 (1H, dd, J=8.8 Hz), 7.77 (1H, d, J=2.0 Hz), 7.86 (1H, d, J=8.8 Hz), 8.50 (1H, s)

Example 64

4-(3,4-Methylenedioxybenzyl)amino-6-ethoxyquinazoline

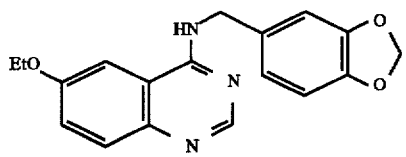

molecular formula; $C_{18}H_{17}N_3O_3$ yield (%); 44 m.p. (°C.); 190~191

Mass; 324 (M+H)$^+$

NMR δ(CDCl$_3$); 1.46 (3H, t, J=6.8 Hz), 4.10 (2H, q, J=6.8 Hz), 4.77 (2H, d, J=5.2 Hz), 5.68 (1H, brs), 5.97 (2H, s), 6.80 (1H, d, J=8.0 Hz), 6.87~6.92 (3H, m), 7.39 (1H, dd, J=9.2 Hz, 2.8 Hz), 7.79 (1H, d, J=9.2 Hz), 8.62 (1H, s)

Example 65

4-(3,4-Methylenedioxybenzyl)amino-6-cyanoquinazoline

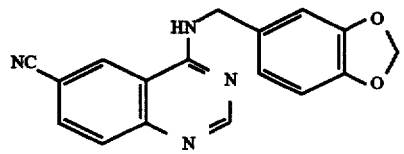

15 ml of isopropyl alcohol, 75 mg of triethylamine and 125 mg of piperonylamine were added to 140 mg of 4-chloro-6-cyanoquinazoline. The obtained mixture was heated under reflux for 5 hours and filtered to recover a precipitate. This precipitate was introduced to a silica gel column, followed by eluting with ethyl acetate to give 200 mg of the title compound.

molecular formula; $C_{17}H_{2}N_4O_2$ yield (%); 89 m.p. (°C.); 243~244

Mass; 305 (M+1)$^+$

NMR δ(DMSO-d$_6$); 4.67 (2H, d, J=5.6 Hz), 5.96 (2H, s), 6.84 (2H, s), 6.95 (1H, s), 7.77 (1H, d, J=8.4 Hz), 8.56 (1H, s), 8.89 (1H, s), 9.04 (1H, br)

Examples 66 to 87

The following compounds were prepared in a similar manner to that of Example 65.

Example 66

4-[3-(1-Imidazolyl)propyl]amino-6-cyanoquinazoline

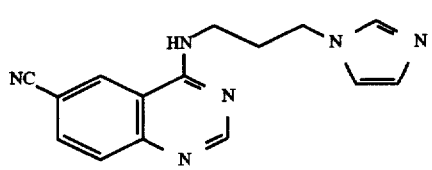

molecular formula; $C_{15}H_4N_6$
yield (%); 22
m.p. (°C.); 196~197
Mass m/e; 279 (M+1)
NMR δ(CDCl$_3$); 2.27 (2H, quintet, J=6.4 Hz), 3.66 (2H, q, J=6.4 Hz), 4.17 (2H, t, J=6.4 Hz), 7.07 (1H, s), 7.11 (1H, s). 7.82 (1H, s), 7.82 (1H, s), 8.09 (1H, s), 8.37 (1H, brs), 8.66 (1H, s), 8.84 (1H, s)

Example 67

4-(Benzimidazol-5-yl)methylamino-6-cyanoquinazoline

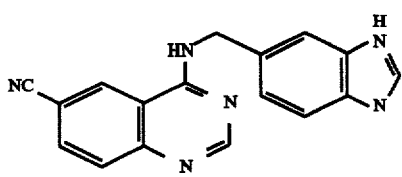

molecular formula; $C_{17}H_{12}N_6$
yield (%); 68
m.p. (°C.); 274~277
Mass; 301 (M+1)$^+$
NMR δ(DMSO-d$_6$); 4.88 (2H, d, J=5.6 Hz), 7.21~7.24 (1H, m), 7.35~7.76 (2H, m), 7.78 (1H, d, J=8.8 Hz), 7.06 (1H, dd, J=8.8 Hz, 1.6 Hz), 8.15 (1H, s), 8.57 (1H, s), 8.92 (1H, s), 9.14 (1H, m), 12.32 (1H, m)

Example 68

4-(3,4-Methylenedioxybenzyl)amino-6-ethoxycarbonylquinazoline

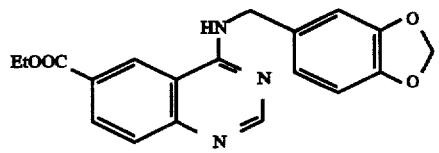

molecular formula; $C_{19}H_{17}N_3O_4$
yield (%); 48
m.p. (°C.); 156~157
Mass; 352 (M+H)$^+$
NMR δ(CDCl$_3$); 1.43 (3H, t, J=7.2 Hz), 4.44 (2H, q, J=7.2 Hz), 4.79 (2H, d, J=5.2 Hz), 5.98 (2H, s), 6.14 (1H, brs), 6.82 (1H, d, J=8.0 Hz), 6.89 (1H, d, J=8.0 Hz), 6.90 (1H, s), 7.87 (1H, d, J=8.8 Hz), 8.33 (1H, d, J=8.8 Hz), 8.46 (1H, s), 8.74 (1H, s)

Example 69

4-(3,4-Methylenedioxybenzyl)amino-6-methylquinazoline

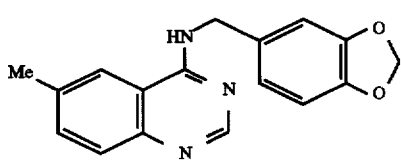

molecular formula; $C_{17}H_{15}N_3O_2$
yield (%); 68
m.p. (°C.); 203~204
Mass; 294 (M+H)$^+$
NMR δ(CDCl$_3$); 2.49 (3H, s), 4.76 (2H, d, J=5.6 Hz), 5.79 (1H, brs), 5.96 (2H, s), 6.81 (1H, d, J=8.0 Hz), 6.88 (1H, d, J=8.0 Hz), 6.91 (1H, s), 7.44 (1H, s), 7.57 (1H, d, J=8.4 Hz), 7.76 (1H, d, J=8.4 Hz), 8.66 (1H, s)

Example 70

4-(3,4-Methylenedioxybenzyl)amino-6,7-dimethoxyquinazoline

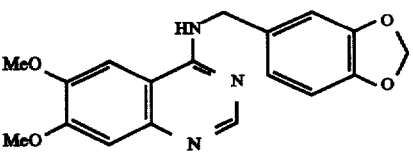

molecular formula; $C_{18}H_{17}N_3O_4$
yield (%); 77
m.p. (°C.); 221~222
Mass; 340 (M+H)$^+$
NMR δ(DMSO-d$_6$); 3.88 (3H, s), 3.89 (3H, s), 4.68 (2H, d, J=6.0 Hz), 5.97 (2H, s), 6.85 (2H, s), 6.94 (1H, s), 7.09 (1H, s), 7.64 (1H, s), 8.33 (1H, s), 8.37 (1H, t, J=6.0 Hz)

Example 71

4-(3,4-Methylenedioxybenzyl)amino-6,8-dimethoxyquinazoline

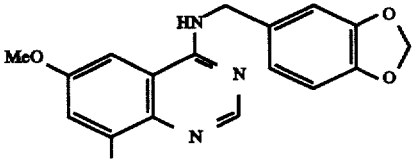

molecular formula; $C_{18}H_{17}N_3O_4$
yield (%); 88
m.p. (°C.); 217~218
Mass; 340 (M+H)$^+$
NMR δ(CDCl$_3$); 3.89 (3H, s), 4.01 (3H, s), 4.77 (2H, d, J=5.2 Hz), 5.63 (1H, brs), 5.97 (2H, s), 6.42 (1H, d, J=2.4 Hz), 6.77 (1H, d, J=2.4 Hz), 6.80 (1H, d, (J=7.6 Hz), 6.88 (1H, dd, J=7.6 Hz, 1.6 Hz), 6.92 (1H, d, J=1.6 Hz), 8.65 (1H, s)

Example 72

4-(4-Methylenedioxybenzyl)amino-5,6-dimethoxyquinazoline

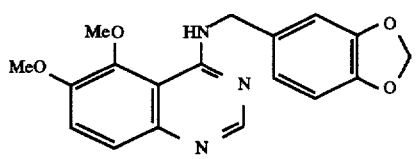

molecular formula; $C_{18}H_{17}N_3O_4$ yield (%); 74 m.p. (°C.); 122~123

Mass; 340 (M+1)$^+$

NMR δ(CDCl$_3$); 3.97 (6H, s), 4.77 (22H, d, J=5.2 Hz), 5.97 (2H, s), 6.81 (1H, d, J=8.0 Hz), 6.86 (1H, dd, J=8.0 Hz, 1.6 Hz), 6.88 (1H, d, J=1.6 Hz), 7.49 (1H, d, J=8.8 Hz), 7.82 (1H, d, J=8.8 Hz), 8.51 (1H, s), 8.64 (1H, brs)

Example 73

4-(3,4-Methylenedioxybenzyl)amino-6-acetamido-7-methoxyquinazoline

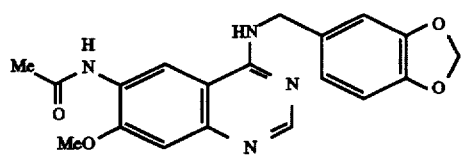

molecular formula; $C_{19}H_{18}N_4O_4$ yield (%); 66 m.p. (°C.); 164~165

Mass; 367 (M+H)$^+$

NMR δ(CDCl$_3$); 2.26 (3H, s), 4.04 (3H, s), 4.76 (2H, d, J=5.6 Hz), 5.95 (2H, s), 6.22 (1H, brs), 6.77 (1H, d, J=8.0 Hz), 6.85 (1H, d, J=8.0 Hz), 6.89 (1H, s), 7.31 (1H, s), 8.02 (1H, brs), 8.59 (1H, s), 8.81 (1H, s)

Example 74

4-(34-Methylenedioxybenzyl)amino-6-methylthio-7-methoxyquinazoline

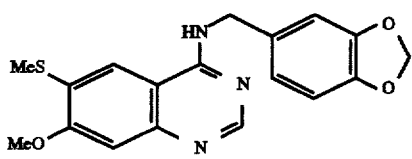

molecular formula; $C_{18}H_{17}N_3O_3S$ yield (%); 39 m.p. (°C.); 200~205 (dec.)

Mass; 356 (M+H)$^+$

NMR δ(CDCl$_3$); 2.50 (3H, s), 4.01 (3H, s), 4.78 (2H, d, J=5.6 Hz), 5.95 (2H, s), 6.13 (1H, brs), 6.79 (1H, d, J=8.0 Hz), 6.88 (1H, d, J=8.0 Hz), 6.91 (1H, s), 7.15 (1H, s), 7.33 (1H, s), 8.56 (1H, s)

Example 75

4-(4-Methylededioxybenzyl)aminoquinazoline

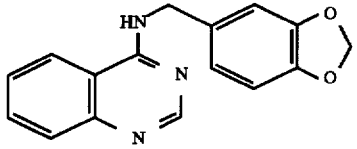

molecular formula; $C_{16}H_{13}N_3O_2$ yield (%); 69 m.p. (°C.); 197~198

Mass; 280 (M+H)$^+$

NMR δ(CDCl$_3$); 4.78 (2H, d, J=5.2 Hz), 5.85 (1H, brs), 5.96 (2H, s), 6.80 (1H, d, J=8.0 Hz), 6.88 (1H, d, J=8.0 Hz), 6.91 (1H, s), 7.46 (1H, t, J=8.0 Hz), 7.68 (1H, d, J=8.0 Hz), 7.75 (1H, t, J=8.0 Hz), 7.87 (1H, d, J=8.0 Hz), 8.71 (1H, s)

Example 76

4-(3,4-Methylededioxybenzyl)amino-8-methoxyquinazoline

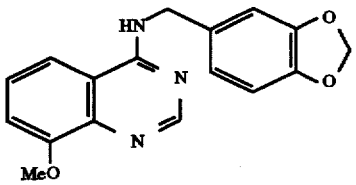

molecular formula; $C_{17}H_{15}N_3O_3$ yield (%); 76 m.p. (°C.); 195~196

Mass; 310 (M+H)$^+$

NMR δ(CDCl$_3$); 4.03 (3H, s), 4.78 (2H, d, J=5.6 Hz), 5.94 (2H, s), 6.77 (1H, d, J=8.0 Hz), 6.89 (1H, d, J=8.0 Hz), 6.92 (1H, s), 6.95 (1H, brs), 7.12 (1H, d, J=8.0 Hz), 7.39 (1H, t, J=8.0 Hz), 7.48 (1H, d, J=8.0 Hz), 8.70 (1H, s)

Example 77

4-(3,4-Methylenedioxybenzyl)amino-7-chloroquinazoline

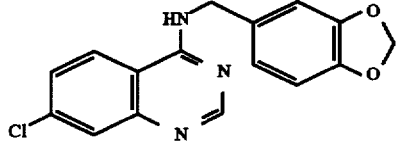

molecular formula; $C_{21}H_{22}N_3O_2Cl$ yield (%); 62 m.p. (°C.); 209~210

Mass; 314 (M+H)$^+$

NMR δ(CDCl$_3$); 4.77 (2H, d, J=5.6 Hz), 5.95 (2H, s), 6.78 (1H, d, J=8.0 Hz), 6.88 (1H, d, J=8.0 Hz), 6.92 (1H, s), 7.39 (1H, dd, J=8.8 Hz, 2.0 Hz), 7.4 (1H, brs), 7.83 (1H, d, J=2.0 Hz), 7.96 (1H, d, J=8.8 Hz), 8.63 (1H, s)

Example 78

4-(3,4-Methylenedioxybenzyl)aminobenzo[g]quinazoline

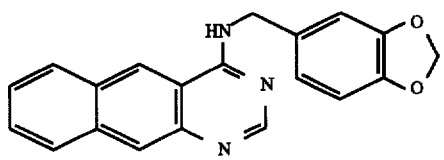

molecular formula; C$_{20}$H$_{15}$N$_3$O$_2$ (329)
yield (%); 45
m.p. (°C.); 265 (dec.)
Mass; 330 (M+1)$^+$
NMR δ(DMSO-D$_6$); 4.92 (2H, d, J=6.0 Hz), 5.97 (2H, s), 6.88 (1H, d, J=8.0 Hz), 6.94 (1H, dd, J=8.0 Hz, 1.6 Hz), 7.06 (1H, d, J=1.6 Hz), 7.68~7.81 (2H, m), 8.11 (1H, d, J=8.4 Hz), 8.21 (1H, d, J=8.4 Hz), 8.33 (1H, s), 8.90 (1H, s), 9.36 (1H, s), 11.09 (1H, br)

Example 79

4-(3,4-Methylenedioxybenzyl)amino-6,7-methylenedioxyquinazoline

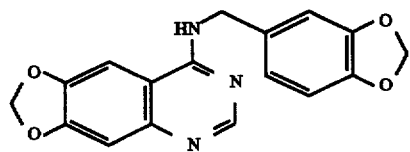

molecular formula; C$_{17}$H$_{13}$N$_{13}$O$_4$ (323)
yield (%); 55
m.p. (°C.); 229~231
Mass; 324 (M+1)$^+$
NMR δ(DMSO-d$_6$); 4.62 (2H, d, J=5.6 Hz), 5.94 (2H, s), 6.16 (2H, s), 6.79 (1H, d, J=8.0 Hz), 6.82 (1H, dd, J=8.0 Hz, 2.0 Hz), 6.89 (1H, d, J=2.0 Hz), 7.06 (1H, s), 7.68 (1H, s), 8.26 (1H, brt, J=5.6 Hz), 8.28 (1H, s)

Example 80

4-(3,4,5-Trimethoxybenzyl)amino-6,7-methylenedioxyquinazoline

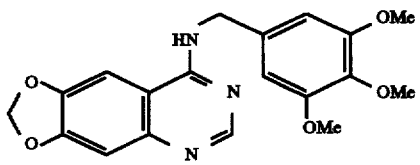

molecular formula; C$_{19}$H$_{19}$N$_3$O$_5$ (369)
yield (%); 59
m.p. (°C.); 240~241
Mass; 370 (M+1)$^+$
NMR δ(DMSO-d$_6$); 3.61 (3H, s), 3.70 (6H, s), 4.65 (2H, d, J=6.0 Hz), 6.16 (2H, s), 6.675 (2H, s), 7.06 (1H, s), 7.72 (1H, s), 8.23 (1H, brt, J=6.0 Hz), 8.30 (1H, s)

Example 81

2-Methyl-4-(3,4-methylenedioxybenzyl)amino-6,7,8-trimethoxyquinazoline

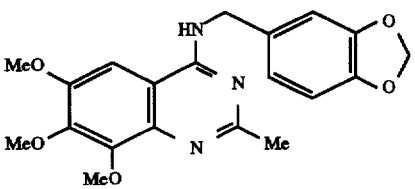

molecular formula; C$_{20}$H$_{21}$N$_3$O$_5$
yield (%); 58
m.p .(°C.); 190~191
Mass; 384 (M+H)$^+$
NMR δ(CDCl$_3$); 2.67 (3H, s), 3.93 (3H, s), 4.01 (3H, s), 4.11 (3H, s), 4.77 (2H, d, J=5.2 Hz), 5.96 (2H, s), 6.70 (1H, s) 6.79 (1H, d, J=7.6 Hz), 6.89 (1H, d, J=7.6 Hz), 6.93 (1H, s)

Example 82

2-Isopropyl-4-(3,4-methylenedioxybenzyl)amino-6-methoxyquinazoline

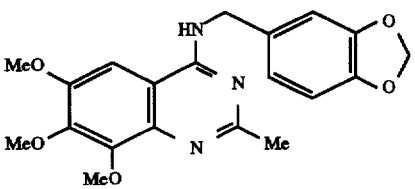

molecular formula; C$_{20}$H$_{21}$N$_3$O$_3$
yield (%); 84
m.p. (°C.); 157~158
Mass; 352 (M+1)$^+$
NMR δ(CDCl$_3$); 1.36 (6H, d, J=6.8 Hz), 3.15 (1H, septet, J=6.8 Hz), 3.88 (3H, s), 4.81 (2H, d, J=5.6 Hz), 5.94 (2H, s), 6.78 (1H, d, J=8.0 Hz), 6.91 (1H, dd, J=8.0 Hz, 2.0 Hz), 6.96 (1H, d, J=2.0 Hz), 6.99 (1H, brd, J=2.4 Hz), 7.32 (1H, dd, J=9.2 Hz, 2.4 Hz), 7.79 (1H, d, J=9.2 Hz)

Example 83

2-(2-Propoxyphenyl)-4-(3,4-methylenedioxybenzyl)amino-6-chloroquinazoline

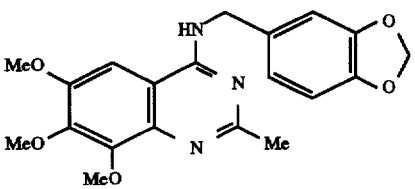

molecular formula; C$_{25}$H$_{22}$N$_3$O$_3$Cl
yield (%); 20
m.p. (°C.); 208~209
Mass; 446 (M+1)$^+$ NMR δ(CDCl₃); 0.97 (3H, t, J=7.6 Hz), 1.71~1.81 (2H, m), 4.01 (2H, t, J=6.4 Hz), 4.81 (2H, brs), 5.80 (1H, br), 5.96 (2H, s), 6.79~7.86 (10H, m)

Example 84

2-(2-Propoxyphenyl)-4-(3,4-methylenedioxybenzyl) aminoquinazoline

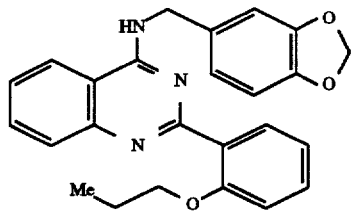

molecular formula; C₂₅H₂₃N₃O₃ (413)
yield (%); 15
m.p. (°C.); 130~131
Mass; 414 (M+1)⁺
NMR δ(CDCl₃); 0.96 (3H, t, J=7.2 Hz), 1.71~1.77 (2H, m), 4.00 (2H, t, J=6.4 Hz), 4.83 (2H, s), 5.95 (2H, s), 6.77~7.93 (12H, m)

Example 85

4-(3,4-Methylenedioxybenzamido)-6,7,8-trimethoxyquinazoline

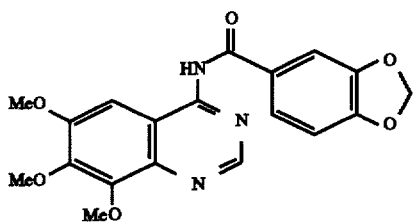

molecular formula; C₁₉H₇N₃O₆
yield (%); 13
m.p. (°C.); 190~192
Mass; 384 (M+H)⁺
NMR δ(CDCl₃); 4.10 (6H, s), 4.12 (3H, s), 6.07 (2H, s), 6.91 (1H, d, J=8.0 Hz), 7.86 (1H, s), 7.90 (1H, s), 8.06 (1H, d, J=8.0 Hz), 8.18 (1H, s)

Example 86

4-(3,4-Methylenedioxybenzyl)oxy-6,7,8-trimethoxyquinazoline

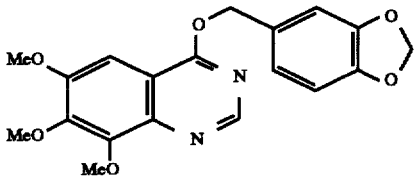

molecular formula; C₁₉H₁₈N₂O₆
yield (%); 49
m.p. (°C.); 141~142

Mass; 371 (M+H)⁺

NMR δ(CDCl₃); 3.97 (3H, s), 4.05 (3H, s), 4.13 (3H, s), 5.53 (2H, s), 5.99 (2H, s), 6.84 (1H, d, J=8.0 Hz), 7.00 (1H, dd, J=8.0 Hz, 2.0 Hz), 7.02 (1H, d, J=2.0 Hz), 7.20 (1H, s), 8.74 (1H, s)

Example 87

4-(3,4-Methylenedioxybenzyl)oxy-6-methylthioquinazoline

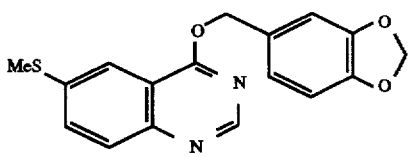

molecular formula; C₁₇H₁₄N₂O₃Cl yield (%); 69 m.p. (°C.); 104~105

Mass; 327 (M+H)⁺

NMR δ(CDCl₃); 2.59 (3H, s), 5.56 (2H, s), 6.00 (2H, s), 6.85 (1H, d, J=8.0 Hz), 7.01 (1H, dd, J=8.0 Hz, 1.6 Hz), 7.03 (1H, d, J=1.6 Hz), 7.72 (1H, dd, J=8.8 Hz, 1.6 Hz), 7.88 (1H, d, J=8.8 Hz), 7.89 (1H, d, J=1.6 Hz), 8.78 (1H, s)

Example 88

2,4,8-Trimethoxyquinazoline

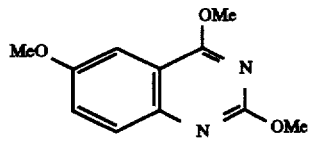

5.0 g (0.022 mol) of 2,4-dichloro-6-methoxyquinazoline was suspended in 150 ml of methanol, followed by the gradual addition of 3.5 g of sodium hydride. The obtained mixture was heated under reflux. After several hours, the reaction mixture was concentrate under a reduced pressure, followed by the addition of water. The crystalline precipitate thus formed was recovered by filtration, washed with water and air-dried to give 4.8 g of the title compound as a crude yellow crystal.

m.p.; 143~144

Mass; 221 (M+1)⁺

NMR δ(CDCl₃); 3.90 (3H, s), 4.08 (3H, s), 4.18 (3H, s), 7.36 (1H, d, J=2.8 Hz), 7.39 (1H, dd, J=8.8 Hz, 2.8 Hz), 7.67 (1H, d, J=2.8 Hz)

Example 89

2,6-Dimethoxy-4-(3,4-methylenedioxybenzyl)aminoquinazoline

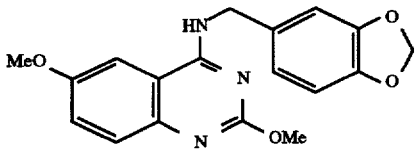

3.75 g (24.8 mmol) of piperonylamine was added to a solution of 2.00 g (8.26 mmol) of the 2,4,6-trimethoxyquinazoline prepared in Example 88 in dimethyl sulfoxide (15 ml). The obtained mixture was stirred under heating at 150° to 160° C. After one hour, the reaction mixture was purified by silica gel column chromatography (ethyl acetate/n-hexane) and recrystallized from ethyl acetate/n-hexane to give 0.50 g of the title compound as a pale-yellow crystal.

molecular formula; $C_{18}H_{17}N_3O_4$ yield (%); 18 m.p. (°C.); 166~167

Mass; 340 (M+1)$^+$

NMR δ(CDCl$_3$); 3.89 (3H, s), 4.03 (3H, s), 4.77 (2H, d, J=5.2 Hz), 5.94 (2H, s), 6.76 (1H, d, J=8.0 Hz), 6.89 (1H, dd, J=8.0 Hz, 1.2 Hz), 6.93 (1H, d, J=1.2 Hz), 7.29 (1H, dd, J=8.8 Hz, 2.8 Hz), 7.32 (1H, brs), 7.59 (1H, d, J=8.8 Hz)

Example 90

2,4-Bisbenzyloxy-6-methoxyquinazoline

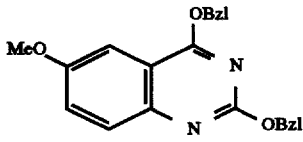

3 ml of benzyl alcohol was dissolved in 50 ml of tetrahydrofuran, followed by the addition of 1.0 g of sodium hydride. The obtained mixture was stirred at 40° to 50° C. for 30 minutes, followed by the addition of 2.50 g (0.0109 mol) of 2,4-dichloro-6-methoxyquinazoline. The obtained mixture was heated under reflux for several hours, followed by the addition of water. The obtained mixture was extracted with chloroform and the organic layer was dried over anhydrous magnesium sulfate and filtered. The filtrate was distilled under a reduced pressure to remove the solvent. The obtained crystalline residue was recrystallized from chloroform/n-hexane to give 3.84 g of the title compound as a yellow crystal.

yield (%); 95 m.p. (°C.); 144~145

Mass; 373 (M+1)$^+$

NMR δ(CDCl$_3$); 3.87 (3H, s), 5.53 (2H, s), 5.62 (2H, s), 7.31~7.55 (12H, m), 7.70 (1H, d, J=8.8 Hz)

Example 91

2-Benzyloxy-4-(4-methylenedioxybenzyl)amino-6-methoxyquinazoline

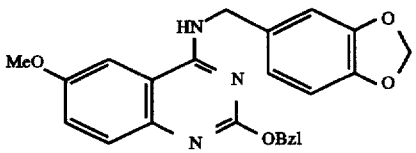

1.25 g (8.27 mmol) of piperonylamine was added to a solution of 1.00 g (2.69 mmol) of the 2,4-bisbenzyloxy-6-methoxyquinazoline prepared in Example 90 in dimethyl sulfoxide (10 ml). The obtained mixture was stirred at 160° to 180° C. After one hour, the reaction mixture was purified by silica gel column chromatography (ethyl acetate/n-hexane) and recrystallized from ethyl acetate/n-hexane to give 0.20 g of the title compound as a colorless needle.

molecular formula; $C_{24}H_{21}N_3O_4$ yield (%); 18 m.p. (°C.); 163~164

Mass; 416 (M+H)$^+$

NMR δ(CDCl$_3$); 3.86 (3H, s), 4.75 (2H, d, J=5.2 Hz), 5.49 (2H, s), 5.68 (1H, brs), 5.96 (2H, s), 6.79 (1H, d, J=8.0 Hz), 6.84~6.87 (3H, m), 7.28~7.36 (4H, m), 7.51~7.53 (2H, m), 7.63 (1H, d, J=9.2 Hz)

Example 92

2,6-Dichloro-4-(3,4-methylenedioxybenzyl)aminoquinazoline

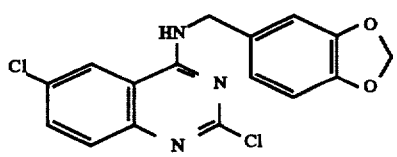

A mixture comprising 3.6 g of 2,4,6-trichloroquinazoline, 2.4 g of piperonylamine, 1.6 g of triethylamine and 50 ml of isopropyl alcohol was heated under reflux for 1.5 hours and hot-filtered to give 5.2 g of the title compound as a filter cake.

molecular formula; $C_{16}H_{11}N_3O_2Cl_2$ yield (%); 98 m.p. (°C.); 215

Mass; 349 (M+1)$^+$

NMR δ(DMSO-D$_6$); 4.61 (2H, s), 5.97 (2H, s), 6.85 (2H, s), 6.95 (1H, s), 7.63 (1H, d, J=8.8 Hz), 7.80 (1H, dd, J=8.8 Hz, 2.4 Hz), 8.45 (1H, d, J=2.4 Hz), 9.24 (1H, br)

Example 93

2-Chloro-4-(3,4-methylenedioxybenzyl)amino-6-cyanoquinazoline

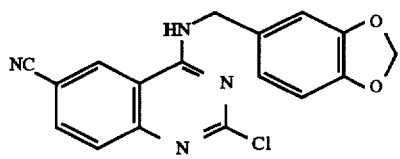

35 ml of isopropyl alcohol, 900 mg of triethylamine and 1.35 g of piperonylamine were added to 2 g of 2,4-dichloro-6-cyanoquinazoline. The obtained mixture was heated under reflux for 1.5 hours and hot-filtered to recover a precipitate. Thus, 2.4 g of the title compound was obtained.

molecular formula; $C_{17}H_{11}N_4O_2Cl$ yield (%); 79 m.p. (°C.); 234–236 (dec.)

Mass; 339 (M+1)$^+$

NMR δ(DMSO-d$_6$); 4.63 (2H, d, J=5.6 Hz), 5.97 (2H, s), 6.86 (2H, s), 6.97 (1H, s), 7.72 (1H, d, J=8.4 Hz), 8.10 (1H, dd, J=8.4 Hz, 1.8 Hz), 8.90 (1H, d, J=1.8 Hz), 9.50 (1H, br)

Example 94

2-Chloro-4-(3-chloro-4-methoxybenzyl)amino-6-cyanoquinazoline

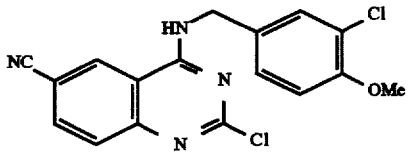

3.9 g of 3-chloro-4-methoxybenzylamine, 3.97 g of triethylamine and 200 ml of 2-propanol were added to 4 g of 2,4-dichloro-6-cyanoquinazoline. The obtained mixture was refluxed for 30 minutes, cooled to room temperature and filtered to recover a crystalline precipitate. The precipitate was washed with water and chloroform successively to give 5.563 g of the title compound.

molecular formula; $C_{17}H_{12}N_4OCl_2$ yield (%); 87 m.p. (°C.); 264–266

Mass m/e; 359 (M+1)

NMR δ(CDCl$_3$); 3.90 (3H, s), 4.73 (2H, d, J=5.2 Hz), 6.92 (1H, d, J=8.4), 7.33 (1H, dd, J=8.4 Hz, 2.0 Hz), 7.45 (1H, d, J=2.0 Hz), 7.74 (1H, d, J=8.4 Hz), 7.83 (1H, dd, J=8.4 Hz, 1.6 Hz), 8.78 (1H, d, J=1.6 Hz), 8.85 (1H, brs)

Examples 95 to 105

The following compounds were prepared in a similar manner to those of Examples 88 to 94.

Example 95

2-Chloro-4-(3,4-methylenedioxybenzyl)amino-6,7,8-trimethoxyquinazoline

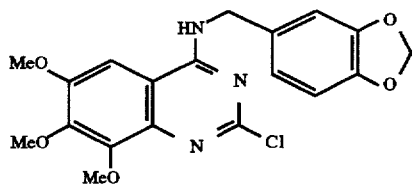

molecular formula; $C_{19}H_{18}N_3O_5Cl$ yield (%); 50 m.p. (°C.); 193–194

Mass; 404 (M+H)$^+$

NMR δ(CDCl$_3$); 3.94 (3H, s), 4.03 (3H, s), 4.10 (3H, s), 4.75 (2H, d, J=5.2 Hz), 5.65 (1H, brs), 5.98 (2H, s), 6.59 (1H, s), 6.81 (1H, d, J=8.0 Hz), 6.89 (1H, d, J=8.0 Hz), 6.91 (1H, s)

Example 96

2-Chloro-4-(3-chloro-4-methoxybenzyl)amino-6,7,8-trimethoxyquinazoline

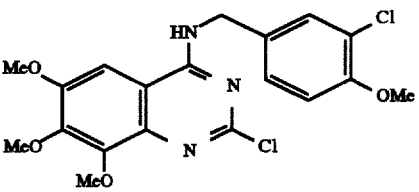

molecular formula; $C_{19}H_{19}Cl_2N_3O_4$ yield (%); 45 m.p. (°C.); 199–200

Mass; 424 (M+1)$^+$

NMR δ(CDCl$_3$); 3.89 (3H, s), 3.95 (3H, s), 4.02 (3H, s), 4.08 (3H, s), 4.76 (2H, d, J=5.6 Hz), 6.39 (1H, brs), 6.83 (1H, s), 6.89 (1H, d, J=8.3 Hz), 7.31 (1H, dd, J=8.4 Hz, 2.0 Hz), 7.40 (1H, d, J=2.0 Hz)

Example 97

2-(Chloro-4-(3,4-methylenedioxybenzyl)amino-6,7-dimethoxyquinazoline

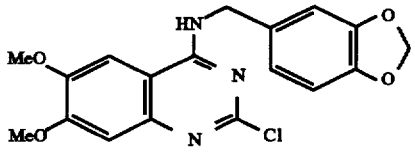

molecular formula; $C_{18}H_{16}N_3O_4Cl$ yield (%); 97 m.p. (°C.); 177–178

Mass; 374 (M+H)$^+$

NMR δ(CDCl$_3$); 3.95 (3H, s), 3.97 (3H, s), 4.75 (2H, d, J=5.2 Hz), 5.74 (1H, brt, J=5.2 Hz), 5.97 (2H, s), 6.80 (1H, d, J=8.0 Hz), 6.81 (1H, s), 6.88 (1H, dd, J=8.0 Hz, 2.0 Hz), 6.91 (1H, d, J=2.0 Hz), 7.14 (1H, s)

Example 98

2-Chloro-4-(3,4-methylenedioxybenzyl)amino-6-methoxyquinazoline

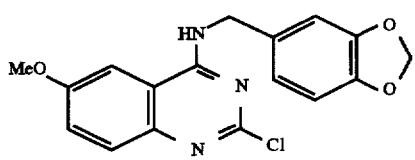

molecular formula; $C_{17}H_{14}N_3O_3Cl$ yield (%); 80 m.p. (°C.); 202~203

Mass; 344 (M+1)$^+$

NMR δ(CDCl$_3$); 3.91 (3H, s), 4.77 (2H, d, J=5.6 Hz), 5.94 (2H, s), 6.76 (1H, d, J=8.0 Hz), 6.91 (1H, dd, J=8.0 Hz, 1.6 Hz), 6.95 (1H, d, J=1.6 Hz), 7.35 (1H, dd, J=9.2 Hz, 2.8 Hz), 7.46 (1H, brd, J=2.8 Hz), 7.69 (1H, d, J=9.2 Hz), 7.90 (1H, brs)

Example 99

2-Chloro-4-(3-chloro-4-methoxybenzyl)amino-6-methoxyquinazoline

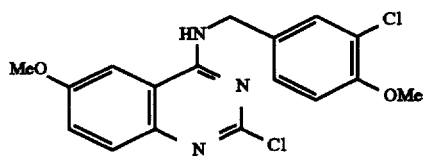

molecular formula; $C_{17}H_{15}N_3O_2Cl_2$ yield (%); 88 m.p. (°C.); 171~172

Mass; 364 (M+1)$^+$

NMR δ(DMSO); 3.83 (3H, s), 3.88 (3H, s), 4.68 (2H, d, J=5.6 Hz), 7.13 (1H, d, J=8.8 Hz), 7.33 (1H, dd, J=2.4 Hz, 8.8 Hz), 7.44 (1H, dd, J=2.8 Hz, 9.2 Hz), 7.46 (1H, d, J=2.4 Hz), 7.58 (1H, d, J=9.2 Hz), 7.72 (1H, d, J=2.8 Hz), 9.05 (1H, t, J=5.6 Hz)

Example 100

2,6-Dichloro-4-benzylaminoquinazoline

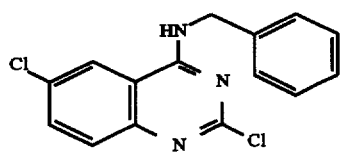

molecular formula; $C_{15}H_{11}N_3Cl_2$ yield (%); 77 m.p. (°C.); 227~228

NMR δ(CDCl$_3$); 4.85 (2H, d, J=5.2 Hz), 5.97 (1H, brs), 7.33~7.43 (5H, m), 7.62 (1H, d, J=2.0 Hz), 7.68 (1H, dd, J=8.8 Hz, 2.0 Hz), 7.74 (1H, d, J=8.8 Hz)

Example 101

2,6-Dichloro-4-[2-(3,4-methylenedixoyphenyl)ethyl]aminoquinazoline

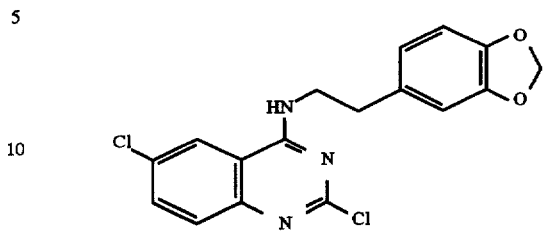

molecular formula; $C_{17}H_{13}N_3O_2Cl_2$ yield (%); 71 m.p. (°C.); 228~229

NMR δ(DMSO-d$_6$); 2.88 (2H, t, J=7.4 Hz), 3.68 (2H, m), 5.96 (2H, s), 6.70 (1H, dd, J=8.0 Hz, 1.6 Hz), 6.81 (1H, d, J=8.0 Hz), 6.87 (1H, d, J=1.6 Hz), 7.63 (1H, d, J=8.8 Hz), 7.80 (1H, dd, J=8.8 Hz, 2.0 Hz), 8.40 (1H, d, J=2.0 Hz), 8.86 (1H, d, J=5.2 Hz)

Example 102

2,6-Dichloro-4-(3-chloro-4-methoxybenzyl)aminoquinazoline

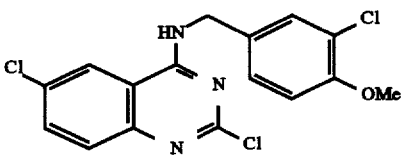

molecular formula; $C_{16}H_{12}N_3OCl_3$ yield (%); 93 m.p. (°C.); 207~208

Mass m/e; 368 (M+1)

NMR δ(CDCl$_3$); 3.90 (3H, s), 4.73 (2H, d, J=5.6 Hz), 6.91 (1H, d, J=8.4 Hz), 7.32 (1H, d, J=8.4 Hz, 2.0 Hz), 7.45 (1H, d, J=2.0 Hz), 7.62 (1H, dd, J=8.8 Hz, 2.0 Hz), 7.66 (1H, d, J=8.8 Hz), 8.07 (1H, brs), 8.16 (1H, d, J=2.0 Hz)

Example 103

2,6-Dichloro-4-(benzimidazol-5-yl)methylaminoquinazoline

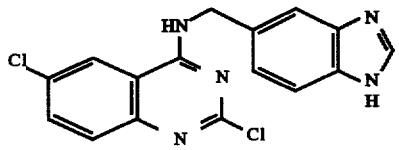

molecular formula; $C_{16}H_{11}N_5Cl_2$ (344.205)

yield (%); 81 m.p. (°C.); >290

Mass; 344 (M+1)$^+$

NMR δ(DMSO); 4.85 (2H, d, J=6.0 Hz), 7.25 (1H, dd, J=1.6 Hz, 6.4 Hz), 7.57 (1H, d, J=6.4 Hz), 7.60 (1H, s), 7.66 (1H, d, J=8.8 Hz), 7.83 (1H, dd, J=2.0 Hz, 8.8 Hz), 8.21 (1H, s), 8.44 (1H, brs), 8.52 (1H, d, J=2.0 Hz), 9.37 (1H, t, J=6.0 Hz)

Example 104

2-Chloro-4-(benzimidazol-5-yl)methylamino-6-cyanoquinazoline

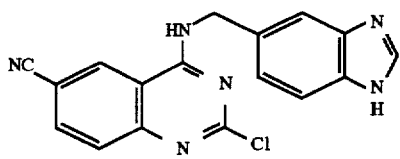

molecular formula; $C_{17}H_{11}N_6Cl$ (334.5)
yield (%); 58
m p.(°C.); >290
Mass; 335 (M+1)$^+$
NMR δ(DMSO-d$_6$); 4.81 (2H, s), 7.21~7.68 (3H, m), 7.73 (1H, d, J=8.8 Hz), 8.10 (1H, d, J=8.8 Hz), 8.17 (1H, s), 8.91 (1H, s), 9.55 (1H, br)

Example 105

2-Chloro-4-[N-(2-hydroxyethyl)-(3,4-methylenedioxybenzyl)amino]-6,7,8-trimethoxyquinazoline

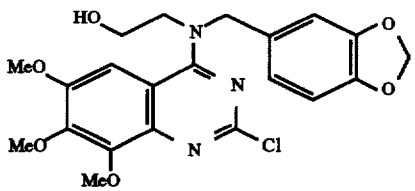

molecular formula; $C_{21}H_{22}N_3O_6Cl$
yield (%); 55
Mass; 448 (M+H)$^+$
NMR δ(CDCl$_3$); 3.38 (3H, s), 3.88 (2H, t, J=4.4 Hz), 4.01 (2H, t, J=4.4 Hz), 4.03 (3H, s), 4.07 (3H, s), 4.92 (2H, s), 6.01 (2H, s), 6.88~6.91 (3H, m), 7.00 (1H, s)

Example 106

2-Formyl-4-(3,4-methylenedioxybenzyl)amino-8-chloroquinazoline

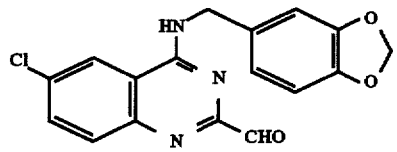

0.50 g (0.0013 mol) of 2-ethoxycarbonyl-4-(3,4-methylenedioxybenzyl)amino-6-chloroquinazoline was dissolved in a solvent mixture comprising 20 ml of methylene chloride and 20 ml of tetrahydrofuran. 2.6 ml of a 1.0M solution of diisobutylaluminum hydride in toluene was dropped into the solution prepared above at −78° C. under stirring. The obtained mixture was stirred at −78° C. for several hours, followed by the addition of 20 ml of methanol. The obtained mixture was distilled under a reduced pressure to remove the solvent. The residue was purified by silica gel column chromatography and recrystallized from ethyl acetate/n-hexane to give 0.23 g of the title compound as a pale-yellow crystal.

yield(%); 52
m.p. (°C.); 200~202 (dec.)
Mass; 342 (M+1)$^+$
NMR δ(CDCl$_3$); 4.86 (2H, d, J=5.2 Hz), 5.98 (2H, s), 6.81 (1H, d, J=7.6 Hz), 6.90 (1H, d, J=7.6 Hz), 6.92 (1H, s), 7.72 (1H, d, J=2.0 Hz), 7.77 (1H, dd, J=8.8 Hz, 2.0 Hz), 8.01 (1H, d, J=8.8 Hz), 10.05 (1H, s)

Example 107

2-Ethoxycarbonyl-4-(3,4-methylenedioxybenzyl)amino-6-chloroquinazoline

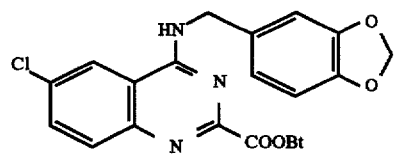

2.72 g (0.0100 mol) of 2-ethoxycarbonyl-4,6-dichloroquinazoline, 1.75 g (0.0116 mol) of piperonylamine and 1.60 g (0.0151 mol) of sodium carbonate were mixed with 100 ml of isopropyl alcohol. The obtained mixture was heated under reflux for 24 hours and distilled under a reduced pressure to remove the solvent. The residue was purified by silica gel column chromatography and recrystallized from chloroform/n-hexane to give 3.56 g of the title compound as a colorless needle.

molecular formula; $C_{19}H_{16}N_3O_4Cl$
yield (%); 92
m.p. (°C.); 212~213
Mass; 386 (M+H)$^+$
NMR δ(CDCl$_3$); 1.49 (3H, t, J=7.2 Hz), 1.54 (2H, q, J=7.2 Hz), 4.83 (2H, d, J=5.6 Hz), 5.96 (1H, brs), 5.97 (2H, s), 6.80 (1H, d, J=8.0 Hz), 6.91 (1H, dd, J=8.0 Hz, 1.6 Hz), 6.97 (1H, d, J=1.6 Hz), 7.70 (1H, d, J=2.0 Hz), 7.72 (1H, dd, J=8.8 Hz, 2.0 Hz), 8.00 (1H, d, J=8.8 Hz)

Examples 108 to 111

The following compounds were prepared in a similar manner to that of Examples 106 or 107.

Example 108

2-Ethoxycarbonyl-4-(3-chloro-4-methoxybenzyl)amino-6-chloroquinazoline

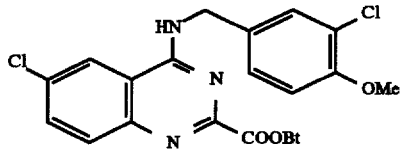

molecular formula; $C_{19}H_{17}N_3O_3Cl_2$
yield (%); 88
m.p. (°C.); 185~186
Mass; 406 (M+1)$^+$
NMR δ(CDCl$_3$); 1.49 (3H, t, J=7.2 Hz), 3.90 (3H, s), 4.54 (2H, q, J=7.2 Hz), 4.84 (2H, d, J=5.2 Hz), 6.09 (1H, brs), 6.90 (1H, d, J=8.4 Hz), 7.33 (1H, dd, J=8.4 Hz, 2.4 Hz), 7.48 (1H, d, J=2.4 Hz), 7.72 (1H, dd, J=8.8 Hz, 2.4 Hz), 7.74 (1H, d, J=2.4 Hz), 7.99 (1H, d, J=8.8 Hz)

Example 109

2-Ethoxycarbonyl-4-(3,4-methylenedioxybenzyl)
amino-6,7,8-trimethoxyquinazoline

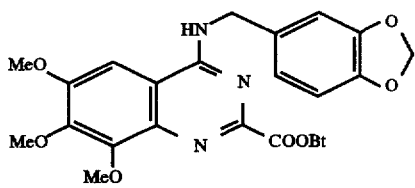

molecular formula; $C_{22}H_{23}N_3O_7$
yield (%); quantitative
m.p. (°C.); 163–165 (dec.)
Mass; 442 (M+1)$^+$
NMR δ(CDCl$_3$); 1.45 (3H, t, J=7.2 Hz), 3.94 (3H, s), 4.02 (3H, s), 4.18 (3H, s), 4.46 (2H, q, J=7.2 Hz), 4.80 (2H, d, J=5.2 Hz), 5.89 (1H, brt, J=5.2 Hz), 5.94 (2H, s), 6.74 (1H, d, J=7.6 Hz), 6.76 (1H, s), 6.86 (1H, dd, J=7.6 Hz, 1.6 Hz), 6.94 (1H, d, J=1.6 Hz)

Example 110

2-Ethoxycarbonyl-4-(3-chloro-4-methoxybenzyl)
amino-6-methoxyquinazoline

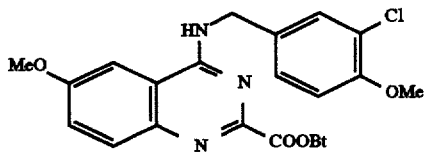

molecular formula; $C_{20}H_{20}N_3O_4Cl$
yield (%); 73
m.p. (°C.); 192–193
Mass; 402 (M+1)$^+$
NMR δ(CDCl$_3$); 1.49 (3H, t, J=7.2 Hz), 3.90 (3H, s), 3.91 (3H, s), 4.53 (2H, q, J=7.2 Hz), 4.86 (2H, d, J=5.6 Hz), 5.90 (1H, brt, J=5.6 Hz), 6.90 (1H, d, J=8.4 Hz), 6.96 (1H, d, J=2.4 Hz), 7.36 (1H, dd, J=8.4 Hz, 2.4 Hz), 7.44 (1H, dd, J=9.2 Hz, 2.4 Hz), 7.49 (1H, d, J=2.4 Hz), 8.00 (1H, d, J=9.2 Hz)

Example 111

2-Ethoxycarbonyl-4-(benzimidazol-5-ylmethyl)
amino-6-methoxyquinazoline

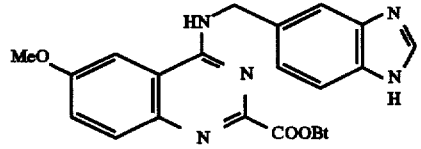

molecular formula; $C_{20}H_{19}N_5O_3$
yield (%); 48
m.p. (°C.); 244–245 (dec.)
Mass; 378 (M+1)$^+$
NMR δ(DMSO-d$_6$); 1.35 (3H, t, J=7.2 Hz), 3.90 (3H, s), 4.33 (2H, q, J=7.2 Hz), 4.94 (2H, d, J=6.0 Hz), 7.31 (1H, d, J=8.0 Hz), 7.47 (1H, dd, J=8.8 Hz, 2.8 Hz), 7.53 (1H, d, J=8.0 Hz), 7.65 (1H, brs), 7.77 (1H, d, J=8.8 Hz), 7.78 (1H, s), 8.17 (1H, s), 8.89 (1H, brt, J=6.0 Hz)

Example 112

(E)-2-(2-Ethoxycarbonyl-1-propenyl)-4-(3,4-
methylenedioxybenzyl)amino-6-chloroquinazoline

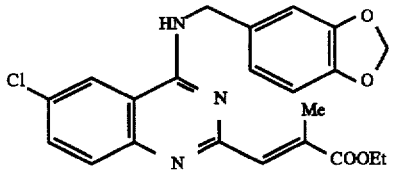

0.52 g (0.013 mol) of sodium hydride was added to a solution of 4.00 g (0.0117 mol) of 2-formyl-4-(3,4-methylenedioxybenzyl)amino-6-chloroquinazoline in 250 ml of tetrahydrofuran. 2.8 ml (0.013 mol) of triethyl 2-phosphonopropionate was dropped into the mixture prepared above under stirring and cooling with ice. The mixture thus prepared was stirred under cooling with ice for a while, heated to room temperature and stirred for additional one hour, followed by the addition of 1.5 ml of 8M hydrochloric acid/ethanol. The obtained mixture was passed through a small amount of silica gel and distilled under a reduced pressure to remove the solvent. The residue was purified by silica gel column chromatography (ethyl acetate/n-hexane) and recrystallized from chloroform/n-hexane to give 2.00 g of the title compound.

molecular formula; $C_{22}H_{20}N_3O_4Cl$
yield (%); 40
m.p. (°C.); 179–180 (dec.)
Mass; 426 (M+1)$^+$
NMR δ(CDCl$_3$); 1.35 (3H, t, J=7.2 Hz), 2.50 (3H, d, J=1.6 Hz), 4.29 (2H, q, J=7.2 Hz), 4.78 (2H, d, J=5.2 Hz), 5.77 (1H, brt, J=5.2 Hz), 5.97 (2H, s), 6.81 (1H, d, J=8.0 Hz), 6.87 (1H, dd, J=8.0 Hz, 1.6 Hz), 6.89 (1H, d, J=1.6 Hz), 7.62 (1H, q, J=1.6 Hz), 7.64 (1H, d, J=2.0 Hz), 7.68 (1H, dd, J=8.8 Hz, 2.0 Hz), 7.81 (1H, d, J=8.8 Hz)

Examples 113 to 119

The following compounds were prepared in a similar manner to that of Example 112.

Example 113

(Z)-2-(2-Ethoxycarbonyl-1-propenyl)-4-(3,4-
methylenedioxybenzyl)amino-6-chloroquinazoline

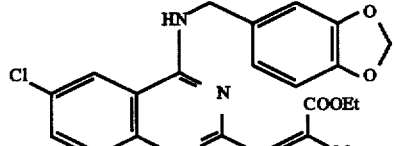

molecular formula; $C_{22}H_{20}N_3O_4Cl$
yield (%); 13
amt. of product(g); 0.64
m.p. (°C.); 162–164 (dec.)
Mass; 426 (M+1)$^+$ NMR δ(CDCl₃); 1.20 (3H, t, J=7.2 Hz), 2.17 (3H, d, J=1.6 Hz), 4.21 (2H, q, J=7.2 Hz), 4.70 (2H, d, J=4.8 Hz), 5.64 (1H, brs), 5.97 (2H, s), 6.53 (1H, q, J=1.6 Hz), 6.81 (1H, d, J=7.6 Hz), 6.85 (1H, dd, J=7.6 Hz, 1.6 Hz), 6.87 (1H, d, J=1.6 Hz), 7.58 (1H, d, J=2.4 Hz), 7.62 (1H, dd, J=8.8 Hz, 2.4 Hz), 7.71 (1H, d, J=8.8 Hz)

Example 114

(E)-2-(2-Ethoxycarbonylvinyl)-4-(3,4-methylenedioxybenzyl)amino-6-chloroquinazoline

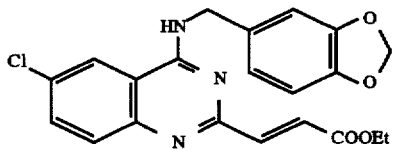

molecular formula; C₂₁H₁₈N₃O₄Cl yield (%); 67 m.p. (°C.); 195~196

Mass; 412 (M+1)⁺

NMR δ(CDCl₃); 1.35 (3H, t, J=7.2 Hz), 4.29 (2H, q, J=7.2 Hz), 4.80 (2H, d, J=5.2 Hz), 5.77 (1H, brs), 5.97 (2H, s), 6.81 (1H, d, J=7.6 Hz), 6.89 (1H, d, J=7.6 Hz), 6.90 (1H, s), 7.21 (1H, d, J=15.6 Hz), 7.64 (1H, d, J=2.0 Hz), 7.66 (1H, d, J=15.6 Hz), 7.68 (1H, dd, J=9.2 Hz, 2.0 Hz), 7.82 (1H, d, J=9.2 Hz)

Example 115

(E)-2-(2-Ethoxycarbonylvinyl)-4-(3-chloro-4-methoxybenzyl)amino-6-chloroquinazoline

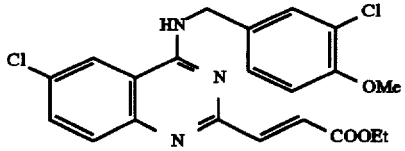

molecular formula; C₂₁H₁₉N₃O₄Cl₂ yield (%); 74 m.p. (°C.); 211~212

Mass; 432 (M+1)⁺

NMR δ(CDCl₃); 1.35 (3H, t, J=7.2 Hz), 3.89 (3H, s), 4.28 (2H, q, J=7.2 Hz), 4.79 (2H, d, J=5.6 Hz), 6.91 (1H, d, J=8.4 Hz), 7.16 (1H, d, J=15.6 Hz), 7.33 (1H, dd, J=8.4 Hz, 2.0 Hz), 7.46 (1H, d, J=2.0 Hz), 7.62 (1H, d, J=15.6 Hz), 7.64 (1H, dd, J=8.8 Hz, 2.4 Hz), 7.75 (1H, d, J=8.8 Hz), 7.77 (1H, brs), 8.16 (1H, d, J=2.4 Hz)

Example 116

(E)-2-(2-Ethoxycarbonyl-1-propenyl)-4-(3-chloro-4-methoxybenzyl)amino-6-chloroquinazoline

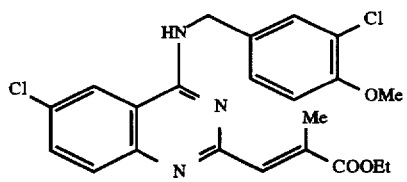

molecular formula; C₂₂H₂₁N₃O₃Cl₂ yield (%); 54 m.p. (°C.); 154~155

Mass; 446 (M+1)⁺

NMR δ(CDCl₃); 1.35 (3H, t, J=7.2 Hz), 2.48 (3H, d, J=1.6 Hz), 3.91 (3H, s), 4.29 (2H, q, J=7.2 Hz), 4.80 (2H, d, J=5.2 Hz), 5.82 (1H, brt, J=5.2 Hz), 6.92 (1H, d, J=8.8 Hz), 7.27 (1H, dd, J=8.8 Hz, 2.0 Hz), 7.42 (1H, d, J=2.0 Hz), 7.62 (1H, q, J=1.6 Hz), 7.67 (1H, d, J=2.4 Hz), 7.69 (1H, dd, J=8.8 Hz, 2.4 Hz), 7.82 (1H, d, J=8.8 Hz)

Example 117

(Z)-2-(2-Ethoxycarbonyl-1-propenyl)-4-(3-chloro-4-methoxybenzyl)amino-6-chloroquinazoline

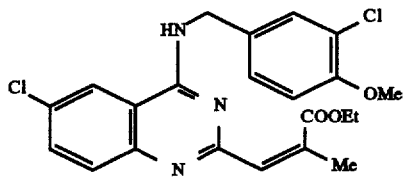

molecular formula; C₂₂H₂₁N₃O₄Cl₂ yield (%); 11 m.p. (°C.); 141~142

Mass; 446 (M+1)⁺

NMR δ(CDCl₃); 1.19 (3H, t, J=7.2 Hz), 2.17 (3H, d, J=1.6 Hz), 3.91 (3H, s), 4.19 (2H, q, J=7.2 Hz), 4.73 (2H, d, J=5.2 Hz), 5.69 (1H, brt, J=5.2 Hz), 6.53 (1H, q, J=1.6 Hz), 6.92 (1H, d, J=8.4 Hz), 7.26 (1H, dd, J=8.4 Hz, 2.0 Hz), 7.40 (1H, d, J=2.0 Hz), 7.60 (1H, d, J=2.0 Hz), 7.63 (1H, dd, J=8.8 Hz, 2.0 Hz), 7.71 (1H, d, J=8.8 Hz)

Example 118

(E)-2-(2-Ethoxycarbonyl-1-propenyl)-4-(3,4-methylenedioxybenzyl)amino-6,7,8-tribethoxyquinazoline

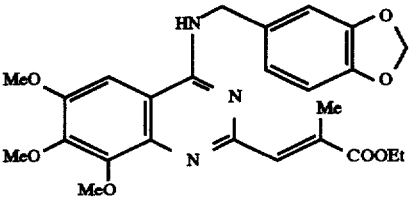

molecular formula; C₂₅H₂₇N₃O₇ yield (%); 51 m.p. (°C.); 175~176

Mass; 482 (M+1)+

NMR δ(CDCl₃); 1.35 (3H, t, J=7.2 Hz), 2.52 (3H, d, J=1.6 Hz), 3.95 (3H, s), 4.04 (3H, s), 4.14 (3H, s), 4.28 (2H, q, J=7.2 Hz), 4.80 (2H, d, J=5.2 Hz), 5.60 (1H, brt, J=5.2 Hz), 5.96 (2H, s), 6.67 (1H, s), 6.80 (1H, d, J=8.0 Hz), 6.87 (1H, dd, J=8.0 Hz, 1.6 Hz), 6.90 (1H, d, J=1.6 Hz), 7.69 (1H, q, J=1.6 Hz)

Example 119

(Z)-2-(2-Ethoxycarbonyl-1-propenyl)-4-(3,4-methylenedioxybenzyl)amino-6,7,8-trimethoxyquinazoline

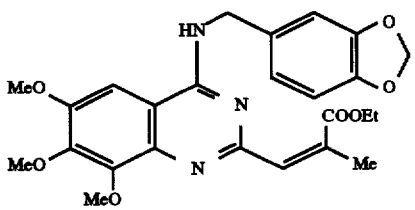

molecular formula; C₂₅H₂₇N₃O₇ yield (%); 11 m.p. (°C.); 157~158 (dec.)

Mass; 482 (M+1)+

NMR δ(CDCl₃); 1.19 (3H, t, J=7.2 Hz), 2.16 (3H, s), 3.92 (3H, s), 4.02 (3H, s), 4.09 (3H, s), 4.21 (2H, q, J=7.2 Hz), 4.72 (2H, d, J=5.2 Hz), 5.43 (1H, brs), 5.96 (2H, s), 6.59~6.61 (2H, m), 6.80 (1H, d, J=8.0 Hz), 6.86~6.89 (2H, m)

Example 120

(E)-2-(2-Carboxy-1-propenyl)-4-(3,4-methylenedioxybenzyl)amino-6-chloroquinazoline

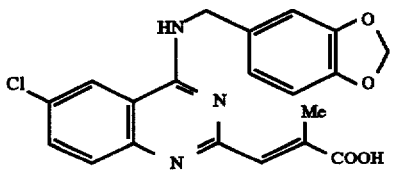

1.00 g (0.0023 mol) of (E)-2-(2-ethoxycarbonylpropenyl)-4-(3,4-methylenedioxybenzyl)amino-6-chloroquinazoline was dissolved in a mixture comprising 5 ml of tetrahydrofuran and 20 ml of ethanol, followed by the addition of 20 ml of a 1N aqueous solution of sodium hydroxide. The obtained mixture was stirred at room temperature for several hours, neutralized with 20 ml of 1N hydrochloric acid and concentrated under a reduced pressure. The crystal thus formed was recovered by filtration, washed with water and air-dried to give 0.85 g of the title compound.

molecular formula; C₂₀H₁₆N₃O₄Cl yield (%); 91 m.p. (°C.); 145~146

Mass; 398 (M+1)+

NMR δ(DMSO-d₆); 2.36 (3H, d, J=1.6 Hz), 4.70 (2H, d, J=5.6 Hz), 5.97 (2H, s), 6.85 (2H, s), 6.95 (1H, s), 7.34 (1H, q, J=1.6 Hz), 7.72 (1H, d, J=8.8 Hz), 7.79 (1H, dd, J=8.8 Hz, 2.0 Hz), 8.46 (1H, d, J=2.0 Hz), 8.86 (1H, brt, J=5.6 Hz)

Examples 121 to 128

The following compounds were prepared in a similar manner to that of Example 120.

Example 121

2-Carboxy-4-(3,4-methylenedioxybenzyl)amino-6-chloroquinazoline

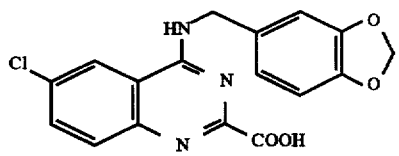

molecular formula; C₁₇H₁₂N₃O₄Cl yield (%); quantitative m.p. (°C.); 240 (dec.)

Mass; 402 (M−1+2Na)+

NMR δ(DMSO-d₆); 4.71 (2H, d, J=5.6 Hz), 5.96 (2H, s), 6.83 (1H, d, J=8.0 Hz), 6.89 (1H, dd, J=8.0 Hz, 1.2 Hz), 7.06 (1H, d, J=1.2 Hz), 7.75 (1H, dd, J=8.8 Hz, 2.4 Hz), 7.90 (1H, d, J=8.8 Hz), 8.48 (1H, d, J=2.4 Hz), 8.82 (1H, brt, J=5.6 Hz)

Example 122

(E)-2-(2-Carboxyvinyl)-4-(3,4-methylenedioxybenzyl)amino-6-chloroquinazoline

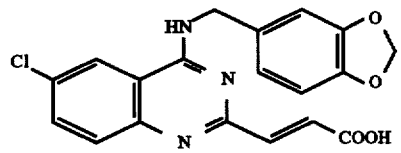

molecular formula; C₁₉H₁₄N₃O₄Cl yield (%); 43 m.p. (°C.); 114~115

Mass; 428 (M−1+2Na)+

NMR δ(DMSO-d₆); 4.71 (2H, d, J=5.6 Hz), 5.96 (2H, s), 6.84 (1H, d, J=8.0 Hz), 6.90 (1H, dd, J=8.0 Hz, 1.6 Hz), 6.99 (1H, d, J=1.6 Hz), 7.02 (1H, d, J=15.6 Hz), 7.23 (1H, d, J=15.6 Hz), 7.73 (1H, d, J=9.2 Hz), 7.78 (1H, dd, J=9.2 Hz, 2.0 Hz), 8.44 (1H, d, J=2.0 Hz), 8.89 (1H, brt, J=5.6 Hz)

Example 123

(Z)-2-(2-carboxy-1-propenyl)-4-(3,4-methylenedioxybenzyl)amino-6-chloroquinazoline

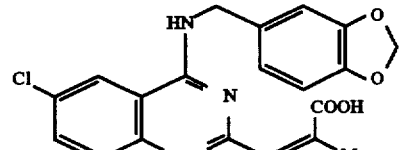

molecular formula; C₂₀H₁₆N₃O₄Cl yield (%); quantitative m.p. (°C.); 195~196

Mass; 398 (M+1)+

NMR δ(DMSO-d₆); 2.10 (3H, d, J=1.6 Hz), 4.70 (2H, d, J=5.6 Hz), 5.97 (2H, s), 6.56 (1H, d, J=1.6 Hz), 6.86 (1H, d, J=8.0 Hz), 6.91 (1H, dd, J=8.0 Hz, 1.6 Hz), 7.00 (1H, d, J=1.6 Hz), 7.65 (1H, d, J=9.2 Hz), 7.81 (1H, dd, J=9.2 Hz, 2.4 Hz), 8.46 (1H, d, J=2.4 Hz), 8.96 (1H, brt, J=5.6 Hz)

Example 124

(E)-2-(2-carboxyvinyl)-4-(3-chloro-4-methoxybenzyl)amino-6-chloroquinazoline

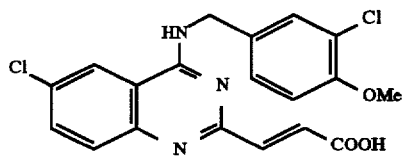

molecular formula; $C_{19}H_{15}N_3O_3Cl_2$
yield (%); quantitative
m.p. (°C.); 109~110
Mass; 448 (M−1+2Na)⁺
NMR δ(DMSO-d₆); 3.81 (3H, s), 4.73 (2H, d, J=5.6 Hz), 6.95 (1H, d, J=15.6 Hz), 7.05 (1H, d, J=15.6 Hz), 7.08 (1H, d, J=8.4 Hz), 7.37 (1H, dd, J=8.4 Hz, 2.0 Hz), 7.48 (1H, d, J=2.0 Hz), 7.68 (1H, d, J=8.8 Hz), 7.73 (1H, dd, J=8.8 Hz, 2.0 Hz), 8.42 (1H, d, J=2.0 Hz), 8.91 (1H, brt, J=5.6 Hz)

Example 125

(E)-2-(2-Carboxy-1-propenyl)-4-(3-chloro-4-methoxybenzyl)amino-6-chloroquinazoline

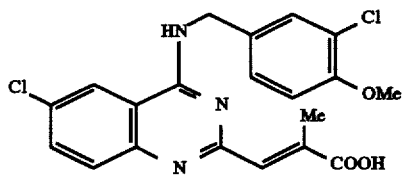

molecular formula; $C_{20}H_{17}N_3O_3Cl_2$
yield (%); quantitative
m.p. (°C.); 151~152
Mass; 462 (M−1+2Na)
NMR δ(DMSO-d₆); 2.33 (3H, d, J=1.2 Hz), 3.82 (3H, s), 4.72 (2H, d, J=5.6 Hz), 7.09 (1H, d, J=8.4 Hz), 7.20 (1H, d, J=1.2 Hz), 7.32 (1H, dd, J=8.4 Hz, 2.0 Hz), 7.44 (1H, d, J=2.0 Hz), 7.67 (1H, d, J=8.8 Hz), 7.74 (1H, dd, J=8.8 Hz, 2.4 Hz), 8.43 (1H, d, J=2.4 Hz), 8.87 (1H, brt, J=5.6 Hz)

Example 126

(Z)-2-(2-Carboxy-1-propenyl)-4-(3-chloro-4-methoxybenzyl)amino-6-chloroquinazoline

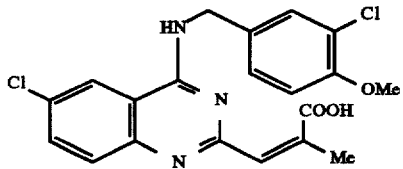

molecular formula; $C_{20}H_{17}N_3O_3Cl_2$
yield (%); quantitative m.p. (°C.); 207~208 (dec.)

Mass; 418 (M+1)⁺

NMR δ(DMSO-d₆); 2.10 (3H, d, J=1.4 Hz), 3.83 (3H, s), 4.72 (2H, d, J=5.2 Hz), 6.54 (1H, d, J=1.4 Hz), 7.10 (1H, d, J=8.4 Hz), 7.38 (1H, dd, J=8.4 Hz, 2.4 Hz), 7.49 (1H, d, J=2.4 Hz), 7.65 (1H, d, J=8.8 Hz), 7.81 (1H, dd, J=8.8 Hz, 2.4 Hz), 8.44 (1H, d, J=2.4 Hz), 8.95 (1H, brt, J=5.2 Hz)

Example 127

(E)-2-(2-Carboxy-1-propenyl)-4-(3,4-methylenedioxybenzyl)amino-6,7,8-trimethoxyquinazoline

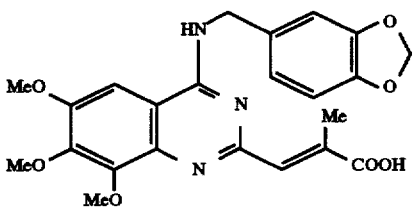

molecular formula; $C_{23}H_{23}N_3O_7$ yield (%); 91 m.p. (°C.); 200~201 (dec.)

Mass; 454 (M+1)⁺

NMR δ(DMSO-d₆); 2.38 (3H, s), 3.89 (3H, s), 3.92 (3H, s), 4.01 (3H, s), 4.71 (2H, d, J=5.6 Hz), 5.97 (2H, s), 6.85 (2H, s), 6.93 (1H, s), 7.37 (1H, s), 7.53 (1H, s), 8.53 (2H, brt, J=5.6 Hz), 12.55 (1H, brs)

Example 128

(Z)-2-(2-Carboxy-1-propenyl)-4-(3,4-methylenedioxybenzyl)amino-6,7,8-trimethoxyquinazoline

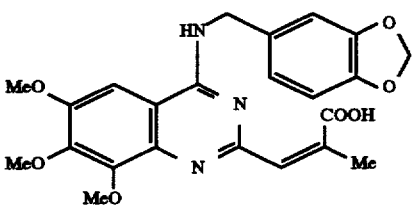

molecular formula; $C_{23}H_{23}N_3O_7$ yield (%); 90 m.p. (°C.); 237~238 (dec.)

Mass; 454 (M+1)⁺

NMR δ(DMSO-d₆); 2.11 (3H, d, J=1.2 Hz), 3.92 ((3H, s), 3.93 (3H, s), 3.94 (3H, s), 4.76 (2H, d, J=5.6 Hz), 5.98 (2H, s), 6.8~6.9 (3H, m), 6.97 (1H, s), 7.61 (1H, s), 9.08 (1H, brt, J=5.6 Hz)

Example 129

4-(α-Carboxy-3,4-methylenedioxybenzyl)amino-6-chloroquinazoline

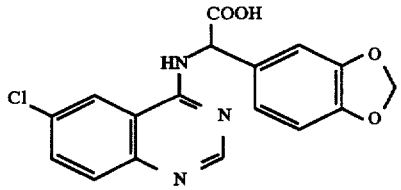

10 ml of ethanol, 5 ml of water and 20 mg of sodium hydroxide were added to 100 mg of 4-(α-ethoxycarbonyl-3,4-methylenedioxybenzyl)amino-6-chloroquinazoline. The obtained mixture was refluxed for 10 minutes and concentrated under a reduced pressure, followed by the addition of 20 ml of water. The obtained mixture was neutralized with 1N hydrochloric acid. The crystal thus precipitated was recovered by filtration. Thus, 45 mg of the title compound was obtained.

molecular formula; $C_{17}H_{12}N_3O_4Cl$ yield (%); 49 m.p. (°C.); 235–236

Mass m/e; 358 (M+1)

NMR δ(DMSO-$d_6$); 5.75 (1H, d, J=6.4 Hz), 6.01 (2H, s), 6.89 (1H, d, J=8.0 Hz), 7.00 (1H, d, J=8.0 Hz), 7.08 (1H, s), 7.70 (1H, d, J=8.8 Hz), 7.75 (1H, dd, J=1.6 Hz, 8.8 Hz), 8.49 (1H, s), 8.59 (1H, d, J=6.4 Hz), 8.70 (1H, d, J=1.6 Hz)

Examples 130 to 131

The following compounds were prepared in a similar manner to that of Example 129.

Example 130

4-[N-(Carboxymethyl)-(3,4-methylenedioxybenzyl)amino]-6,7,8-trimethoxyquinazoline

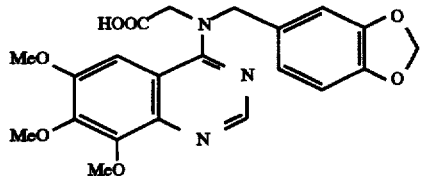

molecular formula; $C_{21}H_{21}N_3O_7$ yield (%); 90 m.p. (°C.); 134–136

Mass; 428 (M+H)$^+$

NMR δ(CDCl$_3$); 3.43 (3H, s), 4.06 (3H, s), 4.17 (3H, s), 4.62 (2H, s), 5.16 (2H, s), 6.03 (2H, s), 6.87 (1H, s), 6.91 (2H, s), 7.06 (1H, s), 8.87 (1H, s)

Example 131

4-(3,4-Methylenedioxybenzyl)amino-6-carboxyquinazoline

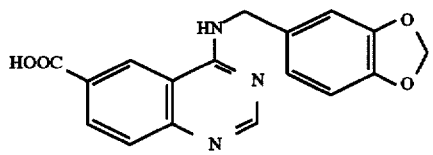

molecular formula; $C_{17}H_{13}N_3O_4$ yield (%); 98 m.p. (°C.); 247–248 (dec.)

Mass; 324 (M+H)$^+$

NMR δ(DMSO-$d_6$); 4.86 (2H, d, J=5.6 Hz), 5.99 (2H, s), 6.89 (1H, d, J=8.0 Hz), 6.92 (1H, d, J=8.0 Hz), 7.02 (1H, s), 7.92 (1H, d, J=8.8 Hz), 8.46 (1H, d, J=8.8 Hz), 8.96 (1H, s), 9.20 (1H, s), 10.88 (1H, brs)

Example 132

4-(α-Carbamoyl-3,4-methylenedioxybenzyl)amino-6-chloroquinazoline

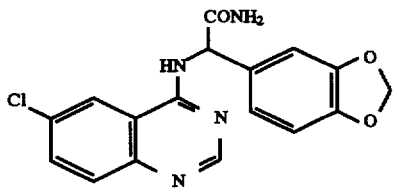

20 ml of a 10% solution of ammonia in ethanol was added to 200 mg of 4-(α-ethoxycarbonyl-3,4-methylenedioxybenzyl)amino-6-chloroquinazoline. The obtained mixture was stirred at room temperature for 3 days. The crystal thus precipitated was recovered by filtration. Thus, 60 mg of the title compound was obtained.

molecular formula; $C_{17}H_{13}N_4O_3Cl$ yield (%); 32 m.p. (°C.); 230–231

Mass m/e; 357 (M+1)

NMR δ(CDCl$_3$+DMSO-$d_6$); 5.96 (3H, m), 6.42 (1H, brs), 6.79 (1H, d, J=8.0 Hz), 7.09 (1H, dd, J=8.0 Hz, 1.6 Hz), 7.14 (1H, d, J=1.6 Hz), 7.15 (1H, brs), 7.67 (1H, dd, J=8.8 Hz, 2.0 Hz), 7.75 (1H, d, J=8.8 Hz), 8.28 (1H, d, J=2.0 Hz), 8.57 (1H, s)

Examples 133 and 134

The following compounds were prepared in a similar manner to that of Example 132.

Example 133

4-(3,4-Methylenedioxybenzyl)amino-6-carbamoylquinazoline

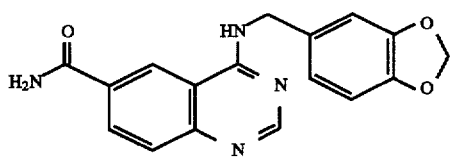

molecular formula; C$_{17}$H$_{14}$N$_4$O$_3$
Mass; 323 (M+H)$^+$
NMR δ(DMSO-d$_6$); 4.68 (2H, d, J=6.0 Hz), 5.97 (2H, s), 6.85 (1H, d, J=8.0 Hz), 6.88 (1H, d, J=8.0 Hz), 6.97 (1H, s), 7.55 (1H, brs), 7.70 (1H, d, J=8.4 Hz), 7.97 (1H, brs), 8.18 (1H, dd, J=8.4 Hz, 1.6 Hz), 8.50 (1H, s), 8.84 (1H, d, J=1.6 Hz), 8.92 (1H, brt, J=6.0 Hz)

Example 134

2-Carbamoyl-4-(3,4-methylenedioxybenzyl)amino-6-chloroquinazoline

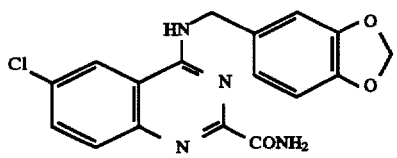

molecular formula; C$_{17}$H$_{13}$ClN$_4$O$_3$
yield (%); 71
m.p. (°C.); 245–247 (dec.)
Mass; 357 (M+1)
NMR δ(DMSO-d$_6$); 4.77 (2H, d, J=5.2 Hz), 5.97 (2H, s), 6.85 (1H, d, J=8.0 Hz), 6.92 (1H, d, J=8.0 Hz), 7.04 (1H, s), 7.66 (1H, brs), 7.83 (2H, m), 8.07 (1H, brs), 8.49 (1H, s), 8.99 (1H, brs)

Example 135

4-(α-Hydroxymethyl-3,4-methylenedioxybenzyl)amino-6-chloroquinazoline

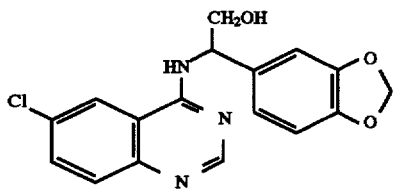

10 ml of ethanol and 197 mg of sodium borohydride were added to 200 mg of 4-(α-ethoxycarbonyl-3,4-methylenedioxybenzyl)amino- 6-chloroquinazoline. The obtained mixture was refluxed for 30 minutes, followed by the addition of 5 ml of water. The obtained mixture was concentrated under a reduced pressure, followed by the addition of 10 ml of water. The crystal thus precipitated was recovered by filtration. Thus, 30 mg of the title compound was obtained.

molecular formula; C$_{17}$H$_{14}$N$_3$O$_3$Cl
yield (%); 17
m.p. (°C.); 204–205
Mass m/e; 344 (M+1)
NMR δ(CDCl$_3$(+DMSO-d$_6$)); 3.95 (2H, m), 5.43 (1H, q, J=4.4 Hz), 5.92 (1H, d, J=1.6 Hz), 5.93 (1H, d, J=1.6 Hz), 6.76 (1H, d, J=8.0 Hz), 6.90 (1H, dd, J=8.0 Hz, 1.6 Hz), 6.95 (1H, d, J=1.6 Hz), 7.60 (1H, brs), 7.65 (1H, dd, J=8.4 Hz, 2.4 Hz), 7.74 (1H, d, J=8.4 Hz), 8.31 (1H, d, J=2.4 Hz), 8.53 (1H, s)

Example 136

4-[(3,4-Methylenedioxybenzyl)amino-6-hydroxymethylquinazoline

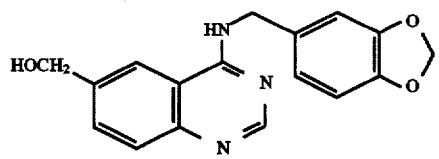

The title compound was prepared in a similar manner to that of Example 135.

molecular formula; C$_{17}$H$_{15}$N$_3$O$_3$
yield (%); 34
m.p. (°C.); 176–177
Mass m/e; 310 (M+1)
NMR δ(DMSO-d$_6$); 4.62 (2H, d, J=5.6 Hz), 4.65 (2H, d, J=5.6 Hz), 5.36 (1H, t, J=5.6 Hz), 5.94 (2H, s), 6.82 (1H, s), 6.82 (1H, s), 6.92 (1H, s), 7.63 (1H, d, J=8.4 Hz), 7.70 (1H, d, J=8.4 Hz), 8.20 (1H, s), 8.41 (1H, s), 8.74 (1H, t, J=5.6 Hz)

Example 137

4-(3,4-Methylenedioxybenzyl)amino-6-methylsulfinylquinazoline

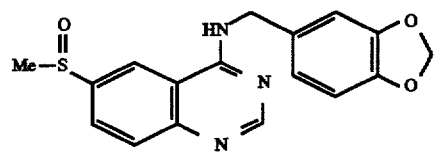

A solution of 1.20 g (6.95 mmol) of m-chloroperbenzoic acid in 30 ml of chloroform was dropped into a solution of 1.80 g (5.53 mmol) of 4-(3,4-methylenedioxybenzyl)amino-6-methylthioquinazoline in 100 ml of chloroform under cooling with ice and stirring. The obtained mixture was stirred under cooling with ice for several hours, washed with a saturated aqueous solution of sodium hydrogencarbonate, dried over anhydrous magnesium sulfate and filtered. The filtrate was purified by silica gel column chromatography (ethyl acetate/acetone) and recrystallized from chloroform/n-hexane to give 1.51 g of the title compound as a pale-yellow crystal.

molecular formula; C$_{17}$H$_{15}$N$_3$O$_3$S
yield (%); 80
m.p. (°C.); 154–155
Mass; 342 (M+H)$^+$
NMR δ(CDCl$_3$); 2.75 (3H, s), 4.80 (2H, d, J=5.2 Hz), 5.96 (2H, s), 6.80 (1H, d, J=8.0 Hz), 6.89 (1H, d, J=8.0 Hz), 6.91

(1H, s), 7.06 (1H, brs), 7.64 (1H, d, J=8.8 Hz), 7.98 (1H, d, J=8.8 Hz), 8.43 (1H, s), 8.74 (1H, s)

Example 138

4-(3,4-Methylenedioxybenzyl)amino-6-methysulfonylquinazoline

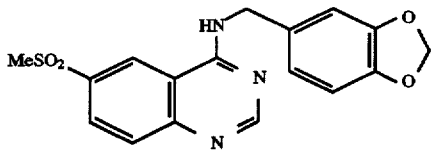

A solution of 0.65 g (3.8 mmol) of m-chloroperbenzoic acid in 20 ml of chloroform was dropped into a solution of 1.00 g (2.93 mmol) of the 4-(3,4-methylenedioxybenzyl)amino-6-methylsulfinylquinazoline prepared in Example 137 under stirring at room temperature. The obtained mixture was stirred at room temperature for several hours, washed with a saturated aqueous solution of sodium hydrogencarbonate, dried over anhydrous magnesium sulfate and filtered. The filtrate was purified by silica gel column chromatography (ethyl acetate) and recrystallized from chloroform/n-hexane to give 0.85 g of the title compound as a yellow crystal.

molecular formula; $C_{17}H_{15}N_3O_4S$ yield (%); 81 m.p. (°C.); 192–193

Mass; 358 $(M+H)^+$

NMR $\delta(CDCl_3)$; 3.13 (3H, s), 4.80 (2H, d, J=5.2 Hz), 5.95 (2H, s), 6.79 (1H, d, J=8.0 Hz), 6.91 (1H, d, J=8.0 Hz), 6.95 (1H, s), 8.05 (1H, d, J=8.8 Hz), 8.17 (1H, d, J=8.8 Hz), 8.72 (1H, s), 8.81 (1H, brs), 8.98 (1H, s)

Example 139

2-Hydroxymethyl-4-(3,4-methylenedioxybenzyl)amino-6-methoxyquinazoline

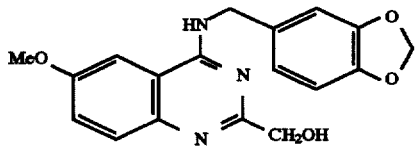

1.5 g of 10% palladium/carbon powder was added to a solution of 1.26 g (2.93 mmol) of 2-benzoyloxymethyl-4-(3,4-methylenedioxybenzyl)amino-6-methoxyquinazoline in an ethyl acetate/ethanol (20 ml-20 ml) mixture. The obtained mixture was stirred at room temperature in a stream of hydrogen for 24 hours and filtered through Celite. The filter cake was washed with hot ethyl acetate/ethanol. The filtrate and the washings were distilled under a reduced pressure to remove the solvent. Thus 0.89 g of the title compound was obtained as a pale-yellow crystal.

molecular formula; $C_{18}H_{17}N_3O_4$ yield (%); 89 m.p. (°C.); 216–218

Mass; 340 $(M+H)^+$

NMR $\delta(CDCl_3)$; 3.91 (3H, s), 4.15 (1H, brs), 4.68 (2H, brs), 4.77 (2H, d, J=5.6 Hz), 5.95 (2H, s), 6.79 (1H, d, 7.6 Hz), 6.85 (1H, brs), 6.88 (1H, dd, J=7.6 Hz, 1.6 Hz), 6.92 (1H, d, J=1.6 Hz), 7.21 (1H, d, J=2.8 Hz), 7.37 (1H, dd, J=9.2 Hz, 2.8 Hz), 7.72 (1H, d, J=9.2 Hz)

Example 140

2-Hydroxy-4-(3,4-methylenedioxybenzyl)amino-6-methoxyquinazoline

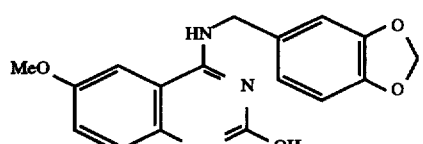

The title compound was prepared in a similar manner to that of Example 139.

molecular formula; $C_{17}H_{15}N_3O_4$ yield (%); 16 m.p. (°C.); 215–217 (dec.)

Mass; 326 $(M+H)^+$

NMR $\delta(DMSO-d_6)$; 3.79 (3H, s), 4.62 (2H, d, J=5.6 Hz), 5.98 (2H, s), 6.84–6.87 (2H, m), 6.94 (1H, s), 7.09 (1H, d, J=8.8 Hz), 7.22 (1H, dd, J=8.8 Hz, 2.8 Hz), 7.60 (1H, d, J=2.8 Hz), 8.65 (1H, brt, J=5.6 Hz), 10.55 (1H, s)

Example 141

2-Formyl-4-(3,4-methylenedioxybenzyl)amino-6-methoxyquinazoline

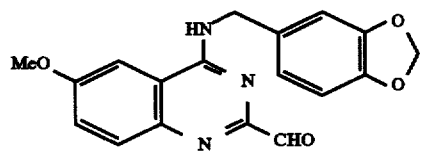

A solution of 1.5 ml of dimethyl sulfoxide in 5 ml of methylene chloride was dropped into a solution of 1.0 ml (11 mmol) of oxalyl chloride in 10 ml of methylene chloride under stirring at −78° C. The obtained mixture was stirred at −78° C. for 15 minutes, followed by the dropwise addition of a solution of 0.74 g (2.2 mmol) of 2-hydroxymethyl-4-(3,4-methylenedioxybenzyl)amino-6-methoxyquinazoline in 7 ml of dimethyl sulfoxide. After the mixture thus obtained had been stirred at −78° C. for 20 minutes, 5 ml of triethylamine was dropped into the resulting mixture. The mixture thus prepared was stirred for 30 minutes, while raising the temperature to room temperature. Water was added to the reaction mixture and the resulting mixture was extracted with chloroform. The organic layer was dried over anhydrous magnesium sulfate and filtered. The filtrate was distilled under a reduced pressure to remove the solvent. Thus, 0.74 g of the title compound was obtained as a crude brown oil.

molecular formula; $C_{18}H_{15}N_3O_4$ yield (%); quantitative

NMR $\delta(CDCl_3)$; 3.93 (3H, s), 4.86 (2H, d, J=5.6 Hz), 5.95 (2H, s), 6.28 (1H, brs), 6.78 (1H, d, J=8.0 Hz), 6.89 (1H, dd, J=8.0 Hz, 1.6 Hz), 6.92 (1H, d, J=1.6 Hz), 7.09 (1H, d, J=2.8 Hz), 7.47 (1H, dd, J=9.2 Hz, 2.8 Hz), 7.97 (1H, d, J=9.2 Hz), 10.02 (1H, s)

Example 142

2-Carboxy-4-(3,4-methylenedioxybenzyl)amino-6-methoxyquinazoline

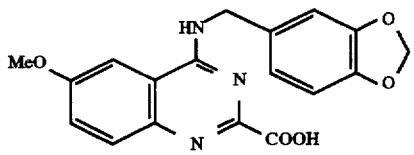

1.00 g of silver (I) oxide and 15 ml of a 1N aqueous solution of sodium hydroxide were added to a solution of 0.59 g (1.8 mmol) of the 2-formyl-4-(3,4-methylenedioxybenzyl)amino-6-methoxyquinazoline prepared in Example 141 in 20 ml of 1,4-dioxane. The obtained mixture was stirred at 60° C. After 30 minutes, the reaction mixture was filtered through Celite and the filter cake was washed with a small amount of dioxane and water. The filtrate and washings were neutralized with 1N hydrochloric acid and extracted with chloroform/ethanol. The organic layer was dried over anhydrous magnesium sulfate and filtered. The filtrate was distilled under a reduced pressure to remove the solvent. The crystal thus formed was recovered by filtration and washed with chloroform to give 0.34 g of the title compound as a pale-yellow crystal.

molecular formula; $C_{18}H_{15}N_3O_5$ yield (%); 55 m.p. (°C.); 190~191 (dec.)

Mass; 354 (M+H)$^+$

NMR δ(DMSO-d$_6$); 3.90 (3H, s), 4.77 (2H, d, J=5.6 Hz), 5.97 (2H, s), 6.86 (1H, d, J=8.0 Hz), 6.92 (1H, d, J=8.0 Hz), 7.05 (1H, s), 7.49 (1H, dd, J=9.2 Hz, 2.8 Hz), 7.76 (1H, d, J=2.8 Hz), 7.79 (1H, d, J=9.2 Hz), 8.91 (1H, brt, J=5.6 Hz)

Examples 143 to 145

The following compounds were prepared in a similar manner to that of Example 141 or 142.

Example 143

4-(3-Formylbenzyl)amino-6,7,8-trimethoxyquinazoline

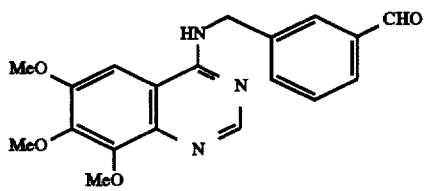

molecular formula; $C_{19}H_{19}N_3O_4$ yield (%); quantitative m.p. (°C.); oily substance NMR δ(CDCl$_3$); 3.96 (3H, s), 4.04 (3H, s), 4.13 (3H, s), 4.97 (2H, d, J=5.6 Hz), 5.97 (1H, brt, J=5.6 Hz), 6.76 (1H, s), 7.53 (1H, t, J=7.6 Hz), 7.70 (1H, d, J=7.6 Hz), 7.81 (1H, d, J=7.6 Hz), 7.91 (1H, s), 8.64 (1H, s), 10.00 (1H, s)

Example 144

4-(3-Carboxybenzyl)amino-6,7,8-trimethoxyquinazoline

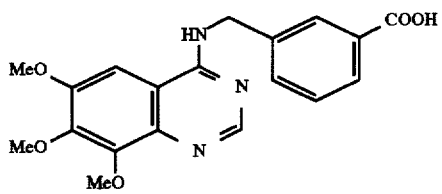

molecular formula; $C_{19}H_{19}N_3O_5$ yield (%); 45 m.p. (°C.); 245~246 (dec.)

Mass; 370 (M+H)$^+$

NMR δ(DMSO-d$_6$); 3.89 (3H, s), 3.93 (3H, s), 3.98 (3H, s), 4.86 (2H, d, J=5.6 Hz), 7.46 (1H, d, J=7.6 Hz), 7.56 (1H, s), 7.62 (1H, d, J=7.6 Hz), 7.83 (1H, d, J=7.6 Hz), 7.95 (1H, s), 8.39 (1H, s), 8.83 (1H, brs)

Example 145

4-(4-Acetylbenzyl)amino-6-methoxyquinazoline

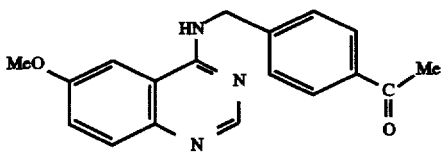

molecular formula; $C_{18}H_{17}N_3O_2$ yield (%); 41 m.p. (°C.); 204~206

Mass; 308 (M+H)$^+$

NMR δ(CDCl$_3$); 2.60 (3H, s), 3.91 (3H, s), 4.97 (2H, d, J=5.6 Hz), 5.96 (1H, brs), 6.98 (1H, s), 7.42 (1H, d, J=9.2 Hz), 7.50 (2H, d, J=8.0 Hz), 7.82 (1H, d, J=9.2 Hz), 7.94 (2H, d, J=8.0 Hz), 8.61 (11H, s)

Example 146

2-Hydroxyiminomethyl-4-(3,4-methylenedioxybenzyl)amino-6-chloroquinazoline

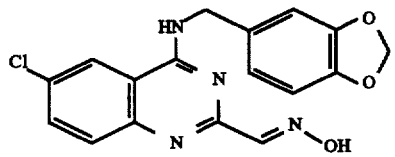

0.60 g of hydroxylamine hydrochloride and 3.0 ml of a 1N aqueous solution of sodium hydroxide were added to a solution of 1.00 g (2.93 mmol) of 2-formyl-4-(3,4-methylenedioxybenzyl)amino-6-chloroquinazoline in 30 ml of ethanol. The obtained mixture was stirred at 60° C. for 30 minutes and cooled by allowing to stand. The crystal thus precipitated was recovered by filtration, washed with ethanol and n-hexane and air-dried to give 1.00 g of the title compound as a white crystal.

molecular formula; $C_{17}H_{13}N_4O_3Cl$ yield (%); 96 m.p. (°C.); 245~246 (dec.)

Mass; 357 (M+1)

NMR δ(DMSO-d₆); 4.69 (2H, d, J=6.0 Hz), 5.96 (2H, s), 6.84 (1H, d, J=7.6 Hz), 6.91 (1H, d, J=7.6 Hz, 1.6 Hz), 7.05 (1H, d, J=1.6 Hz), 7.72 (1H, d, J=8.8 Hz), 7.78 (1H, dd, J=8.8 Hz, 2.0 Hz), 7.96 (1H, s), 8.45 (1H, d, J=2.0 Hz), 8.91 (1H, brt, J=6.0 Hz), 11.83 (1H, s)

Examples 147 to 149

The following compounds were prepared in a similar manner to that of Example 146.

Example 147

2-Hydroxyiminomethyl-4-(3,4-methylenedioxybenzyl)amino-6-methoxyquinazoline

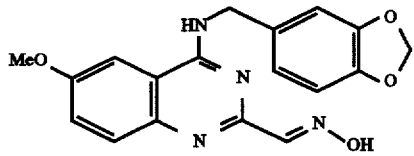

molecular formula; C₁₈H₁₆N₄O₄ yield (%); 46 m.p. (°C.); 229~230 (dec.)

Mass; 353 (M+H)⁺

NMR δ(DMSO-d₆); 3.88 (3H, s), 4.72 (2H, d, J=5.6 Hz), 5.96 (2H, s), 6.85 (1H, d, J=8.0 Hz), 6.91 (1H, d, J=8.0 Hz), 7.05 (1H, s), 7.40 (1H, dd, J=9.2 Hz, 2.8 Hz), 7.66 (1H, d, J=9.2 Hz), 7.69 (1H, d, J=2.8 Hz), 7.94 (1H, s), 8.62 (1H, brt, J=5.6 Hz), 11.63 (1H, s)

Example 148

4-(3-Hydroxyiminomethylbenzyl)amino-6,7,8-trimethoxyquinazoline

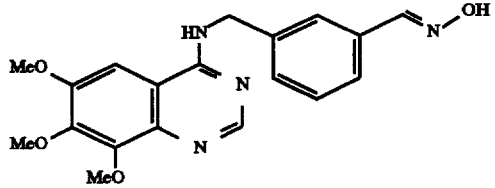

molecular formula; C₁₉H₂₀N₄O₄ yield (%); 56 m.p. (°C.); 231~232 (dec.)

Mass; 369 (M+H)⁺

NMR δ(DMSO-d₆); 3.88 (3H, s), 3.91 (3H, s), 3.98 (3H, s), 4.80 (2H, d, J=6.0 Hz), 7.3~7.5 (3H, m), 7.52 (1H, s), 7.60 (1H, s), 8.11 (1H, s), 8.35 (1H, s), 8.60 (1H, brs), 11.17 (1H, s)

Example 149

4-[4-(1-Hydroxyiminoethyl)benzyl]amino-6-methoxyquinazoline

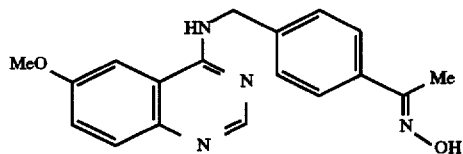

molecular formula; C₁₈H₁₈N₄O₂ yield (%); quantitative m.p. (°C.); 245~246 (dec.)

Mass; 323 (M+H)⁺

NMR δ(DMSO-d₆); 2.13 (3H, s), 3.95 (3H, s), 4.97 (2H, d, J=5.6 Hz), 7.44 (2H, d, J=8.4 Hz), 7.63 (2H, d, J=8.4 Hz), 7.68 (1H, dd, J=9.2 Hz, 2.8 Hz), 7.83 (1H, d, J=9.2Hz), 8.14 (1H, d, J=2.8Hz), 8.84 (1H, s), 10.75 (1H, brs), 11.18 (1H, s)

Example 150

2-Ethoxycarbonylmethoxyiminomethyl-4-(3,4-methylenedioxybenzyl)amino-6-chloroquinazoline

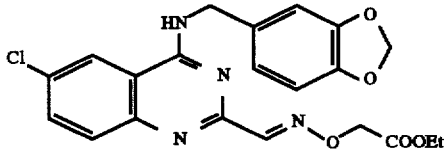

0.10 g (2.5 mmol) of sodium hydride was added to a suspension of 0.50 g (1.4 mmol) of 2-hydroxyiminomethyl-4-(3,4-methylenedioxybenzyl)amino-6-chloroquinazoline in 25 ml of dimethylformamide. The obtained mixture was stirred. After 30 minutes, 25 ml (2.3 mmol) of ethyl bromoacetate was dropped into the mixture. The mixture thus obtained was stirred at room temperature for several hours, followed by the addition of water. The obtained mixture was extracted with ethyl acetate. The organic layer was dried over anhydrous magnesium sulfate and filtered. The filtrate was distilled under a reducer pressure to remove the solvent. The residue was purified by silica gel column chromatography (ethyl acetate/n-hexane) to give 0.52 g of the title compound as a pale-yellow crystal.

molecular formula; C₂₁H₁₉N₄O₅Cl yield (%); 84 m.p. (°C.); 154~155

Mass; 443 (M+1)

NMR δ(CDCl₃); 1.29 (3H, t, J=7.2 Hz), 4.23 (2H, q, J=7.2 Hz), 4.74 (2H, d, J=5.2 Hz), 4.88 (2H, s), 5.96 (2H, s), 6.03 (1H, brt, J=5.2 Hz), 6.78 (1H, d, J=7.6 Hz), 6.87 (1H, d, J=7.6 Hz, 1.6 Hz), 6.93 (1H, d, J=1.6 Hz), 7.65 (1H, dd, J=8.8 Hz, 2.0 Hz), 7.70 (1H, d, J=2.0 Hz), 7.84 (1H, d, J=8.8 Hz), 8.25 (1H, s)

Example 151

4-(3-Amino-4-chlorobenzyl)amino-6-chloroquinazoline

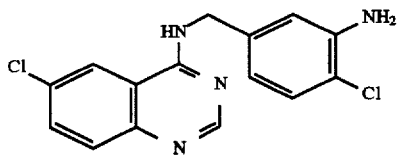

A mixture comprising 1.00 g (2.86 mmol) of 4-(4-chloro-3-nitrobenzyl)amino-6-chloroquinazoline, 0.85 g of powdered iron, 10 ml of acetic acid and 50 ml of ethanol was heated under reflux for several hours and distilled under a reduced pressure to remove the solvent. The residue was purified by silica gel column chromatography (ethyl acetate/n-hexane) to give 0.91 g of the title compound as a pale-yellow crystal.

molecular formula; $C_{15}H_{12}N_4Cl_2$ yield (%); quantitative m.p. (°C.); 226–229 (dec.)

Mass; 319 $(M+H)^{30}$

NMR $\delta(CDCl_3)$; 4.19 (2H, brs), 4.73 (2H, d, J=6.0 Hz), 6.71 (1H, dd, J=8.0 Hz, 2.0 Hz), 6.83 (1H, d, J=2.0 Hz), 7.18 (1H, d, J=8.0 Hz), 7.64 (1H, dd, J=8.8 Hz, 2.0 Hz), 7.72 (1H, brs), 7.74 (1H, d, J=8.8 Hz), 8.19 (1H, d, J=2.0 Hz), 8.60 (1H, s)

Example 152

4-(4-Chloro-3-formamidobenzyl)amino-6-chloroquinazoline

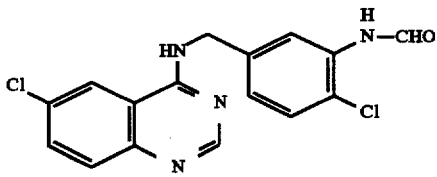

0.90 g (2.82 mmol) of the 4-(3-amino-4-chlorobenzyl)amino-6-chloroquinazoline prepared in Example 151 was dissolved in 15 ml of formic acid, followed by the addition of 1 ml of acetic anhydride. The obtained mixture was stirred at room temperature for several hours and distilled under a reduced pressure to remove the solvent. The residue was purified by silica gel column chromatography (ethyl acetate) and recrystallized from ethyl acetate to give 0.64 g of the title compound as a pale yellow crystal.

molecular formula; $C_{16}H_{12}N_4OCl_2$ yield (%); 65 m.p. (°C.); 229–230

Mass; 347 $(M+H)^+$

NMR $\delta(DMSO-d_6)$; 4.74 (2H, d, J=5.6 Hz), 7.15 (1H, dd, J=8.4 Hz, 2.0 Hz), 7.43 (1H, d, J=8.4 Hz), 7.72 (1H, d, J=8.8 Hz), 7.80 (1H, dd, J=8.8 Hz, 2.0 Hz), 8.16 (1H, d, J=2.0 Hz), 8.32 (1H, d, J=2.0 Hz), 8.45 (1H, s), 8.46 (1H, s), 8.95 (1H, brs), 9.83 (1H, brs)

Example 153

4-(3-Formamido-4-methoxybenzyl)amino-6-chloroquinazoline

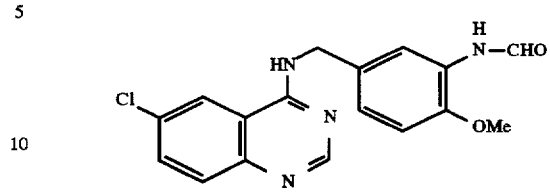

1 g of powdered iron was added in portions to a mixture comprising 1 g of 4-(3-nitro-4-methoxybenzyl)amino-6-chloroguinazoline, 4 ml of acetic acid, 4 ml of water and 40 ml of ethanol, while heating the mixture under mild reflux. The obtained mixture was heated under reflux for 2 hours and filtered to remove insolubles. Concentrated hydrochloric acid was added in portions to the brown filtrate obtained above to give a yellow transparent solution. This solution was cooled with ice to precipitate crystals. The crystals were recovered by filtration and dried to give 1.1 g of 4-(3-amino-4-methoxybenzyl)amino-6-chloroquinazoline hydrochloride. This hydrochloride was dissolved in ethanol/water and the obtained solution was made alkaline by adding a 15% aqueous solution of sodium hydroxide in portions. Water was added to the resulting alkaline solution in portions to precipitate crystals. The crystals were recovered by filtration, washed with water and dried to give 770 mg of 4-(3-amino-4-methoxybenzyl)amine-6-chloroquinazoline (an aniline derivative). Separately, 1 ml of formic acid was dropped into 2 ml of acetic anhydride under cooling with ice and the obtained mixture was heated at 50° C. for 15 minutes and immediately cooled with ice, followed by the addition of the above aniline derivative as such (in a crystalline state). The obtained mixture was reacted at that temperature for one hour and at room temperature for one hour, followed by the addition of water. The crystals thus formed were recovered by filtration, washed with water and dried to give 130 mg of the title compound.

molecular formula; $C_{17}H_{15}N_4O_2Cl$ (342.786)

yield (%); 60 m.p. (°C.); 208–209

Mass; 343 $(MH)^+$

NMR $\delta(DMSO-d_6)$; 3.82 (3H, s), 4.68 (2H, d, J=5.7 Hz), 6.98 (1H, d, J=8.2 Hz), 7.09 (1H, dd, J=2.0 Hz, 8.2 Hz), 7.71 (1H, d, J=9.0 Hz), 7.79 (1H, dd, J=2.4 Hz, 9.0 Hz), 8.23 (1H, d, J=2.0 Hz), 8.27 (1H, d, J=2.4 Hz), 8.47 (2H, s), 8.88 (1H, t, J=5.7 Hz), 9.62 (1H, brs)

Example 154

4-(3-Methanesulfonylamino-4-chlorobenzyl)amino-6-chloroquinazoline

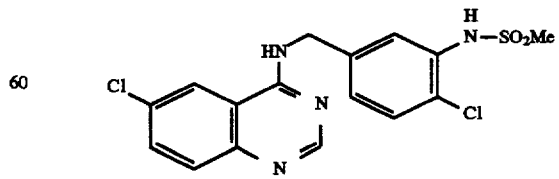

75 µl of methanesulfonyl chloride was added to a mixture comprising 100 mg of 4-(3-amino-4-chlorobenzyl)amino-6- chloroquinazoline and 3 ml of pyridine. The obtained mixture was stirred at room temperature for 1.5 hours. 20 ml of water was added in portions to the reaction mixture to precipitate crystals. The crystals were recovered by filtration, washed with water and dried to give 109 mg of the title compound.

molecular formula; $C_{16}H_{14}N_4O_2SCl_2$ (397.284)

yield (%); 88 m.p. (°C.); 209~210

Mass; 397 (MH)⁺

NMR δ(DMSO-d₆); 3.01 (3H, s), 4.75 (2H, d, J=5.7 Hz), 7.23 (1H, dd, J=2.2 Hz, 8.2 Hz), 7.45 (1H, d, J=8.2 Hz), 7.46 (1H, d, J=2.2 Hz), 7.73 (1H, d, J=9.0 Hz), 7.81 (1H, dd, J=2.4 Hz, 9.0 Hz), 8.45 (1H, d, J=2.4 Hz), 8.47 (1H, s), 8.97 (1H, brt, J=5.7 Hz), 9.4 (1H, brs)

Examples 155 to 161

The following compounds were prepared in a similar manner to those of Examples 151 to 154.

Example 155

4-(3-Amino-4-hydroxybenzyl)amino-6,7,8-trimethoxyquinazoline

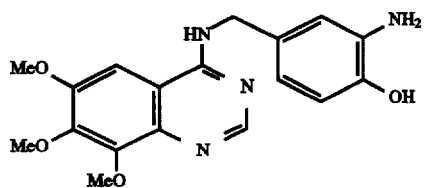

molecular formula; $C_{18}H_{20}N_4O_4$ yield (%); quantitative m.p. (°C.); amorphous Mass; 357 (M+H)⁺

NMR δ(CDCl₃); 3.68 (1H, brs), 3.82 (1H, brs), 3.95 (3H, s), 4.02 (3H, s), 4.11 (3H, s), 4.68 (2H, d, J=4.4 Hz), 6.61 (1H, brs), 6.64 (1H, d, J=7.6 Hz), 6.77 (1H, d, J=7.6 Hz), 7.01 (1H, s), 8.50 (1H, brs), 8.60 (1H, s)

Example 156

4-(3-Ethoxycarbonylamino-4-ethoxycarbonyloxybenzyl)amino-6,7,8-trimethoxyquinazoline

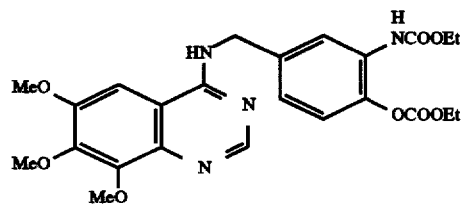

molecular formula; $C_{24}H_{28}N_4O_8$ yield (%); 54 m.p. (°C.); 229–230 (dec.)

Mass; 501 (M+H)⁺

NMR δ(CDCl₃); 1.31 (3H, t, J=7.2 Hz), 1.40 (3H, t, J=7.2 Hz), 3.95 (3H, s), 4.03 (3H, s), 4.11 (3H, s), 4.21 (2H, q, J=7.2 Hz), 4.35 (2H, q, J=7.2 Hz), 4.81 (1H, d, J=5.2 Hz), 5.80 (1H, brt, J=5.2 Hz), 6.74 (1H, s), 6.87 (1H, s), 7.13 (1H, d, J=8.0 Hz), 7.20 (1H, d, J=8.0 Hz), 8.18 (1H, brs), 8.64 (1H, s)

Example 157

4-[Benzoxazol-2(3H)-on-5-ylmethyl]amino-6,7,8-trimethoxyquinazoline

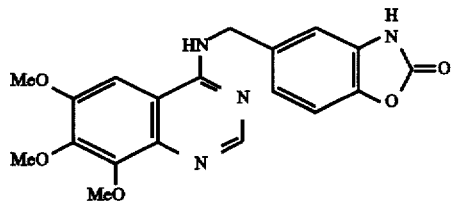

molecular formula; $C_{19}H_{18}N_4O_5$ yield (%); 62 m.p. (°C.); 232~233 (dec.)

Mass; 383 (M+H)⁺

NMR δ(DMSO-d₆); 3.87 (3H, s), 3.90 (3H, s), 3.96 (3H, s), 4.78 (2H, d, J=5.6 Hz), 7.06 (1H, s), 7.07 (1H, d, J=8.0 Hz), 7.20 (1H, d, J=8.0 Hz), 7.50 (1H, s), 8.35 (1H, s), 8.58 (1H, brt, J=5.6 Hz), 11.48 (1H, brs)

Example 158

4-(4-Hydroxy-3-methanesulfonylaminobenzyl)amino-6,7,8-trimethoxyquinazoline

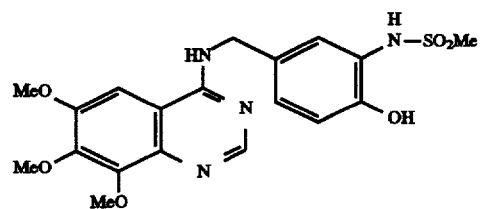

molecular formula; $C_{19}H_{22}N_4O_6S$ yield (%); 56 m.p. (°C.); 215~216 (dec.)

Mass; 435 (M+H)⁺

NMR δ(DMSO-d₆); 2.91 (3H, s), 3.86 (3H, s), 3.89 (3H, s), 3.96 (3H, s), 4.65 (2H, d, J=5.6 Hz), 6.83 (1H, d, J=8.0 Hz), 7.04 (1H, dd, J=8.0 Hz, 2.0 Hz), 7.22 (1H, d, J=2.0 Hz), 7.50 (1H, s), 8.34 (1H, s), 8.52 (1H, brt, J=5.6 Hz), 8.66 (1H, brs), 6.75 (1H, brs)

Example 159

4-(3-Amino-4-chlorobenzyl)amino-6,7,8-trimethoxyquinazoline

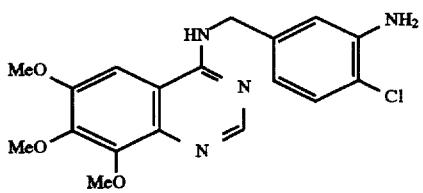

molecular formula; $C_{18}H_{19}N_4O_3Cl$
yield (%); 86
m.p. (°C.); 181~182 (dec.)
Mass; 375 (M+H)$^+$
NMR δ(CDCl$_3$); 3.95 (3H, s), 4.03 (3H, s), 4.08 (2H, brs), 4.13 (3H, s), 4.75 (2H, d, J=5.6 Hz), 5.65 (1H, brs), 6.67 (1H, s), 6.72 (1H, dd, J=8.0 Hz, 2.0 Hz), 6.81 (1H, d, J=2.0 Hz), 7.23 (1H, d, J=8.0 Hz), 8.65 (1H, s)

Example 160

4-(4-Chloro-3-formamidobenzyl)amino-6,7,8-trimethoxyquinazoline

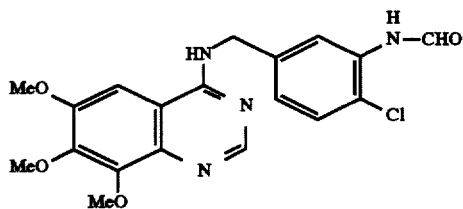

molecular formula; $C_{19}H_{19}N_4O_4Cl$
yield (%); 68
m.p. (°C.); 202~204 (dec.)
Mass; 403 (M+H)$^+$
NMR δ(DMSO-d$_6$); 3.88 (3H, s), 3.91 (3H, s), 3.98 (3H, s), 4.75 (2H, d, J=5.6 Hz), 7.14 (1H, dd, J=8.4 Hz, 2.0 Hz), 7.42 (2H, d, J=8.4 Hz), 7.52 (1H, s), 8.15 (1H, d, J=2.0 Hz), 8.32 (1H, s), 8.35 (1H, s), 8.67 (1H, brs), 9.83 (1H, brs)

Example 161

4-(3-Acetamido-4-chlorobenzyl)amino-6-chloroquinazoline

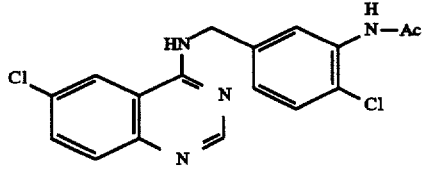

molecular formula; $C_{17}H_{14}N_4OCl_2$ (361.232)
yield (%); 77
m.p. (°C.); 267~268
Mass; 361 (MH)$^+$
NMR δ(DMSO-d$_6$); 2.06 (3H, s), 4.74 (2H, d, J=5.7 Hz), 7.17 (1H, dd, J=2.0 Hz, 8.2 Hz), 7.42 (1H, d, J=8.2 Hz), 7.69 (1H, brs), 7.72 (1H, d, J=9.0 Hz), 7.81 (1H, dd, J=2.4 Hz, 9.0 Hz), 8.45 (1H, d, J=2.4 Hz), 8.46 (1H, s), 8.96 (1H, brt, J=5.7 Hz), 9.48 (1H, brs)

Example 162

4-(3,4-Dihydroxybenzyl)amino-6,7,8-trimethoxyquinazoline hydrochloride

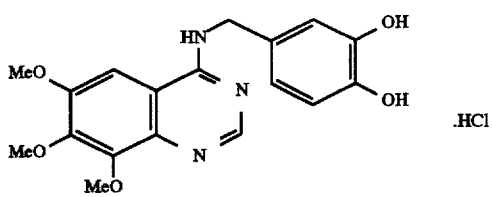

30 ml of a 1.0M solution of boron trichloride in methylene chloride was dropped into a solution of 2.00 g (5.41 mmol) of 4-(3,4-methylenedioxybenzyl)amino-6,7,8-trimethoxyquinazoline in 150 ml of chloroform under stirring at room temperature. The obtained mixture was stirred at room temperature for 2 days, followed by the addition of methanol and the obtained mixture was distilled under a reduced pressure to remove the solvent. This procedure was repeated thrice and the obtained residue was purified by silica gel column chromatography (chloroform/n-hexane). Hydrochloric acid/ethanol was added to the eluate and the obtained mixture was distilled under a reduced pressure to remove the solvent, followed by the addition of ethanol. The crystals thus formed were recovered by filtration. Thus, 0.59 g of the title compound was obtained as a colorless needle.

molecular formula; $C_{18}H_{19}N_3O_5·HCl$
yield (%); 28
m.p. (°C.); 204~205 (dec.)
Mass; 358 (M+H)$^+$
NMR δ(DMSO-d$_6$); 3.98 (3H, s), 3.99 (3H, s), 3.99 (3H, s), 4.78 (2H, d, J=5.6 Hz), 6.65~7.71 (2H, m), 6.79 (1H, s), 7.94 (1H, s), 8.71 (1H, s), 8.90 (2H, brs), 10.54 (1H, brs), 14.06 (1H, brs)

Example 163

4-(3,4-Dihydroxybenzyl)amino-6-chloroquinazoline hydrochloride

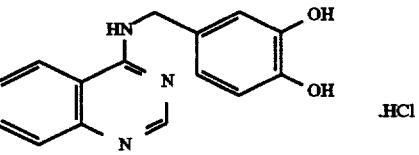

40 ml of a 1.0M solution of boron trichloride in methylene chloride was dropped into a solution of 2.00 g (6.37 mmol) of 4-(3,4-methylenedioxybenzyl)amino-6-chloroquinazoline in 150 ml of chloroform under stirring at room temperature. The obtained mixture was stirred at room temperature for 2 days, followed by the addition of methanol, and the obtained mixture was distilled under a reduced pressure to remove the solvent. This procedure was repeated twice. The crystals thus precipitated were washed with methanol and recrystallized from ethanol to give 1.53 g of the title compound as a yellow crystal.

molecular formula; $C_{15}H_{12}N_3O_2Cl·HCl$ yield (%); 71
m.p. (°C.); 154~155 (dec.)
Mass; 302 (M+H)⁺
NMR δ(DMSO-d₆); 4.74 (2H, d, J=5.6 Hz), 7.67 (1H, dd, J=8.0 Hz, 2.0 Hz), 6.70 (1H, d, J=8.0 Hz), 6.81 (1H, d, J=2.0 Hz), 7.87 (1H, d, J=8.8 Hz), 8.02 (1H, dd, J=8.8 Hz, 2.0 Hz), 8.76 (1H, d, J=2.0 Hz), 8.85 (1H, s), 8.90 (2H, brs), 10.42 (1H, brs)

Example 164

2-(2-Methoxyethoxy)-4-(3,4-methylenedioxybenzyl) amino-6-chloroquinazoline

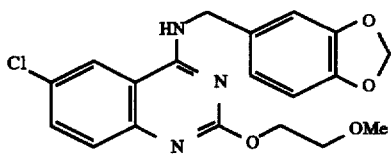

A mixture comprising 20 ml of ethylene glycol monomethyl ether and 70 mg of 55% sodium hydride was heated to 100° C., followed by the addition of a mixture comprising 500 mg of 2,6-dichloro-4-(3,4-methylenedioxybenzyl) aminoquinazoline and 5 ml of ethylene glycol monomethyl ether. The obtained mixture was heated under reflux for 2 hours and poured into 50 ml of water. The obtained mixture was extracted with 50 ml of ethyl acetate twice. The organic layers were together washed with 70 ml of an aqueous solution of sodium chloride twice, dried over magnesium sulfate and concentrated under a reduced pressure to give a crystalline residue. This residue was reprecipitated from ethyl acetate/n-hexane to give 420 mg of the title compound.

molecular formula; C₁₉H₁₈N₃O₄Cl
yield (%); 75
m.p. (°C.); 138~139
Mass; 388 (M+1)⁺
NMR δ(CDCl₃); 3.43 (3H, s), 3.78~3.81 (2H, m), 4.57~4.61 (2H, m), 4.73 (2H, d, J=5.2 Hz), 5.72 (1H, br), 5.96 (2H, s), 6.79~6.87 (3H, m), 7.52~7.58 (3H, m)

Examples 165 to 177

The following compounds were prepared in a similar manner to those of Examples 162 to 164.

Example 165

2-Methoxy-4-(3,4-methylenediokybenzyl)amino-6-chloroquinazoline

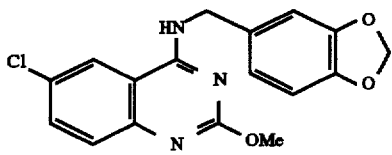

molecular formula; C₁₇H₁₄N₃O₃Cl
yield (%); 15
m.p. (°C.); 187~189
Mass; 344 (M+1)⁺
NMR δ(CDCl₃); 4.03 (3H, s), 4.50 (2H, d, J=5.6 Hz), 5.91 (1H, br), 5.96 (2H, s), 6.78 (1H, d, J=7.6 Hz), 6.81 (1H, dd, J=7.6 Hz, 1.6 Hz), 6.82 (1H, d, J=1.6 Hz), 7.58~7.60 (3H, m)

Example 166

2-Methoxy-4-(3,4-methylenedioxybenzyl)amino-6-cyanoquinazoline

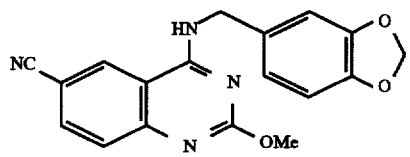

molecular formula; C₁₈H₁₄N₄O₃ (334)
yield (%); 23
m.p. (°C.); 224 (dec.)
Mass; 335 (M+1)⁺
NMR δ(DMSO-d₆); 3.87 (3H, s), 4.60 (2H, brs), 5.95 (2H, s), 6.84 (2H, s), 6.95 (1H, s), 7.55 (1H, d, J=8.8 Hz), 7.94 (1H, dd, J=8.8 Hz, 1.6 Hz), 8.83 (1H, d, J=1.6 Hz), 9.18 (1H, br)

Example 167

2,7,8-Tetramethoxy-4-(3,4-methylenedioxybenzyl) aminoquinazoline

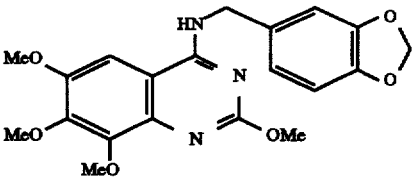

molecular formula; C₂₀H₂₁N₃O₆
yield (%); 28
m.p. (°C.); 128~129
Mass; 400 (M+H)⁺
NMR δ(CDCl₃); 3.91 (3H, s), 4.04 (3H, s), 4.07 (3H, s), 4.14 (3H, s), 4.75 (2H, d, J=5.2 Hz), 5.51 (1H, brs), 5.97 (2H, s), 6.60 (1H, s), 6.80 (1H, d, J=8.0 Hz), 6.87 (1H, dd, J=8.0 Hz, 2.0 Hz), 6.90 (1H, d, J=2.0 Hz)

Example 168

2-(2-Hydroxyethoxy-4-(3,4-methylenedioxybenzyl) amino-6-chloroquinazoline

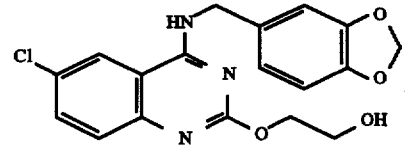

molecular formula; C₁₈H₁₆N₃O₄Cl (373.5)
yield (%); 97
m.p. (°C.); 191~193
Mass; 374 (M+1)⁺
NMR δ(DMSO-d₆); 3.65~3.69 (2H, m), 4.27 (2H, dd, J=8.8 Hz, 5.6 Hz), 4.60 (2H, d, J=5.2 Hz), 4.82 (1H, t, J=5.6 Hz), 5.95 (2H, s), 6.81~6.84 (2H, m), 6.92 (1H, s), 7.47 (1H, d, J=8.8 Hz), 7.65 (1H, dd, J=8.8 Hz, 2.2 Hz), 8.34 (1H, d, J=2.2 Hz), 8.82 (1H, br)

Example 169

2-(2-Hydroxyethoxy)-4-(3,4-methylenedioxybenzyl)amino-6-cyanoquinazoline

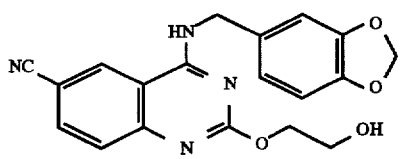

molecular formula; C₁₉H₁₆N₄O₄ (364)
yield (%); 94
m.p. (°C.); 227~229
Mass; 365 (M+1)⁺
NMR δ(DMSO-d₆); 3.68 (2H, t, J=5.2 Hz), 4.30 (2H, t, J=5.2 Hz), 4.44 (1H, brs), 5.97 (2H, s), 6.82 (2H, s), 6.95 (1H, s), 7.54 (1H, d, J=8.4 Hz), 7.95 (1H, dd, J=8.4 Hz, 1.6 Hz), 8.78 (1H, d, J=1.6 Hz), 9.04 (1H, br)

Example 170

2-(2-Methoxyethoxy)-4-(3,4-methylenedioxybenzyl)amino-6-methoxyquinazoline

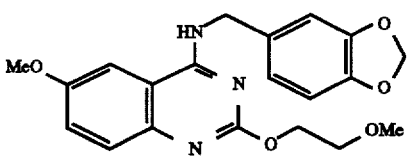

molecular formula; C₂₀H₂₁N₃O₅ (383)
yield (%); 68
m.p. (°C.); 118~119
Mass; 384 (M+1)⁺
NMR δ(DMSO-d₆); 3.26 (3H, s), 3.60 (2H, t, J=4.8 Hz), 3.61 (3H, s), 4.33 (2H, t, J=4.8 Hz), 4.63 (2H, d, J=6.0 Hz), 5.95 (2H, s), 6.81 (1H, d, J=7.6 Hz), 6.84 (1H, dd, J=7.6 Hz, 0.4 Hz), 6.91 (1H, d, J=0.4 Hz), 7.29 (1H, dd, J=8.8 Hz, 2.8 Hz), 7.40 (1H, d, J=8.8 Hz), 7.63 (1H, d, J=2.8 Hz), 8.62 (1H, br)

Example 171

2-(2-Methoxyethoxy)-4-(benzimidazol-5-yl)methylamino-6-cyanoquinazoline

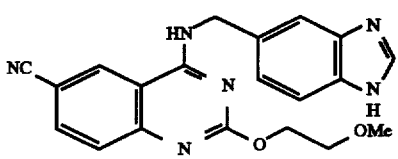

molecular formula; C₂₀H₁₈N₆O₂ (374)
yield (%); 68
m.p. (°C.); 267 (dec.)
Mass; 375 (M+1)⁺
NMR δ(DMSO-d₆); 3.21 (3H, s), 3.60 (2H, s), 4.40 (2H, s), 4.82 (2H, s), 7.17~7.66 (4H, m), 7.94 (1H, d, J=9.6 Hz), 8.16 (1H, s), 8.81 (1H, s), 9.15 (1H, br)

Example 172

2-Propoxy-4-(3,4-methylenedioxybenzyl)amino-6,7,8-trimethoxyquinazoline

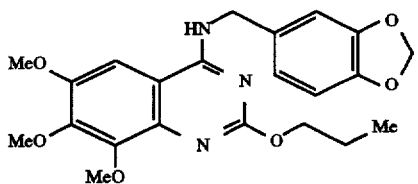

molecular formula; C₂₂H₂₅N₃O₆
yield (%); 6
m.p. (°C.); 122~123
Mass; 428 (M+H)⁺
NMR δ(CDCl₃); 1.05 (3H, t, J=7.4 Hz), 1.89 (2H, m), 3.90 (3H, s), 4.03 (3H, s), 4.13 (3H, s), 4.41 (2H, t, J=7.0 Hz), 4.76 (2H, d, J=5.2 Hz), 5.49 (1H, brs), 5.97 (2H, s), 6.60 (1H, s), 6.80 (1H, d, J=8.0 Hz), 6.87 (1H, d, J=8.0 Hz), 6.90 (1H, s)

Example 173

2-(3-Hydroxypropoxy)-4-(3,4-methylenedioxybenzyl)amino-6-chloroquinazoline

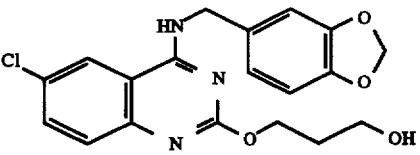

molecular formula; C₁₉H₁₈N₃O₄Cl (387.5)
yield (%); 60
m.p. (°C.); 118~120
Mass; 388 (M+1)⁺
NMR δ(CDCl₃); 2.02 (2H, tt, J=5.6 Hz, 5.6 Hz), 3.70 (2H, t, J=5.6 Hz), 3.95 (1H, br), 4.66 (2H, t, J=5.6 Hz), 4.71 (2H, d, J=5.2 Hz), 5.95 (2H, s), 6.08 (1H, br), 6.77 (1H, d, J=8.0 Hz), 6.83 (1H, d, J=8.0 Hz), 6.85 (1H, s), 7.51 (1H, d, J=8.8 Hz), 7.56 (1H, dd, J=8.8 Hz, 2.0 Hz), 7.61 (1H, d, J=2.0 Hz)

Example 174

2-(4-Hydroxybutoxy)-4-(3,4-methylenedioxybenzyl)amino-6-chloroquinazoline

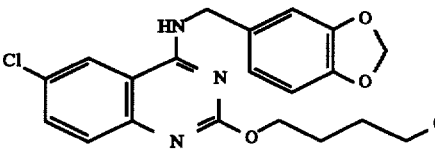

molecular formula; C₂₀H₂₀N₃O₄Cl (401.5)
yield (%); 23
m.p. (°C.); 121~124
Mass; 402 (M+1)⁺
NMR δ(CDCl₃); 1.47~1.73 (4H, m), 3.40~3.47 (2H, m), 4.20 (2H, t, J=6.7 Hz), 4.55 (2H, d, J=5.2 Hz), 5.72 (2H, s), 6.56 (1H, d, J=8.0 Hz), 6.66 (1H, dd, J=8.0 Hz, 1.6 Hz), 6.71 (1H, d, J=1.6 Hz), 7.30 (2H, s), 7.88 (1H, brt, J=5.2 Hz), 7.99 (1H, s)

Example 175

2-(4-Methoxybutoxy)-4-(3,4-methylenedioxybenzyl)amino-6-chloroquinazoline

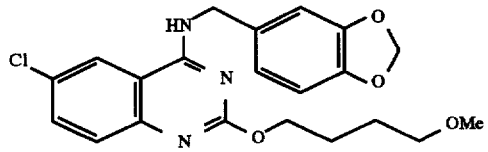

molecular formula; C$_{21}$H$_{22}$N$_3$O$_4$Cl (415.5)

yield (%); 26 m.p. (°C.); 120~123

Mass; 416 (M+1)$^+$

NMR δ(CDCl$_3$); 1.77 (2H, tt, J=8.8 Hz, 6.8 Hz), 1.90 (2H, tt, J=8.8 Hz, 6.8 Hz), 3.34 (3H, s), 3.44 (2H, t, J=6.8 Hz), 4.44 (2H, t, J=6.8 Hz), 4.72 (2H, d, J=5.2 Hz), 5.71 (1H, br), 5.96 (2H, s), 6.79 (1H, d, J=8.0 Hz), 6.84 (1H, dd, J=8.0 Hz, 1.8 Hz), 6.87 (1H, d, J=1.8 Hz), 7.53~7.59 (3H, m)

Example 176

2-(6-Hydroxybenzyloxy)-4-(3,4-methylenedioxybenzyl)amino-6-chloroquinazoline

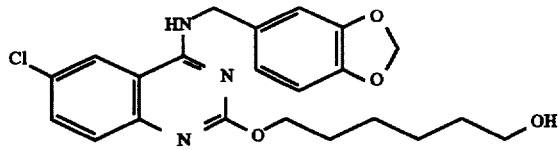

molecular formula; C$_{22}$H$_{24}$N$_3$O$_4$Cl (429.5)

yield (%); 66 m.p. (°C.); 144~146

Mass; 430 (M+1)$^+$

NMR δ(CDCl$_3$); 1.14~1.40 (6H, m), 1.58~1.64 (2H, m), 3.06 (1H, br), 3.38 (2H, br), 4.17 (2H, t, J=6.8 Hz), 4.52 (2H, d, J=5.6 Hz), 5.73 (2H, s), 6.56 (1H, d, J=8.0 Hz), 6.66 (1H, dd, J=8.0 Hz, 1.6 Hz), 6.71 (1H, d, J=1.6 Hz), 7.30 (2H, s), 7.85 (1H, br), 7.96 (1H, s)

Example 177

2-Hydroxy-4-(3,4-methylenedioxybenzyl)amino-6-chloroquinazoline

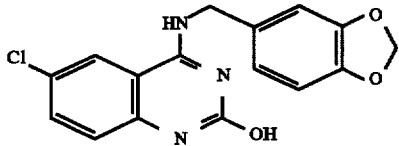

molecular formula; C$_{16}$H$_{12}$N$_3$O$_3$Cl (329.5)

m.p. (°C.); 257 (dec.)

NMR δ(DMSO-d$_6$); 4.668 (2H, d, J=5.6 Hz), 5.967 (2H, s), 6.846~6.905 (2H, m), 6.995 (1H, s), 7.821~7.859 (2H, m), 8.508 (1H, s), 10.103 (1H, br), 11.916 (1H, s)

Example 178

2-(2,3-Dihydroxypropyl)oxy-4-(3,4-methylenedioxybenzyl)amino-6-chloroquinazoline

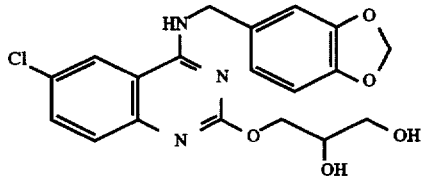

100 mg of sodium hydride was added to a mixture comprising 300 mg of 5-hydroxy-2-phenyl-1,3-dioxane and 5 ml of dimethylformamide. The obtained mixture was heated to 80° C. After the bubbling had been discontinued, 300 mg of 2,6-dichloro-4-(3,4-methylenedioxybenzyl)aminoquinazoline was added in a crystalline state. The obtained mixture was heated at 140° C. for 2 hours and cooled, followed by the addition of water. The obtained mixture was extracted with ethyl acetate. The extract was purified by silica gel column chromatography using an ethyl acetate/benzene mixture to give 118 mg of 2-(2-phenyl-1,3-dioxan-5-yl)oxy-4-(3,4-methylenedioxybenzyl)amino-6-chloroquinazoline. 100 mg of this compound was hydrolyzed with concentrated hydrochloric acid/ethanol by a conventional process to give 60 mg of the title compound through rearrangement.

molecular formula; C$_{19}$H$_{18}$ClN$_3$O$_5$ yield (%); 73 m.p. (°C.); 106~107

Mass; 404 (MH$^+$)

NMR δ(DMSO-d$_6$); 3.42 (2H, t, J=5.7 Hz), 3.79 (1H, sextet, J=5 Hz), 4.17 (1H, dd, J=6.6 Hz, 11.0 Hz), 4.31 (1H, dd, J=4.2 Hz, 11.0 Hz), 4.63 (2H, d, J=5.7 Hz), 4.66 (1H, t, J=6.0 Hz), 4.94 (1H, d, J=5.3 Hz), 5.98 (2H, s), 6.85 (2H, s), 6.95 (1H, s), 7.49 (1H, d, J=9.0 Hz), 7.68 (1H, dd, J=2.4 Hz, 9.0 Hz), 8.37 (1H, d, J=2.4 Hz), 8.83 (1H, t, J=5.7 Hz)

Example 179

2-(3-Carboxypropyl)oxy-4-(3,4-methylenedioxybenzyl)amino-6-cyanoquinazoline

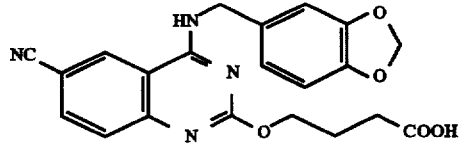

250 μl of dimethyl sulfoxide was slowly dropped into a mixture comprising 150 μl of oxalyl chloride and 15 ml of methylene chloride which had been preliminarily cooled in a dry ice/acetone bath. After 10 minutes, a solution of 500 mg of 2-(2-hydroxyethyl)oxy-4-(3,4-methylenedioxybenzyl)amino-6-cyanoquinazoline in 1 ml of dimethyl sulfoxide was dropped into the mixture prepared above at the same temperature and after 10 minutes, 1.4 ml of N,N-diisopropylethylamine was dropped thereinto at the same temperature. The obtained mixture was stirred at the same temperature for 10 minutes and brought to room temperature. After 20 minutes, 600 mg of ethoxycarbonylmethylenetriphenylphosphorane was added in a crystalline state to the resulting mixture to conduct a reaction for 30 minutes, followed by the addition of water. The obtained mixture was extracted with ethyl acetate and the extract was purified by silica gel column chromatography using an ethyl acetate/benzene mixture to give 400 mg of 2-(3-ethoxycarbonyl-2-propenyl)oxy-4-(3,4-methylenedioxybenzyl)amino-6-cyanoquinazoline (cis/trans mixture).

The whole of the above compound was dissolved in 30 ml of ethyl acetate and catalytically reduced with a 10% palladium/carbon catalyst under normal pressure. The reaction mixture was purified by silica gel column chromatography using an ethyl acetate/benzene mixture to give 250 mg of 2-(3-ethoxycarbonylpropyl)oxy-4-(3,4-methylenedioxybenzyl)amino-6-cyanoquinazoline (a saturated ester).

250 mg of the above saturated ester was dissolved in 50 ml of ethanol, followed by the addition of 1.7 ml of a 1N aqueous solution of sodium hydroxide. The obtained mixture was reacted at room temperature for 10 hours and then at 40° C. for 2 hours, cooled and neutralized by the addition of 1.7 ml of 1N aqueous hydrochloric acid, followed by the addition of water. The crystals thus formed were recovered by filtration and recrystallized from ethanol/water to give 200 mg of the title compound.

molecular formula; $C_{21}H_{18}N_4O_5$ (406.398)

yield (%); 86 m.p. (°C.); >290

Mass; 407 (MH⁺)

NMR δ(DMSO); 1.93 (2H, quintet, J=7 Hz), 2.35 (2H, t, J=7.3 Hz), 4.32 (2H, t, J=6.6 Hz), 4.64 (2H, d, J=5.7 Hz), 5.98 (2H, s), 6.87 (2H, s), 6.97 (1H, s), 7.56 (1H, d, J=8.8 Hz), 7.96 (1H, dd, J=1.8 Hz, 8.8 Hz), 8.80 (1H, d, J=1.8 Hz), 9.05 (1H, t, J=5.7 Hz)

Example 180

2-Methylthio-4-(3,4-methylenedioxybenzyl)amino-6-chloroquinazoline

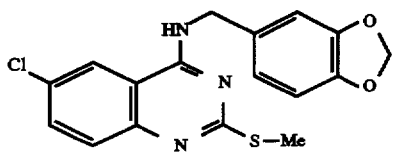

20 ml of N,N-dimethylformamide and 221 mg of sodium thiomethoxide were added to 1 g of 2,6-dichloro-4-(3,4-methylenedioxybenzyl)aminoquinazoline. The obtained mixture was stirred at 110° C. for one hour, neutralized with 1N hydrochloric acid and stirred at room temperature for one hour, followed by the addition of water. The crystals thus precipitated were recovered by filtration to give 780 mg of the title compound.

molecular formula; $C_{17}H_{14}ClN_3O_2S$ yield (%); 76 m.p. (°C.); 214~216

Mass m/e; 360 (M+1)

NMR δ(CDCl₃); 2.66 (3H, s), 4.85 (2H, d, J=5.6 Hz), 5.93 (2H, s), 6.73 (1H, d, J=8.0 Hz), 6.89 (1H, d, J=8.0 Hz), 6.93 (1H, s), 7.64 (1H, dd, J=8.8 Hz, 2.0 Hz), 8.16 (1H, d, J=8.8 Hz), 8.77 (1H, d, J=2.0 Hz)

Example 181

2-Morpholino-4-(3,4-methylenedioxybenzyl)amino-6-cyanoquinazoline

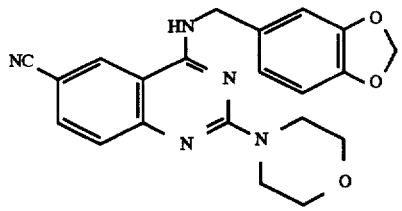

A mixture comprising 338 mg of 2-chloro-4-(3,4-methylenedioxybenzyl)amino-6-cyanoquinazoline, 435 mg of morpholine and 20 ml of isopropyl alcohol was heated under reflux for 3 hours, followed by the addition of 30 ml of water under heating. The precipitate thus formed was recovered by filtration and washed with 30 ml of water and 30 ml of ethyl acetate. Thus, 310 mg of the title compound was obtained.

molecular formula; $C_{21}H_{19}N_5O_3$ (389)

yield (%); 80 m.p. (°C.); 270~272 (dec.)

Mass; 390 (M+1)⁺

NMR δ(DMSO-d₆); 3.57~3.61 (4H, m), 3.73~3.79 (4H, m), 4.57 (2H, d, J=5.6 Hz), 5.95 (2H, s), 6.82 (1H, d, J=8.0 Hz), 6.85 (1H, d, J=8.0 Hz), 6.93 (1H, s), 7.27 (1H, d, J=8.8 Hz), 7.74 (1H, dd, J=8.8 Hz, 1.6 Hz), 8.56 (1H, d, J=1.6 Hz), 8.75 (1H, brt, J=5.6 Hz)

Examples 182 to 183

The following compounds were prepared in a similar manner to that of Example 181.

Example 182

2-Morpholino-4-(3,4-methylenedioxybenzyl)amino-6-chloroquinazoline

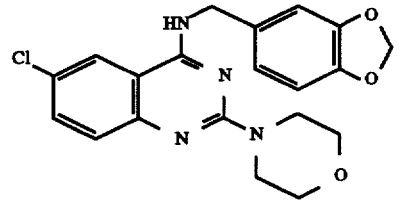

molecular formula; $C_{20}H_{19}N_4O_3Cl$ (398.850)

yield (%); 96 m.p. (°C.); 208~209

Mass; 399 (MH)⁺

NMR δ(DMSO-d₆); 3.61 (4H, t, J=5 Hz), 3.72 (4H, t, J=5 Hz), 4.58 (2H, d, J=5.7 Hz), 5.97 (2H, s), 6.85 (2H, s), 6.95 (1H, s), 7.28 (1H, d, J=9.0 Hz), 7.51 (1H, dd, J=2.4 Hz, 9.0 Hz), 8.18 (1H, d, J=2.4 Hz), 8.60 (1H, t, J=5.7 Hz)

Example 183

2-Morpholino-4-(3-chloro-4-methoxybenzyl)amino-6-cyanoquinazoline

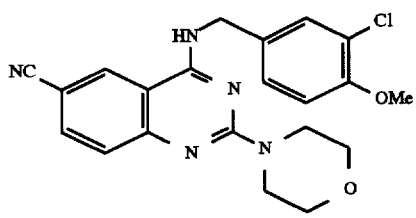

molecular formula; $C_{21}H_{20}N_5O_2Cl$ (407.5)

yield (%); 51 m.p. (°C.); 222~223

Mass; 410 (M+1)$^+$

NMR δ(DMSO-d$_6$); 3.56~3.61 (4H, m), 3.74~3.80 (4H, m), 3.80 (3H, s), 4.58 (2H, d, J=5.2 Hz), 7.27~7.32 (2H, m), 7.44 (1H, d, J=1.6 Hz), 7.75 (1H, dd, J=8.8 Hz, 1.6 Hz), 8.55 (1H, d, J=1.6 Hz), 8.80 (1H, brt, J=5.2 Hz)

Example 184

2-(4-Hydroxypiperidino)-4-(3,4-methylenedioxybenzyl)amino-6-cyanoquinazoline

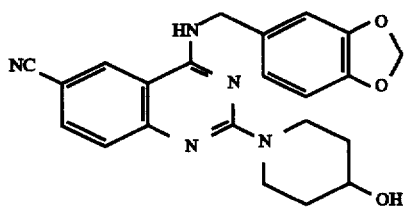

A mixture comprising 339 mg of 2-chloro-4-(3,4-methylenedioxybenzyl)amino-6-cyanoquinazoline, 500 mg of 4-hydroxypiperidine and 20 ml of N,N-dimethylformamide was heated under reflux for 5 hours and poured into 50 ml of water, followed by the addition of 50 ml of ethyl acetate. The obtained mixture was filtered to remove insolubles. The organic layer of the filtrate was dried over magnesium sulfate and concentrated under a reduced pressure to give a crystalline residue. This residue was washed with chloroform to give 145 mg of the title compound.

molecular formula; $C_{22}H_{21}N_5O_3$ (403)

yield (%); 36 m.p. (°C.); 229

Mass; 404 (M+1)$^+$

NMR δ(DMSO-d$_6$); 1.19~1.30 (2H, m), 1.64~1.77 (2H, m), 3.21~3.30 (2H, m), 3.63~3.75 (1H, m), 4.34~4.38 (2H, m), 4.55 (2H, d, J=5.6 Hz), 4.66 (1H, d, J=4.0 Hz), 5.94 (2H, s), 6.80~6.86 (2H, m), 6.93 (1H, d, J=0.8 Hz), 7.24 (1H, d, J=8.4 Hz), 7.70 (1H, dd, J=8.4 Hz, 1.6 Hz), 8.52 (1H, d, J=1.6 Hz), 8.70 (1H, br)

Examples 185 to 191

The following compounds were prepared in a similar manner to that of Example 184.

Example 185

2-(4-Hydroxypiperidino)-4-(3,4-methylenedioxybenzyl)amino-6-chloroquinazoline

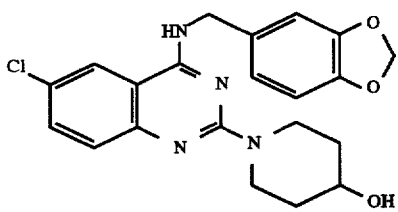

molecular formula; $C_{21}H_{21}N_4O_3Cl$ (412.877)

yield (%); 56 m.p. (°C.); 157~158

Mass; 413 (MH$^+$)

NMR δ(DMSO-d$_6$); 1.2~1.3 (2H, m), 1.6~1.8 (2H, m), 3.1~3.2 (2H, m), 3.6~3.7 (1H, m), 4.3~4.4 (2H, m), 4.55 (2H, d, J=5.7 Hz), 4.65 (1H, d, J=4.4 Hz), 5.96 (2H, s), 6.84 (2H, s), 6.95 (1H, s), 7.24 (1H, d, J=9.0 Hz), 7.47 (1H, dd, J=2.4 Hz, 9.0 Hz), 8.13 (1H, d, J=2.4 Hz), 8.53 (1H, t, J=5.7 Hz)

Example 186

2-(4-Hydroxypiperidino)-4-(3-chloro-4-methoxybenzyl)amino-6-cyanoquinazoline

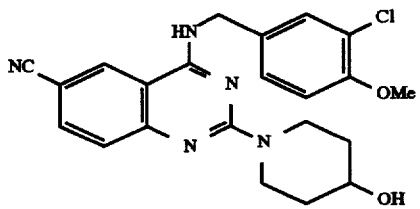

molecular formula; $C_{22}H_{22}N_5O_2Cl$ (423.5)

yield (%); 80 m.p. (°C.); 207~208

Mass; 424 (M+1)$^+$

NMR δ(DMSO-d$_6$); 1.18~1.30 (2H, m), 1.65~1.76 (2H, m), 3.21~3.33 (2H, m), 3.30 (3H, s), 3.64~3.72 (1H, m), 4.29~4.37 (2H, m), 4.57 (2H, d, J=5.6 Hz), 4.66 (1H, d, J=1.8 Hz), 7.07 (1H, d, J=8.4 Hz), 7.24 (1H, d, J=8.8 Hz), 7.29 (1H, dd, J=8.4 Hz, 2.0 Hz), 7.43 (1H, d, J=2.0 Hz), 7.71 (1H, dd, J=8.8 Hz, 2.0 Hz), 8.51 (1H, d, J=2.0 Hz), 8.74 (1H, brt, J=1.8 Hz)

Example 187

2-(2-Hydroxyethyl)amino-4-(3,4-methylenedioxybenzyl)amino-6,7,8-trimethoxyquinazoline

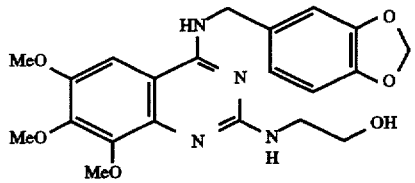

molecular formula; $C_{21}H_{24}N_4O_6$
yield (%); 38
m.p. (°C.); amorphous
Mass; 429 (M+H)⁺
NMR δ(CDCl₃); 3.60 (2H, m), 3.88 (3H, s & 1H, m), 3.99 (3H, s), 4.01 (3H, s), 4.67 (2H, d, J=5.6 Hz), 5.32 (1H, brs), 5.53 (1H, brs), 5.97 (2H, s), 6.55 (1H, s), 6.80 (1H, d, J=8.0 Hz), 6.85 (1H, d, J=8.0 Hz), 6.89 (1H, s)

Example 188

2-(2-Hydroxyethyl)amino-4-(3,4-methylenedioxybenzyl)amino-6-chloroquinazoline

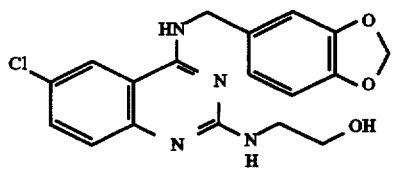

molecular formula; $C_{18}H_{17}N_4O_3Cl$
yield (%); 47
m.p. (°C.); 138~139
Mass m/e; 373 (M+1)
NMR δ(CDCl₃(+DMSO-d₆)); 3.60 (2H, m), 3.79 (2H, t, J=4.8 Hz), 4.65 (2H, d, J=5.2 Hz), 5.94 (2H, s), 6.76 (1H, d, J=8.0 Hz), 6.85 (1H, dd, J=8.0 Hz, 2.0 Hz), 6.90 (1H, d, J=2.0 Hz), 7.34 (1H, d, J=8.8 Hz), 7.44 (1H, dd, J=8.8 Hz, 2.4 Hz), 8.02 (2H, brs)

Example 189

2-[N-(2-Hydroxyethyl)-N-methylamino]-4-(3,4-methylenedioxybenzyl)amino-6-chloroquinazoline

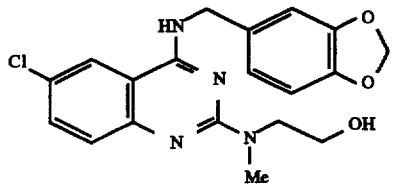

molecular formula; $C_{19}H_{19}N_4O_3C$
yield (%); 48
m.p. (°C.); 146~148
Mass m/e; 387 (M+1)
NMR δ(CDCl₃(+DMSO-d₆)); 3.27 (3H, s), 3.82 (2H, t, J=4.8 Hz), 3.89 (2H, t, J=4.8 Hz), 4.67 (2H, d, J=5.6 Hz), 5.95 (2H, s), 6.77 (1H, d, J=8.0 Hz), 6.86 (1H, dd, J=8.0 Hz, 1.6 Hz), 6.90 (1H, d, J=1.6 Hz), 7.43 (2H, m), 7.76 (1H, brs)

Example 190

2-(9-Hydroxymethylpyrrolidin-1-yl)-4-(3,4-methylenedioxyybenzyl)amino-6-chloroquinazoline

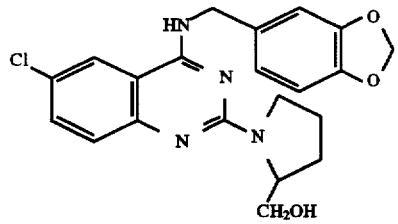

molecular formula; $C_{21}H_{21}N_4O_3Cl$ (412.877)
yield (%); 70
m.p. (°C.); 182~183
Mass; 413 (MH⁺)
NMR δ(DMSO-d₆); 1.8~2.0 (4H, br 2 peaks), 3.4~3.7 (3H, br 2 peaks), 4.1~4.2 (1H, brs), 4.58 (2H, d, J=5.8 Hz), 5.96 (2H, s), 6.84 (1H, d, J=8.0 Hz), 6.88 (1H, dd, J=1.3 Hz, 8.0 Hz), 6.96 (1H, d, J=1.3 Hz), 7.23 (1H, d, J=8.8 Hz), 7.47 (1H, dd, J=2.4 Hz, 8.8 Hz), 8.15 (1H, d, J=2.4 Hz), 8.4~8.6 (1H, brs)

Example 191

2-Bis(2-hydroxyethyl)amino-4-(3,4-methylenedioxybenzyl)amino-6-chloroquinazoline

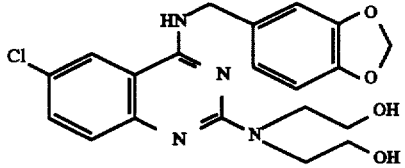

molecular formula; $C_{20}H_{21}N_4O_4Cl$ (416.865)
yield (%); 56
m.p. (°C.); 167~168
Mass; 417 (MH⁺)
NMR δ(DMSO-d₆); 3.5~3.7 (8H, br 2 peaks), 4.56 (2H, d, J=5.7 Hz), 5.96 (2H, s), 6.85 (2H, s), 6.93 (1H, s), 7.22 (1H, d, J=9.0 Hz), 7.47 (1H, dd, J=2.4 Hz, 9.0 Hz), 8.15 (1H, d, J=2.4 Hz), 8.55 (1H, brt, J=5.7 Hz)

Example 192

2-(1-Imidazolyl)-4-(3,4-methylenedioxybenzyl)amino-6-chloroquinazoline

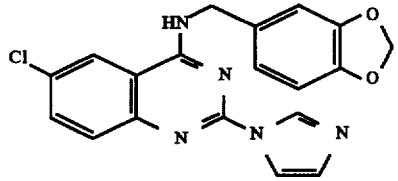

103 mg of imidazole was added to a suspension of 66 mg of sodium hydride in 6 ml of dimethylformamide at 0° C.

The obtained mixture was stirred for 10 minutes. 500 mg of 2,6-dichloro-4-(3,4-methylenedioxybenzyl)amino-6-chloroquinazoline was added to the resulting mixture at room temperature. The mixture thus prepared was stirred at 100° C. for 20 minutes, followed by the addition of water. The crystals precipitated were recovered by filtration and washed with water and ethanol/acetone successively to give 325 mg of the title compound.

molecular formula; $C_{19}H_{14}N_5O_2Cl$ yield (%); 59 m.p. (°C.); 275~276 (dec.)

Mass m/e; 380 (M+1)

NMR δ(DMSO-d$_6$); 4.74 (2H, d, J=5.6 Hz), 5.96 (2H, s), 6.85 (1H, d, J=8.0 Hz), 6.95 (1H, dd, J=8.0 Hz, 1.6 Hz), 7.03 (1H, d, J=1.6 Hz), 7.08 (1H, d, J=1.2 Hz), 7.68 (1H, d, J=8.8 Hz), 7.78 (1H, dd, J=8.8 Hz, 2.4 Hz), 7.94 (1H, d, J=1.2 Hz), 8.47 (1H, d, J=2.4 Hz), 8.58 (1H, t, J=2.4 Hz), 9.28 (1H, t, J=5.6 Hz)

Examples 193 to 197

The following compounds were prepared in a similar manner to that of Example 192.

Example 193

2-(Imidazol-1-yl)-4-(3,4-methylenedioxybenzyl)amino-6-cyanoquinazoline

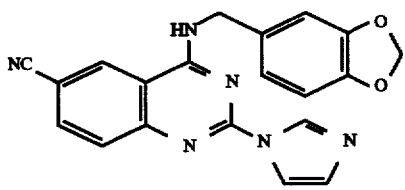

molecular formula; $C_{20}H_{14}N_6O_2$ (370)

yield (%); 81 m.p. (°C.); >290

Mass; 371 (M+1)$^+$

NMR δ(DMSO-d$_6$); 4.74 (2H, d, J=6.0 Hz), 5.95 (2H, s), 6.86 (1H, d, J=8.0 Hz), 6.95 (1H, dd, J=8.0 Hz, 1.6 Hz), 7.04 (1H, d, J=1.6 Hz), 7.09 (1H, d, J=1.6 Hz), 7.73 (1H, d, J=8.4 Hz), 7.95 (1H, d, J=1.6 Hz), 8.06 (1H, dd, J=8.4 Hz, 1.6 Hz), 8.61 (1H, d, J=1.6 Hz), 8.87 (1H, d, J=1.6 Hz), 9.47 (1H, brt, J=6.0 Hz)

Example 194

2-Pentylamino-4-(3,4-methylenedioxybenzyl)amino-6-chloroquinazoline

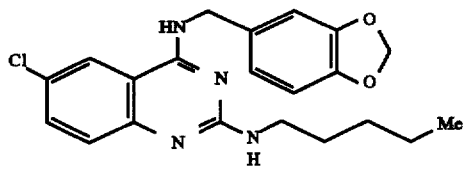

molecular formula; $C_{21}H_{23}N_4O_2Cl$ yield (%); 97 m.p. (°C.); 194~195

Mass m/e; 399 (M+1)

NMR δ(CDCl$_3$); 0.86 (3H, t, J=7.2 Hz), 1.29 (4H, m), 1.58 (2H, quintet, J=6.8 Hz), 3.47 (2H, q, J=6.8 Hz), 4.78 (2H, d, J=5.6 Hz), 5.87 (2H, s), 6.66 (1H, d, J=8.0 Hz), 6.89 (1H, d, J=8.0 Hz), 6.94 (1H, s), 7.26 (1H, d, J=8.8 Hz), 7.41 (1H, d, J=8.8 Hz), 7.90 (1H, t, J=5.6 Hz), 8.55 (1H, s), 9.53 (1H, brs)

Example 195

2-(2-Aminoethyl)amino-4-(3,4-methylenedioxybenzyl)amino-6,7,8-trimethoxyquinazoline

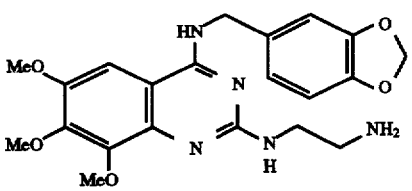

molecular formula; $C_{21}H_{25}N_5O_5$ yield (%); 87 m.p. (°C.); amorphous

Mass; 428 (M+H)$^+$

NMR δ(CDCl$_3$); 1.44 (2H, s), 2.93 (2H, t, J=6.0 Hz), 3.57 (2H, brs), 3.88 (3H, s), 4.00 (3H, s), 4.07 (3H, s), 4.70 (2H, d, J=4.8 Hz), 5.16 (1H, brs), 5.51 (1H, brs), 5.96 (2H, s), 6.56 (1H, s), 6.80 (1H, d, J=8.0 Hz), 6.86 (1H, d, J=8.0 Hz), 6.90 (1H, s)

Example 196

2-Hydrazino-4-(3,4-methylenedioxybenzyl)amino-6,7,8-trimethoxyquinazoline

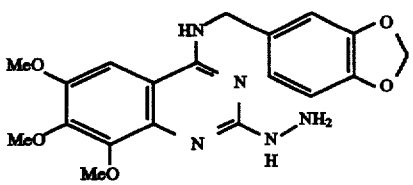

molecular formula; $C_{19}H_{21}N_5O_5$ yield (%); 12 m.p. (°C.); oily substance

Mass; 400 (M+H)$^+$

NMR δ(CDCl$_3$); 3.88 (3H, s), 3.99 (3H, s), 4.05 (3H, s), 4.66 (2H, d, J=3.6 Hz), 5.92 (2H, s), 6.75 (1H, d, J=8.0 Hz), 6.83 (1H, d, J=8.0 Hz), 6.87 (1H, s), 7.04 (2H, brs)

Example 197

2-Carbamoylmethyl)amino-4-(3,4-methylenedioxybenzyl)amino-6-chloroquinazoline

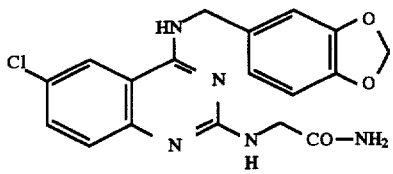

molecular formula; $C_{18}H_{16}N_5O_3Cl$
yield (%); 63
m.p. (°C.); 259~260 (dec.)
Mass m/e; 386 (M+1)
NMR δ(DMSO-d$_6$); 4.02 (2H, d, J=4.8 Hz), 4.66 (2H, d, J=5.6 Hz), 5.97 (2H, s), 6.86 (1H, d, J=8.0 Hz), 6.91 (1H, d, J=8.0 Hz), 6.99 (1H, s), 7.19 (1H, s), 7.50 (1H, d, J=8.8 Hz), 7.61 (1H, s), 7.83 (1H, d, J=8.8 Hz), 8.09 (1H, brs), 8.49 (1H, brs), 10.03 (1H, brs)

Example 198

2-(3,4-Methylenedioxybenzyl)amino-4,6,7,8-tetramethoxyquinazoline

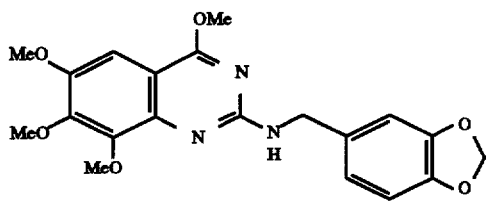

1.00 g (3.51 mmol) of 2-chloro-4,6,7,8-tetramethoxyquinazoline, 0.60 g (3.97 mmol) of piperonylamine and 0.60 g of sodium carbonate were mixed with 30 ml of isopropyl alcohol. The obtained mixture was heated under reflux for 24 hours and distilled under a reduced pressure to remove the solvent. The residue was purified by silica gel column chromatography (ethyl acetate/n-hexane) to give 0.12 g of the title compound as an oily substance.

molecular formula; $C_{20}H_{21}N_3O_6$
yield (%); 9
m.p. (°C.); oily substance
NMR δ(CDCl$_3$); 3.91 (3H, s), 4.02 (3H, s), 4.04 (6H, s), 4.63 (2H, d, J=6.0 Hz), 5.30 (1H, brs), 5.93 (2H, s), 6.75 (1H, d, J=8.0 Hz), 6.86 (1H, dd, J=8.0 Hz, 1.6 Hz), 6.92 (1H, d, J=1.6 Hz), 7.06 (1H, s)

Example 199

2-Chloro-4,6,7,8-tetramethoxyquinazoline

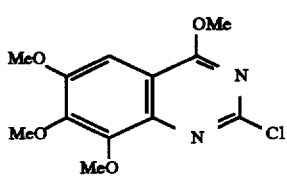

5.00 g (17.3 mmol) of 2,4-dichloro-6,7,8-trimethoxyquinazoline was suspended in 100 ml of methanol, followed by the gradual addition of 1.5 g of sodium hydride. The obtained mixture was heated under reflux. After several hours, the reaction mixture was concentrated under a reduced pressure, followed by the addition of water. The crystal thus precipitated was recovered by filtration, washed with water and air-dried to give 4.80 g of the title compound as a pale-pink crystal.

yield (%); 97
m.p. (°C.); 119~120
Mass; 285 (M+1)$^+$
NMR δ(CDCl$_3$); 3.98 (3H, s), 4.06 (3H, s), 4.12 (3H, s), 4.19 (3H, s), 7.17 (1H, s)

Example 200

2-Amino-4-(3,4-methylenedioxybenzyl)amino-6-chloroquinazoline

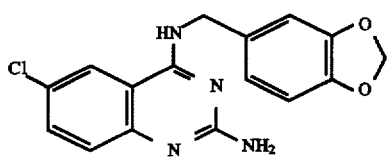

2.0 g of 2,6-dichloro-4-(3,4-methylenedioxybenzyl)aminoquinazoline was heated to 120° C. in 50 ml of ethanolic ammonia put in a pressure vessel for 18 hours, cooled and concentrated under a reduced pressure. The obtained residue was introduced to a silica gel column and eluted with a chloroform/methanol (9:1) mixture to give 830 mg of the title compound.

molecular formula; $C_{16}H_{13}N_4O_2Cl$
yield (%); 44
m.p. (°C.); 285 (dec.)
Mass; 329 (M+1)$^+$
NMR δ(CDCl$_3$); 4.67 (2H, d, J=5.6 Hz), 4.98 (2H, br), 5.74 (1H, br), 5.96 (2H, s), 6.78 (1H, d, J=7.6 Hz), 6.83 (1H, dd, J=7.6 Hz, 1.6 Hz), 6.86 (1H, d, J=1.6 Hz), 7.38 (1H, d, J=9.6 Hz), 7.46~7.49 (2H, m)

Example 201

2-Amino-4-(3,4-methylenedioxybenzyl)amino-6-cyanoquinazoline

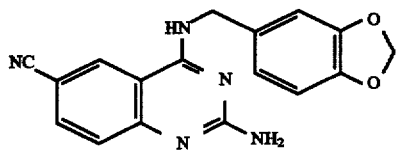

The title compound was prepared in a similar manner to those of Examples 199 and 200.

molecular formula; $C_{17}H_{13}N_5O_2$ (319)
yield (%); 60
m.p. (°C.); 284 (dec.)
Mass; 320 (M+1)$^+$
NMR δ(CDCl$_3$); 4.31 (2H, d, J=5.6 Hz), 5.25 (2H, brs), 5.58 (2H, s), 6.40 (1H, d, J=7.6 Hz), 6.51 (1H, dd, J=7.6 Hz, 1.2 Hz), 6.57 (1H, d, J=1.2 Hz), 6.95 (1H, d, J=8.4 Hz), 7.25 (1H, dd, J=8.4 Hz, 1.6 Hz), 8.00 (1H, br), 8.20 (1H, d, J=1.6 Hz)

Example 202

2-(Methylcarbamoyl)amino-4-(3,4-methylenedioxybenzyl)amino-6-chloroquinazoline

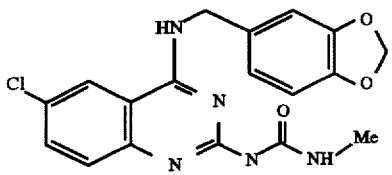

4 ml of dimethyl sulfoxide and 260 mg of methyl isocyanate were added to 500 mg of 2-amino-4-(3,4-methylenedioxybenzyl)amino-6-chloroquinazoline. The obtained mixture was stirred at 50° C. for 3 hours and distilled under a reduced pressure to remove excess methyl isocyanate, followed by the addition of chloroform and water. The mixture thus obtained was filtered and the filtrate was extracted with chloroform twice. The organic layers were combined, washed with water twice, dried over magnesium sulfate and distilled under a reduced pressure to remove the solvent. The residue was purified by silica gel column chromatography (benzene/acetone) and recrystallized (from benzene/chloroform/ethanol) to give 72 mg of the title compound.

molecular formula; $C_{18}H_{16}N_5O_3Cl$
yield (%); 12
m.p. (°C.); 245–247
Mass m/e; 386 (M+1)
NMR δ(DMSO-d$_6$); 2.75 (3H, d, J=4.4 Hz), 4.56 (2H, d, J=6.0 Hz), 5.95 (2H, s), 6.82 (1H, d, J=8.4 Hz), 6.92 (1H, d, J=8.4 Hz), 7.11 (1H, s), 7.56 (1H, d, J=8.8 Hz), 7.67 (1H, dd, J=8.8 Hz, 1.6 Hz), 8.27 (1H, d, J=1.6 Hz), 8.90 (1H, t, J=6.0 Hz), 9.20 (1H, s), 9.38 (1H, d, J=4.4 Hz)

Examples 203 and 204

The following compounds were prepared in a similar manner to that of Example 202.

Example 203

2-Bis(methylcarbamoyl)amino-4-(3,4-methylenedioxybenzyl)amino-6-chloroquinazoline

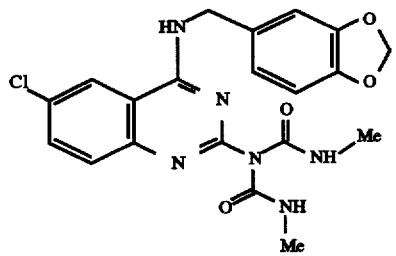

molecular formula; $C_{20}H_{19}N_6O_4Cl$
yield (%); 8
amt. of product (mg); 45
m.p. (°C.); 243–245
Mass m/e; 443 (M+1)
NMR δ(DMSO-d$_6$); 2.71 (6H, d, J=4.8 Hz), 4.53 (2H, d, J=6.0 Hz), 5.94 (2H, s), 6.80 (1H, d, J=8.0 Hz), 6.85 (1H, d, J=8.0 Hz), 6.95 (1H, s), 7.66 (1H, d, J=8.8 Hz), 7.72 (1H, dd, J=8.8 Hz, 2.0 Hz), 8.32 (1H, dd, J=2.0 Hz), 8.85 (1H, dd, J=4.8 Hz), 9.01 (1H, t, J=6.0 Hz)

Example 204

2-(n-Butylcarbamoyl)amino-4-(3,4-methylenedioxybenzyl)amino-6-chloroquinazoline

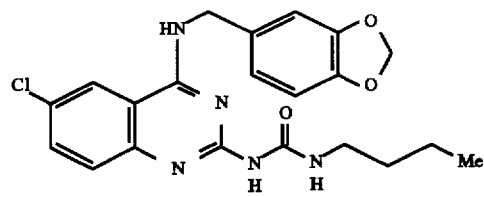

molecular formula; $C_{21}H_{22}N_5O_3Cl$
yield (%); 40
m.p. (°C.); 209–210
Mass m/e; 428 (M+1)
NMR δ(DMSO-d$_6$); 0.89 (3H, t, J=7.2 Hz), 1.33 (2H, sextet, J=7.2 Hz), 1.45 (2H, quintet, J=7.2 Hz), 3.18 (2H, t, J=7.2 Hz), 4.56 (2H, d, J=6.0 Hz), 5.95 (2H, s), 6.83 (1H, d, J=8.0 Hz), 6.91 (1H, d, J=8.0 Hz), 7.09 (1H, s), 7.46 (1H, d, J=8.8 Hz), 7.66 (1H, dd, J=8.8 Hz, 2.0 Hz), 8.27 (1H, d, J=2.0 Hz), 8.90 (1H, t, J=6.0 Hz), 9.17 (1H, s), 9.58 (1H, t, J=7.2 Hz)

Example 205

2-(4-Ethoxycarbonylpiperidino)-4-(3,4-methylenedioxybenzyl)amino-6-chloroquinazoline

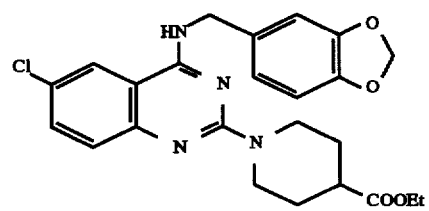

3.61 g of methyl isonipecotate, 2.32 g of triethylamine and 5 ml of 2-propanol were added to 1 g of 2,6-dichloro-4-(3,4-methylenedioxybenzyl)aminoquinazoline prepared in Example 92. The obtained mixture was refluxed for 100 minutes. The mixture thus obtained was extracted with chloroform twice. The organic layers were combined, washed with water, dried over magnesium sulfate and freed from the solvent by distillation. The residue was recrystallized (from ethanol/water) to give 1.31 g of the title compound.

molecular formula; $C_{24}H_{25}ClN_4O_4$
yield (%); 97
m.p. (°C.); 118–119
Mass; 469 (M+1)
NMR δ(DMSO-d$_6$); 1.18 (3H, t, J=7.2 Hz), 1.42 (2H, m), 2.58 (1H, m), 2.98 (2H, m), 4.06 (2H, q, J=7.2 Hz), 4.56 (2H, m, J=5.6 Hz), 4.62 (2H, m), 5.96 (2H, s), 6.82 (1H, d, J=8.0 Hz), 6.86 (1H, dd, J=8.0 Hz, 1.6 Hz), 6.94 (1H, d, J=1.6 Hz), 7.26 (1H, d, J=9.2 Hz), 7.48 (1H, dd, J=9.2 Hz, 2.4 Hz), 8.15 (1H, d, J=2.4 Hz), 8.56 (1H, brt, J=5.6 Hz)

Example 206

2-(4-Ethoxycarbonylpiperidino)-4-(3,4-methylenedioxybenzyl)amino-6-chloroquinazoline hydrochloride

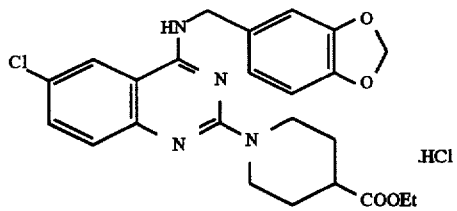

The title compound was prepared from the 2-(4-Ethoxycarbonylpiperidino)-4-(3,4-methylenedioxybenzyl)amino-6-chloroquinazoline prepared in Example 205 by the use of ethanol-hydrochloric acid-ethanol.

molecular formula; $C_{24}H_{25}ClN_4O_4 \cdot HCl$ yield (%); 97 m.p. (°C.); 174~175

NMR δ(DMSO-$d_6$); 1.20(3H, t, J=7.2 Hz), 1.59(2H, m), 1.97(2H, m), 2.75(1H, m), 3.31(2H, m), 4.09(2H, q, J=7.2 Hz), 4.53(2H, m), 4.67(2H, d, J=5.6 Hz), 5.98(2H, s), 6.86(1H, d, J=8.0 Hz), 6.90(1H, dd, J=8.0 Hz, 1.6 Hz), 7.01(1H, d, J=1.6 Hz), 7.83(1H, dd, J=8.8 Hz, 2.0 Hz), 7.91(1H, d, J=8.8 Hz), 8.52(1H, d, J=2.0 Hz), 10.15(1H, brs), 12.28(11H, brs)

Example 207

2-(4-Ethoxycarbonylpiperidino)-4-(3,4-methylenedioxybenzyl)amino-6-cyanoquinazoline

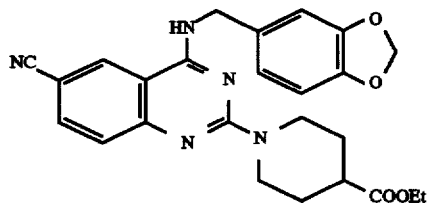

3.71 g of ethyl isonipecotate, 2.38 g of triethylamine and 10 ml of 2-propanol were added to 1 g of 2-chloro-4-(3,4-methylenedioxybenzyl)amino-6-cyanoquinazoline. The obtained mixture was refluxed for 1 hour and cooled to room temperature. The crystals thus precipitated were recovered by filtration and washed with water and ether successively to give 1.126 g of the title compound.

molecular formula; $C_{25}H_{25}N_5O_4$ yield (%); 83 m.p. (°C.); 192~193

Mass; 460 (M+1)

NMR δ(CDCl$_3$); 1.26 (3H, t, J=7.2 Hz), 1.71 (2H, m), 1.99 (2H, m), 2.59 (1H, m), 3.12 (2H, brt, J=12.0 Hz), 4.15 (2H, q, J=7.2 Hz), 4.67 (2H, d, J=5.2 Hz), 4.82 (2H, dt, J=13.2 Hz, 3.6 Hz), 5.96 (2H, s), 6.79 (1H, d, J=8.0 Hz), 6.85 (1H, dd, J=8.0 Hz, 1.6 Hz), 6.88 (1H, d, J=1.6 Hz), 7.42 (1H, brs), 7.61 (1H, dd, J=8.8 Hz, 1.6 Hz), 7.84 (1H, brs)

Example 208

2-(4-Ethoxycarbonylpiperidino)-4-(3-chloro-4-methoxybenzyl)amino-6-cyanoquinazoline

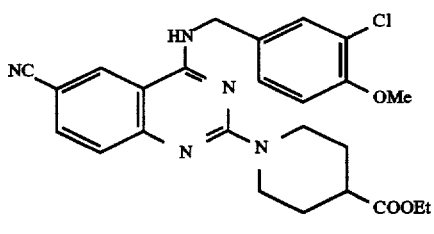

3.5 g of ethyl isonipecotate, 2.25 g of triethylamine and 30 ml of 2-propanol were added to 1 g of 2-chloro-4-(3-chloro-4-methoxybenzyl)amino-6-cyanoquinazoline. The obtained mixture was refluxed for 30 minutes and cooled to room temperature. The crystals thus precipitated were recovered by filtration and washed with water and ethanol successively to give 1.13 g of the title compound.

molecular formula; $C_{25}H_{26}N_5O_3Cl$ yield (%); 85 m.p. (°C.); 202~203

Mass; 480 (M+1)

NMR δ(CDCl$_3$); 1.26 (3H, t, J=7.2 Hz), 1.72 (2H, m), 1.99 (2H, m), 2.59 (1H, m), 3.13 (2H, brt, J=11.2 Hz), 3.90 (3H, s), 4.15 (2H, q, J=7.2 Hz), 4.69 (2H, d, J=5.6 Hz), 4.80 (2H, m), 6.91 (1H, d, J=8.4 Hz), 7.25 (1H, dd, J=8.4 Hz, 2.4 Hz), 7.42 (1H, d, J=2.4 Hz), 7.43 (1H, brs), 7.61 (1H, dd, J=8.8 Hz, 1.6 Hz), 7.87 (1H, brs)

Example 209

2-[N-(3-Ethoxycarbonylpropyl)-N-methylamino]-4-(-3,4-methylenedioxybenzyl)amino-6-cyanoquinazoline

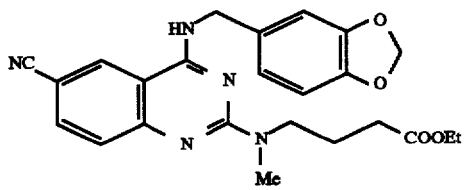

858 mg of ethyl N-methyl-4-aminobutyrate hydrochloride, 238 mg of triethylamine, 4 ml of 2-propanol and 2 ml of N,N-dimethylformamide were added to 400 mg of 2-chloro-4-(3,4-methylenedioxybenzyl)amino-6-cyanoquinazoline. The obtained mixture was refluxed for 1 hour, cooled to room temperature and filtered. The filtrate was distilled under a reduced pressure to remove the solvent and the residue was recrystallized (from ethanol/water) to give 410 mg of the title compound.

molecular formula; $C_{24}H_{25}N_5O_4$ yield (%); 78 m.p. (°C.); 152~153

Mass; 448 (M+1)

NMR δ(CDCl$_3$); 1.22 (3H, t, J=6.8 Hz), 1.97 (2H, brs), 2.30 (2H, brs), 3.24 (3H, s), 3.75 (2H, brs), 4.10 (2H, q, J=6.8 Hz), 4.68 (2H, d, J=5.2 Hz), 5.96 (2H, s), 6.79 (1H, d, J=8.0 Hz), 6.84 (1H, d, J=8.0 Hz), 6.87 (1H, s), 7.42 (1H, brs), 7.60 (1H, d, J=8.8 Hz), 7.81 (1H, brs)

Examples 210 to 221

The following compounds were prepared in a similar manner to that of Examples 205 to 209.

Example 210

2-(4-Ethoxycarbonylpiperidino)-4-(3,4-methylenedioxybenzyl)amino-6,7,8-trimethoxyquinazoline hydrochloride

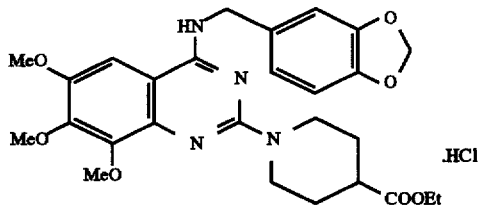

molecular formula; $C_{27}H_{32}N_4O_7 \cdot HCl$ yield (%); 65 m.p. (°C.); 148~150

Mass; 525 (M+1)

NMR δ(CDCl$_3$); 1.275 (3H, t, J=7.2 Hz), 1.76 (2H, m), 2.03 (2H, m), 2.63 (1H, m), 3.38 (2H, m), 3.99 (3H, s), 4.08 (3H, s), 4.12 (3H, s), 4.17 (2H, q, J=7.2 Hz), 4.28 (2H, m), 4.63 (2H, d, J=6.0 Hz), 5.88 (2H, s), 6.68 (1H, d, J=8.0 Hz), 6.92 (1H, dd, J=8.0 Hz, 1.6 Hz), 6.97 (1H, d, J=1.6 Hz), 8.23 (1H, s), 9.38 (1H, brs), 11.1 (1H, s)

Example 211

2-(4-Ethoxycarbonylpiperidino)-4-(3-chloro-4-methoxybenzyl)amino-6,7,8-trimethoxyquinazoline hydrochloride

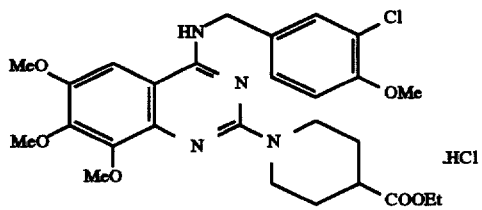

molecular formula; $C_{27}H_{33}N_4O_6Cl \cdot HCl$ yield (%); 93 m.p. (°C.); 177~178

Mass; 545 (M+1)

NMR δ(CDCl$_3$); 1.27 (3H, t, J=7.2 Hz), 1.80 (2H, m), 2.06 (2H, m), 2.67 (1H, m), 3.40 (2H, m), 3.82 (3H, s), 3.98 (3H, s), 4.07 (3H, s), 4.11 (3H, s), 4.17 (2H, q, J=7.2 Hz), 4.27 (2H, m), 4.65 (2H, d, J=6.0 Hz), 6.84 (1H, d, J=8.8 Hz), 7.40 (1H, d, J=2.0 Hz), 7.48 (1H, dd, J=8.8 Hz, 2.0 Hz), 8.23 (1H, s), 9.26 (1H, s), 11.27 (1H, brs)

Example 212

2-(4-Ethoxycarbonylpiperidino)-4-(3-chloro-4-methoxybenzyl)amino-6-chloroquinazoline

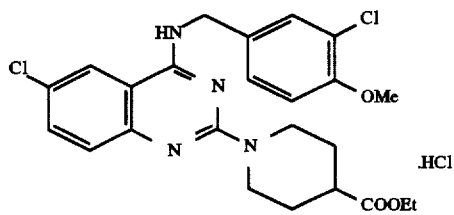

molecular formula; $C_{24}H_{26}N_4O_3Cl_2 \cdot HCl$ yield (%); 97 m.p. (°C.); 201~204

Mass; 489 (M+1)

NMR δ(DMSO-d$_6$); 1.17 (3H, t, J=7.2 Hz), 1.56 (2H, m), 1.93 (2H, m), 2.71 (1H, m), 3.30 (2H, m), 3.80 (3H, s), 4.06 (2H, q, J=7.2 Hz), 4.48 (2H, m), 4.66 (2H, d, J=5.2 Hz), 7.09 (1H, d, J=8.4 Hz), 7.34 (1H, dd, J=8.4 Hz, 2.0 Hz), 7.49 (1H, d, J=2.0 Hz), 7.83 (2H, brs), 8.48 (1H, brs), 10.8 (1H, brs)

Example 213

2-(Ethoxycarbonylmethyl)amino-4-(3,4-methylenendioxybenzyl)amino-6-chloroquinazoline

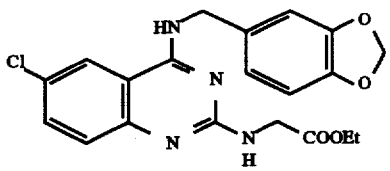

molecular formula; $C_{20}H_{19}N_4O_4Cl$ yield (%); 55 m.p. (°C.); 218~219 (dec.)

Mass m/e; 415 (M+1)

NMR δ(DMSO-d$_6$); 1.13 (3H, t, J=7.2 Hz), 4.07 (2H, q, J=7.2 Hz), 4.18 (2H, brs), 4.63 (2H, brd, J=4.0 Hz), 5.97 (2H, s), 6.85~6.92 (3H, m), 7.53 (1H, brs), 7.84 (1H, brd, J=8.0 Hz), 8.35 (1H, brs), 8.50 (2H, m)

Example 214

2-(3-Ethoxycarbonylpropyl)amino-4-(3,4-methylenedioxybenzyl)amino-6-chloroquinazoline

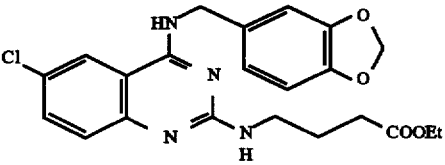

molecular formula; $C_{22}H_{23}N_4O_4Cl$ yield (%); 44 m.p. (C); 96~98

Mass m/e; 443 (M+1)

NMR δ(CDCl$_3$); 1.24 (3H, t, J=68.8 Hz), 1.96 (2H, quintent, J=7.2 Hz), 2.41 (2H, t, J=7.2 Hz), 3.54 (2H, q, J=7.2 Hz), 4.12 (2H, q, J=6.8 Hz), 4.66 (2H, q, J=5.2 Hz), 5.97 (2H, s), 6.79 (1H, d, J=8.0 Hz), 6.84 (1H, d, J=8.0 Hz), 6.87 (1H, s), 7.30 (1H, d, J=8.0 Hz), 7.44 (1H, s), 7.47 (1H, d, J=8.0 Hz)

Example 215

2-[N-(3-Ethoxycarbonylpropyl)-N-methylamino]-4-(4-methylenedioxybenzyl)amino-6-chloroquinazoline hydrochloride molecular formula; C₂₃H₂₅N₄O₄Cl.HCl yield (%); 67 m.p. (°C.); 182~183

Mass; 457 (M+1)

NMR δ(CDCl₃+DMSO-d₆); 1.23 (3H, t, J=7.2 Hz), 1.90 (2H, brs), 2.25 (2H, brs), 2.84 (3H, brs), 3.56 (2H, brs), 4.10 (2H, q, J=7.2 Hz), 4.70 (2H, d, J=5.6 Hz), 5.94 (2H, s), 6.76 (1H, d, J=7.6 Hz), 6.87 (2H, m), 7.54 (1H, dd, J=9.2 Hz, 2.0 Hz), 8.40 (1H, d, J=2.0 Hz), 8.66 (1H, d, J=9.2 Hz), 9.69 (1H, brs)

Example 216

2-(5-Ethoxycarbonylpentyl)amino-4-(3,4-methylenedioxybenzyl)amino-6-chloroquinazoline molecular formula; C₂₄H₂₇N₄O₄Cl yield (%); 46 m.p. (°C.); 109~110

Mass m/e; 471 (M+1)

NMR δ(CDCl₃); 1.25 (3H, t, J=7.2 Hz), 1.43 (2H, quintet, J=7.6 Hz), 1.66 (4H, m), 2.31 (2H, t, J=7.6 Hz), 3.49 (2H, q, J=7.6 Hz), 4.12 (2H, q, J=7.2 Hz), 4.68 (2H, d, J=5.2 Hz), 5.97 (2H, s), 6.79 (1H, d, J=8.0 Hz), 6.84 (1H, d, J=8.0 Hz), 6.87 (1H, s), 7.43 (3H, m)

Example 217

(S)-2-(N-2-Ethoxycarbonylpyrrolidin-1-yl)-4-(3,4-methylenedioxybenzyl)amino-6-chloroquinazoline hydrochloride molecular formula; C₂₃H₂₁N₄O₄Cl.HCl yield (%); 52 m.p. (°C.); 206~208

Mass; 455 (M+1)

NMR δ(CDCl₃); 1.19 (3H, t, J=7.2 Hz), 2.17 (3H, m), 2.32 (1H, m), 4.12 (2H, m), 4.24 (2H, m), 4.62 (2H, m), 4.67 (1H, m), 5.93 (2H, s), 6.77 (1H, d, J=8.0 Hz), 6.86 (1H, dd, J=8.0 Hz, 1.6 Hz), 6.89 (1H, d, J=1.6 Hz), 7.54 (1H, d, J=8.8 Hz), 8.38 (1H, s), 8.64 (1H, d, J=8.8 Hz), 9.67 (1H, brs), 13.38 (1H, brs)

Example 218

2-(N-Ethoxycarbonylmethyl-N-methylamino)-4-(3,4-methylenedioxybenzyl)amino-6-cyanoquinazoline molecular formula; C₂₂H₂₁N₅O₄ yield (%); 75 m.p. (°C.); 171~172

Mass; 420 (M+1)

NMR δ(DMSO-d₆); 1.12 (3H, m), 3.18 (3H, s), 4.03 (2H, m), 4.38 (2H, m), 4.51 (2H, m), 5.95 (2H, s), 6.84 (3H, m), 7.30 (1H, m), 7.76 (1H, m), 8.58 (1H, s), 8.79 (1H, m)

Example 219

2-[N-Ethyl-N-(3-ethoxycarbonylpropyl)amino]-4-(3,4-methylenedioxybenzyl)amino-6-cyanoquinazoline molecular formula; C₂₅H₂₇N₅O₄ (461.522)

yield (%); 61 m.p. (°C.); 142~143

Mass; 462 (M+1)

NMR δ(DMSO-d₆); 1.0~1.15 (3H, br 2 peaks), 1.13 (3H, t, J=7.1 Hz), 1.65~1.9 (2H, br 2 peaks), 2.15~2.35 (2H, br 2 peaks), 3.58 (4H, brs), 4.01 (2H, q, J=7.1 Hz), 4.58 (2H, d, J=5.7 Hz), 5.96 (2H, s), 6.84 (2H, s), 6.93 (1H, s), 7.25 (1H, brs), 7.72 (1H, dd, J=1.8 Hz, 8.8 Hz), 8.56 (1H, d, J=1.8 Hz), 8.72 (1H, t, J=5.7 Hz)

Example 220

2-(N-(3-Ethoxycarbonylpropyl)-N-methylamino]-4-(3-chloro-6-cyanoquinazoline

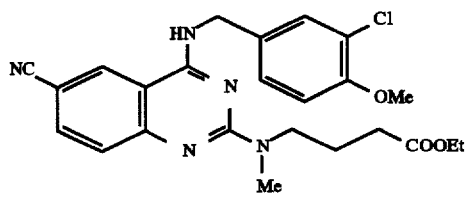

molecular formula; C₂₄H₂₆N₅O₃Cl yield (%); 72 m.p. (°C.); 127~128

Mass; 468 (M+1)

NMR δ(DMSO-d₆); 1.11 (3H, t, J=7.2 Hz), 1.74 (2H, brs), 2.14 (2H, brs), 3.09 (3H, s), 3.62 (2H, brs), 3.81 (3H, s), 3.98 (2H, q, J=7.2 Hz), 4.61 (2H, d, J=6.0 Hz), 7.07 (1H, d, J=8.8 Hz), 7.20~7.36 (2H, m), 7.42 (1H, s), 7.72 (1H, d, J=8.8 Hz), 8.55 (1H, s), 8.75 (1H, t, J=6.0 Hz)

Example 221

(S)-2-(N-2-Ethoxycarbonylpyrrolidin-1-yl)-4-(3,4-methylenedioxybenzyl)amino-6-cyanoquinazoline hydrochloride

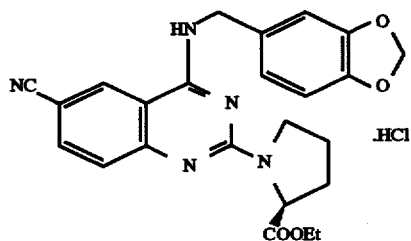

molecular formula; C₂₄H₂₃N₅O₄·HCl yield (%); 44 m.p. (°C.); 231~232

Mass; 446 (M+1)

NMR δ(CDCl₃); 1.21 (3H, t, J=7.2 Hz), 2.19 (3H, m), 2.36 (1H, m), 4.15 (2H, m), 4.28 (2H, m), 4.62 (2H, m), 4.76 (1H, m), 5.95 (2H, s), 6.79 (1H, d, J=8.0 Hz), 6.86 (1H, d, J=8.0 Hz), 6.88 (1H, s), 7.80 (1H, dd, J=8.8 Hz, 1.6 Hz), 8.82 (1H, d, J=1.6 Hz), 8.87 (1H, d, J=8.8 Hz), 9.85 (1H, brs), 13.81 (1H, s)

Example 222

2-(4-Carboxypiperidino)-4-(3,4-methylenedioxybenzyl)amino-6-chloroquinazoline

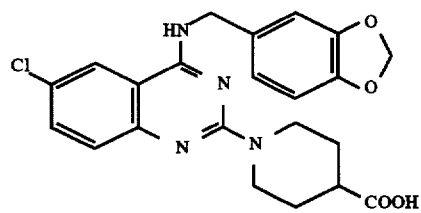

10 ml of ethanol, 5 ml of water and 820 mg of sodium hydroxide were added to 1 g of 2-(4-ethoxycarbonylpiperidino)-4-(3,4-methylenedioxybenzyl)amino-6-chloroquinazoline. The obtained mixture was refluxed for 20 minutes, concentrated under a reduced pressure and neutralized with 1N hydrochloric acid. The crystals thus precipitated were recovered by filtration to give 920 mg of the title compound.

molecular formula; C₂₂H₂₁N₄O₄Cl yield (%); 98 m.p. (°C.); 221~222

Mass m/e; 441 (M+1)

NMR δ(DMSO-d₆); 1.38 (2H, m), 1.80 (2H, dd, J=13.2 Hz, 2.4 Hz), 2.48 (1H, m), 2.96 (2H, t, J=12.0 Hz), 4.54 (2H, d, J=5.6 Hz), 4.56 (2H, dt, J=12.0 Hz, 3.2 Hz), 5.94 (2H, s), 6.81 (1H, d, J=8.0 Hz), 6.84 (1H, d, J=8.0 Hz), 6.93 (1H, s), 7.24 (1H, d, J=9.2 Hz), 7.46 (1H, dd, J=9.2 Hz, 2.0 Hz), 8.13 (1H, d, J=2.0 Hz), 8.55 (1H, t, J=5.6 Hz)

Example 223

Sodium 2-(4-Carboxypiperidino)-4-(3,4-methylenedioxybenzyl)amino-6-chloroquinazoline

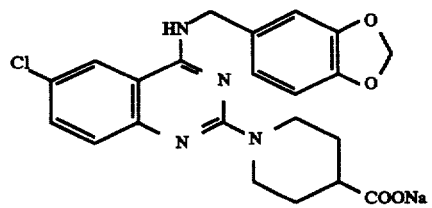

12 ml of a 1N aqueous solution of sodium hydroxide and 40 ml of water were added to 5.00 g (11.3 mmol) of the 2-(4-carboxypiperidino)-4-(3,4-methylenedioxybenzyl)amino-6-chloroquinazoline prepared in Example 222. The obtained mixture was dissolved by heating and cooled by allowing to stand. The crystals thus precipitated were recovered by filtration under suction, washed with a small amount of water, and vacuum-dried in the presence of phosphorus pentaoxide to give 4.34 g of the title compound.

molecular formula; C₂₂H₂₀ClN₄O₄Na yield (%); 98

NMR δ(DMSO-d₆); 1.42(2H, m), 1.73(2H, m), 2.06(1H, m), 2.95(2H, m), 4.52(2H, m), 4.56(2H, d, J=5.6 Hz), 5.95(2H, s), 6.81(1H, d, J=8.0 Hz), 6.86(1H, dd, J=8.0 Hz, 1.6 Hz), 6.95(1H, d, J=1.6 Hz), 7.22(1H, d, J=9.2 Hz), 7.44(1H, dd, J=9.2 Hz, 2.4 Hz), 8.13(1H, d, J=2.4 Hz), 8.58(1H, brt, J=5.6 Hz)

Example 224

Potassium 2-(4-Carboxypiperidino)-4-(3,4-methylenedioxybenzyl)amino-6-chloroquinazoline

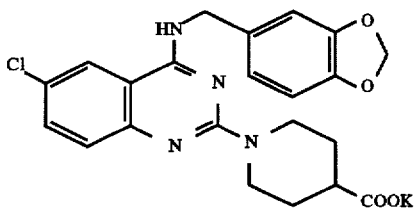

12.5 ml of a 1N aqueous solution of potassium hydroxide and 40 ml of water were added to 5.50 g (12.5 mmol) of the 2-(4-carboxypiperidino)-4-(3,4-methylenedioxybenzylamino)-6-chloroquinazoline prepared in Example 222. The obtained mixture was dissolved by heating and filtered. The filtrate was concentrated in a vacuum. Ethanol and ether were added to the obtained residue to precipitate crystals. The crystals were recovered by filtration, washed with ether, and vacuum-dried in the presence of phosphorus pentaoxide to give 4.69 g of the title compound.

molecular formula; $C_{22}H_{20}ClN_4O_4K$
yield (%); 78
m.p. (°C.); 230–234 (dec.)
NMR δ(DMSO-$d_6$); 1.39(2H, m), 1.69(2H, m), 1.96(1H, m), 2.94(2H, m), 4.48(2H, m), 4.55(2H, d, J=5.6 Hz), 5.96(2H, s), 6.81(1H, d, J=8.0 Hz), 6.86(1H, dd, J=8.0 Hz, 1.6 Hz), 6.94(1H, d,J=1.6 Hz), 7.22(1H, d, J=8.8 Hz), 7.43(1H, dd, J=8.8 Hz, 2.4 Hz), 8.11(1H, d, J=2.4 Hz), 8.50(1H, brt, J=5.6 Hz)

Example 225

2-(4-Carboxypiperidino)-4-(3,4-methylenedioxybenzyl)amino-6-chlororquinazoline hydrochloride

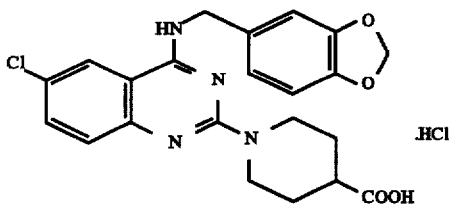

2.00 g (4.54 mmol) of the 2-(4-carboxypiperidino)-4-(3,4-methylenedioxybenzylamino)-6-chloroquinazoline prepared in Example 222 was dissolved in a mixture comprising 25 ml of tetrahydrofuran and 25 ml of ethanol under heating, followed by the dropwise addition of 1.0 ml of an 8M ethanolic solution of hydrochloric acid. The obtained mixture was cooled by allowing to stand to precipitate crystals. The crystals were recovered by filtration, washed with tetrahydrofuran, and air-dried to give 1.87 g of the title compound.

molecular formula; $C_{22}H_{21}N_4O_4Cl.HCl$
yield (%); 86
m.p. (°C.); 284–286
NMR δ(DMSO-$d_6$); 1.58(2H, m), 1.96(2H, m), 2.65(1H, m), 3.3(2H, m), 4.47(2H, m), 4.67(2H, d, J=5.8 Hz), 5.98 (2H, s), 6.87(1H, d, J=8.0 Hz), 6.90(1H, dd, J=8.0 Hz, 1.6 Hz), 7.00(1H, d, J=1.6 Hz), 7.83(2H, brs), 8.49(1H,brs), 10.09(1H, brs), 12.11(1H, brs), 12.40(1H, brs)

Example 226

2-(4-(Carboxypiperidino)-4-(3,4-methylenedioxybenzyl)amino-6-chloroquinazoline methanesulfonate

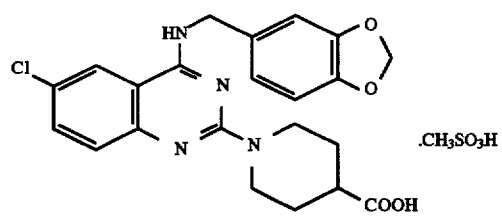

2.00 g (4.54 mmol) of the 2-(4-carboxypiperidino)-4-(3, 4-methylenedioxybenzylamino)-6-chloroquinazoline prepared in Example 222 was dissolved in a mixture comprising 25 ml of tetrahydrofuran and 25 ml of ethanol under heating, followed by the dropwise addition of 0.31 ml (4.78 mmol) of methanesulfonic acid. The obtained mixture was cooled by allowing to stand to precipitate crystals. The crystals were recovered by filtration, washed with tetrahydrofuran, and air-dried to give 2.21 g of the title compound.

molecular formula; $C_{22}H_{21}N_4O_4Cl.CH_4O_3S$
yield (%); 91
m.p. (°C.); 265–266
NMR δ(DMSO-$d_6$); 1.59(2H, m), 1.97(2H, m), 2.32(3H, s), 2.65(1H, m), 3.3(2H, m), 4.40(2H, m), 4.68(2H, d, J=5.6 Hz), 5.98(2H, s), 6.87(1H, d, J=8.0 Hz), 6.90(1H, dd, J=8.0 Hz, 1.6 Hz), 6.98(1H, d, J=1.66 Hz), 7.67(1H, d, J=8.8 Hz), 7.84(1H, dd, J=8.0 Hz, 2.0 Hz), 8.42(1H, d, J=2.0 Hz), 9.95(1H,brs), 11.76(1H, brs), 12.37(1H, brs)

Example 227

2-(4-Carboxypiperidino)-4-(3,4-methylenedioxybenzyl)amino-6-cyanoquinazoline

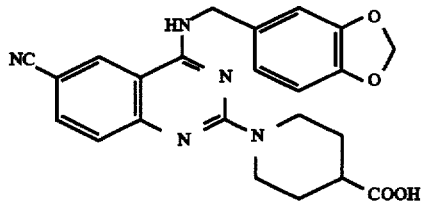

20 ml of ethanol and 2.0 ml of a 1N aqueous solution of sodium hydroxide were added to 318 mg of 2-(4-ethoxycarbonylpiperidino)-4-(3,4-methylenedioxybenzyl)amino-6-cyanoquinazoline. The obtained mixture was stirred at 50° C. for 30 minutes and neutralized with 1N hydrochloric acid. The crystal thus precipitated was recovered by filtration and purified by silica gel column chromatography (chloroform/methanol) to give 116 mg of the title compound.

molecular formula; $C_{23}H_{21}N_5O_4$
yield (%); 39
m.p. (°C.); 269–271

Mass m/e; 432 (M+1)

NMR δ(DMSO-d₆); 1.40 (2H, m), 1.79 (2H, m), 2.41 (1H, m), 3.04 (1H, dt, J=11.2 Hz, 1.2 Hz), 4.55 (2H, d, J=5.6 Hz), 4.57 (2H, m), 5.95 (2H, s), 6.82 (1H, d, J=8.0 Hz), 6.84 (1H, d, J=8.0 Hz), 6.94 (1H, s), 7.25 (1H, d, J=8.8 Hz), 7.71 (1H, d, J=8.8 Hz), 8.53 (1H, s), 8.72 (1H, t, J=5.6 Hz)

Example 228

2-(4-Carboxypiperidino)-4-(3-chloro-4-methoxybenzyl)amino-6-cyanoquinazoline

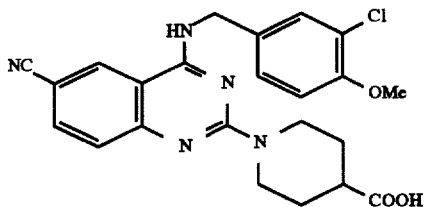

30 ml of tetrahydrofuran, 30 ml of ethanol and 14 ml of a 1N aqueous solution of sodium hydroxide were added to 1.0 g of 2-(4-ethoxycarbonylpiperidino)-4-(3-chloro-4-methoxybenzyl)amino-6-cyanoquinazoline. The obtained mixture was stirred at room temperature for 16 hours and neutralized with 1N hydrochloric acid, followed by the addition of 100 ml of water. The crystals thus precipitated were recovered by filtration and recrystallized from tetrahydrofuran/ethanol/water to give 860 mg of the title compound.

molecular formula; C₂₃H₂₂N₅O₃Cl yield (%); 91 m.p. (°C.); 277~278 (dec.)

Mass m/e; 452 (M+1)

NMR δ(DMSO-d₆); 1.40 (2H, m), 1.84 (2H, m), 2.51 (1H, m), 3.05 (2H, dt, J=12 Hz, 2.4 Hz), 3.82 (3H, s), 4.59 (2H, d, J=5.6 Hz), 4.63 (2H, m), 7.08 (1H, d, J=8.4 Hz), 7.28 (1H, d, J=8.8 Hz), 7.32 (1H, dd, J=8.4 Hz, 2.0 Hz), 7.45 (1H, d, J=2.0 Hz), 7.74 (1H, dd, J=8.8 Hz, 2.0 Hz), 8.54 (1H, d, J=2.0 Hz), 8.79 (1H, t, J=5.6 Hz)

Example 229

Sodium 2-(4-Carboxypiperidino)-4-(3-chloro-4-methoxybenzyl)amino-6-cyanoquinazoline

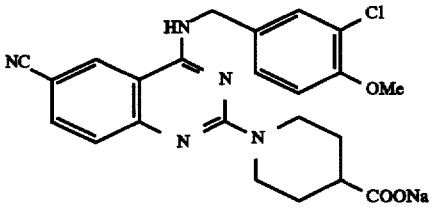

1.00 g (2.21 mmol) of the 2-(4-carboxypiperidino)-4-(3-chloro-4-methoxybenzyl)amino-6-cyanoquinazoline prepared in Example 228 was dissolved in a mixture comprising 30 ml of tetrahydrofuran and 40 ml of ethanol under heating, followed by the addition of 2.3 ml of a 1N aqueous solution of sodium hydroxide and 100 ml of water. The obtained mixture was concentrated in a vacuum to precipitate crystals. The crystals were recovered by filtration, washed with water, and air-dried to give 0.45 g of the title compound.

molecular formula; C₂₃H₂₁N₅O₃ClNa yield (%); 43

NMR δ(DMSO-d₆); 1.45 (2H, m), 1.75 (2H, m), 2.12 (1H, m), 3.06 (2H, m), 3.81 (3H, s), 4.52 (2H, m), 4.58 (2H, d, J=5.6 Hz), 7.07 (1H, d, J=8.8 Hz), 7.24 (1H, d, J=8.4 Hz), 7.32 (1H, dd, J=8.4 Hz, 2.0 Hz), 7.45 (1H, d, J=2.0 Hz), 7.69 (1H, dd, J=8.8 Hz, 2.0 Hz), 8.54 (1H, d, J=2.0 Hz), 8.86 (1H, brt, J=5.6 Hz)

Example 230

2-[N-(3-Carboxypropyl)-N-methylamino]-4-(3,4-methylenedioxybenzyl)amino-6-cyanoquinazoline

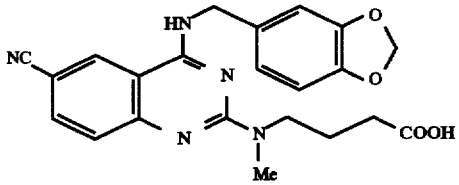

20 ml of ethanol and 2.61 ml of a 1N aqueous solution of sodium hydroxide were added to 389 mg of 2-(N-(3-ethoxycarbonylpropyl)-N-methoxyamino]-4-(3,4-methylenedioxybenzyl)amino-6-cyanoquinazoline. The obtained mixture was stirred at room temperature for 4 hours and at 50° C. for 10 minutes and neutralized with 1N hydrochloric acid. The crystals precipitated were recovered by filtration, purified by silica gel column chromatography (chloroform/methanol) and recrystallized from ethanol/acetone/water to give 305 mg of the title compound.

molecular formula; C₂₂H₂₁N₅O₄ yield (%); 84 m.p. (°C.); 138~140

Mass m/e; 420 (M+1)

NMR δ(CDCl₃(+DMSO-d₆);); 1.96 (2H, brs), 2.31 (brs), 3.24 (3H, s), 3.76 (2H, brs), 4.67 (2H, d, J=5.6 Hz), 5.94 (2H, s), 6.77 (1H, d, J=8.0 Hz), 6.86 (1H, d, J=8.0 Hz), 6.91 (1H, s), 7.58 (1H, brs), 7.61 (1H, d, J=8.4 Hz), 8.48 (2H, m)

Examples 231 to 245

The following compounds were prepared in a similar manner to those of Examples 222 to 230.

Example 231

2-(4-Carboxypiperidino)-4-(3,4-methylenedioxybenzyl)amino-6,7,8-trimethoxyquinazoline

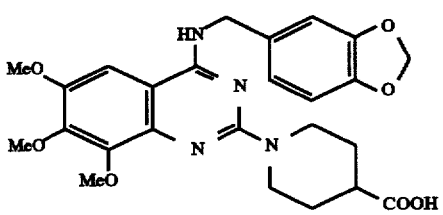

molecular formula; C₂₅H₂₈N₄O₇ yield (%); 73 m.p. (°C.); 216~217

Mass m/e; 297 (M+1)

NMR δ(CDCl₃); 1.80 (2H, m), 2.05 (2H, m), 2.65 (1H, m), 3.39 (2H, dt, J=10.8 Hz, 2.8 Hz), 3.98 (3H, s), 4.07 (3H, s), 4.13 (3H, s), 4.26 (2H, m), 4.70 (2H, d, J=6.0 Hz), 5.88 (2H, s), 6.69 (1H, d, J=7.6 Hz), 6.95 (1H, dd, J=7.6 Hz, 1.6 Hz), 7.02 (1H, d, J=1.6 Hz), 8.38 (1H, s), 9.36 (1H, s), 11.24 (1H, t, J=6.0 Hz)

Example 232

2-(4-Carboxypiperidino)-4-(3-chloro-4-methoxybenzyl)amino-6,7,8-trimethoxyquinazoline

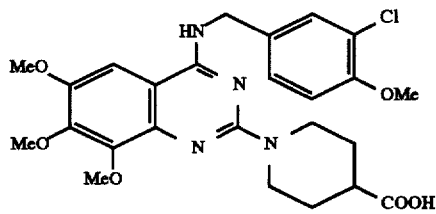

molecular formula; C₂₅H₂₉N₄O₆Cl yield (%); 90 m.p. (°C.); 197~198

Mass m/e; 517 (M+1)

NMR δ(DMSO-d₆); 1.45 (2H, brs), 1.90 (2H, brs), 2.59 (1H, brs), 3.22 (2H, brs), 3.80 (3H, s), 3.90 (6H, s), 3.92 (3H, s), 4.39 (2H, brs), 4.65 (2H, d, J=5.2 Hz), 7.05 (1H, d, J=8.4 Hz), 7.33 (1H, d, J=8.4 Hz), 7.45 (1H, s), 7.76 (1H, brs), 10.70 (1H, brs)

Example 233

2-(4-Carboxypiperidino)-4-(3,4-methylenedioxybenzyl)amino-6-methoxyquinazoline

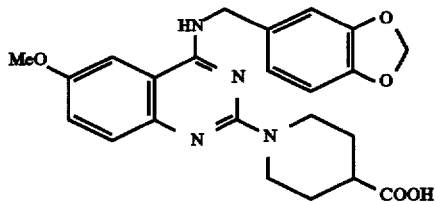

molecular formula; C₂₃H₂₄N₄O₅ (436)

yield (%); 79 m.p. (°C.); 263 (dec.)

Mass; 437 (M+1)⁺

NMR δ(DMSO-d₆); 1.51~1.59 (2H, m), 1.86~1.95 (2H, m), 2.59~2.64 (1H, m), 3.21~3.28 (2H, m), 4.39~4.44 (2H, m), 4.67 (2H, d, J=5.6 Hz), 5.78 (2H, s), 6.85 (1H, d, J=7.6 Hz), 6.89 (1H, d, J=7.6 Hz), 6.99 (1H, s), 7.42 (1H, dd, J=9.2 Hz, 1.6 Hz), 7.72 (1H, d, J=9.2 Hz), 7.86 (1H, d, J=1.6 Hz), 10.02 (1H, br), 11.89 (1H, s)

Example 234

2-(4-Carboxypiperidino)-4-(3-chloro-4-mehtoxybenzyl)amino-6-methoxyquinazoline

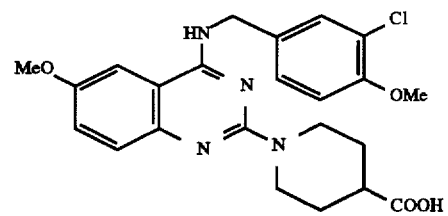

molecular formula; C₂₃H₂₅N₄O₄Cl (456.930)

yield (%); 81 m.p. (°C.); 245 (dec.)

Mass; 457 (MH⁺)

NMR; 1.3~1.5 (2H, m), 1.79 (2H, d, J=10 Hz), 2.4~2.5 (1H, m), 2.91 (2H, t, J=11 Hz), 3.81 (3H, s), 4.56 (2H, d, J=13 Hz), 4.60 (2H, d, J=5.7 Hz), 7.09 (1H, d, J=8.6 Hz), 7.18 (1H, dd, J=2.7 Hz, 9.2 Hz), 7.24 (1H, d, J=9.2 Hz), 7.32 (1H, dd, J=2.2 Hz, 8.6 Hz), 7.45 (1H, d, J=2.2 Hz), 7.49 (1H, d, J=2.7 Hz), 8.42 (1H, t, J=5.7 Hz), 12.15 (1H, brs)

Example 235

2-(4-Carboxypiperidino)-4-(3-chloro-4-methoxybenzyl)amino-6-chloroquinazoline

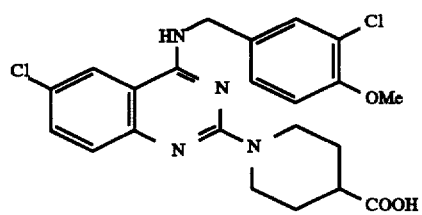

molecular formula; C₂₂H₂₂N₄O₃Cl₂ yield (%); 92 m.p. (°C.); 280~281

Mass m/e; 461 (M+1)

NMR δ(DMSO-d₆); 1.59 (2H, m), 1.94 (2H, brd, J=11.6 Hz), 2.62 (1H, brs), 3.32 (2H, m), 3.79 (3H, s), 4.52 (2H, d, J=13.6 Hz), 4.64 (2H, d, J=4.8 Hz), 6.99 (1H, d, J=8.4 Hz), 7.30 (1H, d, J=8.4 Hz), 7.42 (1H, s), 7.69 (1H, d, J=8.8 Hz), 8.00 (1H, d, J=8.8 Hz), 8.51 (1H, s), 10.24 (1H, s), 12.42 (1H, s)

Example 236

2-(4-Carboxypiperidino)-4-(benzimidazol-5-yl)methylamino-6-chloroquinazoline

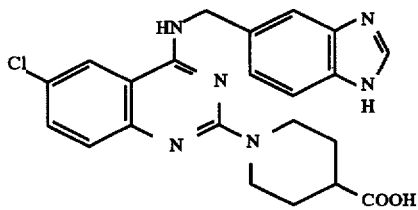

molecular formula; $C_{22}H_{21}N_6O_2Cl$ (436.903)
yield (%); 99
m.p. (°C.); 230 (dec.)
Mass; 437 (MH)$^+$
NMR δ(DMSO-$d_6$); 1.3–1.5 (2H, m), 1.82 (2H, d, J=10 Hz), 2.4–2.5 (1H, m), 2.98 (2H, t, J=11 Hz), 4.60 (2H, d, J=13 Hz), 4.77 (2H, d, J=5.7 Hz), 7.2–7.3 (2H, m), 7.45–7.6 (3H, m), 8.16 (1H, s), 8.19 (1H, d, J=2.4 Hz), 8.68 (1H, t, J=5.7 Hz), 12.17 (1H, brs), 12.33 (1H, brs)

Example 237

2-(Carboxymethyl)amino-4-(3,4-methylenedioxybenzyl)amino-6-chloroquinazoline

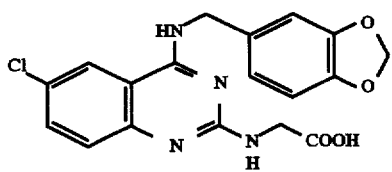

molecular formula; $C_{18}H_{15}N_4O_4Cl$
yield (%); 64
m.p. (°C.); 260–261 (dec.)
Mass m/e; 387 (M+1)
NMR δ(DMSO-$d_6$); 4.00 (2H, brs), 4.57 (2H, d, J=5.6 Hz), 5.93 (2H, s), 6.79 (1H, d, J=8.0 Hz), 6.86 (1H, d, J=8.0 Hz), 6.95 (1H, s), 7.35 (1H, brs), 7.50 (1H, brs), 8.30–8.50 (2H, m)

Example 238

2-(3-Carboxypropyl)amino-4-(3,4-methylenedioxybenzyl)amino-6-chloroquinazoline

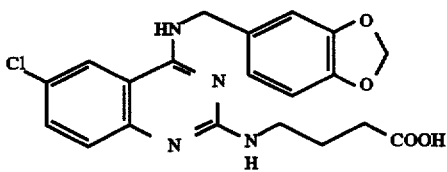

molecular formula; $C_{20}H_{19}N_4O_4Cl$
yield (%); 88
m.p. (°C.); 170–172
Mass m/e; 415 (M+1)
NMR δ(DMSO-$d_6$); 1.71 (2H, brs), 2.23 (2H, brs), 3.27 (2H, brs), 4.56 (2H, d, J=5.6 Hz), 5.95 (2H, s), 6.82 (3H, m), 6.95 (1H, s), 7.20. (1 h, brs), 7.46 (1H, dd, J=8.8 Hz, 1.6 Hz), 8.12 (1H, d, J=1.6 Hz)

Example 239

2-(5-Carboxypentyl)amino-4-(3,4-methylenedioxybenzyl)amino-6-chloroquinazoline

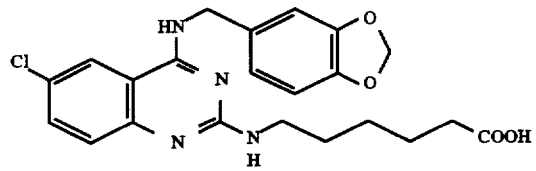

molecular formula; $C_{22}H_{23}N_4O_4Cl$
yield (%); 80
m.p. (°C.); 190–192
Mass m/e; 443 (M+1)
NMR δ(DMSO-$d_6$); 1.25 (2H, brs), 1.47 (4H, brs), 2.16 (2H, brs), 3.31 (2H, brs), 4.60 (2H, brs), 5.94 (2H, s), 6.84 (2H, s), 6.96 (1H, s), 7.33 (1H, brs), 7.60 (1H, brs), 8.25 (1H, brs)

Example 240

2-[N-(3-Carboxypropyl)-N-methylamino]-4-(3,4-methylenedioxybenzyl)amino-6-chloroquinazoline

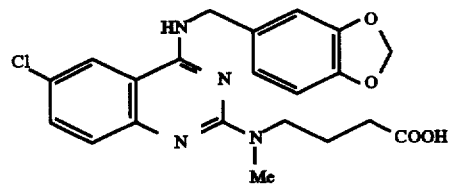

molecular formula; $C_{21}H_{21}N_4O_4Cl$
yield (%); 92
m.p. (°C.); 143–144
Mass m/e; 429 (M+1)
NMR δ(DMSO-$d_6$(+CD$_3$OD)); 1.79 (2H, brs), 2.20 (2H, brs), 3.21 (3H, s), 3.71 (2H, t, J=7.2 Hz), 4.65 (2H, s), 5.95 (2H, s), 6.81 (1H, d, J=8.0 Hz), 6.86 (1H, d, J=8.0 Hz), 6.95 (1H, s), 7.79 (1H, d, J=8.8 Hz), 7.85 (1H, d, J=8.8 Hz), 8.49 (1H, s)

Example 241

2-(N-Carboxymethyl-N-methylamino)-4-(3,4-methylenedioxybenzyl)amino-6-cyanoquinazoline

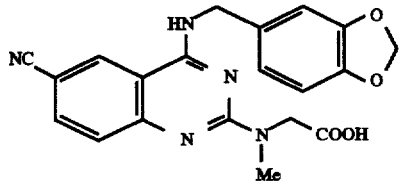

molecular formula; $C_{20}H_{17}N_5O_4$
yield (%); 68
m.p. (°C.); 268–270

Mass m/e; 392 (M+1)

NMR δ(DMSO-d₆); 3.11 (3H, s), 4.13 (2H, brs), 4.56 (2H, m), 5.94 (2H, s), 6.83 (2H, m), 6.93 (1H, d, J=14.4 Hz), 7.20 (1H, m), 7.66 (1H, m), 8.51 (1H, s), 8.62 (1H, m)

Example 242

2-[N-Ethyl-N-(3-carboxypropyl)amino]-4-(3,4-methylenedioxybenzyl)amino-8-cyanoquinazoline

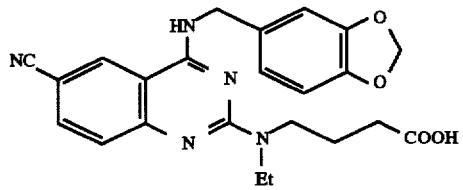

molecular formula; C₂₃H₂₃N₅O₄ (433.468)

yield (%); 96 m.p. (°C.); 186–187

Mass; 434 (M+1)

NMR δ(DMSO-d₆); 1.0–1.15 (3H, br 2 peaks), 1.65–1.85 (2H, br 2 peaks), 2.1–2.25 (2H, br 2 peaks), 3.57 (4H, brs), 4.58 (2H, d, J=5.7 Hz), 5.96 (2H, s), 6.84 (2H, s), 6.93 (1H, s), 7.26 (1H, d, J=8.8 Hz), 7.72 (1H, dd, J=1.8 Hz, 8.8 Hz), 8.56 (1H, d, J=1.8 Hz), 8.71 (1H, brs)

Example 243

2-[N-(3-Carboxypropyl)-N-methylamino]-4-(3-chloro-4-methoxybenzyl)amino-6-cyanoquinazoline

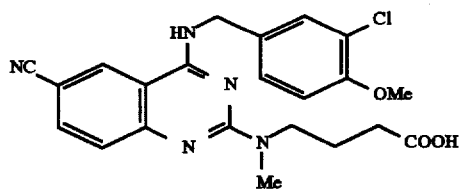

molecular formula; C₂₂H₂₂N₅O₃Cl yield (%); 88 m.p. (°C.); 108–109

Mass; 440 (M+1)

NMR δ(DMSO-d₆); 1.73 (2H, brs), 2.13 (2H, brs), 3.11 (3H, s), 3.63 (2H, brs), 3.82 (3H, s), 4.61 (2H, d, J=5.6 Hz), 7.07 (2H, d, J=8.4 Hz), 7.27 (1H, d, J=8.8 Hz), 7.31 (2H, d, J=8.4 Hz), 7.43 (3H, s), 7.72 (2H, s), 8.55 (3H, s), 8.74 (1H, brt, J=5.6 Hz), 12.02 (1H, brs)

Example 244

2-(4-Carboxypiperidino)-4-(benzimidazol-5-yl)methylamino-6-cyanoquinazoline

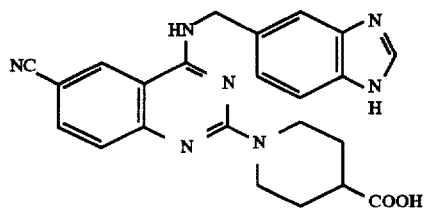

molecular formula; C₂₃H₂₁N₇O₂ (427)

yield (%); 50 m.p. (°C.); >290

Mass; 428 (M⁺+1)

NMR δ(DMSO-d₆); 1.29–1.42 (2H, m), 1.76–2.20 (2H, m), 2.39–2.51 (2H, m), 2.99–3.07 (3H, m), 4.60–4.64 (2H, m), 4.76 (2H, d, J=5.6 Hz), 7.23 (1H, d, J=8.4 Hz), 7.25 (1H, d, J=8.8 Hz), 7.51 (1H, d, J=8.4 Hz), 7.56 (1H, s), 7.71 (1H, dd, J=8.4 Hz, 1.6 Hz), 8.14 (1H, s), 8.57 (1H, d, J=1.6 Hz), 8.82 (1H, brt, J=5.6 Hz)

Example 245

2-(4-Carboxypiperidino)-4-(3,4-methylenedioxybenzyl)amino-6-carbamoylquinazoline

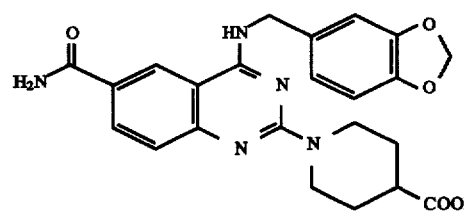

molecular formula; C₂₃H₂₃N₅O₅ (449)

yield (%); 6 m.p. (°C.); 180–182 (dec.)

Mass; 450 (M+1)

NMR δ(DMSO-d₆); 1.39 (2H, m), 1.81 (2H, m), 2.48 (1H, m), 2.99 (2H, m), 4.55 (2H, d, J=5.6 Hz), 4.62 (2H, m), 5.93 (2H, s), 6.81 (1H, d, J=7.6 Hz), 6.85 (1H, dd, J=7.6 Hz, 1.6 Hz), 6.95 (1H, d, J=1.6 Hz), 7.20 (1H, d, J=8.8 Hz), 7.27 (1H, br), 7.71 (1H, br), 7.92 (1H, dd, J=8.8 Hz, 2.0 Hz), 8.57 (1H, d, J=2.0 Hz), 8.59 (1H, brt, J=5.6 Hz), 12.09 (1H, br)

Example 246

2-Benzyloxymethyl-4-chloro-6-methoxyquinazoline

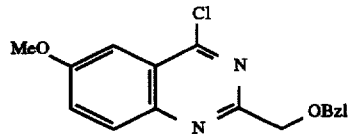

30 ml of phosphorus oxychloride was added to a suspension of 1.50 g (5.06 mmol) of 2-benzyloxymethyl-6-methoxyquinazolin-4(3H)-one in 75 ml of acetonitrile. The obtained mixture was heated under reflux. After one hour, the reaction mixture was distilled under a reduced pressure to remove the solvent and the obtained residue was dissolved in chloroform. The obtained solution was washed with a saturated aqueous solution of sodium hydrogencarbonate. The organic layer was dried over anhydrous magnesium sulfate and filtered. The filtrate was distilled under a reduced pressure to remove the solvent. The residue was purified by silica gel column chromatography (ethyl acetate/n-hexane) to give 1.10 g of the title compound as a yellow crystal.

yield (%); 69
m.p. (°C.); 49–50
Mass; 315 (M+1)⁺
NMR δ(CDCl₃); 3.98 (3H, s), 4.79 (2H, s), 4.84 (2H, s), 7.42 (1H, d, J=2.8 Hz), 7.26–7.46 (5H, m), 7.57 (1H, dd, J=9.2 Hz, 2.8 Hz), 8.01 (1H, d, J=9.2 Hz)

Example 247

2-Benzyloxymethyl-4-(3,4-methylenedioxybenzyl)amino-6-methoxyquinazoline

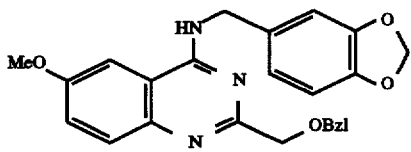

0.74 g (2.4 mmol) of the 2-benzyloxymethyl-4-chloro-6-methoxyquinazoline prepared in Example 246, 0.55 g (3.6 mmol) of piperonylamine and 0.50 g of sodium carbonate were mixed with 20 ml of isopropyl alcohol. The obtained mixture was heated under reflux. After 6 hours, the reaction mixture was distilled under a reduced pressure to remove the solvent and the residue was purified by silica gel column chromatography (ethyl acetate/n-hexane) and recrystallized from chloroform/n-hexane to give 1.01 g of the title compound as a yellow crystal.

molecular formula; C₂₅H₂₃N₃O₄
yield (%); quantitative
m.p. (°C.); 158–159
NMR δ(CDCl₃); 3.91 (3H, s), 4.69 (2H, s), 4.77 (2H, s), 4.79 (2H, d, J=5.6 Hz), 5.94 (2H, s), 6.77 (1H, d, J=7.6 Hz), 6.90 (1H, dd, J=7.6 Hz, 1.6 Hz), 6.94 (1H, d, J=1.6 Hz), 7.10 (1H, brs), 7.25–7.35 (5H, m), 7.41–7.44 (2H, m), 7.81 (1H, d, J=9.2 Hz)

Example 248

2,6-Dichloro-4-(3,4-methylenedioxybenzyl)oxyquinazoline

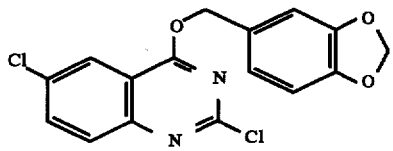

molecular formula; C₁₆H₁₀Cl₂N₂O₃
yield (%); 55
m.p. (°C.); 141–142
Mass m/e; 349 (M+1)

NMR δ(CDCl); 5.54(2H, s), 6.01(2H, s), 6.86(1H, d, J=8.8 Hz), 7.01(1H, d, J=8.8 Hz), 7.02(1H, s), 7.76(1H, dd, J=8.0 Hz, 2.4 Hz), 7.8(1H, dd, J=8.0 Hz, 0.8 Hz), 8.09(1H, dd, J=2.4 Hz, 0.8 Hz)

Example 249

2-(4-Carboxypiperidino)-4-(3,4-methylenedioxybenzyl)oxy-6-chloroquinazoline

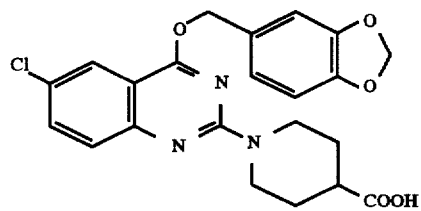

molecular formula; C₂₂H₂₀ClN₃O₅
yield (%); 84
m.p.(°C.); 145–147
Mass m/e; 442 (M+1)
NMR δ(DMSO-d₆); 1.47(2H, m), 1.88(2H, m), 2.49(1H, m), 3.10(2H, brt, J=13.2 Hz), 4.60(2H, brd, J=13.2 Hz), 5.43(2H, s), 6.01(2H, s), 6.91(1H, d, J=8.0 Hz), 7.02(1H, d, J=8.0 Hz), 7.11(1H, s), 7.39(1H, d, J=8.8 Hz), 7.61(1H, dd, J=8.8 Hz, 2.4 Hz), 7.77(1H, d, J=2.4 Hz)

Example 250

2,6-Dichloro-4-(3,4-methylenedioxybenzyl)thioquinazoline

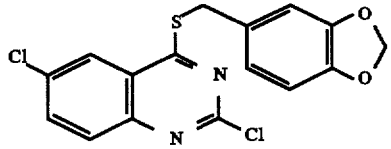

molecular formula; C₁₆H₁₀Cl₂N₂O₂S
yield (%); 92
m.p. (°C.); 180–182
Mass m/e; 365 (M+1)
NMR δ(CDCl₃); 4.55 (2H, s), 5.96 (2H, s), 6.77 (1H, d, J=8.4 Hz), 6.96 (1H, s), 6.96 (1H, d, J=8.4 Hz), 7.77 (1H, dd, J=8.8 Hz, 2.0 Hz), 7.82 (1H, d, J=8.8 Hz), 7.99 (1H, dd, J=2.0 Hz)

Example 251

2-(4-Carboxypiperidino)-4-(3,4-methylenedioxybenzyl)thio-6-chloroquinazoline

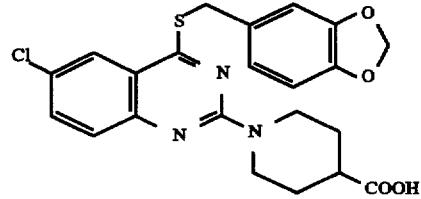

molecular formula; C₂₂H₂₀ClN₃O₄S
yield (%); 98 m.p. (°C.); 153~154

Mass m/e; 458 (M+1)

NMR δ(DMSO-d₆); 1.50(2H, m), 1.82(2H, m), 2.39(1H, brs), 3.18(2H, m), 4.48(2H, s), 4.55(2H, brs), 5.96(2H, s), 6.82(1H, d, J=8.0 Hz), 6.92(1H, d, J=8.0 Hz), 6.99(1H, s), 7.41(1H, brd, J=8.8 Hz), 7.82(1H, brd, J=8.8 Hz), 7.69(1H, brs)

Example 252

2-(4-Nitroxypiperidino)-4-(3,4-methylenedioxybenzyl)amino-6-chloroquinazoline

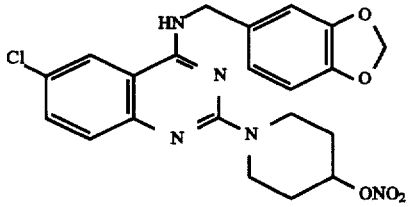

molecular formula; $C_{21}H_{20}ClN_5O_5$ yield (%); 11 m.p. (°C.); oily substance

Mass m/e; 458 (MH⁺)

NMR δ(CDCl₃); 1.71~1.82(2H, m), 2.02~2.10(2H, m), 3.56~3.63(2H, m), 4.39~4.44(2H, m), 4.66(2H, d, J=5.2 Hz), 5.18~5.22(1H, m), 5.61(1H, brt, J=5.2 Hz), 5.96(2H, s), 6.79(1H, d, J=7.6 Hz), 6.84(1H, dd, J=7.6 Hz, 1.2 Hz), 6.87(1H, d, J=1.2 Hz), 7.39(1H, d, J=8.8 Hz), 7.43~7.47(2H, m)

Example 253

2,6-Dichloro-4-(4-methylenedioxybenzyl)aminoquinoline

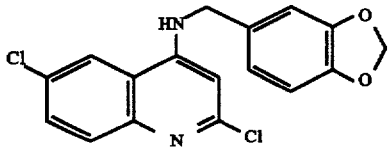

a) 2,4,6-Trichloroquinoline

The title compound was prepared from methyl 5-chloroanthranilate in a similar manner to that described in Journal of American Chemical Society, 68, 1285 (1946).

NMR δ(CDCl₃); 7.55(1H, s), 7.74(1H, dd, J=9.0 Hz, 2.2 Hz), 7.98(1H, d, J=9.0 Hz), 8.19(1H, d, J=2.2 Hz)

b) 2,6-Dichloro-4-(3,4-methylenedioxybenzyl)aminoquinoline

A reaction of a mixture comprising 500 mg of the compound prepared in the step (a), 350 mg of 3,4-methylenedioxybenzylamine, 1 ml of N,N-diisopropylethylamine and 4 ml of N-methyl-2-pyrrolidone was conducted on an oil bath of 130° C. for 10 hours. Water was added to the reaction mixture and the obtained mixture was extracted with ethyl acetate. The ethyl acetate layer was washed with water and a saturated aqueous solution of sodium chloride, dried over anhydrous magnesium sulfate, and concentrated. The residue was subjected to column chromatography with 5 to 20% ethyl acetate/hexane to give 430 mg of the title compound as a highly polar component.

molecular formula; $C_{17}H_{12}Cl_2N_2O_3$ m.p. (°C.); 198~199

Mass m/e; 347 (M+1)

NMR δ(CDCl₃); 4.39(2H, d, J=4.9 Hz), 5.21(1H, t, J=4.9 Hz), 6.00(2H, s), 6.47(1H, s), 6.82~6.87(3H, m), 7.58(1H, dd, J=9.0 Hz, 2.2 Hz), 7.65(1H, d, J=2.2 Hz), 7.84(1H, d, J=9.0 Hz)

Simultaneously, 190 mg of 4,6-dichloro-2-(3,4-methylenedioxybenzyl)aminoquinoline was obtained as a lowly polar component.

NMR δ(CDCl₃); 4.58(2H, d, J=5.7 Hz), 5.00(1H, brt, J=5.7 Hz), 5.94(2H, s), 6.74(1H, s), 6.77(1H, d, J=7.9 Hz), 6.84(1H, dd, J=7.9 Hz, 1.6 Hz), 6.88(1H, d, J=1.6 Hz), 7.50(1H, dd, J=9.0 Hz, 2.4 Hz), 7.62(1H, d, J=9.0 Hz), 7.96(1H, d, J=2.4 Hz)

Example 254

2,6-Dichloro-4-(3-chloro-4-methoxybenzylamino)quinoline

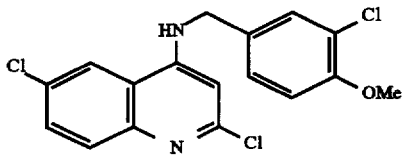

The titled compound was prepared in a similar manner to that of Example 253.

molecular formula; $C_{17}H_{13}Cl_3N_2O$ yield (%); 59 m.p. (°C.); 204~205

NMR δ(CDCl₃); 3.91(3H, s), 3.40(3H, s), 4.38(2H, d, J=5.1 Hz), 4.97(1H, t, J=5.1 Hz), 5.93(1H, s), 6.93(1H, d, J=8.4 Hz), 7.24(1H, dd, J=8.4 Hz, 2.2 Hz), 7.40(1H, d, J=2.2 Hz), 7.50(1H, dd, J=8.8 Hz, 2.2 Hz), 7.59(1H, d, J=2.2 Hz), 7.71 (1H, d, J=8.8 Hz)

Example 255

2-(4-Carboxypiperidino)-4-(3,4-methylenedioxybenzyl)amino-6chloroquinoline

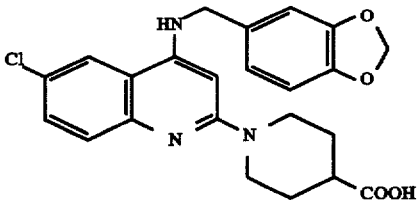

a) 2-(4-Ethoxycarbonylpiperidino)-4-methylenedioxybenzyl)amino-6-chloroquinoline A reaction of a mixture comprising 130 mg of 2,6-dichloro-4-(3,4-methylenedioxybenzyl)aminoquinoline, 500 82 1 of ethyl isonipecotate and 1 ml of N-methyl-2-pyrrolidone was conduct on an oil bath at 150° C. for 3 hours. The reaction mixture was cooled, followed by the addition of water. The resulting mixture was extracted with ethyl acetate and the ethyl acetate layer was washed with water and a saturated aqueous solution of sodium chloride, dried over anhydrous magnesium sulfate, and concentrated. The residue was purified by silica gel column chromatography with 20 to 50% ethyl acetate/hexane to give 150 mg of the title compound.

NMR δ(CDCl₃); 1.26(3H, t, J=7.1 Hz), 1.70~1.81(2H, m), 1.95~2.02(2H, m), 2.54(1H, tt, J=11.2 Hz, 3.8 Hz), 2.97~3.06(2H, m), 4.14(2H, q, J=7.1 Hz), 4.32~4.39(4H, m), 4.86(1H, t, J=5.5 Hz), 5.98(3H, s), 6.81(1H, d, J=7.7 Hz), 6.84~6.89(2H, m), 7.39(1H, dd, J=9.0 Hz, 2.4 Hz), 7.47(1H, d, J=2.4 Hz), 7.55(1H, d, J=9.0 Hz)

b) 2-(4-Carboxypiperidino)-4-(3,4-methylenedioxybenzyl)amino-6-chloroquinoline

A reaction of a mixture comprising 150 mg of the compound prepared in the step (a), 1 ml of a 1N aqueous solution of sodium hydroxide and 10 ml of ethanol was conducted on an oil bath at 60° C. for 2 hours. The reaction mixture was concentrated, followed by the addition of water. The resulting mixture was neutralized by the addition of 1 ml of 1N hydrochloric acid to precipitate crystals. The crystals were recovered by filtration, washed with water, and dried to give 130 mg of the title compound.

molecular formula; $C_{23}H_{22}ClN_3O_4$
yield (%); 92
m.p. (°C.); 235~237
Mass m/e; 440 (M+1)
NMR δ(DMSO-d₆); 1.37~1.50(2H, m), 1.77~1.86(2H, m), 2.89~3.00(2H, br, 3 peak), 4.20~4.28(2H, br, 2 peak), 4.42(2H, d, J=5.7 Hz), 5.96(2H, s), 5.97(1H, s), 6.85(1H, d, J=7.9 Hz), 6.92(1H, dd, J=7.9 Hz, 1.5 Hz), 6.98(1H, d, J=1.5 Hz), 7.42(2H, brs), 7.58(1H, brs), 8.15(1H, brs)

Example 256

2-(4-Carboxypiperidino)-4-(3-chloro-4-methoxybenzyl)amino-6-chloroquinoline

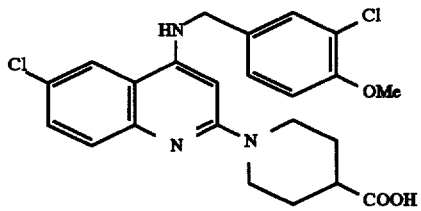

The title compound was prepared in a similar manner to that of Example 255.

molecular formula; $C_{23}H_{23}Cl_2N_3O_3$
m.p. (°C.); 282~283
Mass m/e; 460 (M+1)
NMR δ(DMSO-d₆); 1.36~1.48(2H, m), 1.76~1.84(2H, m), 2.43~2.53(1H, m), 2.91(2H, t, J=11.2 Hz), 4.26(2H, brd, J=13.2 Hz), 4.44(2H, d, J=5.9 Hz), 5.97(1H, s), 7.10(1H, d, J=8.6 Hz), 7.36(1H, dd, J=8.6 Hz, 2.2 Hz), 7.38(2H, s), 7.50(2H, brs and d, J=2.2 Hz), 8.11(1H, s)

Example 257

2-Methoxy-4-(3-chloro-4-methoxybenzyl)amino-6-chloroquinoline

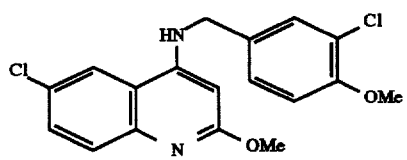

A mixture comprising 200 mg of 2,6-dichloro-4-(3-chloro-4-methoxybenzyl)aminoquinoline, 0.5 ml of methanol, 200 mg of potassium t-butoxide and 3 ml of 1,4-dioxane was heated under reflux for one hour and cooled, followed by the addition of water. The resulting mixture was extracted with ethyl acetate and the ethyl acetate layer was washed with a saturated aqueous solution of sodium chloride, dried over anhydrous magnesium sulfate, and concentrated. The residue was purified by silica gel column chromatography with 10 to 30% ethyl acetate/hexane and recrystallized from ethyl acetate/hexane to give 150 mg of the title compound.

molecular formula; $C_{18}H_{16}Cl_2N_2O_2$
yield (%); 76
m.p. (°C.); 170~171
NMR δ(CDCl₃); 3.93(3H, s), 4.42(2H, d, J=5.2 Hz), 5.22(1H, t, J=5.2 Hz), 6.46(1H, s), 6.96(1H, d, J=8.4 Hz), 7.25(1H, dd, J=8.4 Hz, 2.2 Hz), 7.41(1H, d, J=2.2 Hz), 7.59(1H, dd, J=9.0 Hz, 2.2 Hz), 7.66(1H, d, J=2.2 Hz), 7.85(1H, d, J=9.0 Hz)

Example 258

2-(3,4-Methylenedioxybenzylamino)-4-(4-carboxypiperidino)-6-chloroquinoline

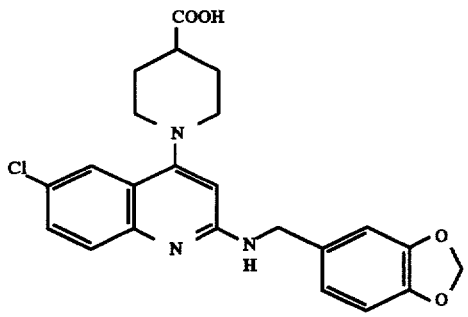

130 mg of the title compound was prepared from 140 mg of the 4,6-dichloro-2-(3,4-methylenedioxybenzyl)aminoquinoline prepared in the step (b) of Example 253 as a by-product in a similar manner to that of Example 255.

molecular formula; $C_{23}H_{22}ClN_3O_4$
yield (%); 99
m.p. (°C.); 270~272
Mass m/e; 440 (M+1)
NMR δ(DMSO-d₆); 1.78~1.89(2H, m), 1.96~2.04(2H, m), 2.70~2.79(2H, m), 3.26~3.36(2H, m), 4.49(2H, d, J=5.7 Hz), 5.96(2H, s), 6.37(1H, s), 6.85(2H, s), 6.94(1H, s), 7.37(1H, t, J=5.7 Hz), 7.41(1H, dd, J=8.8 Hz, 2.4 Hz), 7.46(1H, d, J=8.8 Hz), 7.60(1H, d, J=2.4 Hz)

Example 259

2-Chloro-4-(3-chloro-4-methoxybenzyl)amino-6-cyanoquinoline

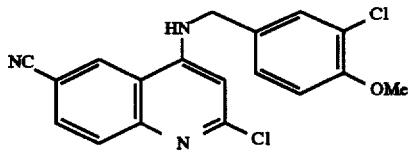

a) 4-Hydroxyquinoline-2-one-6-carboxylic acid

The title compound was prepared from dimethyl 4-aminobenzene-1,4-dicarboxylate in a similar manner to that described in Journal of American Chemical Society, 68, 1285 (1946), NMR δ(DMSO-d₆); 5.79(1H, s), 7.31(1H, d, J=8.6 Hz), 8.02(1H, dd, J=8.6 Hz, 2.0 Hz), 8.39(1H, d, J=2.0 Hz), 11.51(1H, s), 11.63(1H, brs), 12.86(1H, brs)

b) 2,4-Dichloroquinoline-6-carboxamide

A mixture comprising 9 g of the compound prepared in the step (a) and 50 ml of phosphorus oxychloride was heated under reflux for one hour. The reaction mixture was concentrated and ethyl acetate/acetone was added to the obtained residue to form a homogeneous suspension. This suspension was gradually poured into concentrated aqueous ammonia cooled with ice under stirring. After 30 minutes, the crystals thus precipitated were recovered by filtration, washed with water and ethyl acetate, and dried to give 8.96 g of the title compound.

NMR δ(DMSO-d₆); 7.72(1H, brs), 8.06(1H, s), 8.10(1H, d, J=8.8 Hz), 8.34(1H, dd, J=8.8 Hz, 2.0 Hz), 8.43(1H, brs), 8.73(1H, d, J=2.0 Hz)

c) 2,4-Dichloro-6-cyanoquinoline

A mixture comprising 3 g of the compound prepared in the step (b), 300 mg of lithium chloride and 30 ml of phosphorus oxychloride was heated under reflux for 2 hours. The reaction mixture was concentrated, followed by the addition of 120 ml of benzene. The resulting mixture was washed with a saturated aqueous solution of sodium hydrogencarbonate. The benzene layer was washed with a saturated aqueous solution of sodium chloride, dried over anhydrous magnesium sulfate, and filtered through a silica gel bed. The silica gel was further washed with benzene. The benzene solutions were combined and concentrated and the residue was recrystallized from ethyl acetate/hexane to give 2.15 g of the title compound.

NMR δ(CDCl₃); 7.65(1H, s), 7.95(1H, dd, J=8.8 Hz, 1.8 Hz), 8.14(1H, d, J=8.8 Hz), 8.60(1H, d, J=1.8 Hz)

d) 2-Chloro-4-(3-chloro-4-methoxybenzyl)amino-6-cyanoquinoline

A reaction of a mixture comprising 1 g of the compound prepared in the step (c), 1 g of 3-chloro-4-methoxybenzylamine hydrochloride, 2.4 ml of N,N-diisopropylethylamine and 10 ml of N-methyl-2-pyrrolidone was conducted on an oil bath at 130° C. for one hour. The reaction mixture was cooled, followed by the addition of water and ethyl acetate. The crystals thus precipitated were recovered by filtration, washed with water and ethyl acetate, and dried to give 610 mg of the title compound.

molecular formula; C₁₈H₁₃Cl₂N₃O yield (%); 38 m.p. (°C.); 254~255

NMR δ(CDCl₃); 3.94(3H, s), 4.45(2H, d, J=4.9 Hz), 5.41(1H, d, J=4.9 Hz), 6.54(1H, s), 6.98(1H, d, J=8.4 Hz), 7.26(1H, dd, J=8.4 Hz, 2.2 Hz), 7.41(1H, d, J=2.2 Hz), 7.80(1H, d, J=8.8 Hz, 1.6 Hz), 7.97(1H, d, J=8.8 Hz), 8.08(1H, d, J=1.6 Hz)

Example 260

2-(4-Carboxypiperidino)-4-(3-chloro-4-methoxybenzyl)amino-6-cyanoquinoline

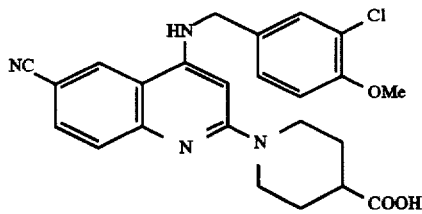

a) 2-(4-Ethoxycarbonylpiperidino)-4-(3-chloro-4-methoxybenzylamino)-6-cyanoquinoline A mixture comprising 750 mg of 2-chloro-4-(3-chloro-4-methoxybenzyl)amino-6-cyanoquinoline, 1.6 ml of isonipecotic acid and 5 ml of N-methyl-2-pyrrolidone was heated on an oil bath at 130° C. for 3 hours and cooled, followed by the addition of water. The resulting mixture was extracted with ethyl acetate and the ethyl acetate layer was washed with water and a saturated aqueous solution of sodium chloride, dried over anhydrous magnesium sulfate, and concentrated. The residue was subjected to silica gel column chromatography (20 to 40% ethyl acetate/hexane) and thereafter recrystallized from ethyl acetate/hexane to give 860 mg of the title compound.

NMR δ(CDCl₃); 1.26(3H, t, J=7.1 Hz), 1.68~1.79(2H, m), 1.95~2.03(2H, m), 2.58(1H, tt, J=11.0 Hz, 4.0 Hz), 3.03~3.12(2H, m), 3.92(3H, s), 4.15(2H, q, J=7.1 Hz), 4.36~4.43(4H, m), 5.08(1H, t, J=5.1 Hz), 5.94(1H, s), 6.95 (1H, d, J=8.4 Hz), 7.26(1H, dd, J=8.4 Hz, 2.2 Hz), 7.42(1H, d, J=2.2 Hz), 7.55~7.61(2H, m), 7.88(1H, s)

b) 2-(4-carboxypiperidino)-4-(3-chloro-4-methoxybenzylamino)-6-cyanoquinoline

A mixture comprising 500 mg of the compound prepared in the step (a), 2 ml of a 1N aqueous solution of sodium hydroxide, 20 ml of tetrahydrofuran and 25 ml of ethanol was reacted at 50° C. for 2 hours, followed by the addition of 2 ml of 1N hydrochloric acid. About 20 ml of the solvents was distilled away to precipitate crystals. The crystals were recovered by filtration, washed with water and ethyl acetate, and dried to give 460 mg of the title compound.

molecular formula; C₂₄H₂₃ClN₄O₃ yield (%); 98 m.p. (°C.); 274~276 (dec.)

NMR δ(DMSO-d₆); 1.35~1.47(2H, m), 1.79~1.87(2H, m), 2.47~2.56(1H, m), 2.95~3.04(2H, m), 3.81(3H, s), 4.30~4.39(2H, m), 4.46(2H, d, J=5.7 Hz), 6.01(1H, s), 7.11(1H, d, J=8.6 Hz), 7.37(1H, dd, J=8.6 Hz, 2.2 Hz), 7.40(1H, d, J=8.8 Hz), 7.52(1H, d, J=2.2 Hz), 7.65(1H, dd, J=8.8 Hz, 1.6 Hz), 7.68(1H, t, J=5.7 Hz), 8.55(1H, d, J=1.6 Hz), 12.20(1H, brs)

Example 261

2-Chloro-8-(3,4-methoxydioxybenzyl)aminopyrido[2,3-d]pyrimidine

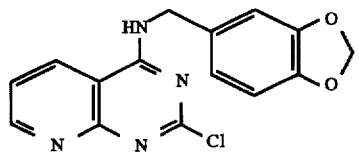

66 mg of triethylamine and 89 mg of piperonylamine were added to a solution of 118 mg of 2,8-dichloropyrido[2,3-d]pyrimidine in 20 ml of tetrahydrofuran. The obtained mixture was stirred at room temperature for 16 hours, followed by the addition of water. The crystals thus precipitated were recovered by filtration, whereby 166 mg of the title compound was obtained.

molecular formula; $C_{15}H_{11}ClN_4O_2$
yield (%); 89
m.p. (°C.); 200~202
Mass m/e; 315 (M+1)
NMR δ(DMSO-d$_6$); 4.64(1H, d, J=5.6 Hz), 5.97(2H, s), 6.85(1H, d, J=8.0 Hz), 6.87(1H, d, J=8.0 Hz), 6.96(1H, s), 7.55(1H, dd, J=8.0 Hz, 4.4 Hz), 8.73(1H, dd, J=8.0 Hz, 1.6 Hz), 8.96(1H, dd, J=4.4 Hz, 1.6 Hz), 9.46(1H, t, J=5.5 Hz)

Example 262

2-(4-Carboxypiperidino)-8-(3,4-methylenedioxybenzyl)aminopyrido[2,3-d]pyrimidine

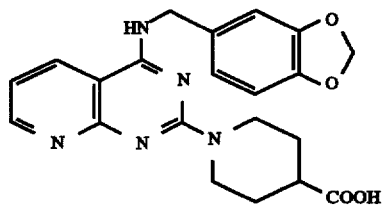

a) 2-(4-ethoxycarbonylpiperidino)-8-(3,4-methylenedioxybenzylamino)pyrido[2,3-d]pyrimidine

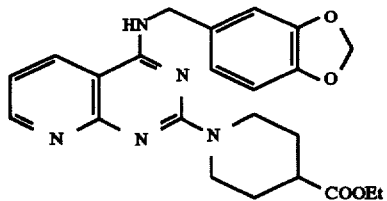

41 mg of triethylamine add 190 mg of ethyl isonipecotate were added to a solution of 127 mg of 2-chloro-8-(3,4-methylenedioxybenzyl)aminopyrido[2,3-d]pyrimidine in 8 ml of tetrahydrofuran. The obtained mixture was refluxed for 2 hours, followed by the addition of water. The resulting mixture was extracted with chloroform twice. The organic layers were combined, dried over magnesium sulfate, and distilled to remove the solvent. The residue was purified by silica gel chromatography (with ethyl acetate) to give 175 mg of the title compound (in a yield of 100%).

b) 2(4-carboxypiperidino)-8-(3,4-methylenedioxybenzyl)aminopyrido[2,3-d]pyrimidine

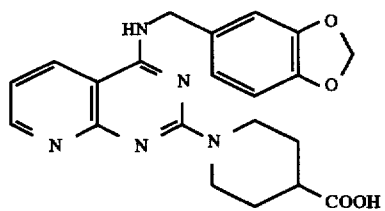

1.56 ml of 1N sodium hydroxide was added to a solution of 170 mg of 2-(4-ethoxycarbonylpiperidino)-8-(3,4-methylenedioxybenzyl)aminopyrido[2,3-d]-pyrimidine in 10 ml of ethanol. The obtained mixture was stirred at room temperature for 6 hours and neutralized by the addition of 1N hydrochloric acid and water. The crystals thus precipitated were recovered by filtration, whereby 121 mg of the title compound was obtained.

molecular formula; $C_{21}H_{21}N_5O_4$
yield (%); 76
m.p. (°C.); 255~256
Mass m/e; 408 (M+1)
NMR δ(DMSO-d$_6$); 1.39(2H, m), 1.80(2H, m), 2.51(1H, m), 3.01(2H, brt, J=11.2Hz), 4.56(2H, d, J=5.6 Hz), 4.61 (2H, brd, J=12.8 Hz), 5.94(2H, s), 6.82(1H, d, J=8.0 Hz), 6.84(1H, d, J=8.0 Hz), 6.93(1H, s), 7.03(1H, dd, J=8.0 Hz, 4.4 Hz), 8.38(1H, dd, J=8.0 Hz, 1.6 Hz), 8.61(1H, dd, J=4.4 Hz, 1.6 Hz), 8.70(1H, t, J=5.6 Hz), 12.16(1H, brs)

Example 293

5-Chloro-2-methanesulfonyl-1-(3,4-methylenedioxybenzyl)benzimidazole

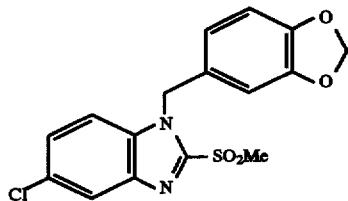

8.89 g of 6-chloro-2-mercaptobenzimidazole was dissolved in 150 ml of dimethylformamide, followed by the addition of 6.65 g of potassium carbonate and 6.15 g of methyl iodide under cooling with ice. The obtained mixture was stirred at that temperature for 50 minutes, followed by the addition of water. The resulting mixture was extracted with ethyl acetate. The ethyl acetate layer was dried and concentrated in a vacuum to give crude 6-chloro-2-methylthiobenzimidazole.

This crude product was dissolved in 100 ml of methylene chloride, followed by the addition of 17.3 g of 80% m-CPBA under cooling with ice. The obtained mixture was stirred at room temperature overnight, followed by the addition of 7 g of sodium thiosulfate. The resulting mixture was stirred at room temperature for 30 minutes, followed by the addition of water. The organic layer was recovered, dried and subjected to silica gel column chromatography to give 10 g of 6-chloro-2-methanesulfonylbenzimidazole.

2.3 g of the 6-chloro-2-methanesulfonylbenzimidazole was dissolved in 30 ml of dimethylformamide, followed by the addition of 480 mg of 60% sodium hydride and 2.04 g of piperonyl chloride under cooling with ice. The obtained mixture was maintained at 80° C. by heating for 4 hours, allowed to stand overnight and filtered to remove insolubles.

The filtrate was concentrated in a vacuum and subjected to silica gel column chromatography to give the title compound.

molecular formula; C₁₆H₁₃ClN₂O₄S
yield (%); 25
m.p. (°C.); 129~131
Mass m/e; 365 (MH⁺)
NMR δ(CDCl₃); 3.48(3H, s), 5.64(2H, s), 5.91(2H, s), 6.73~6.76(3H, m), 7.27(1H, d, J=8.8 Hz), 7.31(1H, dd, J=8.8 Hz, 2.0 Hz), 7.80(1H, d, J=2.0 Hz)

Example 264

6-Chloro-2-methanesulfonyl-1-(3,4-methylenedixoybenzyl)benzimidazole

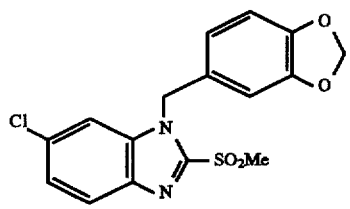

The title compound was obtained by further elution after the elution of the 5-chloro-2-methanesulfonyl-1-(3,4-methylene-dixoybenzyl)benzimidazole in Example 263.

molecular formula; C₁₆H₁₃ClN₂O₄S
yield (%); 22
m.p. (°C.); 140~142
Mass m/e; 365 (MH⁺)
NMR δ(CDCl₃); 3.48(3H, s), 5.62(2H, s), 5.93(2H, s), 6.73~6.77(3H, m), 7.32(1H, d, J=8.4 Hz), 7.33(1H, d, J=1.2 Hz), 7.74(1H, dd, J=8.4 Hz, 1.2 Hz)

Example 265

2-Chloro-2-methoxy-1-(3,4-methylenedioxybenzyl)benzimidazole

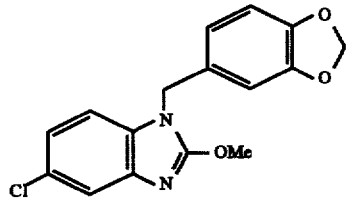

448 mg of a mixture comprising 5-chloro-2-sulfonylmethyl-1-(3,4-methylenedioxybenzyl)benzimidazole and 6-chloro-2-sulfonylmethyl-1-(3,4-methylenedioxybenzyl)benzimidazole was dissolved in 20 ml of methanol, followed by the addition of 10 ml of 28% sodium methoxide. The obtained mixture was heated under reflux for 1.5 hours, cooled with ice, neutralized with 10% aqueous hydrochlic acid, and extracted with ethyl acetate. The ethyl acetate layer was dried and concentrated in a vacuum. The residue was subjected to silica gel column chromatography to give the title compound.

molecular formula; C₁₆H₁₃ClN₂O₃
yield (%); 31
m.p. (°C.); 117~118

Mass m/e; 317 (MH⁺)
NMR δ(CDCl₃); 4.21(3H, s), 5.01(2H, s), 5.92(2H, s), 6.65(1H, d, J=1.6 Hz), 6.68(1H, dd, J=8.0 Hz, 1.6 Hz), 6.73(1H, d, J=8.0 Hz), 6.96(1H, d, J=8.4 Hz), 7.05(1H, dd, J=8.4 Hz, 2.0 Hz), 7.51(1H, d, J=2.0 Hz)

Example 266

6-Chloro-2-methoxy-1-(3,4-methylenedioxybenzyl)benzimidazole

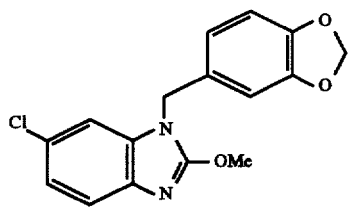

The title compound was obtained by further elution after the elution of the 5-chloro-2-methoxy-1-(3,4-methylenedioxybenzyl)benzimidazole in Example 265.

molecular formula; C₁₆H₁₃ClN₂O₃
yield (%); 26
m.p. (°C.); 133~134
Mass m/e; 317 (MH⁺)
NMR δ(CDCl₃); 4.21(3H, s), 4.99(2H, s), 5.92(2H, s), 6.65(1H, d, J=1.6 Hz), 6.68(1H, dd, J=8.0 Hz, 1.6 Hz), 6.74(1H, d, J=8.0 Hz), 7.05(1H, d, J=1.6 Hz), 7.10(1H, dd, J=8.8 Hz, 1.6 Hz), 7.43(1H, d, J=8.8 Hz)

Example 267 to 280

The following compounds were prepared in a similar manner to those of Examples 263 to 266.

Example 267

1-(3,4-Methylenedioxybenzyl)benzimidazole

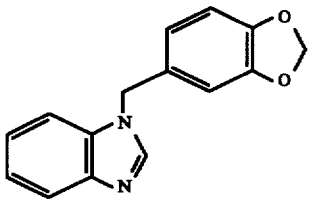

molecular formula; C₁₅H₁₂N₂O₂
yield (%); 34
m.p. (°C.); 107~108
Mass m/e; 253 (MH⁺)
NMR δ(CDCl₃); 5.23(2H, s), 5.92(2H, s), 6.63(1H, d, J=1.6 Hz), 6.70(1H, dd, J=8.0 Hz, 1.6 Hz), 6.76(1H, d, J=8.0 Hz), 7.23~7.32(3H, m), 7.80~7.83(1H, m), 7.9(1H, s)

Example 268

1-(2-Propoxybenzyl)benximidazole

molecular formula; $C_{17}H_{18}N_2O$
yield (%); 89
m.p. (°C.); 85~86
Mass m/e; 267 (MH$^+$)
NMR δ(CDCl$_3$); 1.02(3H, t, J=7.4 Hz), 1.78~1.86(2H, m), 3.95(2H, t, J=6.6 Hz), 5.35(2H, s), 6.86~6.90(2H, m), 7.06~7.09(1H m), 7.23~7.28(3H, m), 7.40~7.43(1H, m), 7.79~7.82(1H, m), 7.99(1H, s)

Example 269

2-(3,4-Methylenedioxybenzyl)benzimidazole

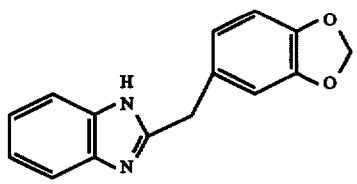

molecular formula; $C_{15}H_{12}N_2O_2$
yield (%); 62
m.p. (°C.); 143~146
Mass m/e; 253 (MH$^+$)
NMR δ(DMSO-d$_6$); 4.43(2H, s), 5.99(2H, s), 6.89~6.94 (2H, m), 7.09(1H, s), 7.48~7.52(2H, m), 7.72~7.76(2H, m)

Example 270

1-(3,4-Methylenedioxybenzyl)-6-methoxybenzimidazole

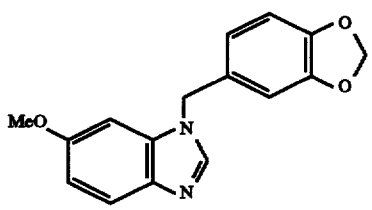

molecular formula; $C_{16}H_{14}N_2O_3$
yield (%); 70
m.p. (°C.); 134~135
Mass m/e; 283 (M+1)$^+$
NMR δ(CDCl$_3$); 3.82(3H, s), 5.21(2H, s), 5.95(2H, s), 6.64(1H, d, J=1.8 Hz), 6.71(1H, dd, J=7.6 Hz, 1.8 Hz), 6.75(1H, d, J=2.4 Hz), 6.78(1H, d, J=7.6 Hz), 6.93(1H, dd, J=8.8 Hz, 2.4 Hz), 7.70(1H, d, J=8.8 Hz), 7.90(1H, s)

Example 271

1-(2-Chloro-4,5-methylenedioxybenzyl)-6-methoxybenzimidazole

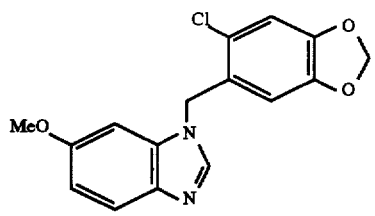

molecular formula; $C_{16}H_{13}ClN_2O_3$
yield (%); 81
m.p. (°C.); 108~109
Mass m/e; 317 (M+1)$^+$
NMR δ(CDCl$_3$); 3.84(3H, s), 5.322(2H, s), 5.97(2H, s), 6.40(1H, s), 6.80(1H, s), 6.91(1H, s), 6.95(1H, d, J=8.8 Hz), 7.72(1H, d, J=8.8 Hz), 7.96(1H, s)

Example 272

1-[2-(3,4-Methylenedioxyphenyl)ethyl]-6-methoxybenzimidazole

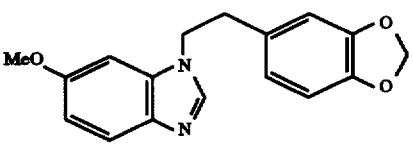

molecular formula; $C_{17}H_{16}N_2O_3$
yield (%); 69
m.p. (°C.); oily substance
Mass m/e; 297 (M+1)$^+$
NMR δ(CDCl$_3$); 3.04(2H, t, J=6.8 Hz), 3.87(3H, s), 4.31(2H, t, J=6.8 Hz), 5.93(2H, s), 6.43(1H, dd, J=8.0 Hz, 2.0 Hz), 6.52(1H, d, J=2.0 Hz), 6.68(1H, d, J=8.0 Hz), 6.77(1H, d, J=2.4 Hz), 6.92(1H, dd, J=8.8 Hz, 2.4 Hz), 7.57(1H, s), 7.67(1H, d, J=8.8 Hz)

Example 273

6-Chloro-1-(3,4-methylenedioxybenzyl)benzimidazole

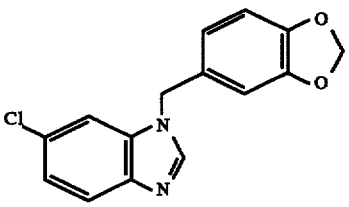

molecular formula; $C_{15}H_{11}N_2O_2$
m.p. (°C.); 122~123
Mass m/e; 287 (MH$^+$)
NMR δ(CDCl$_3$); 5.18(2H, s), 5.94(2H, s), 6.61(1H, d, J=1.2 Hz), 6.68(1H, dd, J=8.0 Hz, 1.2 Hz), 6.77(1H, d, J=8.0 Hz), 7.22~7.40(2H, m), 7.71(1H, d, J=8.8 Hz), 7.90(1H, s)

Example 274

5-Chloro-1-(3,4-methylenedioxybenzyl)benzimidazole

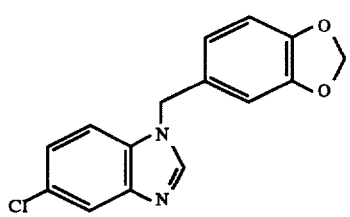

molecular formula; $C_{15}H_{11}ClN_2O_2$
yield (%); 83
m.p. (C); 113~114
Mass m/e; 287 (MH$^+$)
NMR δ(CDCl$_3$); 5.20(2H, s), 5.93(2H, s), 6.60(1H, d, J=1.6 Hz), 6.67(1H, dd, J=7.6 Hz, 1.6 Hz), 7.76(1H, d, J=7.6 Hz), 7.18~7.20(2H, m), 7.78(1H, s), 7.93(1H, s)

Example 275

6-Chloro-[3-(3,4-methylenedioxyphenyl)propyl]benzimidazole

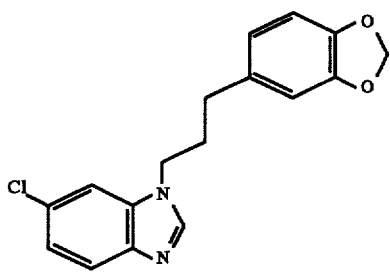

molecular formula; $C_{17}H_{15}ClN_2O_2$
yield (%); 40
m.p. (°C.); 107~109
Mass m/e; 315 (MH$^+$)
NMR δ(CDCl$_3$); 2.13~2.21(2H, m), 2.54(2H, t, J=7.4 Hz), 4.11(2H, t, J=7.2 Hz), 5.94(2H, s), 6.59(1H, dd, J=8.0 Hz, 1.6 Hz), 6.64(1H, d, J=1.6 Hz), 6.75(1H, d, J=8.0 Hz), 7.24(1H, dd, J=8.4 Hz, 2.0 Hz), 7.31(1H, d, J=2.0 Hz), 7.71(1H, d, J=8.4 Hz), 7.84(1H, s)

Example 276

6-Chloro-2-formyl-1-(3,4-methylenedioxybenzyl)benzimidazole

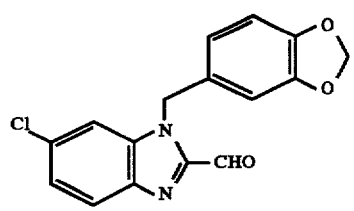

molecular formula; $C_{16}H_{11}ClN_2O_3$
yield (%); 55 m.p. (°C.); 120~122

Mass m/e; 315 (MH$^+$)

NMR δ(CDCl$_3$); 5.71(2H, s), 5.93(2H, s), 6.64(1H, d, J=1.6 Hz), 6.70(1H, dd, J=7.6 Hz, 1.6 Hz), 6.75(1H, d, J=7.6 Hz), 7.36(1H, dd, J=8.8 Hz, 2.0 Hz), 7.46(1H, d, J=2.0 Hz), 7.86(1H, d, J=8.8 Hz),

Example 277

2-Amino-6-chloro-1-(3,4-methylenedioxybenzyl)benzimidazole

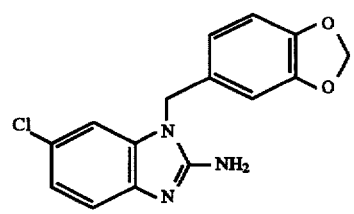

molecular formula; $C_{15}H_{12}ClN_3O_2$ yield (%); 10 m.p. (°C.); 223~224

Mass m/e; 302 (MH$^+$)

NMR δ(DMSO-d$_6$); 5.13(2H, s), 5.95(2H, s), 6.68~6.71 (3H, m), 6.77(1H, d, J=1.6 Hz), 6.84(1H, d, J=7.6 Hz), 6.90(1H, dd, J=8.4 Hz, 2.4 Hz), 7.07(1H, d, J=8.4 Hz), 7.18 (H, d, J=2.4 Hz)

Example 278

6-Chloro-2-(imidazol-1-yl)-1-(3,4-methylenedioxybenzyl)benzimidazole

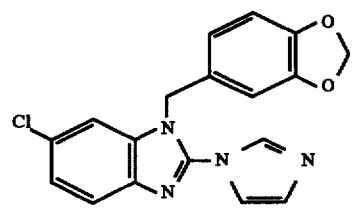

molecular formula; $C_{18}H_{13}ClN_4O_2$ yield (%); 41 m.p. (°C.); 127~129

Mass m/e; 353 (MH$^+$)

NMR δ(CDCl$_3$); 5.20(2H, s), 5.97(2H, s), 6.48~6.50(2H, m), 6.76(1H, d, J=7.2 Hz), 7.23~7.35(4H, m), 7.72(1H, d, J=8.4 Hz), 7.89(1H, s)

Example 279

2-(4-Carboxypiperidino)-5-chloro-1-(3,4-methylenedioxybenzyl)benzimidazole

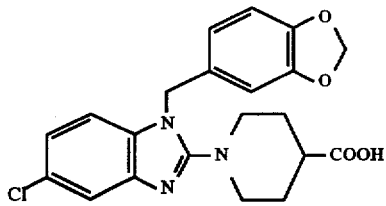

molecular formula; $C_{21}H_{20}ClN_3O_4$ yield (%); 84 m.p. (°C.); 201~202

Mass m/e; 414 (MH$^+$)

NMR δ(DMSO-d$_6$); 1.64~1.77(2H, m), 1.84~1.90(2H, m), 2.40~2.46(1H, m), 2.92~3.00(2H, m), 3.43~3.47(2H, m), 5.15(2H, s), 5.96(2H, s), 6.60(1H, dd, J=8.0 Hz, 1.6 Hz), 6.72(1H, d, J=1.6 Hz), 6.82(1H, d, J=8.0 Hz), 7.03(1H, dd, J=8.4 Hz, 2.0 Hz), 7.18(1H, d, J=8.4 Hz), 7.42(1H, d, J=2.0 Hz)

Example 280

2-(4-Carboxypiperidino)-6-chloro-1-(3,4-methylenedioxybenzyl)benzimidazole

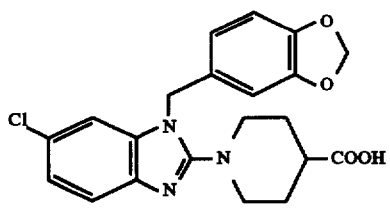

molecular formula; $C_{21}H_{20}ClN_3O_4$ m.p. (°C.); amorphous

Mass m/e; 414 (MH$^+$)

NMR δ(DMSO-d$_6$); 1.70~1.79(2H, m), 1.80~1.89(2H, m), 2.31~2.42(1H, m), 2.90~2.97(2H, m), 3.39~3.45(2H, m), 5.15(2H, s), 5.96(2H, s), 6.61(1H, d, J=8.0 Hz), 6.73 (1H, s), 6.83(1H, d, J=8.0 Hz), 7.06(1H, dd, J=8.4 Hz, 2.0 Hz), 7.30(1H, d, J=2.0 Hz), 7.38(1H, d, J=8.4 Hz)

Examples 281 to 291

The following compounds were prepared in a similar manner to those of Examples 88 to 94.

Example 281

2-(4-Carboxypiperidino)-4-(3,5-dichloro-4-methoxybenzylamino)-6-cyanoquinazoline

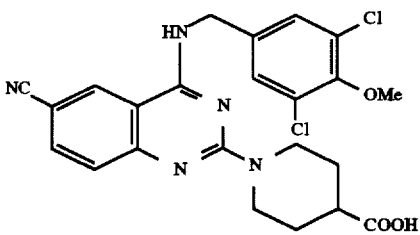

molecular formula; $C_{23}H_{21}Cl_2N_5O_3$ yield (%); 98 m.p. (°C.); 255~256 (dec.)

Mass m/e; 486 (M+1)$^+$

NMR δ(DMSO-d$_6$); 1.36(2H, brm), 1.80(2H, brm), 2.52 (1H, m), 3.03(2H, m), 3.78(3H, s), 4.59(2H d, J=6.0 Hz), 4.59(2H, brm), 7.29(1H, d, J=8.8 Hz), 7.50(2H, s), 7.75(1H, dd, J=8.8 Hz, 1.6 Hz), 8.53(1H, d, J=1.6 Hz), 8.85(1H, brt, J=6.0 Hz), 12.18(1H, brs)

Example 282

2,6-Dichloro-4-(4-ethoxycarbonylpiperidino)quinazoline

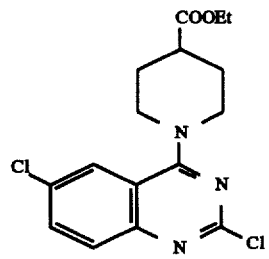

molecular formula; $C_{16}H_{17}Cl_2N_3O_2$ yield (%); 100 m.p. (°C.); 101~103

Mass m/e; 354 (M+1)

NMR δ(CDCl$_3$); 1.30(3H, t, J=7.2 Hz), 1.99(2H, m), 2.14(2H, m), 2.69(1H, m), 3.35(2H, dt, J=11.2 Hz, 2.4 Hz), 4.20(2H, q, J=7.2 Hz), 4.31(2H, dt, J=13.6 Hz, 3.6 Hz), 7.67(1H, dd, J=8.8 Hz, 2.2 Hz), 7.76(1H, d, J=8.8 Hz), 7.79(1H, d, J=2.2 Hz)

Example 283

2-[N-[2-(2-Pyridyl)ethyl]methylamino]-4-(3,4-methylenedioxybenzyl)-]-amino-6-chloroquinazoline dihydrochloride

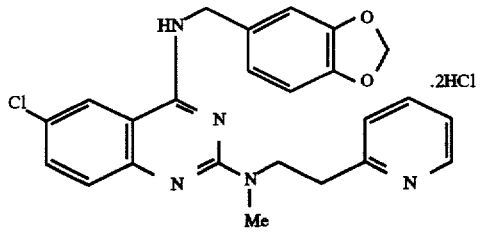

molecular formula; $C_{24}H_{22}ClN_5O_2 \cdot 2HCl$
yield (%); 94
m.p. (°C.); 234~236 (dec.)
Mass m/e; 448 (M+1)⁺
NMR δ(DMSO-d₆); 3.2~3.3(5H, br), 4.12(2H, br), 4.61 (2H, br), 5.97(2H, s), 6.82(1H, brd), 6.88(1H, brd), 7.00(1H, s), 7.74(2H, br), 7.86(1H, dd, J=9.2 Hz, 2.0 Hz), 8.01(1H, br), 8.26(1H, br), 8.57(1H, d, J=2.0 Hz), 8.74(1H, br), 10.16(1H, brs), 12.12(1H, brs)

Example 284

2-(4-Carboxypiperidino)-4-(3,4-dihydroxybenzyl)amino-6-chloroquinazoline

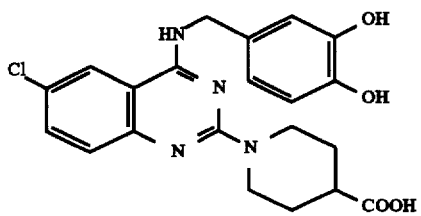

molecular formula; $C_{21}H_{21}ClN_4O_4$
yield (%); 95
m.p. (° C); 216~218 (dec.)
Mass m/e; 429 (MH⁺)
NMR δ(DMSO-d₆); 1.38~1.47(2H, m), 1.80~1.84(2H, m), 2.44~2.49(1H, m), 2.93~3.00(2H, m), 4.48(2H, d, J=5.6 Hz), 4.57~4.61(2H, m), 6.60~6.65(2H, m), 6.74(1H, d, J=1.6 Hz), 7.24(1H, d, J=8.8 Hz), 7.46(1H, dd, J=8.8 Hz, 2.0 Hz), 8.15(1H, d, J=2.0 Hz), 8.48(1H, brs), 8.675(1H, s), 8.75(1H, s), 12.14(1H, brs)

Example 285

2,6-Dichloro-4-(5-hydroxypentyl)aminoquinazoline

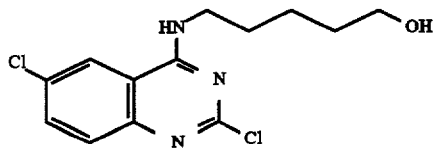

molecular formula; $C_{13}H_{15}Cl_2N_3O$
yield (%); 82 m.p. (°C.); 134~135
Mass m/e; 300 (M+1)⁺
NMR δ(CDCl₃); 1.53(2H, m), 1.65(2H, m), 1.76(2H, m), 3.63(2H, m), 3.66(2H, m), 7.61(1H, dd, J=8.8 Hz, 2.4 Hz), 7.67(1H, d, J=8.8 Hz), 7.85(1H, brs), 8.20(1H, d, J=2.4 Hz)

Example 286

2-(4-Carboxypiperidino)-4-(5-nitroxypentyl)amino-6-chloroquinazoline

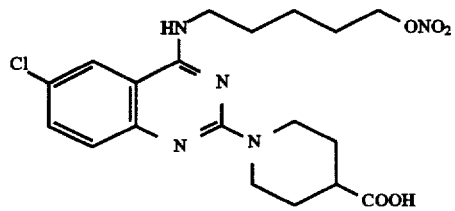

molecular formula; $C_{19}H_{24}ClN_5O_5$
yield (%); 80
m.p. (°C.); 176~179 (dec.)
Mass m/e; 438 (MH⁺)
NMR δ(DMSO-d₆); 1.3~2.00(10H, m), 2.57~2.64(1H, m), 3.18~3.59(4H, m), 4.44~4.58(4H, m), 7.72~7.86(2H, m), 8.39~8.41 (1H, m), 12.31(2H, brs)

Example 287

2-(Carboxymethyl)methylamino-4-(3-pyridylmethyl)amino-6-chloroquinazoline

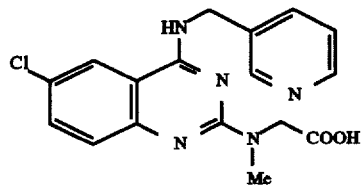

molecular formula; $C_{17}H_{16}ClN_5O_2$
yield (%); 97
m.p. (°C.); 222~223
Mass m/e; 358 (M+1)
NMR δ(DMSO-d₆); 3.10(3H, s), 4.22(2H, brs), 4.63(2H, brs), 7.31(2H, m), 7.48(1H, m), 7.72(1H, m), 8.14(1H, d, J=2.4 Hz), 8.43(1H, d, J=4.8 Hz), 8.59(1H, m), 8.66(1H, brs)

Example 288

2-[N-(3-Carboxypropyl)-N-methylamino]-4-(3-pyridylmethyl)amino-6-chloroquinazoline

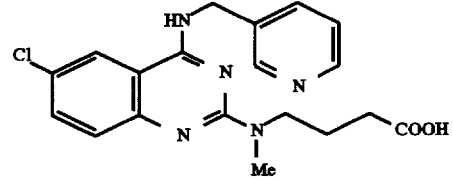

molecular formula; $C_{19}H_{20}ClN_5O_2$
yield (%); 41 m.p. (°C.); 110~112

Mass m/e; 386 (M+1)

NMR δ(DMSO-d₆); 1.67(2H, brs), 2.09(2H, m), 3.02(3H, s), 3.53(2H, t, J=6.8 Hz), 4.67(2H, d, J=5.6 Hz), 7.24(2H, d, J=8.8 Hz), 7.31(1H, dd, J=8.0 Hz, 4.8 Hz), 7.47(1H, dd, J=8.8 Hz, 2.0 Hz), 7.73(1H, d, J=8.0 Hz), 8.13(1H, d, J=2.0 Hz), 8.41 (1H, d, J=4.8 Hz), 8.58(1H, s), 8.62(1H, brs), 12.04(1H, brs)

Example 289

2-(4-Carboxypiperidino)-4-(2-pyridylmethyl)amino-6-chloroquinazoline

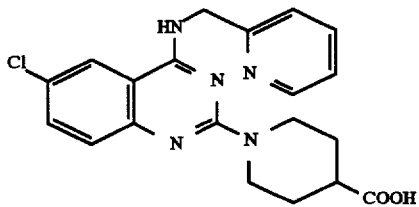

molecular formula; C₂₀H₂₀ClN₅O₂ yield (%); 92 m.p. (°C.); 235~237

Mass m/e; 398 (M+1)

NMR δ(DMSO-d₆); 1.25~1.45 (2H, m), 1.71~1.83(2H, m), 2.45~2.54(1H, m), 2.93~3.10(2H, m), 4.37~4.48(2H, m), 4.77(2H, d, J=5.5 Hz), 7.25(1H, dd, J=7.7 Hz, 5.0 Hz), 7.37(1H, d, J=7.7 Hz), 7.48(1H, brs), 7.63(1H, brs), 7.73 (1H, td, J=7.7 Hz, 1.6 Hz), 8.34(1H, brs), 8.51(1H, brd, J=5.0 Hz), 12.23(1H, brs)

Example 290

2-(4-Carboxypiperidino)-4-(pyridylmethyl)amino-6-chloroquinazoline

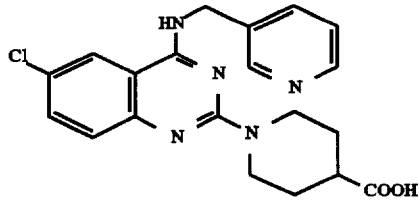

molecular formula; C₂₀H₂₀ClN₅O₂ yield (%); 93 m.p. (°C.); >250

Mass m/e; 398 (M+1)

NMR δ(DMSO-d₆); 1.45~1.60(2H, m), 1.84~1.97(2H, m), 2.58~2.68(1H, m), 3.25~3.45(2H, m), 4.45~4.54(2H, m), 4.80(2H, d, J=5.7 Hz), 7.41(1H, dd, J=7.9 Hz, 4.8 Hz), 7.82(1H, dd, J=9.0 Hz, 2.0 Hz), 7.86~7.96(2H, m), 8.50(1H, d, J=4.8 Hz), 8.55(1H d, J=1.6 Hz), 8.69(1H, s)

Example 291

2-(4-Carboxypiperidino)-4-(4-pyridylmethyl)amino-6-chloroquinazoline

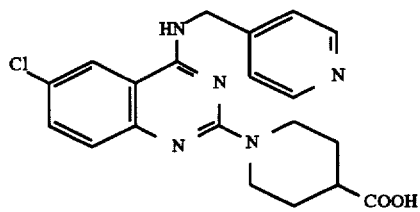

molecular formula; C₂₀H₂₀ClN₅O₂ yield (%); 89 m.p. (°C.); 167~168

Mass m/e; 398 (M+1)

NMR δ(DMSO-d₆); 1.24~1.36(2H, m), 1.68~1.77(2H, m), 2.40~2.49(1H, m), 2.86~2.96(2H, m), 4.42~4.50(2H, m), 4.66(2H, d, J=5.7 Hz), 7.28(1H, d, J=9.0 Hz), 7.34(2H, d, J=6.0 Hz), 7.51(1H, dd, J=9.0 Hz, 2.4 Hz), 8.18(1H, d, J=2.4 Hz), 8.47(2H, d, J=6.0 Hz), 8.74(1H, t, J=5.7 Hz)

Example 292

2-(6-Nitroxyhexyloxy)-4-(3,4-methylenedioxybenzyl)amino-6-chloroquinazoline

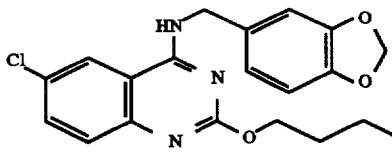

860 mg of 2-(6-hydroxyhexyloxy)-4-(3,4-methylenedioxybenzyl)amino-6-chloroquinazoline was dissolved in 15 ml of pyridine, followed by the addition of 570 mg of methyl chloride under cooling with ice. The obtained mixture was stirred for 10 hours, followed by the addition of water. The resulting mixture was extracted with ethyl acetate. The ethyl acetate layer was dried and concentrated to give 1.2 g of crude 2-(6-tosyloxyhexyloxy)-4-(3,4-methylenedioxybenzyl)amino-6-chloroquinazoline.

3 g of sodium iodide and 30 ml of dimethylformamide were added to the crude product. The obtained mixture was maintained at 60° C. by heating for one hour, followed by the addition of water. The resulting mixture was extracted with ethyl acetate. The organic layer was washed with an aqueous solution of sodium chloride, dried and concentrated. The residue was purified by silica gel column chromatography to give 450 mg of 2-(6-iodohexyloxy)-4-(3,4-methylenedioxybenzyl)amino-6-chloroquinazoline.

410 mg of the 2-(6-iodohexyloxy)-4-(3,4-methylenedioxybenzyl)amino-6-chloroquinazoline was suspended in 15 ml of acetonitrile, followed by the addition of 900 mg of silver nitrate. The obtained mixture was maintained at 60° C. by heating for one hour, followed by the addition of water and ethyl acetate. The resulting mixture was filtered through Celite to remove insolubles. The organic layer was recovered, dried and subjected to silica gel column chromatography to give 340 mg of the title compound.

molecular formula; C₂₂H₂₃ClN₄O₆ (474.5)

yield (%); 95 m.p. (°C.); 121~122

Mass; 475 (MH⁺)

NMR δ(CDCl₃); 1.42~1.59 (4H, m), 1.70~1.89 (4H, m), 4.43 (4H, q, J=6.8 Hz), 4.73 (2H, d, J=4.4 Hz), 5.95 (2H, s), 6.28 (1H, br), 6.77 (1H, d, J=8.0 Hz), 6.83 (1H, d, J=8.0 Hz), 6.85 (1H, s), 7.54 (1H, d, J=8.8 Hz), 7.58 (1H, d, J=8.8 Hz), 7.66 (1H, s)

Example 293

Sodium 2-(3-sulfoxypropoxy)-4-(3,4methylenedioxybenzyl)amino-6-chloroquinazoline

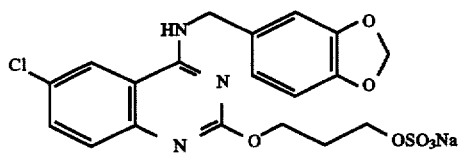

1 g of 2-(3-hydroxypropoxy)-4-(3,4-methylenedioxybenzyl)amino-6-chloroquinazoline and 540 mg of sulfur trioxide/trimethylamine complex were suspended in 10 ml of pyridine. The obtained suspension was stirred at room temperature overnight, followed by the addition of ethyl acetate. The crystals thus precipitated were recovered by filtration, suspended in methanol and dissolved therein by the addition of 1N sodium hydroxide. Ether was added to the obtained solution to precipitate crystals. The crystals were recovered by filtration, whereby 400 mg (32%) of the title compound was obtained.

molecular formula; C₁₉H₁₇ClN₃NaO₇S (489.5)

yield (%); 32 m.p. (°C.); 190~192 (dec.)

Mass; 490 (MH⁺)

NMR δ(DMSO-d₆); 1.90~1.95 (2H, m), 3.82 (2H, t, J=6.4 Hz), 4.28 (2H, t, J=6.8 Hz), 4.61 (2H, d, J=5.6 Hz), 5.95 (2H, s), 6.84 (2H, s), 6.98 (1H, s), 7.50 (1H, d, J=8.8 Hz), 7.64 (1H, dd, J=8.8 Hz, 2.4 Hz), 8.84 (1H, d, J=2.4 Hz), 8.79 (1H, t, J=1.6 Hz)

Example 294

2-(4-Ethoxycarboxypiperidino)carbonyl-4-(3,4-methylenedioxybenzyl)amino-6-chloroquinazoline hydrochloride

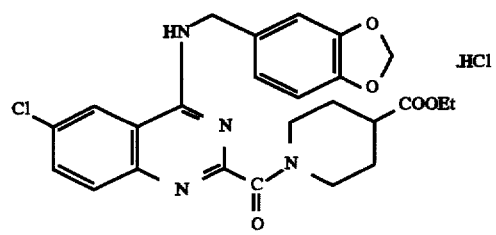

A solution of 0.50 ml (3.3 mmol) of diethyl cyanophosphate in 3 ml of dimethylformamide and 0.50 ml (3.6 mmol) of triethylamine were dropped, in this order, into a solution of 0.78 g (2.2 mmol) of 2-carboxy-4-(3,4-methylenedioxybenzyl)amino-6-chloroquinazoline and 0.50 g (3.2 mmol) of ethyl isonipecotate in 7 μl of dimethylformamide under cooling with ice and stirring. The obtained mixture was stirred under cooling with ice for 30 minutes and thereafter at room temperature for 3 hours, followed by the addition of water. The resulting mixture was extracted with ethyl acetate and the organic layer was dried over anhydrous magnesium sulfate and filtered. The filtrate was distilled in a vacuum to remove the solvent. The residue was recrystallized from hydrochloric acid/ethanol/ether to give 0.96 g of the title compound.

molecular formula; C₂₅H₂₅ClN₄O₅.HCl yield (%); 82 m.p. (°C.); 205~206 (dec.)

Mass m/e; 497 (M+1)⁺

NMR δ(DMSO-d₆); 1.18(3H, t, J=7.2 Hz), 1.51(2H, m), 1.70(1H, m), 1.95(1H, m), 2.66(1H, m), 3.02(1H, m), 3.11 (1H, m), 3.62(1H, m), 4.08(2H, q, J=7.2 Hz), 4.31(1H, m), 4.71(1H, dd, J=14.9 Hz, 6.0 Hz), 4.78(1H, dd, J=14.9 Hz, 6.0 Hz), 5.97(2H, s), 6.84(1H, d, J=8.0 Hz), 6.87(1H, dd, J=8.0 Hz, 1.2 Hz), 6.97(1H, d, J=1.2 Hz), 7.82(1H, d, J=9.2 Hz), 7.97(1H, dd, J=9.2 Hz), 2.0 Hz), 8.67(1H, d, J=2.5 Hz), 10.13(1H, brs)

Example 295

2-[N-(2-Sulfoethyl)carbamoyl]-4-(3,4-methylenedioxybenzyl)amino-6-chloroquinazoline hydrochloride

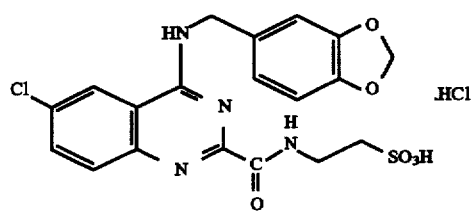

0.60 ml (3.8 mmol) of diethyl cyanophosphate and 0.90 ml (6.4 mmol) of triethylamine were dropped, in this order, into a solution of 0.50 g (1.4 mmol) of 2-carboxy-4-(3,4-methylenedioxybenzyl)amino-6-chloroquinazoline and 0.28 g (1.9 mmol) of sodium 2-aminothanesulfonate in 15 ml of dimethylformamide under cooling with ice and stirring. The obtained mixture was stirred at room temperature for several days, followed by the addition of 10 ml of 1N hydrochloric acid and water. The crystals thus precipitated were recovered by filtration, washed with water and air-dried to give 0.61 g of the title compound.

molecular formula; C₁₉H₁₇ClN₄O₆S.HCl yield (%); 93

NMR δ(DMSO-d₆); 2.76(2H, t, J=6.4 Hz), 3.67(2H, q, J=6.4 Hz), 5.01(2H, d, J=5.6 Hz), 5.99(2H, s), 6.88(1H, d, J=7.6 Hz), 7.05(1H, dd J=7.6 Hz, 1.6 Hz), 7.11(1H, d, J=1.6 Hz), 8.09(1H, dd, J=8.8 Hz, 2.0 Hz), 8.13(1H, d, J=8.8 Hz), 8.68(1H, d, J=2.0 Hz), 9.97(1H, t, J=5.6 Hz), 10.55(1H, brs)

Example 296

2-(4-cis-Carboxycyclohexyl)-4-(3,4-methylenedioxybenzyl)amino-6-chloroquinazoline

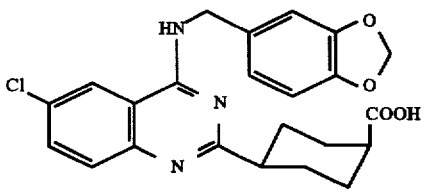

a) 2-(4-Ethoxycarbonylcyclohexylcarbonyl)amino-5-chlorobenzamide 1.5 g of 4-ethoxycarbonylcyclohexanecarbonyl chloride was added to a mixture comprising 1.23 g of 2-amino-5-chlorobenzamide hydrochloride, 3 ml of N,N-diisopropylethylamine and 100 ml of tetrahydrofuran at room temperature. The obtained mixture was reacted at room temperature overnight, followed by the addition of water. The resulting mixture was extracted with ethyl acetate. The organic layer was washed with water and a saturated aqueous solution of sodium chloride, dried over magnesium sulfate, and concentrated. The residue was subjected to silica gel chromatography with 30 to 35% ethyl acetate/hexane to give 1.5 g of the title compound (as a cis/trans mixture), b) 2-(4-Ethoxycarbonylcyclohexyl)-6-chloroquinazoline-4-one 1.3 g of the compound prepared in the step (a) was suspended in 20 ml of ethanol. 320 mg of potassium t-butoxide was added to the obtained suspension in three portions at room temperature. The resulting mixture was reacted at room temperature overnight. The reaction mixture was partially concentrated, followed by the addition of water and 3.5 ml of 1N hydrochloric acid in this order. The crystals thus precipitated were recovered by filtration, washed with water, and vacuum-dried over phosphorus pentaoxide to give 1.16 g of the title compound (as a cis/trans mixture), c) 2-(4-cis-Ethoxycarbonylcyclohexyl)-4,6-dichloroquinazoline 20 ml of phosphorus oxychloride was added to 1.0 g of the compound prepared in the step (b), The obtained mixture was heated under reflux for 2 hours and concentrated. 50 ml of chloroform was added to the residue to form a solution, which was poured into a saturated aqueous solution of sodium hydrogen-carbonate cooled with ice. The chloroform layer was recovered and the aqueous layer was extracted with 30 ml of chloroform. The chloroform layers were combined, washed with a saturated aqueous solution of sodium chloride, dried over magnesium sulfate, and filtered through a silica gel bed. The silica gel was washed with 10% ethyl acetate/hexane. The washings and the filtrate were combined and concentrated. The residue was subjected to silica gel column chromatography with 5% ethyl acetate/hexane to give 145 mg of the title compound.

NMR δ(CDCl₃); 1.28(3H, t, J=7.2 Hz), 1.69~1.78(2H, m), 1.92~2.02(2H, m), 2.05~2.21(4H, m), 2.61~2.68(1H, m), 3.05~3.13(1H, m), 4.17(2H, q, J=7.2 Hz), 7.83(1H, dd, J=9.2 Hz, 2.4 Hz), 7.94(1H, d, J=9.2 Hz), 8.19(1H, d, J=2.4 Hz)

Simultaneously, 470 mg of 2-(4-trans-ethoxycarbonylcyclohexyl)-4,6-dichloroquinazoline was obtained as a more highly polar component.

NMR δ(CDCl₃); 1.28(3H, t, J=7.2 Hz), 1.57~1.69(2H, m), 1.71~1.84(2H, m), 2.13~2.24(4H, m), 1.41(1H, tt, J=12.2 Hz, 3.5 Hz), 2.99(1H, tt, J=12.2 Hz, 3.5 Hz), 4.15 (2H, q, J=7.2 Hz), 7.84(1H, dd, J=9.2 Hz, 2.4 Hz), 7.94(1H, d, J=9.2 Hz), 8.20(1H, d, J=2.4 Hz)

d) 2-(4-cis-Ethoxycarbonylcyclohexyl)-4-(3,4-methylenedioxybenzyl)amino-6-chloroquinazoline A mixture comprising 145 mg of the compound prepared in the step (c), 80 mg of 3,4-methylenedioxybenzylamine, 20 μl of triethylamine and 5 ml of isopropyl alcohol was maintained at 80° C. for 3 hours (to conduct a reaction. The reaction mixture was concentrated and extracted with ethyl acetate/water. The ethyl acetate layer was washed with water and a saturated aqueous solution of sodium chloride, dried over anhydrous magnesium sulfate, and concentrated. The residue was subjected to silica gel column chromatography with 15% ethyl acetate/hexane to give 190 mg of the title compound.

NMR δ(CDCl₃); 1.25(3H, t, J=7.2 Hz), 1.66~1.75(2H, m), 1.84~1.72(2H, m), 2.05~2.23(4H, m), 2.60~2.66(1H, m), 2.85~2.93(1H, m), 4.15(2H, q, J=7.2 Hz), 4.74(2H, d, J=5.6 Hz), 5.72(1H, t, J=5.6 Hz), 5.96(2H, s), 6.79(1H, d, J=8.0 Hz), 6.85~6.90(2H, m), 7.58~7.62(2H, m), 7.74(1H, d, J=9.6 Hz)

e) 2,4-cis-Carboxycyclohexyl)-4-(3,4-methylenedioxybenzyl)amino-6-chloroquinazoline 25 ml of ethanol and 2 ml of a 1N aqueous solution of sodium hydroxide were added to the compound prepared in the step (d). The obtained mixture was maintained at 60° C. for 8 hours and thereafter heated under reflux for 3 hours to conduct a reaction. The reaction mixture was cooled to room temperature, followed by the addition of 2 ml of 1N aqueous hydrochloric acid. The resulting mixture was partially concentrated to precipitate crystals. The crystals were recovered by filtration, washed with water and diethyl ether, and vacuum-dried over phosphorus pentaoxide to give 138 mg of the title compound.

molecular formula; $C_{23}H_{22}ClN_3O_4$
yield (%); 77
m.p. (°C.); 152~153
Mass m/e; 440 (M+1)

NMR δ(DMSO-d₆); 1.54~1.64(2H, m), 1.66~1.76(2H, m), 1.89~2.02(4H, m), 2.69~2.77(1H, m), 4.63(2H, d, J=5.6 Hz), 5.96(2H, s), 6.84(1H, d, J=8.0 Hz), 6.89(1H, dd, J=8.0 Hz, 1.6 Hz), 6.95(1H, d, J=1.6 Hz), 7.63(1H, d, J=8.6 Hz), 7.71(1H, dd, J=8.8 Hz, 2.4 Hz), 8.36(1H, d, J=2.4 Hz), 8.71(1H, t, J=5.6 Hz)

Example 297

2-(4-trans-Carboxycyclohexyl)-4-(3,4-methylenedioxybenzyl)amino-6-chloroquinazoline

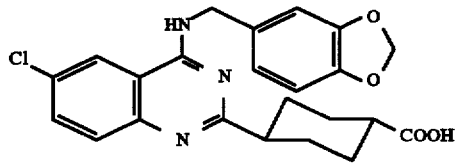

a) 2-(4-trans-Ethoxycarbonylcyclohexyl)-4-(3,4-methylenedioxybenzyl)amino-6-chloroquinazoline 145 mg of the trans isomer prepared in the step (c) of Example 296 was treated in a similar manner to that of the step (d) of Example 296 to give 180 mg of the title compound.

NMR δ(CDCl₃); 1.27(3H, t, J=7.2 Hz), 1.54~1.67(2H, m), 1.70~1.83(2H, m), 2.08~2.17(4H, m), 2.39(1H, tt, J=12.2 Hz, 3.2 Hz), 2.79(1H, tt, J=12.2 Hz, 3.2 Hz), 4.14

(2H, q, J=7.2 Hz), 4.76(2H, d, J=5.5 Hz), 5.82(1H, t, J=5.5 Hz), 5.96(2H, s), 6.79(1H, d, J=7.9 Hz), 6.86(1H, dd, J=7.9 Hz, 1.6 Hz), 6.90(1H, d, J=1.6 Hz), 7.59~7.63(2H, m), 7.73(1H, d, J=7.9 Hz)

b) 2-(4-Trans-carboxycyclohexyl)-4-(3,4-methylenedioxybenzyl)amino-6-chloroquinazoline The compound prepared in the step (a) was hydrolyzed in a similar manner to that of the step (e) of Example 296 to give 163 mg of the title compound.

molecular formula; $C_{23}H_{22}ClN_3O_4$
yield (%); 96
m.p. (°C.); 245~246
Mass m/e; 440 (M+1)

NMR δ(DMSO-d₆); 1.38~1.50(2H, m), 1.55~1.68(2H, m), 1.94~2.04(4H, m), 2.34(1H, t, J=11.9 Hz, 3.1 Hz), 2.60(1H, tt, J=11.9 Hz, 3.1 Hz), 4.66(2H, d, J=5.7 Hz), 5.97(2H, s), 6.85(1H, d, J=8.1 Hz), 6.88(1H, dd, J=8.1 Hz, 1.5 Hz), 6.98(1H, d, J=1.5 Hz), 7.63(1H, d, J=9.0 Hz), 7.72(1H, dd, J=9.0 Hz, 2.4 Hz), 8.37(1H, d, J=2.4 Hz), 8.71(1H, brt, J=5.7 Hz), 12.04(1H, s)

Example 298

2-(4-trans-Carboxycyclohexyl)-3,4-methylenedioxybenzyl)amino-6-cyanoquinazoline

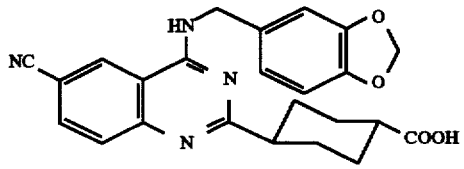

a) 4-(4-methoxycarbonylcyclohexanecarbonyl)aminobenzene-1,3-dicarboxamide 5.1 g of 4-methoxycarbonylcyclohexanecarbonyl chloride was added to a mixture comprising 3.6 g of 4-aminobenzene-1,3-dicarboxamide, 5 ml of N,N-dimethylaniline and 50 ml of tetrahydrofuran at room temperature. The obtained mixture was reacted as such overnight, followed by the addition of water. The crystals thus precipitated were recovered by filtration, washed with water and diethyl ether, and dried to give 5.77 g of the title compound.

b) 2-(4-Methoxycarbonylcyclohexyl)-6-carbamoylquinazoline-4-one 5.7 g of the compound prepared in the step (a) was suspended in 200 ml of methanol, followed by the addition of 1.84 g of potassium t-butoxide. The obtained mixture was reacted at room temperature overnight, followed by the addition of water. The resulting mixture was acidified with concentrated hydrochloric acid to precipitate crystals. The crystals were recovered by filtration, washed with water and diethyl ether, and dried to give 5.04 g of the title compound.

c) 2-(4-trans-Methoxycarbonylcyclohexyl)-4-chloro-6-cyanoquinazoline

A mixture comprising 2.0 g of the compound prepared in the step (b), 2.0 g of lithium chloride and 40 ml of phosphorus oxychloride was heated under reflux for 6 hours and filtered to remove insolubles. The filtrate was concentrated and the residue was subjected to silica gel column chromatography with 10% ethyl acetate/hexane, whereby the trans isomer was separated from the cis isomer. 180 mg of the title compound was obtained.

NMR δ(CDCl₃); 1.57~1.70(2H, m), 1.72~1.84(2H, m), 2.12~2.26(4H, m), 2.43(1H, tt, J=12.3 Hz, 3.2 Hz), 3.03(1H, tt, J=11.9 Hz, 3.0 Hz), 3.71(3H, s), 8.04(1H, dd, J=8.8 Hz, 1.6 Hz), 8.08(1H, dd, J=8.8 Hz, 0.5 Hz), 8.62(1H, dd, J=1.6 Hz, 0.5 Hz)

d) 2-(4-trans-Methoxycarbonylcyclohexyl)-4-(3,4-methylenedioxybenzyl)amino-6-cyanoquinazoline A mixture comprising 180 mg of the compound prepared in the step (c), 100 mg of 3,4-methylenedioxybenzylamine, 200 Al of triethylamine and 5 ml of isopropyl alcohol was maintained at 80° C. for one hour to conduct a reaction. The reaction mixture was concentrated and extracted with ethyl acetate/water. The ethyl acetate layer was washed with a saturated aqueous solution of sodium chloride, dried over anhydrous magnesium sulfate, and concentrated. The residue was subjected to silica gel column chromatography with 10% ethyl acetate/benzene to give 157 mg of the title compound.

NMR δ(CDCl₃); 1.55~1.68(2H, m), 1.70~1.82(2H, m), 2.10~2.18(4H, m), 2.42(1H, tt, J=12.3 Hz, 3.2 Hz), 2.81(1H, tt, J=11.9 Hz, 3.0 Hz), 3.70(3H, s), 4.78(2H, d, J=5.5 Hz), 6.96(2H, s), 6.20(1H, t, J=5.5 Hz), 6.80(1H, d, J=7.9 Hz), 6.88(1H, dd, J=7.9 Hz, 1.6 Hz), 6.90(1H, d, J=1.6), 7.82(2H, s), 8.11(1H, s)

e) 2-(4-trans-carboxycyclohexyl)-4-(3,4-methylenedioxybenzyl)amino-6-cyanoquinazoline A mixture comprising 157 mg of the compound prepared in the step (d), 1 ml of a 1N aqueous solution of sodium hydroxide, 3 ml of methanol and 6 ml of tetrahydrofuran was reacted at room temperature for 24 hours. 1 ml of ON hydrochloric acid and 5 ml of water were added to the reaction mixture in this order to precipitate crystals. The crystals were recovered by filtration, washed with water, and dried to give 138 mg of the title compound.

molecular formula; $C_{24}H_{22}N_4O_4$
yield (%); 91
m.p. (°C.); 269~270
Mass m/e; 431 (M+1)

NMR δ(DMSO-d₆); 1.38~1.50(2H, m), 1.55~1.68(2H, m), 1.95~2.04(4H, m), 2.24(1H, tt, J=11.9 Hz, 3.1 Hz), 2.63(1H, tt, J=11.9 Hz, 3.1 Hz), 4.68(2H, d, J=5.7 Hz), 5.97(2H, s), 6.86(1H, d, J=7.9 Hz), 6.90(1H, dd, J=7.9 Hz, 1.5 Hz), 6.99(1H, d, J=1.5 Hz), 7.71(1H, d, J=8.8 Hz), 8.01(1H, dd, J=8.8 Hz, 1.6 Hz), 8.82(1H, d, J=1.6 Hz), 8.95(1H, t, J=5.7 Hz)

Example 299

2-Carbamoylmethyl-4-(3,4-methylenedioxybenzyl)amino-6-chloroquinazoline

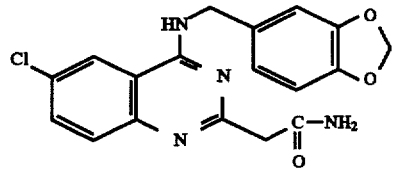

a) 2-Ethoxycarbonylmethyl-4-(3,4-methylenedioxybenzyl)amino-6-chloroquinazoline

The title compound was prepared in a similar manner to that of Example 296.

NMR δ(CDCl₃); 1.27(3H, t, J=7.1 Hz), 3.93(2H, s), 4.22(2H, q, J=7.1 Hz), 4.71(2H, d, J=5.5 Hz), 5.83(1H, t, J=5.5 Hz), 5.96(2H, s), 6.78(1H, d, J=7.9 Hz), 6.85(1H, dd, J=7.9 Hz, 1.6 Hz), 6.89(1H, d, J=1.6 Hz), 7.60~7.65(2H, m), 7.74(1H, d, J=9.0 Hz), b) 2-Carbamoylmethyl-4-(3,4-methylenedioxybenzyl)amino-6-chloroquinazoline A mixture comprising 200 mg of the compound prepared in the step (a) and 20 ml of ethanol was cooled with ice. Ammonium gas was introduced into the resulting mixture to saturate the mixture therewith. The resulting mixture was gradually brought to room temperature and reacted for 3 days. The reaction mixture was concentrated and the residue was subjected to silica gel column chromatography with 0 to 20% ethanol/ethyl acetate to give 24 mg of the title compound.

Example 300

2-(4-Cyanopiperidino)-4-(3,4-methylenedioxybenzyl)amino-6-chloroquinazoline

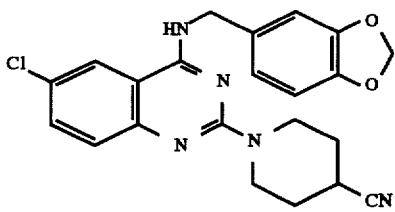

75 ml of thionyl chloride and 150 ml of acetonitrile were added to 3.8 g (0.0086 mol) of 2-(4-carbamoylpiperidino)-4-(3, 4-methylenedioxybenzyl)amino- 6-chloroquinazoline. The mixture thus obtained was heated under reflux for one hour. The reaction mixture was distilled under a reduced pressure to remove the solvent. A saturated aqueous solution of sodium hydrogencarbonate and triethylamine were added to the residue and the resultant mixture was etracted with ethyl acetate. The organic layer was washed with a saturated aqueous solution of sodium chloride, dried over anhydrous magnesium sulfate, filtered and distilled under a reduced pressure to remove the solvent. The obtained residue was purified by a silica gel column chromatography (ethyl acetate-n-hexane) and recrystallized from chloroform-n-hexane to give 3.1 g of the title compound.

molecular formula; $C_{22}H_{20}ClN_5O_2$ yield (%); 85 m.p. (°C.); 169–170

NMR δ(CDCl$_3$); 1.88 (2H, m), 1.95 (2H, m), 2.87 (1H, m), 3.73 (2H, m), 4.25 (2H, m), 4.67 (2H, d, J=5.6 Hz), 5.65 (1H, t, J=5.6 Hz), 5.97 (2H, s), 6.79 (1H, d, J=8.0 Hz), 6.84 ((1H, dd, J=8.0 Hz, 1.6 Hz), 6.87 (1H, d, J=1.6 Hz), 7.39 (1H, d, J=8.8 Hz), 7.44 (1H, d, J=2.4 Hz), 7.46 (1H, dd, J=8.8 Hz, 2.4 Hz)

Example 301

2-[4-(1H-tetrazol-5-yl)piperidino]-4-(3, 4methylenedioxybenzyl)amino-6-chloroquinazoline hydrochloride

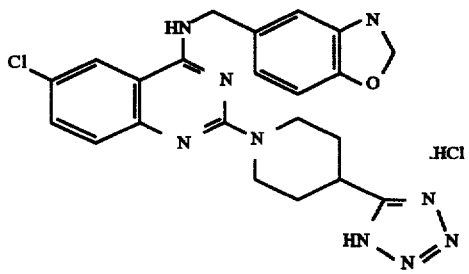

10 ml of toluene was added to a mixture comprising 0.50 g (0.0012 mol) of 2-(4-cyanopiperidino)-4-(3,4-methylenedioxybenzyl)amino-6-chloroquinazoline and 0.50 g (0.0024 mol) of trimethyl stannylazide. The mixture thus obtained was heated under reflux for two days. The reaction mixture was distilled under a reduced pressure to remove the solvent. The residue was suspended in 10 ml of ethanol, followed by the addition of 10 ml of 1N hydrochloric acid. The mixture thus obtained was stirred at room temperature for several hours. The mixture was filtered to recover the crystal. The crystal was washed with water and air-dried to give 0.60 g of the title compound.

molecular formula; $C_{22}H_{21}ClN_8O_2$·HCl yield (%); quantitative m.p. (°C.); 212–214

Mass m/e; 465 (M+1)$^+$

NMR δ(DMSO-d$_6$); 1.80 (2H, m), 2.17 (2H, m), 3.45 (2H, m), 4.62 (2H, m), 4.69 (2H, d, J=5.6 Hz), 5.97 (2H, s), 6.86 (1H, d, J=7.6 Hz), 6.91 ((1H, dd, J=7.6 Hz, 1.6 Hz), 7.01 (1H, d, J=1.6 Hz), 7.84 (1H, dd, J=8.8 Hz, 1.6 Hz), 7.88 (1H, d, J=8.8 Hz), 8.51 (1H, d, J=1.6 Hz), 10.13 (1H, brs), 12.28 (1H, brs)

Example 302

2-(1 H-tetrazol-5-yl)-4-(3,4-methylenedioxybenzyl) amino-6-chloroquinazoline hydrochloride

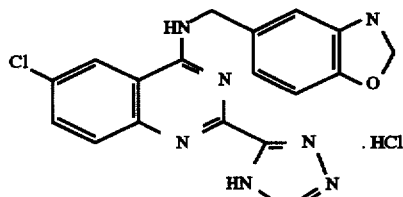

The title compound was prepared in a similar manner to that of Example 301.

molecular formula; $C_{17}H_{12}ClN_7O_2$·HCl yield (%); 37 m.p. (°C.); 201–204 (dec.)

Mass m/e; 382 (MH)$^+$

NMR δ(DMSO-d$_6$); 4.90 (2H, d, J=5.6 Hz), 5.97 (2H, s), 6.87 (1H, d, J=8.0 Hz), 6.98 ((1H, dd, J=8.0 Hz, 2.0 Hz), 7.11 (1H, d, J=2.0 Hz), 7.92–7.94 (2H, m), 8.60 (1H, d, J=1.6 Hz), 9.53 (1H, brs)

Examples 303 to 410

The following compounds were each prepared by any method described above.

Example 303

2-Chloro-4-(4-methylenedioxybenzyl)amino-6-methoxy-6cyclopentyloxyquinazoline

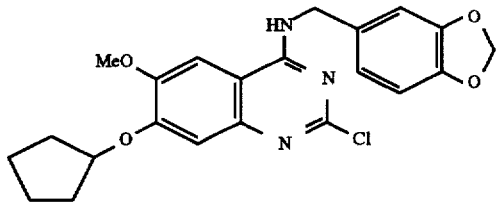

molecular formula; C$_{22}$H$_{22}$ClN$_3$O$_4$ yield (%); 88 m.p. (°C.); 176~177

Mass; 428 (M+1)$^+$

NMR δ(CDCl$_3$); 1.64 (2H, m), 1.82 (2H, m), 1.93 (2H, m), 2.02 (2H, m), 3.90 (3H, s), 4.74 (2H, d, J=5.6 Hz), 4.85 (1H, m), 5.72 (1H, t, J=5.6 Hz), 5.96 (2H, s), 6.79 (1H, d, J=7.6 Hz), 6.79 ((1H, s), 6.87 (1H, dd, J=7.6 Hz, 1.6 Hz), 6.90 (1H, d, J=1.6 Hz), 7.11 (Hz, s)

TABLE 7

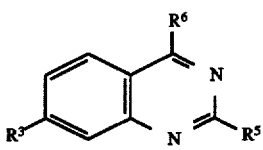

| Ex. | R$^3$ | R$^5$ | R$^6$ | m.p. (°C.) | yield (%) | Mass | NMR | note |
|---|---|---|---|---|---|---|---|---|
| 304 | Cl | HN-CH$_2$-(1,3-benzodioxol-5-yl) | -N(piperidine)-COOH | 264–265 | 97 | 441(M+1) | δ (DMSO-d$_6$): 1.70(2H, brs), 1.90(2H, m), 2.54(1H, m) 3.11(2H, m), 3.98(2H, m) 4.40(2H, d, J=6.4Hz), 5.93(2H, s) 6.80(2H, brs), 6.84(1H, brs) 7.02(1H, m), 7.28(1H, m), 7.44(1H, brs) 7.68(1H, d, J=8.8Hz), 12.24(1H, brs) | |
| 305 | Cl | -N(piperidine)-COOH | HN-CH$_2$-(1,3-benzodioxol-5-yl) | 258–259 | 97 | 441(M+1) | δ (DMSO-d$_6$): 1.36(2H, m), 1.79(2H, m), 2.47(1H, m) 2.96(2H, t, J=11.2Hz) 4.55(2H, d, J=5.6Hz), 4.58(2H, m) 5.93(2H, s), 6.82(2H, s) 6.92(1H, s) 7.05(1H, dd, J=8.8Hz, 2.4Hz) 7.23(1H, d, J=2.4Hz) 8.00(1H, d, J=8.8Hz) 8.58(1H, t, J=5.6Hz), 12.15(1H, brs) | |

TABLE 8

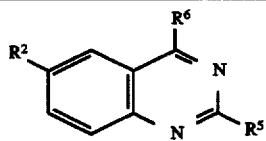

| Ex. | R$^2$ | R$^5$ | R$^6$ | m.p. (°C.) | yield (%) | Mass | NMR | note |
|---|---|---|---|---|---|---|---|---|
| 306 | CN | -N(piperidine)-COOEt | Me-N(CH$_2$-(3-Cl-4-OMe-phenyl)) | amorphous | 93 | 494(MH$^+$) | δ (CDCl$_3$): 1.25(3H, t, J=7.2Hz), 1.64–1.77(2H, m) 1.94–2.01(2H, m), 2.52–2.61(1H, m) 3.04–3.14(2H, m), 3.25(3H, s) 3.91(3H, s), 4.14(3H, q, J=7.2Hz) 4.72–4.81(2H, m), 4.74(2H, s) 6.93(1H, d, J=8.4Hz) 7.19(1H, dd, J=8.4Hz, 2.0Hz) 7.37(1H, d, J=2.0Hz) 7.43 (1H, d, J=8.4Hz) 7.58(1H, dd, J=8.4Hz, 2.0Hz) 8.06(1H, d, J=2.0Hz) | |

TABLE 8-continued

| Ex. | R² R⁵ | R⁶ | m.p. (°C.) | yield (%) | Mass | NMR | note |
|---|---|---|---|---|---|---|---|
| 307 | CN, —N(piperidine)—COOH | Me-N(Me)-CH₂-(3,4-methylenedioxyphenyl) | 196–198 | 44 | 446(MH⁺) | δ (DMSO-$d_6$): 1.35–1.50(2H, m), 1.79–1.86(2H, m) 2.50–2.55(1H, m), 2.99–3.08(2H, m) 3.30(3H, s), 4.54–4.62(2H, m) 4.81(2H, s), 5.98(2H, s) 6.82(1H, dd, J=8.0Hz, 1.6Hz) 6.87(1H, d, J=8.0Hz) 6.92(1H, d, J=1.6Hz) 7.33(1H, d, J=2.4Hz) 7.71(1H, dd, J=8.4Hz, 1.6Hz) 8.27(1H, d, J=1.6Hz) | |

TABLE 9

| Ex. | R² R⁵ | R⁶ | m.p. (°C.) | yield (%) | Mass | NMR | note |
|---|---|---|---|---|---|---|---|
| 308 | Cl, —(CH₂)₃—COOH | HN-CH₂-(3-Cl-4-OMe-phenyl) | 180–181 | 99 | 420(M+1) | δ (DMSO-$d_6$): 1.97(2H, quintet, J=7.4Hz) 2.26(2H, t, J=7.4Hz) 2.72(2H, t, J=7.4Hz) 3.82(3H, s), 4.67(2H, d, J=5.7Hz) 7.08(1H, d, J=8.6Hz) 7.34(1H, dd, J=8.6Hz, 2.2Hz) 7.47(1H, d, J=2.2Hz) 7.64(1H, d, J=9.0Hz) 7.74(1H, dd, J=9.0Hz, 2.4Hz) 8.37(1H, d, J=2.4Hz) 8.76(1H, t, J=5.7Hz) | |
| 309 | Cl, —N(piperidine)—COOH | HN-(CH₂)₄-OH | >250 | 17 | 393(MH⁺) | δ(DMSO-$d_6$): 1.28–1.88(10H, m), 2.46–2.48(1H, m) 2.91–3.01(2H, m), 3.35–3.42(4H, m) 4.39(1H, brs), 4.57–4.63(2H, m) 7.22(1H, d, J=8.8Hz) 7.43(1H, dd, J=8.8Hz, 2.4Hz) 8.11(1H, brt, J=4.0Hz) 8.15(1H, d, J=2.4Hz) | |

TABLE 10

| Ex. | R² | R⁵ | R⁶ | m.p. (°C.) | yield (%) | Mass | NMR | note |
|---|---|---|---|---|---|---|---|---|
| 310 | Cl | -N⌐⌐-COOH (piperidine-4-carboxylic acid) | Me-N(CH₂Ph) (N-methyl-N-benzylamino) | >250 | 100 | 361(MH⁺) | δ (DMSO): 0.23–0.29(2H, m), 0.41–0.48(2H, m) 1.11–1.22(1H, m), 1.40–1.52(2H, m) 1.81–1.87(2H, m), 2.45–2.52(1H, m) 2.93–3.01(2H, m), 3.26–3.35(2H, m) 4.60–4.67(2H, m) 7.25(1H, d, J=9.2Hz) 7.47(1H, dd, J=9.2Hz, 2.4Hz) 8.14(1H, m), 8.16(1H, d, J=2.4Hz) 12.18(1H, brs) | |
| 311 | Cl | Cl | -N⌐⌐-COOH (piperidine-4-carboxylic acid) | 172–174 | 43 | 326(M+1) | δ (DMSO-d₆): 1.75(2H, m), 1.98(2H, m), 2.64(1H, m) 3.39(2H, m), 4.23(2H, brd, J=13.2Hz) 7.71(1H, d, J=8.8Hz) 7.84(1H, dd, J=8.8Hz, 2.0Hz) 7.93(1H, d, J=2.0Hz) | |

TABLE 11

| Ex. | R² | R⁵ | R⁶ | m.p. (°C.) | yield (%) | Mass | NMR | note |
|---|---|---|---|---|---|---|---|---|
| 312 | Cl | -N⌐⌐-COOH (piperidine-4-carboxylic acid) | -N⌐⌐-COOH (piperidine-4-carboxylic acid) | 260–262 | 91 | 419(M+1) | δ (DMSO-d₆): 1.60(2H, m), 1.74(2H, m) 1.97(4H, brt, J=15.2Hz), 2.68(2H, m) 3.32(2H, t, J=11.6Hz) 3.53(2H, t, J=11.6Hz) 4.36(2H, d, J=13.6Hz) 4.57(2H, d, J=13.2Hz) 7.82(1H, d, J=9.2Hz) 7.86(1H, s), 8.18(1H, d, J=9.2Hz) 13.0(1H, brs) | hydrochloride |
| 313 | Cl | -NH-CH₂-(1,3-benzodioxol-5-yl) | -N⌐⌐-COOEt (piperidine-4-carboxylic acid ethyl ester) | 159–160 | 56 | 469(M+1)⁺ | δ (DMSO-d₆): 1.21(3H, t, J=7.2Hz), 1.75(2H, brm) 1.95(2H, brm), 2.65(1H, m) 3.14(2H, brm), 4.00(2H, brm) 4.10(2H, q, J=7.2Hz) 4.43(2H, d, J=6.0Hz), 5.94(2H, s) 6.80(2H, brs), 6.91(1H, brs) 7.34(1H, brd, J=9.2Hz) 7.43(1H, brs) 7.51(1H, dd, J=9.2Hz, 2.4Hz) 7.62(1H, d, J=2.4Hz) | |

TABLE 12
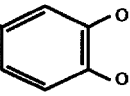
| Ex. | R² R⁵ | R⁶ | m.p. (°C.) | yield (%) | Mass | NMR | note |
|---|---|---|---|---|---|---|---|
| 314 | Cl, 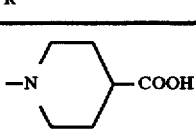 | 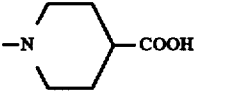 | 238–239 (decomp.) | 68 | 441 (M+1)⁺ | δ (DMSO-d₆): 1.75(2H, brm), 1.94(2H, brm) 2.56(1H, m), 3.14(2H, brm) 3.99(2H, brm), 4.43(2H, d, J=6.4Hz) 5.94 (2H, s), 6.81 (2H, brs) 6.91 (1H, brs), 7.34 (1H, brd, J=8.8Hz) 7.43 (1H, brs) 7.51 (1H, dd, J=8.8 Hz, 2.4Hz) 7.62(1H, d, J=2.4Hz) | |
| 315 | Cl, 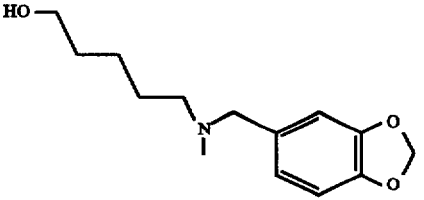 | 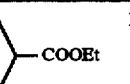 | 170 (decomp.) | 68 | 527 (MH⁺) | δ (DMSO): 1.22–1.33(2H, m), 1.36–1.51 (4H, m) 1.69–1.82(4H, m), 2.52–2.81(1H, m) 2.97–3.06 (2H, m), 3.32–3.52(4H, m) 4.29–4.52(3H, m), 4.72(2H, brs) 5.98(2H, s), 6.80–6.92 (2H, m) 7.29 (1H, d, J=9.2 Hz), 7.45(1H, dd, J=9.2Hz, 1.2Hz) 7.60 (1H, d, J=1.2Hz) | |
TABLE 13
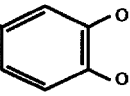
| Ex. | R² R⁵ | R⁶ | m.p. (°C.) | yield (%) | Mass | NMR | note |
|---|---|---|---|---|---|---|---|
| 316 | CN, 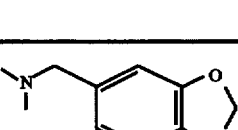 | 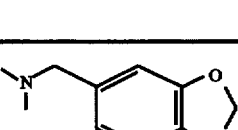 | oily substance | quantitative | 474 (MH⁺) | δ (CDCl₃): 1.26(3H, t, J=7.2Hz) 1.66–1.77(2H, m), 1.93–2.01(2H, m) 2.51–2.62(1H, m), 3.09–3.13(2H, m) 3.23(3H, s), 4.14(2H, q, J=7.2Hz) 4.74–4.80(2H, m), 4.79(2H, s) 5.98(2H, s), 6.80–6.84(3H, m) 7.42(1H, d, J=8.8Hz) 7.57(1H, dd, J=8.8Hz, 2.0Hz), 8.05(1H, d, J=2.0Hz) | |

TABLE 14

| Ex. | R² | R⁵ | R⁶ | m.p. (°C.) | yield (%) | Mass | NMR | note |
|---|---|---|---|---|---|---|---|---|
| 317 | Cl | —N⟨piperidine⟩—COOH | HN-CH₂-C₆H₃(OMe)(OH) | 244–245 | quantitative | 443 (M+1)⁺ | δ (DMSO-d₆): 1.49(2H, m), 1.88(2H, m), 2.53(1H, m) 3.08(2H, m), 3.74(3H, s) 4.58(2H, d, J=5.2Hz), 4.61(2H, m) 6.71(1H, d, J=8.0Hz) 6.80(1H, dd, J=8.0Hz, 2.0Hz), 6.99(1H, d, J=2.0Hz), 7.38(1H, brs) 7.56(1H, brs), 8.25(1H, brs) 8.86(1H, s), 12.19(1H, brs) | |
| 318 | Cl | —N⟨piperidine⟩—COOH | HN-CH₂-C₆H₃(OH)(OMe) | 254–255 (decomp.) | 92 | 443 (M+1)⁺ | δ (DMSO-d₆): 1.48(2H, m), 1.88(2H, m), 2.54(1H, m) 3.10(2H, m), 3.72(3H, s), 4.54(2H, m) 4.56(2H, d, J=5.6Hz) 6.77(1H, dd, J=8.0Hz, 2.0Hz) 6.82(1H, d, J=2.0Hz) 6.84(1H, d, J=8.0Hz) 7.45(1H, brs), 7.60(1H, brs) 8.28(1H, brs), 8.90 (1H, s) 12.21(1H, brs) | |

TABLE 15

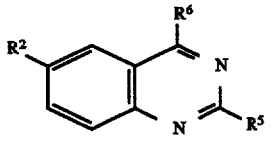

| Ex. | R² | R⁵ | R⁶ | m.p. (°C.) | yield (%) | Mass | NMR | note |
|---|---|---|---|---|---|---|---|---|
| 319 | Cl | Cl | HN-CH₂-C₆H₃(OH)(OMe) | 193–194 | 58 | 350(M+1)⁺ | δ (DMSO-d₆): 3.71(3H, s), 4.57(2H, d, J=5.6Hz) 6.74(1H, dd, J=8.4Hz, 2.0Hz) 6.77(1H, d, J=2.0Hz) 6.84(1H, d, J=8.4Hz) 7.62(1H, d, J=8.8Hz) 7.79(1H, dd, J=8.8Hz, 2.4Hz) 8.46(1H, d, J=2.4Hz) 8.91(1H, s), 9.22(1H, t, J=5.6Hz) | |

TABLE 16

[Structure: R2-substituted benzene fused with pyrimidine ring bearing R6 and R5 substituents]

| Ex. | R² | R⁵ | R⁶ | m.p. (°C.) | yield (%) | Mass | NMR | note |
|---|---|---|---|---|---|---|---|---|
| 320 | Cl | —N(piperidine)—COOEt | HN—CH₂—(3-OMe, 4-OH-phenyl) | 173–174 | 78 | 471 (M+1)⁺ | δ (CDCl₃): 1.26(3H, t, J=7.2Hz), 1.72(2H, m) 1.98(2H, m), 2.56(1H, m), 3.05(2H, m) 3.88(3H, s), 4.15(2H, q, J=7.2Hz) 4.68(2H, d, J=5.2Hz), 4.82(2H, m) 5.56(1H, t, J=5.2Hz), 5.65(1H, brs) 6.90(3H, m), 7.39(1H, d, J=8.8Hz) 7.42(1H, d, J=2.4Hz) 7.44(1H, dd, J=8.8Hz, 2.4Hz) | |
| 321 | Cl | —N(piperidine)—COOEt | HN—CH₂—(3-OH, 4-OMe-phenyl) | 170–171 | 91 | 471 (M+1)⁺ | δ (CDCl₃): 1.26(3H, t, J=7.2Hz), 1.72(2H, m) 1.97(2H, m), 2.55(1H, m), 3.04(1H, m) 3.90(3H, s), 4.15(2H, q, J=7.2Hz) 4.66(2H, d, J=5.2Hz), 4.80(2H, m,) 5.57(1H, t, J=5.2Hz), 5.68(1H, brs) 6.83(1H, d, J=8.0Hz) 6.87(1H, dd, J=8.0Hz, 2.0Hz) 6.97(1H, d, J=2.0Hz), 7.38(1H, d, J=8.8Hz) 7.41(1H, d, J=2.4Hz) 7.43(1H, dd, J=8.8Hz, 2.4Hz) | |

TABLE 17

[Structure: R2-substituted benzene fused with pyrimidine ring bearing R6 and R5 substituents]

| Ex. | R² | R⁵ | R⁶ | m.p. (°C.) | yield (%) | Mass | NMR | note |
|---|---|---|---|---|---|---|---|---|
| 322 | Cl | —N(piperidine)—COOH | HN—CH₂—(3-NO₂, 4-Cl-phenyl) | >260 | 99 | 476(M+1)⁺ | δ DMSO-d₆): 1.53(2H, m), 1.90(2H, m), 2.62(1H, m) 3.29(2H, m), 4.41(2H, m) 4.83(2H, d, J=5.6Hz) 7.74(1H, d, J=8.4Hz) 7.76(1H, dd, J=8.4Hz, 2.0Hz) 7.85(1H, d, J=8.4Hz) 7.90(1H, d, J=8.4Hz) 8.15(1H, d, J=2.0Hz), 8.51(1H, s) 10.34(1H, brs), 12.28(1H, brs) | hydro-chloride |
| 323 | Cl | —N(piperidine)—COOH | HN—CH₂—(3-NH₂, 4-Cl-phenyl) | >260 | 65 | 446(M+1)⁺ | δ DMSO-d₆): 1.58(2H, m), 1.95(2H, m), 2.63(1H, m) 3.32(2H, m), 4.45(2H, m) 4.62(2H, d, J=5.2Hz), 5.33(2H, brs) 6.58(1H, dd, J=8.0Hz, 2.0Hz) 6.79(1H, d, J=2.0Hz) 7.13(1H, d, J=8.0Hz) 7.85(1H, d, J=8.8Hz) 7.89(1H, d, J=8.8Hz) 8.51(1H, s), 10.14(1H, brs) 12.22(1H, brs) | hydro-chloride |

TABLE 18

| Ex. | R² | R⁵ | R⁶ | m.p. (°C.) | yield (%) | Mass | NMR | note |
|---|---|---|---|---|---|---|---|---|
| 324 | Cl | —N⟨piperidine⟩—COOEt | HN-CH₂-C₆H₃(NH₂)(Cl) | 218–219 (decomp.) | 25 | 476 (M+1)⁺ | δ (DMSO-d₆): 1.20(3H, t, J=7.2Hz), 1.57(2H, m) 1.96(2H, m), 2.73(1H, m), 3.31(2H, m) 4.08(2H, q, J=7.2Hz), 4.40(2H, m) 4.61(2H, d, J=5.6Hz) 6.59(1H, dd, J=8.0Hz, 2.0Hz) 6.79(1H, d, J=2.0Hz) 7.13(1H, d, J=8.0Hz) 7.85(1H, dd, J=9.2Hz, 2.4Hz) 7.93(1H, d, J=9.2Hz) 8.53(1H, d, J=2.4Hz) 10.19(1H, brt, J=5.6Hz) 12.31(1H, brs) | |
| 325 | Cl | Cl | HN-CH₂-C₆H₃(OMe)(OH) | 186–187 | 77 | 350 (M+1)⁺ | δ (DMSO-d₆): 3.74(3H, s), 4.58(2H, d, J=5.6Hz) 6.70(1H, d, J=8.0Hz) 6.75(1H, d, J=8.0Hz, 1.6Hz) 7.00(1H, d, J=1.6Hz) 7.61(1H, d, J=8.8Hz) 7.78(1H, dd, J=8.8Hz, 2.4Hz) 8.46(1H, d, J=2.4Hz), 8.87(1H, s) 8.19(1H, t, J=5.6Hz) | |

TABLE 19

| Ex. | R² | R⁵ | R⁶ | m.p. (°C.) | yield (%) | Mass | NMR | note |
|---|---|---|---|---|---|---|---|---|
| 326 | Cl | —N⟨piperidine⟩—COOEt | —N⟨piperidine⟩—COOEt | 175–176 | 76 | 475 (M+1)⁺ | δ (DMSO-d₆): 1.198(3H, t, J=7.2Hz) 1.203(3H, t, J=7.2Hz), 1.65(2H, m) 1.78(2H, m), 2.01(4H, m), 2.76(1H, m) 2.82(1H, m), 3.31(2H, m), 3.55(2H, m) 4.09(2H, q, J=7.2Hz) 4.10(2H, q, J=7.2Hz), 4.41(2H, m) 4.53(2H, m) 7.84(1H, dd, J=8.8Hz, 1.6Hz) 7.90(1H, d, J=1.6Hz) 8.00(1H, d, J=8.8Hz) | hydro-chloride |
| 327 | Cl | Cl | HN-CH₂-C₆H₃(NO₂)(Cl) | 220–221 | 71 | 383 (M+1)⁺ | δ (DMSO-d₆): 4.81(2H, d, J=5.6Hz) 7.67(1H, d, J=8.4Hz) 7.71(1H, dd, J=8.4Hz, 2.0Hz) 7.74(1H, d, J=8.4Hz) 7.84(1H, dd, J=8.4Hz, 2.0Hz) 8.11(1H, d, J=2.0Hz) 8.44(1H, d, J=2.0Hz) 9.39(1H, t, J=5.6Hz) | |

TABLE 20

| Ex. | R² | R⁵ | R⁶ | m.p. (°C.) | yield (%) | Mass | NMR | note |
|---|---|---|---|---|---|---|---|---|
| 328 | Cl | —N⟨piperidine⟩—COOEt | HN-CH₂-(3-NO₂,4-Cl-phenyl) | 230–231 | 73 | 504 (M+1)⁺ | δ (DMSO-d₆): 1.20(3H, t, J=7.2Hz), 1.51(2H, m) 1.89(2H, m), 2.72(1H, m), 3.27(2H, m) 4.08(2H, q, J=7.2Hz), 4.44(2H, m) 4.82(2H, d, J=5.6Hz) 7.73(1H, d, J=8.4Hz) 7.76(1H, dd, J=8.4Hz, 2.0Hz) 7.85(1H, dd, J=8.8Hz, 2.0Hz) 7.92(1H, d, J=8.8Hz) 8.14 (1H, d, J=2.0Hz) 8.52(1H, d, J=2.0Hz), 10.35(1H, brs) 12.35(1H, brs) | hydro-chloride |
| 329 | Cl | —N⟨piperidine⟩—COOH | HN-CH₂-(3-NH₂,4-Cl-phenyl) | >260 | 65 | 446 (M+1)⁺ | δ (DMSO-d₆): 1.58(2H, m), 1.95(2H, m), 2.63(1H, m) 3.32(2H, m), 4.45(2H, m) 4.62(2H, d, J=5.2Hz), 5.33(2H, brs) 6.58(1H, dd, J=8.0Hz, 2.0Hz) 6.79(1H, d, J=2.0Hz) 7.13(1H, d, J=8.0Hz) 7.85(1H, d, J=8.8Hz) 7.89(1H, d, J=8.8Hz), 8.51(1H, s) 10.14(1H, brs), 12.22(1H, brs) | hydro-chloride |

TABLE 21

| Ex. | R² | R⁵ | R⁶ | m.p. (°C.) | yield (%) | Mass | NMR | note |
|---|---|---|---|---|---|---|---|---|
| 330 | OMe | H | N-methylpyrrolidin-2-yl-(benzo[1,3]dioxol-5-yl) | oily substance | 85 | | δ (CDCl₃): 1.95–2.10(3H, m), 2.37(1H, m) 3.58(3H, s), 4.05–4.20(2H, m) 5.58(1H, m), 5.93(1H, s), 5.94 (1H, s) 6.78(1H, d, J=8.4Hz) 6.84(1H, s) 6.85(1H, d, J=8.4 Hz) 7.30(1H, d, J=10.0Hz), 7.35 (1H, s) 7.74(1H, d, J=10.0Hz), 8.53(1H, s) | |
| 331 | Cl | —N⟨piperidine⟩—COOH | HN-(CH₂)₃-O-(benzo[1,3]dioxol-5-yl) | 139–140 | 83 | 485 (M+1)⁺ | δ (DMSO-d₆): 1.44(2H, m), 1.82(2H, m), 2.03 (2H, m) 2.46(1H, m), 2.94(2H, m), 3.59(2H, m) 3.96(2H, t, J= 6.0Hz), 4.62(2H, m) 5.91(2H, s) 6.32(1H, dd, J=8.4Hz, 2.4Hz) 6.56(1H, d, J=2.4Hz) 6.75(1H, d, J=8.4Hz) 7.22(1H, d, J=8.8Hz) 7.44(1H, dd, J=8.8Hz, 2.4Hz) 8.05(1H, brt), 8.08(1H, d, J= 2.4Hz) 12.14(1H, brs) | |

TABLE 22

| Ex. | R² | R⁵ | R⁶ | m.p. (°C.) | yield (%) | Mass | NMR | note |
|---|---|---|---|---|---|---|---|---|
| 332 | Cl | —N⟨piperidine⟩—COOEt | HN(Me)-CH₂CH₂CH₂-O-(benzodioxole) | 184–185 | 97 | 513 (M+1)⁺ | δ (DMSO-d₆): 1.18(3H, t, J=7.2Hz), 1.59 (2H, m), 1.95(2H, m), 2.05 (2H, m), 2.72(1H, m) 3.3(2H, m), 3.71(2H, m) 3.98(2H, t, J=6.0Hz) 4.07(2H, q, J=7.2 Hz), 4.48(2H, m) 5.91(2H, s) 6.29(1H, dd, J=8.4Hz, 2.4Hz) 6.52(1H, d, J=2.4Hz) 6.74(1H, d, J=8.4Hz), 7.81 (2H, brs) 8.41(1H, brs), 9.59 (1H, brs) 12.07(1H, brs) | hydro-chloride |
| 333 | Cl | Cl | HN(Me)-CH₂CH₂CH₂-O-(benzodioxole) | 148–149 | 87 | 392 (M+1)⁺ | δ (CDCl₃): 2.21(2H, m), 3.88(2H, m) 4.16(2H, t, J=5.4Hz), 5.94 (2H, s) 6.39(1H, dd, J=8.4Hz, 2.8Hz) 6.56(1H, d, J=2.8Hz), 6.72(1H, brs) 6.74(1H, d, J= 8.4Hz) 7.63(1H, d, J=2.0Hz) 7.66(1H, dd, J=8.8Hz, 2.0Hz) 7.70(1H, d, J =8.8Hz) | |

TABLE 23

| Ex. | R² | R⁵ | R⁶ | m.p. (°C.) | yield (%) | Mass | NMR | note |
|---|---|---|---|---|---|---|---|---|
| 334 | Cl | —N⟨piperidine⟩—COOH | HN(Me)-CH₂-Ph | 240–241 (decomp.) | 60 | 397 (M+1)⁺ | δ (DMSO-d₆): 1.39(2H, m), 1.80(2H, m), 2.47(1H, m) 2.96(2H, m), 4.57(2H, m) 4.66(2H, d, J=5.6Hz) 7.15–7.45(6H, m) 7.48(1H, dd, J=9.2Hz, 1.6Hz) 8.17(1H, d, J=1.6Hz), 8.64(1H, brs) 12.15(1H, brs) | |
| 335 | CN | —N⟨piperidine⟩—COOH | Me-N(Me)-CH₂-(3-Cl-4-OMe-phenyl) | 176–177 | 40 | 466 (MH⁺) | δ (CDCl₃): 1.62–1.79(2H, m), 1.96–2.03(2H, m) 1.57–1.64(1H, m), 3.08–3.18(2H, m) 3.25(3H, s), 3.91(3H, s) 4.70(4.79(2H, m), 4.80(2H, s) 6.93(1H, d, J=8.4Hz) 7.19(1H, dd, J=8.4Hz, 2.0Hz) 7.36(1H, d, J=2.0Hz) 7.45(1H, d, J=8.8Hz) 7.58(1H, dd, J=8.8Hz, 2.0Hz) 8.06(1H, d, J=2.0Hz) | |

TABLE 24

Structure: benzene ring with R² substituent, fused to a ring with =N-C(R⁵)=N- and =CR⁶ positions (quinazoline-like).

| Ex. | R² | R⁵ | R⁶ | m.p. (°C.) | yield (%) | Mass | NMR | note |
|---|---|---|---|---|---|---|---|---|
| 336 | CN | Cl | Me-N(Me)-CH₂-(3,4-methylenedioxyphenyl) | 156–158 | 89 | 353(MH⁺) | δ (DMSO-d₆): 3.42(3H, s), 4.93(2H, s), 5.99(2H, s), 6.86(1H, dd, J=8.0Hz, 1.6Hz), 6.90(1H, d, J=8.0Hz), 6.98(1H, d, J=1.6Hz), 7.73(1H, d, J=8.4Hz), 8.08(1H, dd, J=8.4Hz, 2.0Hz), 8.63(1H, d, J=2.0Hz) | |
| 337 | CN | Cl | Me-N(Me)-CH₂-(3-Cl-4-OMe-phenyl) | 173–175 | 86 | 373(MH⁺) | δ (DMSO-d₆): 3.44(3H, s), 3.83(3H, s), 4.95(2H, s), 7.13(1H, d, J=8.8Hz), 7.34(1H, dd, J=8.8Hz, 2.4Hz), 7.50(1H, d, J=2.4Hz), 7.74(1H, d, J=8.8Hz), 8.08(1H, dd, J=8.8Hz, 1.6Hz), 8.65(1H, d, J=1.6Hz) | |

TABLE 25

Structure: similar quinazoline core with R², R⁵, R⁶ substituents.

| Ex. | R² | R⁵ | R⁶ | m.p. (°C.) | yield (%) | Mass | NMR | note |
|---|---|---|---|---|---|---|---|---|
| 338 | Cl | —COOH | HN-CH₂-(3-Cl-4-OMe-phenyl) | 187–188 | 93 | 378 (M+1)⁺ | δ (DMSO-d₆): 3.83(3H, s), 4.75(2H, d, J=5.6Hz), 7.10(1H, d, J=8.4Hz), 7.38(1H, dd, J=8.4Hz, 2.4Hz), 7.53(1H, d, J=2.4Hz), 7.84(1H, d, J=8.8Hz), 7.88(1H, dd, J=8.8Hz, 2.0Hz), 8.50(1H, d, J=2.0Hz), 9.15(1H, brt, J=5.6Hz) | |
| 339 | Cl | -(CH₂)₃-COOH | HN-CH₂-(3-Cl-4-OMe-phenyl) | 180–181 | 99 | 420 (M+1)⁺ | δ (DMSO-d₆): 1.97(2H, quintet, J=7.4Hz), 2.26(2H, t, J=7.4Hz), 2.72(2H, t, J=7.4Hz), 3.82(3H, s), 4.67(2H, d, J=5.7Hz), 7.08(1H, d, J=8.6Hz), 7.34(1H, dd, J=8.6Hz, 2.2Hz), 7.47(1H, d, J=2.2Hz), 7.64(1H, d, J=9.0Hz), 7.74(1H, dd, J=9.0Hz, 2.4Hz), 8.37(1H, d, J=2.4Hz), 8.76(1H, t, J=5.7Hz) | |

TABLE 26

Structure: R² on benzene ring, with C(=R⁶)-N=C(R⁵)-N forming fused ring system

| Ex. | R² | R⁵ | R⁶ | m.p. (°C.) | yield (%) | Mass | NMR | note |
|---|---|---|---|---|---|---|---|---|
| 340 | Cl | -N(piperidine)-COOEt | 3,4-methylenedioxyphenyl-CH₂CH₂-NH-CH₂- | 173–174 | 88 | 483 (M+1)⁺ | δ (DMSO-d₆): 1.20(3H, t, J=7.2Hz), 1.67(2H, m) 2.01(2H, m), 2.77(1H, m) 2.89(2H, t, J=7.2Hz), 3.39(2H, m) 3.75(2H, m), 4.10(2H, q, J=7.2Hz) 4.56(2H, m), 5.96(2H, s) 6.69(1H, dd, J=8.0Hz, 1.6Hz) 6.80(1H, d, J=8.0Hz) 6.86(1H, d, J=1.6Hz) 7.83(1H, dd, J=8.8Hz, 2.4Hz) 7.95(1H, d, J=8.8Hz) 8.44(1H, d, J=2.4Hz), 9.69(1H, brs) 12.34(1H, brs) | hydro-chloride |
| 341 | Cl | -N(piperidine)-COOH | 3,4-methylenedioxyphenyl-CH₂CH₂-NH-CH₂- | 186–187 | 75 | 455 (M+1)⁺ | δ (DMSO-d₆): 1.50(2H, m), 1.88(2H, m), 2.52(1H, m) 2.86(2H, t, J=7.4Hz), 3.03(2H, m) 3.63(2H, m), 4.65(2H, m), 5.96(2H, s) 6.69(1H, d, J=8.0Hz) 6.82(1H, d, J=8.0Hz), 6.83(1H, s) 7.27(1H, d, J=9.2Hz) 7.48(1H, dd, J=9.2Hz, 2.4Hz) 8.10(1H, d, J=2.4Hz), 8.17(1H, brs) 12.19(1H, brs) | |

TABLE 27

| Ex. | R² | R⁵ | R⁶ | m.p. (°C.) | yield (%) | Mass | NMR | note |
|---|---|---|---|---|---|---|---|---|
| 342 | Cl | -N(piperidine)-COOEt | PhCH₂-NH-CH₂- | 166–167 | 95 | 425 (M+1)⁺ | δ (DMSO-d₆): 1.19(3H, t, J=7.2Hz), 1.57(2H, m) 1.94(2H, m), 2.73(1H, m), 3.31(2H, m) 4.08(2H, q, J=7.2Hz), 4.48(2H, m) 4.77(2H, d, J=5.6Hz) 7.25–7.45(5H,m), 7.85(2H, s) 8.52(1H, s), 10.19(1H, brs) 12.19(1H, brs) | hydro-chloride |
| 343 | Cl | -N(Me)-CH₂CH₂-COOEt | 3-Cl-4-OMe-phenyl-CH₂-NH- | 212–213 | 41 | 477 (M+1)⁺ | δ (DMSO-d₆): 1.12(3H, t, J=7.2Hz), 1.80(2H, brs) 2.23(2H, brs), 3.24(3H, s) 3.73(2H, brs), 3.82(3H, s) 3.99(2H, q, J=7.2Hz) 4.71(2H, d, J=6.0Hz) 7.09(1H, d, J=8.8Hz) 7.35(1H, d, J=8.4Hz), 7.48(1H, s) | hydro-chloride |

TABLE 28

| Ex. | R² | R⁵ | R⁶ | m.p. (°C.) | yield (%) | Mass | NMR | note |
|---|---|---|---|---|---|---|---|---|
| 344 | Cl | —N(Me)—(CH₂)₃—COOH | HN-CH₂-(3-Cl, 4-OMe-C₆H₃) | 140–141 | 81 | 449(M+1)⁺ | δ DMSO-d₆): 1.74(2H, brm), 1.59(2H, brm) 3.10(3H, s), 3.61(2H, t, J=7.2Hz) 3.81(3H, s), 4.61(2H, d, J=5.6Hz) 7.07(1H, d, J=8.4Hz) 7.31(1H, dd, J=8.4Hz, 2.0Hz) 7.36(1H, brs), 7.43(1H, d, J=2.0Hz) 7.55(1H, brs), 8.20(1H, brs) 12.03(1H, brs) | |
| 345 | CN | Cl | HN-CH₂-(3,5-diCl, 4-OMe-C₆H₂) | 248–249 | 78 | 393(M+1)⁺ | δ (DMSO-d₆): 3.81(3H, s), 4.71(2H, d, J=5.6Hz) 7.55(2H, s), 7.76(1H, d, J=8.4Hz) 8.14(1H, dd, J=8.4Hz, 2.0Hz) 8.88(1H, d, J=2.0Hz) 9.49(1H, brt, J=5.6Hz) | |

TABLE 29

| Ex. | R² | R⁵ | R⁶ | m.p. (°C.) | yield (%) | Mass | NMR | note |
|---|---|---|---|---|---|---|---|---|
| 346 | CN | —N(piperidine)—COOEt | HN-CH₂-(3,5-diCl, 4-OMe-C₆H₂) | 207–208 | 82 | 514 (M+1)⁺ | δ (DMSO-d₆): 1.17(3H, t, J=7.2 Hz), 1.36(2H, brm) 1.82(2H, brm), 2.62 (1H, m) 3.03(2H, m), 3.78(3H, s) 4.05 (2H, q, J=7.2Hz) 4.59(2H, brd, J=5.6 Hz) 4.63(2H, brm), 7.29(1H, d, J=8.8 Hz) 7.50(2H, s) 7.75(1H, dd, J=8.8 Hz, 2.0Hz) 8.53(1H, d, J=2.0Hz) 8.86 (1H, brt, J=5.6Hz) | |
| 347 | Cl | —N(piperidine)—COOH | O₂NO-(CH₂)₅-N(Me)-CH₂-(3,4-methylenedioxy-C₆H₃) | amorphous | 19 | 572 (MH⁺) | δ (CDCl₃): 1.25–2.02(12H, m), 2.47–2.57(1H, m) 3.02–3.18(2H, m), 3.50–3.58(2H, m) 4.42(2H, t, J=6.6 Hz) 4.63–4.74(2H, m), 4.75(2H, s) 5.47 (2H, s), 6.80–6.81 (3H, m) 7.41(1H, dd, J=8.0Hz, 2.0Hz) 7.50(1H, d, J=8.0 Hz) 7.62(1H, d, J=2.0Hz) | |

TABLE 30

[Structure: benzene ring with R² at 5-position, R⁶-CH=N- at top, -N=CH-R⁵ connecting to form ring]

| Ex. | R² | R⁵ | R⁶ | m.p. (°C.) | yield (%) | Mass | NMR | note |
|---|---|---|---|---|---|---|---|---|
| 348 | NC | -N(piperidine-4-yl)-C(=O)-NH-CH₂CH₂-SO₃Na | HN-CH₂-(3-Cl, 4-OMe-phenyl) | >250 | 62 | | δ (DMSO-d₆): 1.40(2H, m), 1.72(2H, m), 2.34(1H, m) 2.54 (2H, t, J=7.2Hz), 2.89 (2H, m) 3.31(2H, m), 3.82(3H, s) 4.59(2H, d, J=5.6Hz), 4.78(2H, m) 7.09(1H, d, J=8.4 Hz) 7.28(1H, d, J=8.4 Hz) 7.32(1H, dd, J= 8.4Hz, 2.0Hz) 7.45 (1H, d, J=2.0Hz) 7.72 (1H, dd, J=8.4Hz, 2.0 Hz) 7.74(1H, t, J= 5.6Hz) 8.54(1H, d, J= 2.0Hz) 8.77(1H, t, J= 5.6Hz) | |
| 349 | Cl | -N(piperidine-4-yl)-COOH | HN-CH₂-(3,4-diOH-phenyl) | 216–218 (decomp.) | 95 | 429 (MH⁺) | δ (DMSO-d₆): 1.38–1.47(2H, m), 1.80–1.84(2H, m), 2.44–2.49(1H, m), 2.93–3.00(2H, m), 4.48(2H, d, J=5.6Hz) 4.57–4.61(2H, m), 6.60–6.65(2H, m), 6.74(1H, d, J=1.6Hz) 7.24(1H, d, J=8.8Hz) 7.46(1H, dd, J=8.8Hz, 2.0Hz) 8.15(1H, d, J=2.0Hz), 8.48(1H, brs) 8.675(1H, s), 8.75 (1H, s) 12.14(1H, brs) | |

TABLE 31

[Structure: benzene ring with R² at 5-, R³ at 4-, R⁴ at 3-position, R⁶-CH=N- fused with -N=CH-]

| Ex. | R² | R³ | R⁴ | R⁶ | m.p. (°C.) | yield (%) | Mass | NMR | note |
|---|---|---|---|---|---|---|---|---|---|
| 350 | MeO | MeO | MeO | HN-CH₂-(cis-bicyclic methylenedioxy cyclopentane) | 163–164 | 70 | 362(M+1)⁺ | δ (CDCl₃): 1.41(2H, m), 2.16(2H, m), 2.60(1H, m) 3.69(2H, m), 4.02(3H, s), 4.03(3H, s) 4.11(3H, s), 4.55(2H, m), 4.63(1H, s) 5.06(1H, s), 5.75(1H, brs) 6.83(1H, brs), 8.59(1H, s) | |
| 351 | MeO | MeO | MeO | HN-CH₂CH₂-(cis-bicyclic methylenedioxy cyclopentane) | 173–174 | 37 | 376(M+1)⁺ | δ (CDCl₃): 1.86(2H, m), 1.79(2H, m) 2.14(2H, dd, J=14.4Hz, 5.6Hz) 2.27(1H, m), 3.68(2H, m), 3.99(3H, s) 4.02(3H, s), 4.11(3H, s), 4.50(2H, m) 4.62(1H, s), 5.03(1H, s), 5.78(1H, brs) 6.76(1H, s), 8.60(1H, s) | |

TABLE 31-continued

| Ex. | R² | R³ | R⁴ | R⁶ | m.p. (°C.) | yield (%) | Mass | NMR | note |
|---|---|---|---|---|---|---|---|---|---|
| 352 | MeO | MeO | MeO | (cyclopentane fused 1,3-dioxolane with -CH₂-NH- substituent, H stereochem shown) | 170–171 | 70 | 362(M+1)⁺ | δ (CDCl₃): 1.87(2H, m), 1.99(2H, m), 2.63(1H, m) 3.73(2H, m), 4.00(3H, s), 4.03(3H, s) 4.11(3H, s), 4.58(2H, m), 4.80(1H, s) 5.17(1H, s), 6.14(1H, brs), 6.80(1H, s) 8.59(1H, s) | |

TABLE 32

| Ex. | R² | R³ | R⁴ | R⁶ | m.p. (°C.) | yield (%) | Mass | NMR | note |
|---|---|---|---|---|---|---|---|---|---|
| 353 | MeO | MeO | MeO | (cyclopentane fused 1,3-dioxolane with -CH₂CH₂-NH- substituent) | 143–144 | 24 | 376(M+1)⁺ | δ (CDCl₃): 1.77(2H, m), 1.80(2H, m), 1.97(2H, m) 2.07(1H, m), 3.64(2H, m), 3.98(3H, s) 4.03(3H, s), 4.10(3H, s), 4.58(2H, m) 4.83(1H, s), 5.12(1H, s), 6.24(1H, brs) 6.92(1H, s), 8.60(1H, s) | |
| 354 | MeO | MeO | MeO | HN-CH₂CH₂CH₂-CN | 139–140 | 88 | 303(M+1)⁺ | δ (CDCl₃): 2.16(2H, quintet, J=6.8Hz) 2.52(1H, t, J=6.8Hz) 3.85(2H, dt, J=6.8Hz, 6.0Hz) 3.99(3H, s), 4.03(3H, s), 4.10(3H, s) 6.29(1H, brs), 6.90(1H, s), 8.60(1H, s) | |
| 355 | MeO | MeO | MeO | HN-CH₂CH₂CH₂CH₂-CN | 160–161 | 94 | 317(M+1)⁺ | δ (CDCl₃): 1.81(2H, m), 1.94(2H, m) 2.47(2H, t, J=6.8Hz) 3.75(2H, dt, J=6.8Hz, 6.0Hz) 4.00(3H, s), 4.03(3H, s), 4.11(3H, s) 5.91(1H, brs), 6.82(1H, s), 8.60(1H, s) | |

TABLE 33

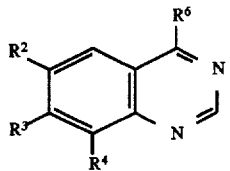

| Ex. | R² | R³ | R⁴ | R⁶ | m.p. (°C.) | yield (%) | Mass | NMR | note |
|---|---|---|---|---|---|---|---|---|---|
| 356 | MeO | MeO | MeO | ![HN-(CH2)5-CN] | 155–156 | 75 | 331(M+1)⁺ | δ (CDCl₃): 1.6–1.8(6H, m), 2.40(2H, t, J=7.0Hz) 3.70(2H, dt, J=7.0Hz, 5.6Hz) 4.00(3H, s), 4.03(3H, s), 4.11(3H, s) 6.00(1H, brs), 6.84(1H, s), 8.60(1H, s) | |

TABLE 34

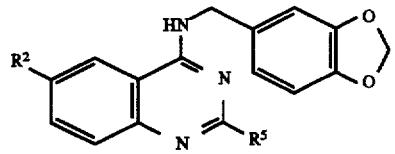

| Ex. | R² | R⁵ | m.p. (°C.) | yield (%) | Mass | NMR | note |
|---|---|---|---|---|---|---|---|
| 357 | Cl | ![piperidine-(CH2)4-COOH] | 225–227 | 85 | 483(M+1) | δ (DMSO-d₆): 0.93(2H, m), 1.18(2H, m), 1.44(1H, m) 1.51(2H, m), 1.64(2H, brd, J=12.0Hz) 2.18(2H, t, J=7.6Hz), 2.75(2H, brt, J=12.0 Hz) 4.53(2H, d, J=5.6Hz), 4.73(2H, brd, J=12.8Hz) 5.94(1H, s), 6.83(2H, s), 6.93 (1H, s) 7.22(1H, d, J=8.8Hz) 7.45(1H, dd, J=8.8Hz, 2.4Hz) 8.11(1H, d, J=2.4Hz), 8.50(1H, t, J=5.6Hz) | |
| 358 | Cl | ![-O-(CH2)3-O-SO2-ONa] | 190–192 (decomp.) | 32 | 490(MH⁺) | δ (DMSO-d₆): 1.90–1.95(2H, m), 3.82(2H, t, J=6.4Hz) 4.28(2H, t, J=6.8Hz), 4.61(2H, d, J=5.6Hz) 5.95(2H, s), 6.04(2H, s), 6.13(1H, s) 7.50(1H, d, J=8.8Hz) 7.64(1H, dd, J=8.8Hz, 2.4Hz) 8.54(1H, d, J=2.4Hz), 8.75(1H, t, J=1.6Hz) | |

TABLE 35

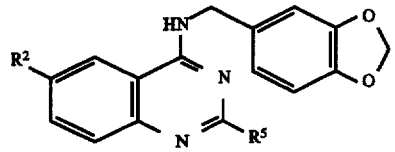

| Ex. | R² | R⁵ | m.p. (°C.) | yield (%) | Mass | NMR | note |
|---|---|---|---|---|---|---|---|
| 359 | Cl | ![-O-(CH2)6-ONO2] | 121–122 | 95 | 475(MH⁺)⁺ | δ (CDCl₃): 1.42–1.59(4H, m), 1.70–1.89(4H, m), 4.43(4H, q, J=6.8Hz), 4.73(2H, d, J=4.4Hz) 5.95(2H, s), 6.28(1H, br) 6.77(1H, d, J=8.0Hz), 6.83(1H, d, J=8.0Hz) 6.85(1H, s), 7.54(1H, d, J=8.8Hz) 7.58(1H, d, J=8.8Hz), 7.66(1H, s) | |

TABLE 35-continued

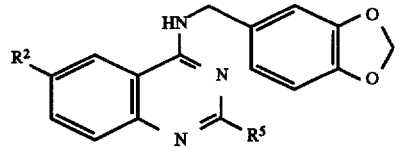

| Ex. | R² | R⁵ | m.p. (°C.) | yield (%) | Mass | NMR | note |
|---|---|---|---|---|---|---|---|
| 360 | Cl | piperazinyl (—N(CH₂CH₂)₂NH) | 173–175 | 98 | 398(M+1) | δ (DMSO-d₆): 2.66(4H, t, J=4.8Hz), 3.66(1H, t, J=4.8Hz) 4.54(2H, d, J=6.0Hz), 5.94(2H, s) 6.83(2H, s), 6.92(1H, s), 7.22(1H, d, J=8.8Hz) 7.46(1H, dd, J=8.8Hz, 2.4Hz) 8.12(1H, d, J=2.4Hz), 8.51(1H, t, J=6.0Hz) | |
| 361 | Cl | 4-(methoxycarbonyl)piperidin-1-yl | 233–234 | 93 | 455(M+1)⁺ | δ (DMSO-d₆): 1.58(2H, m), 1.95(2H, m), 2.75(1H, m) 3.3(2H, m), 3.61(3H, s), 4.46(2H, m) 4.65(2H, d, J=5.6Hz), 5.96(2H, s) 6.84(1H, d, J=8.0Hz) 6.87(1H, dd, J=8.0Hz, 1.2Hz) 6.97(1H, d, J=1.2Hz), 7.78(1H, brd, J=8.8Hz) 7.81(1H, brd, J=8.8Hz), 8.45(1H, brs) 10.05(1H, brs), 12.05(1H, brs) | hydrochloride |

TABLE 36

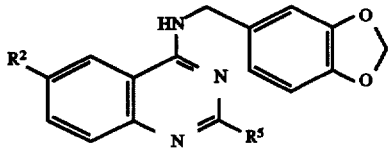

| Ex. | R² | R⁵ | m.p. (°C.) | yield (%) | Mass | NMR | note |
|---|---|---|---|---|---|---|---|
| 362 | Cl | 1-acetyl-4-carboxypiperidin-4-yl | | 12 | | δ (DMSO-d₆): 1.48(2H, m), 1.64(1H, m), 1.85(1H, m) 2.36(1H, m), 2.96(2H, m), 3.28(1H, m) 4.19(1H, m), 4.64(2H, d, J=5.6Hz) 5.95(2H, s), 6.82(2H, s), 6.93(1H, s) 7.71(1H, brd), 7.79(1H, brd), 8.47(1H, s) 9.04(1H, brs) | |
| 363 | H | Cl | 191–192 | 94 | 314(M+1) | δ (CDCl₃): 4.76(2H, d, J=5.2Hz), 5.97(2H, s) 6.15(1H, brs), 6.80(1H, d, J=8.0Hz) 6.87(1H, dd, J=8.0Hz, 1.6Hz) 6.89(1H, d, J=1.6Hz) 7.44(1H, ddd, J=8.0Hz, 6.8Hz, 1.6Hz) 7.66(1H, d, J=8.0Hz), 7.74(1H, t, J=6.8Hz) 7.78(1H, dd, J=6.8Hz, 1.6Hz) | |

TABLE 37

[Structure: R² substituted benzene with C(=NH-CH₂-benzodioxole) and N=C(R⁵)-N ring]

| Ex. | R² | R⁵ | m.p. (°C.) | yield (%) | Mass | NMR | note |
|---|---|---|---|---|---|---|---|
| 364 | H | -N(piperidine)-COOH (4-position) | 159–161 | 97 | 407(M+1) | δ (DMSO-d₆): 1.38(2H, m), 1.79(2H, brd, J=12.8Hz) 2.47(1H, m), 2.94(2H, brt, J=11.2Hz) 4.56(2H, d, J=5.6Hz), 4.61(2H, m) 5.93(2H, s), 6.81(1H, d, J=8.0Hz) 6.84(1H, dd, J=8.0Hz, 1.6Hz) 6.93(1H, d, J=1.6Hz), 7.04(1H, t, J=8.4Hz) 7.24(1H, d, J=8.4Hz), 7.48(1H, t, J=8.4Hz) 7.98(1H, t, J=8.4Hz), 8.47(1H, brs) 12.13(1H, brs) | |
| 365 | Cl | -N(piperidine)(4-CH₃)(4-COOH) | 243–245 | 81 | 455(M+1) | δ (DMSO-d₆): 1.12(3H, s), 1.25(2H, m), 1.88(2H, m) 3.23(2H, m), 4.20(2H, m), 4.53(2H, d, J=6.0Hz) 5.94(2H, s), 6.83(2H, s), 6.92(1H, s) 7.23(1H, d, J=9.2Hz) 7.46(1H, dd, J=9.2Hz, 2.4Hz) 8.12(1H, d, J=2.4Hz), 8.53(1H, t, J=6.0Hz) | |

TABLE 38

[Structure: R² substituted benzene with C(=NH-CH₂-benzodioxole) and N=C(R⁵)-N ring]

| Ex. | R² | R⁵ | m.p. (°C.) | yield (%) | Mass | NMR | note |
|---|---|---|---|---|---|---|---|
| 366 | Cl | -N(piperazine)N-(CH₂)₃-COOH | 174–175 | 99 | 484(M+1) | δ (DMSO-d₆): 1.66(2H, quintet, J=7.2Hz) 2.24(2H, t, J=7.2Hz), 2.29(2H, t, J=7.2Hz) 2.35(4H, m), 3.72(4H, m), 4.55(2H, d, J=5.6Hz) 5.95(2H, s), 6.83(2H, s), 6.93(1H, s) 7.24(1H, d, J=8.8Hz) 7.47(1H, dd, J=8.8Hz, 2.4Hz) 8.14(1H, d, J=2.4Hz), 8.53(1H, t, J=5.6Hz) | |
| 367 | Cl | -N(piperazine)N-Me | 237–239 (decomp.) | quantitative | 412(M+1)⁺ | δ (DMSO-d₆): 2.79(3H, s), 3.14(2H, m), 3.54(2H, m) 3.62(2H, m), 4.71(2H, d, J=5.6Hz), 4.94 (2H, m) 5.99(2H, s), 6.87(1H, d, J=8.0Hz) 6.94(1H, dd, J=8.0Hz, 1.6Hz) 7.03(1H, d, J=1.6Hz), 7.87(1H, brd) 8.07(1H, brs), 8.60(1H, brs), 10.29(1H, brs) 11.36(1H, brs), 13.13(1H, brs) | dihydro-chloride |

TABLE 39

[Structure: R² substituted benzene fused to pyrimidine ring with HN-CH₂-benzo[1,3]dioxole group and R⁵ substituent]

| Ex. | R² | R⁵ | m.p. (°C.) | yield (%) | Mass | NMR | note |
|---|---|---|---|---|---|---|---|
| 368 | Cl | −N(piperazine)N−CH₂−COOH | 193–195 | 86 | 456(M+1) | δ (DMSO-d₆): 2.53(4H, m), 3.00(2H, brs), 3.75(4H, m) 4.53(2H, brd, J=6.0Hz), 5.94(2H, s) 6.82(2H, brs), 6.92(1H, s) 7.23(1H, d, J=8.8Hz), 7.47(1H, brd, J=8.8Hz) 8.14(1H, brs), 8.55(1H, t, J=6.0Hz) | |
| 369 | Cl | −N(piperazine)N−CH₂CH₂−COOH | 174–176 | 90 | 470(M+1) | δ (DMSO-d₆): 2.39(6H, m), 2.56(2H, t, J=7.2Hz) 3.71(2H, brs), 4.55(2H, d, J=5.6Hz) 1.83(2H, s), 6.93(1H, s), 7.24(1H, d, J=8.8Hz) 7.48(1H, dd, J=8.8Hz, 2.4Hz) 8.14(1H, d, J=2.4Hz), 8.55(1H, t, J=5.6Hz) | |
| 370 | Cl | −CONH−CH₂CH₂−phenyl | 166–169 (decomp.) | 80 | 461(MH⁺) | δ (DMSO-d₆): 2.86(2H, t, J=7.2Hz), 3.53(2H, q, J=8.0Hz) 4.74(2H, d, J=5.2Hz), 5.97(2H, s) 6.86–6.89(2H, m), 7.01(1H, d, J=1.2Hz) 7.18–7.32(5H, m), 7.83(1H, d, J=8.8Hz) 7.86(2H, dd, J=8.8Hz, 2.0Hz) 8.50(1H, d, J=2.0Hz), 8.70(1H, brt, J=5.2Hz) 9.02(1H, brt, J=5.0H) | |

TABLE 40

[Structure: R² substituted benzene fused to pyrimidine ring with HN-CH₂-benzo[1,3]dioxole group and R⁵ substituent]

| Ex. | R² | R⁵ | m.p. (°C.) | yield (%) | Mass | NMR | note |
|---|---|---|---|---|---|---|---|
| 371 | Cl | −CONH−CH₂CH₂−OH | 223–225 (decomp.) | 42 | 401(MH⁺) | δ(DMSO-d₆): 3.37(2H, q, J=6.0Hz), 3.53(2H, q, J=5.8Hz) 4.75(2H, d, J=6.0Hz), 4.82(1H, t, J=5.4Hz) 5.97(2H, s), 6.86(1H, d, =8.0Hz) 6.94(1H, dd, J=8.0Hz, 1.6Hz) 7.04(1H, d, J=1.6Hz), 7.81–7.88(2H, m) 8.50(1H, d, J=2.0Hz), 8.64(1H, t, J=6.0Hz) 9.04(1H, t, J=6.0Hz) | |
| 372 | Cl | −C(=N−CN)−O−CH₂CH₂CH₃ | 199–201 (decomp.) | | 424(MH⁺) | δ(DMSO-d₆): 0.99(3H, t, J=7.4Hz), 1.79–1.84(2H, m) 4.41(2H, t, J=6.6Hz), 4.83(2H, d, J=5.6Hz) 5.97(2H, s), 6.85(1H, d, J=28.0Hz) 6.93(1H, dd, J=8.0Hz, 1.6Hz) 7.03(1H, d, J=1.6Hz), 7.87(1H, d, J=8.8Hz) 7.91(1H, dd, J=8.8Hz, 2.2Hz) 8.56(1H, d, J=2.2Hz), 8.727(1H, brt, J=5.6Hz) | |

TABLE 41

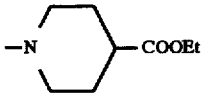

| Ex. | R² | R⁵ | m.p. (°C.) | yield (%) | Mass | NMR | note |
|---|---|---|---|---|---|---|---|
| 373 | Br | Cl | 213–214 | 80 | 392(M + 1)⁺ | δ(DMSO-d₆): 4.63(2H, d, J=5.6Hz), 5.99(2H, s), 6.87(2H, s) 6.97(1H, s), 7.57(1H, d, J=8.8Hz) 7.92(1H, dd, J=8.8Hz, 2.0Hz) 8.61(1H, d, J=2.0Hz), 9.26(1H, t, J=5.6Hz) | |
| 374 | F | Cl | 192–193 | 80 | 332(M + 1)⁺ | δ(DMSO-d₆): 4.65(2H, d, J=5.6Hz), 5.99(2H, s), 6.87(2H, s) 6.97(1H, s), 7.71(2H, m), 8.17(1H, m) 9.14(1H, t, J=5.6Hz) | |
| 375 | Br | —N(piperidine)—COOEt | 239–240 | 80 | 513(M + 1)⁺ | δ(DMSO-d₆): 1.17(3H, t, J=7.2Hz), 1.56(2H, m), 1.94(2H, m) 2.72(1H, m), 3.3(2H, m), 4.06(2H, q, J=7.2Hz) 4.49(2H, m), 4.64(2H, d, J=6.0Hz), 5.95(2H, s) 6.83(1H, d, J=8.0Hz) 6.87(1H, dd, J=8.0Hz, 1.6Hz) 6.97(1H, d, J=1.6Hz), 7.80(1H, d, J=8.8Hz) 7.91(1H, dd, J=8.8Hz, 2.0Hz) 8.60(1H, d, J = 2.0Hz), 10.10(1H, brs) 12.22(1H, brs) | hydrochloride |

TABLE 42

| Ex. | R² | R⁵ | m.p. (°C.) | yield (%) | Mass | NMR | note |
|---|---|---|---|---|---|---|---|
| 376 | Br | —N(piperidine)—COOH | 209–210 | 96 | 485(M + 1)⁺ | δ(DMSO-d₆): 1.38(2H, m), 1.79(2H, m), 2.46(1H, m) 2.95(2H, m), 4.53(2H, d, J=6.0Hz), 4.58(2H, m) 5.93(2H, s), 6.80(1H, d, J=8.0Hz) 6.83(1H, dd, J=8.0Hz, 1.6Hz) 6.91(1H, d, J=1.6Hz), 7.16(1H, d, J=9.2Hz) 7.55(1H, dd, J=9.2Hz, 2.4Hz) 8.24(1H, d, J=2.4Hz), 8.52(1H, t, J=6.0Hz) 12.13(1H, brs) | |
| 377 | piperidin-1-yl | Cl | 200–201 | 36 | 397(M + 1)⁺ | δ(CDCl₃): 1.62(2H, m), 1.73(4H, m), 3.21(4H, t, J=5.4Hz) 4.76(2H, d, J=5.2Hz), 5.80(1H, t, J=5.2Hz) 5.97(2H, s), 6.76(1H, d, J=2.4Hz) 6.81(1H, d, J=8.0Hz) 6.88(1H, dd, J=8.0Hz, 1.2Hz) 6.91(1H, d, J=1.2Hz) 7.48(1H, dd, J=9.2Hz, 2.4Hz) 7.66(1H, d, J=9.2Hz) | |

TABLE 43

| Ex. | R² | R⁵ | m.p. (°C.) | yield (%) | Mass | NMR | note |
|---|---|---|---|---|---|---|---|
| 378 | Me₂N— (Me-N-Me) | Cl | 226–227 (decomp.) | 94 | 357(M + 1)⁺ | δ(DMSO-d₆): 2.99(6H, s), 4.63(2H, d, J=6.0Hz), 5.96(2H, s) 6.84(2H, s), 6.93(1H, s), 7.20(1H, d, J=2.8Hz) 7.37(1H, dd, J=9.2Hz, 2.8Hz) 7.46(1H, d, J=9.2Hz), 8.84(1H, t, J=6.0Hz) | |
| 379 | Cl | —N(piperazinyl)N—C(O)CH₂CH₂COOH | 183–185 | 86 | 498(M + 1) | δ(DMSO-d₆): 2.43(2H, t, J=6.4Hz), 2.56(2H, t, J=6.4Hz) 3.46(4H, brs), 3.71(2H, brs), 3.77(2H, brs) 4.56(2H, d, J=5.6Hz), 5.95(2H, s) 6.83(1H, d, J=8.0Hz), 6.86(1H, d, J=8.0Hz) 6.94(1H, s), 7.27(1H, d, J=8.8Hz) 7.50(1H, dd, J=8.8Hz, 2.0Hz) 8.16(1H, d, J=2.0Hz), 8.61(1H, t, J=5.6Hz) | |

TABLE 44

| Ex. | R² | R⁵ | m.p. (°C.) | yield (%) | Mass | NMR | note |
|---|---|---|---|---|---|---|---|
| 380 | Cl | —N(piperazinyl)N—C(O)CH₂COOH | 193–195 | 85 | 484(M + 1) | δ(DMSO-d₆): 3.44(6H, m), 3.73(2H, m), 3.78(2H, m) 4.56(2H, d, J=5.6Hz), 5.93(2H, s) 6.83(1H, d, J=8.0Hz), 6.85(1H, d, J=8.0Hz) 6.94(1H, s), 7.27(1H, d, J=8.8Hz) 7.50(1H, dd, J=8.8Hz, 2.0Hz) 8.16(1H, d, J=2.0Hz), 8.61(1H, t, J=5.6Hz) | |
| 381 | Cl | —N(piperazinyl)N—C(O)CH₂CH₂CH₃ | 204–205 | 62 | 468(M + 1) | δ(CDCl₃): 1.00(3H, t, J=7.6Hz) 1.70(2H, sextet, J=7.6Hz) 2.36(2H, t, J=7.6Hz), 3.54(2H, brs) 3.69(2H, t, J=4.8Hz), 3.89(2H, t, J=4.8Hz) 3.92(2H, brs), 4.68(2H, d, J=5.2Hz) 5.65(1H, brs), 5.97(2H, s) 6.80(1H, d, J=8.0Hz) 6.84(1H, dd, J=8.0Hz, 0.8Hz) 6.87(1H, d, J=0.8Hz), 7.40(1H, m), 7.46(1H, m) 7.48(1H, m) | |

TABLE 45

Structure: R² substituted benzene with HN-CH₂-benzodioxole group, and N=C-R⁵ group

| Ex. | R² | R⁵ | m.p. (°C.) | yield (%) | Mass | NMR | note |
|---|---|---|---|---|---|---|---|
| 382 | Cl | —N(piperidine)-COOMe (4-position) | 233–234 | 93 | 455(M + 1)⁺ | δ(DMSO-d₆): 1.58(2H, m), 1.95(2H, m), 2.75(1H, m) 3.3(2H, m), 3.61(3H, s), 4.46(2H, m) 4.65(2H, d, J=5.6Hz), 5.96(2H, s) 6.84(1H, d, J=8.0Hz) 6.87(1H, dd, J=8.0Hz, 1.2Hz) 6.97(1H, d, J=1.2Hz), 7.78(1H, brd, J=8.8Hz) 7.81(1H, brd, J=8.8Hz), 8.45(1H, brs) 10.05(1H, brs), 12.05(1H, brs) | hydrochloride |
| 383 | Cl | —N(piperidine)-COOEt (3-position) | amorphous | 99 | 469(M + 1)⁺ | δ(CDCl₃): 1.25(3H, t, J=7.2Hz), 1.54(1H, m), 1.70(1H, m) 1.78(1H, m), 2.11(1H, m), 2.52(1H, m), 2.98(1H, m, 3.14(1H, m ), 4.15(2H, q, J=7.2Hz) 4.66(2H, m), 4.73(1H, m), 4.98(1H, m) 5.61(1H, brt), 5.95(2H, s) 6.78(1H, d, J=8.0Hz) 6.85(1H, dd, J=8.0Hz, 1.6Hz) 6.88(1H, d, J=1.6Hz), 7.37–7.44(3H, m) | |

TABLE 46

Structure: R² substituted benzene with HN-CH₂-benzodioxole group, and N=C-R⁵ group

| Ex. | R² | R⁵ | m.p. (°C.) | yield (%) | Mass | NMR | note |
|---|---|---|---|---|---|---|---|
| 384 | Cl | —N(piperidine)-COOH (3-position) | 275–276 (decomp.) | 98 | 441(M + 1)⁺ | δ(DMSO-d₆); 1.34(1H, m), 1.56(1H, m), 1.65(1H, m) 1.97(1H, m), 2.28(1H, m), 2.85(1H, m) 2.95(1H, m), 4.53(2H, m), 4.57(1H, m) 4.81(1H, m), 5.93(2H, s), 6.78(1H, d, J=8.0Hz) 6.84(1H, dd, J=8.0Hz, 1.6Hz) 6.91(1H, d, J=1.6Hz), 7.24(1H, d, J=8.8Hz) 7.45(1H, dd, J=8.8Hz, 2.4Hz) 8.12(1H, d, J=2.4Hz), 8.55(1H, brs) | |
| 385 | Cl | —CN | 198–199 | 35 | 339(M + 1)⁺ | δ(CDCl₃); 3.18(1H, br), 4.75(2H, d, J=5.2Hz) 5.97(2H, s), 6.17(1H, br) 6.81(1H, d, J=8.4Hz) 6.87(1H, dt, J=8.4Hz, 1.6Hz) 6.88(1H, d, J=1.6Hz), 7.72(1H, d, J=2.0Hz) 7.75(1H, dd, J=8.8Hz, 2.0Hz) 7.85(1H, d, J=2.0Hz) | |

TABLE 47

| Ex. | R² | R⁵ | m.p. (°C.) | yield (%) | Mass | NMR | note |
|---|---|---|---|---|---|---|---|
| 386 | MeS | H | 174–175 | 83 | 326(M + H)⁺ | δ(CDCl₃); 2.59(3H, s), 4.79(2H, d, J=5.6Hz) 5.93(2H, s), 6.77(1H, d, J=8.0Hz) 6.89(1H, d, J=8.0Hz), 6.94(1H, s) 7.62(1H, dd, J=8.8Hz, 2.0Hz) 7.75(1H, d, J=8.8Hz), 7.97(1H, d, J=2.0Hz) 8.10(1H, brs), 8.56(1H, s) | |
| 387 |  | H | 154–155 | 80 | 342(M + H)⁺ | δ(CDCl₃); 2.75(3H, s), 4.80(2H, d, J=5.2Hz) 5.96(2H, s), 6.80(1H, d, J=8.0Hz) 6.89(1H, d, J=8.0Hz), 6.91(1H, s) 7.06(1H, brs), 7.64(1H, d, J=8.8Hz) 7.98(1H, d, J=8.8Hz), 8.43(1H, s), 8.74(1H, s) | |
| 388 | Cl | 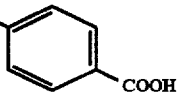 | 154–155 | 71 | 401(M + 1)⁺ | δ(DMSO-d₆); 1.68(2H, m), 3.11(3H, s), 3.40(2H, t, J=6.2Hz) 3.65(2H, t, J=7.0Hz), 4.60(2H, d, J=5.6Hz) 6.83(1H, d, J=7.6Hz) 6.87(1H, dd, J=7.6Hz, 1.2Hz) 6.95(1H, d, J=1.2Hz), 7.31(1H, br) 7.52(1H, br), 8.19(1H, br) | |

TABLE 48

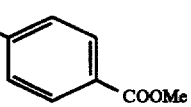

| Ex. | R² | R⁵ | m.p. (°C.) | yield (%) | Mass | NMR | note |
|---|---|---|---|---|---|---|---|
| 389 | Cl | Cl | 194–195 (decomp.) | 48 | 334(M + 1)⁺ | δ(DMSO-d₆); 6.04(2H, s), 6.95(1H, d, J=8.4Hz) 7.11(1H, dd, J=8.4Hz, 2.0Hz) 7.38(1H, d, J=2.0Hz), 7.69(1H, d, J=8.8Hz) 7.86(1H, dd, J=8.8Hz, 2.4Hz) 8.66(1H, d, J=2.4Hz), 10.13(1H, s) | |
| 390 | CN | —O—CH₂—C₆H₄—COOH | 298–300 (decomp.) | 29 | 445(MH⁺) | δ(DMSO-d₆); 4.62(2H, d, J=5.6Hz), 5.47(2H, s), 5.45(2H, s) 6.81–6.82(2H, m), 6.90(1H, s) 7.51(2H, d, J=8.0Hz), 7.57(1H, d, J=8.8Hz) 7.90(2H, d, J=8.0Hz) 7.96(1H, dd, J=8.8Hz, 2.0Hz) 8.79(1H, d, J=2.0Hz), 9.10(1H, brt, J=5.1Hz) | |
| 391 | CN | —O—CH₂—C₆H₄—COOMe | 176–179 | 35 | 469(MH⁺) | δ(CDCl₃); 3.92(3H, s), 4.74(2H, d, J=5.2Hz), 5.58(2H, s) 5.92–5.99(1H, m), 5.99(2H, s) 6.60–6.69(3H, m), 7.57(2H, d, J=8.0Hz) 7.70(1H, d, J=8.8Hz) 7.80(1H, dd, J=8.8Hz, 1.6Hz) 7.95(1H, d, J=1.6Hz), 8.03(2H, d, J=8.0Hz) | |

TABLE 49

[Structure: R² on benzene ring, HN-CH₂-benzodioxole, N=C central, N-C-R⁵]

| Ex. | R² | R⁵ | m.p. (°C.) | yield (%) | Mass | NMR | note |
|---|---|---|---|---|---|---|---|
| 392 | Cl | -N(piperidine-4-yl)-C(O)-NH-CH₂CH₂-SO₃Na | 230 (decomp.) | 51 | | δ(DMSO-d₆); 1.39(2H, m), 1.69(2H, m), 2.31(1H, m) 2.54(2H, t, J=7.2Hz), 2.82(2H, m) 3.31(2H, m), 4.56(2H, d, J=5.6Hz) 4.74(2H, m), 5.96(2H, s), 6.83(1H, d, J=8.0Hz) 6.86(1H, dd, J=8.0Hz, 1.6Hz) 6.94(1H, d, J=1.6Hz), 7.26(1h, d, J=8.8Hz) 7.47(1H, dd, J=8.8Hz, 2.4Hz) 7.72(1H, t, J=5.6Hz), 8.14(1H, d, J=2.4Hz) 8.54(1H, t, J=5.6Hz) | |
| 393 | Cl | -N(piperidine-4-yl)-COOH | 255-256 | 96 | 455(M + 1) | δ(DMSO-d₆); 1.01(2H, m), 1.66(2H, brd, J=13.2Hz) 1.90(1H, brs), 2.12(2H, d, J=7.2Hz) 2.79(2H, brt, J=12.0Hz) 4.53(2H, d, J=5.6Hz), 4.71(2H, brd, J=13.2Hz) 5.94(2H, s), 6.82(2H, m), 6.92(1H, s) 7.22(1H, d, J=8.8Hz) 7.45(1H, dd, J=8.8Hz, 2.4Hz) 8.11(1H, d, J=2.4Hz), 8.51(1H, t, J=5.6Hz) | |

TABLE 50

[Structure: same core as Table 49]

| Ex. | R² | R⁵ | m.p. (°C.) | yield (%) | Mass | NMR | note |
|---|---|---|---|---|---|---|---|
| 394 | Cl | -CH₂-CONH₂ | 222-223 | 13 | 371(M + 1) | δ(DMSO-d₆); 3.54(2H, s), 4.66(2H, d, J=5.7Hz) 5.97(2H, s), 6.84(1H, d, J=7.9Hz) 6.90(1H, dd, J=7.9Hz, 1.6Hz) 6.98(2H, brs, d, J=1.6Hz), 7.43(1H, brs) 7.66(1H, d, J=9.0Hz) 7.76(1H, dd, J=9.0Hz, 3.2Hz) 8.40(1H, d, J=2.2Hz), 8.77(1H, t, J=5.7Hz) | |
| 395 | Cl | -NH-CH₂-benzodioxole | 176-177 | 54 | 463(M + 1) | δ(DMSO-d₆); 4.39(2H, d, J=6.0Hz), 4.55(2H, d, J=5.6Hz) 5.93(4H, d, J=8.0Hz), 6.77(5H, m) 6.80(1H, br), 7.20(2H, br) 7.45(1H, dd, J=8.8Hz, 0.8Hz) 8.11(1H, d, J=2.4Hz), 8.38(1H, br) | |

TABLE 51

(structure shown: R² substituted benzene with HN-CH2-benzodioxole and N=C-R⁵ amidine group)

| Ex. | R² | R⁵ | m.p. (°C.) | yield (%) | Mass | NMR | note |
|---|---|---|---|---|---|---|---|
| 396 | CN | —O—CH2—C6H4—COOMe | 176–179 | 35 | 469(MH⁺) | δ(CDCl3); 3.92(3H, s), 4.74(2H, d, J=5.2Hz), 5.58(2H, s) 5.92–5.99(1H, m), 5.98(2H, s), 6.60–6.69(3H, m), 7.57(2H, d, J=8.0Hz) 7.70(1H, d, J=8.8Hz) 7.80(1H, dd, J=8.8Hz, 1.6Hz) 7.95(1H, d, J=1.6Hz), 8.03(2H, d, J=8.0Hz) | |
| 397 | CN | —O—CH2—C6H4—COOH | 298–300 (decomp.) | 29 | 455(MH⁺) | δ(DMSO-d6); 4.62(2H, d, J=5.6Hz), 5.47(2H, s), 5.45(2H, s) 6.81–6.82(2H, m), 6.90(1H, s) 7.51(2H, d, J=8.0Hz), 7.57(1H, d, J=8.8Hz) 7.90(2H, d, J=8.0Hz) 7.91(1H, dd, J=8.8Hz, 2.0Hz) 8.79(1H, d, J=2.0Hz), 9,10(1H, brt, J=5.1Hz) | |

TABLE 52

(structure shown: R² substituted benzene with HN-CH2-benzodioxole and N=C-R⁵ amidine group)

| Ex. | R² | R⁵ | m.p. (°C.) | yield (%) | Mass | NMR | note |
|---|---|---|---|---|---|---|---|
| 398 | Cl | —N(Me)—CH2CH2—C(Me)(Me)—COOEt | 236–237 | 27 | 485(M+1) | δ(DMSO-d6); 1.10(6H, s), 1.11(3H, t, J=7.2Hz) 1.76(2H, brs), 3.22(3H, s), 3.64(2H, m) 3.97(2H, q, J=7.2Hz), 4.71(2H, d, J=5.6Hz) 5.97(2H, s), 6.84(2H, s), 6.95(1H, s) 7.84(1H, dd, J=9.2Hz, 2.0Hz) 7.93(1h, d, J=9.2Hz), 8.53(1H, d, J=2.0Hz) 10.10(1H, brs), 11.95(1H, brs) | hydrochloride |
| 399 | Cl | —N(Me)—CH2CH2—C(Me)(Me)—COOH | 240–241 (decomp.) | 78 | 457(M+1) | δ(DMSO-d6); 1.086(6H, s), 1.66(2H, m), 3.03(3H, s) 3.54(2H, m), 4.59(2H, d, J=5.6Hz), 5.94(2H, s) 6.82(2H, s), 6.90(1H, s), 7.22(1H, d, J=9.2Hz) 7.45(1H, dd, J=9.2Hz, 2.0Hz) 8.12(1H, d, J=2.0Hz), 8.46(1H, brs) | |

TABLE 53

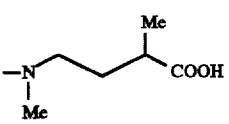

| Ex. | R² | R⁵ | m.p. (°C.) | yield (%) | Mass | NMR | note |
|---|---|---|---|---|---|---|---|
| 400 | Cl | 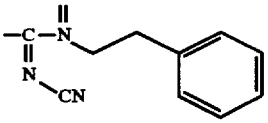 | 148–150 | 21 | 443(M + 1) | δ(DMSO-d₆);<br>1.05(3H, d, J=6.0Hz), 1.51(1H, m), 1.81(1H, m)<br>2.26(1H, m), 3.05(3H, s), 3.57(2H, m)<br>4.57(2H, d, J=5.6Hz), 5.94(2H, s), 6.82(2H, s)<br>6.91(1H, s), 7.23(1H, d, J=8.8Hz)<br>7.46(1H, dd, J=8.8Hz, 1.2Hz)<br>8.13(1H, d, J=1.2Hz), 8.49(1H, brs) | |
| 401 | Cl | 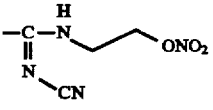 | 180–182 (decomp.) | 80 | 485(MH⁺) | δ(CDCl₃);<br>2.85(2H, t, J=7.0Hz), 3.72–3.78(2H, m)<br>4.85(2H, d, J=5.2Hz), 5.84(2H, s)<br>6.35(1H, brt, J=5.4Hz), 6.66(1H, d, J=8.0Hz)<br>6.78(1H, dd, J=8.0Hz, 1.6Hz)<br>6.82(1H, d, J=1.6Hz), 7.18–7.29(5H, m)<br>7.61(1H, dd, J=8.8Hz, 2.2Hz)<br>7.69–7.72(2H, m), 7.99(1H, br) | |

TABLE 54

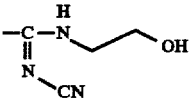

| Ex. | R² | R⁵ | m.p. (°C.) | yield (%) | Mass | NMR | note |
|---|---|---|---|---|---|---|---|
| 402 | Cl | -C(=N-CN)-NH-CH₂CH₂-ONO₂ | 169 (decomp.) | 62 | 470(MH⁺) | δ(DMSO-d₆);<br>3.77–3.81(2H, m), 4.76(2H, t, J=5.2Hz)<br>4.92(2H, d, J=6.0Hz), 5.97(2H, s)<br>6.86(1H, d, J=8.0Hz)<br>6.97(1H, dd, J=8.0Hz, 2.0Hz)<br>7.05(1H, d, J=2.0Hz), 7.83(1H, d, J=8.8Hz)<br>7.92(1H, dd, J=8.8Hz, 2.4Hz)<br>8.56(1H, d, J=2.4Hz), 9.04(1H, t, J=6.0Hz)<br>9.4848(1H, t, J=6.0Hz) | |
| 403 | Cl | -C(=N-CN)-NH-CH₂CH₂-OH | 243–245 (decomp.) | 58 | 425(MH⁺) | δ(DMSO-d₆);<br>3.44–3.48(2H, m), 3.56–3.60(2H, m)<br>4.37–4.51(3H, m), 5.94(2H, s)<br>6.83(1H, d, J=8.0Hz)<br>6.94(1H, dd, J=8.0Hz, 1.6Hz)<br>7.02(1H, d, J=1.6Hz), 7.80(1H, d, J=8.8Hz)<br>7.89(1H, dd, J=8.8Hz, 2.4Hz)<br>8.53(1H, d, J=2.4Hz), 9.20(1H, br) | |

TABLE 55

| Ex. | R² | R⁵ | m.p. (°C.) | yield (%) | Mass | NMR | note |
|---|---|---|---|---|---|---|---|
| 404 | Cl | ⌇OH | 210 213 (decomp.) | | 344(MH⁺) | δ(DMSO-d₆); 4.41(2H, d, J=6.0Hz), 4.66(2H, d, J=5.6Hz) 4.84(1H, t, J=6.0Hz), 5.95(2H, s) 6.83(1H, d, J=7.6Hz) 6.86(1H, dd, J=7.6Hz, 1.6Hz) 6.97(1H, d, J=1.6Hz), 7.67(1H, d, J=8.8Hz) 7.75(1H, dd, J=8.8Hz, 2.4Hz) 8.40(1H, d, J=2.4Hz), 8.78(1H, t, J=5.6Hz) | |
| 405 | Cl | ⌇COOH | 191–192 | 97 | 400(M + 1) | δ(DMSO-d₆); 1.97(2H, quintet, J=7.4Hz) 2.26(2H, t, J=7.4Hz), 2.72(2H, t, J=7.4Hz) 4.65(2H, d, J=5.7Hz), 5.97(2H, s) 6.83(1H, d, J=8.0Hz) 6.88(1H, dd, J=8.0Hz, 1.6Hz) 6.96(1H, d, J=1.6Hz), 7.63(1H, d, J=9.0Hz) 7.73(1H, dd, J=9.0Hz, 2.2Hz) 8.39(1H, d, J=2.2Hz), 8.72(1H, t, J=5.7Hz) | |

TABLE 56

| Ex. | R² | R⁵ | m.p. (°C.) | yield (%) | Mass | NMR | note |
|---|---|---|---|---|---|---|---|
| 406 | CN | ⌇COOH | 245–246 | 55 | 391(M + 1) | δ(DMSO-d₆); 1.98(2H, quintet, J=7.4Hz) 2.29(2H, t, J=7.4Hz), 2.75(2H, t, J=7.4Hz) 4.68(2H, d, J=5.7Hz), 5.97(2H, s) 6.85(1H, d, J=7.9Hz) 6.89(1H, dd, J=7.9Hz, 1.6Hz) 6.98(1H, d, J=8.6Hz), 7.72(1H, d, J=8.6Hz) 8.02(1H, dd, J=8.6Hz, 1.6Hz) 8.84(1H, d, J=1.6Hz), 8.96(1H, t, J=5.7Hz) | |
| 407 | Cl | ⌇COOH | 201–202 | 99 | 386(M + 1) | δ(DMSO-d₆) 2.71(2H, t, J=7.1Hz), 2.96(2H, t, J=7.1Hz) 4.65(2H, d, J=5.7Hz), 5.97(2H, s) 6.85(1H, d, J=7.9Hz) 6.89(1H, dd, J=7.9Hz, 1.6Hz) 6.98(1H, d, J=1.6Hz), 7.62(1H, d, J=9.0Hz) 7.73(1H, dd, J=9.0Hz, 2.2Hz) 8.39(1H, d, J=3.2Hz), 8.73(1H, t, J=5.7Hz) | |

TABLE 57

![structure]

| Ex. | R² | R⁵ | m.p. (°C.) | yield (%) | Mass | NMR | note |
|---|---|---|---|---|---|---|---|
| 408 | Cl | —N⟨piperidine⟩—CONH₂ | 231–232 (decomp.) | 79 | 440(M + 1)⁺ | δ(DMSO-d₆); 1.40(2H, m), 1.71(2H, m), 2.34(1H, m) 2.82(2H, m), 4.56(2H, d, J=5.6Hz), 4.74(2H, m) 5.95(2H, s), 6.73(1H, brs) 6.82(1H, d, J=8.0Hz) 6.86(1H, dd, J=8.0Hz, 1.6Hz) 6.94(1H, d, J=1.6Hz), 7.25(1H, brs) 7.25(1H, d, J=8.8Hz) 7.47(1H, dd, J=8.8Hz, 2.4Hz) 8.14(1H, d, J=2.4Hz), 8.53(1H, brt, J=5.6Hz) | hydrochloride |
| 409 | Cl | —N(Me)—CH₂—C₆H₄—COOEt | 215 (decomp.) | 81 | 505(MH⁺) | δ(DMSO-d₆); 1.27(3H, J=7.0Hz), 3.21(3H, s) 4.30(2H, q, J=7.0Hz), 4.55(2H, brs) 4.97(2H, s), 5.89(2H, s), 6.52–8.42(10H, m) 12.20(1H, brs) | |

TABLE 58

![structure]

| Ex. | R² | R⁵ | m.p. (°C.) | yield (%) | Mass | NMR | note |
|---|---|---|---|---|---|---|---|
| 410 | Cl | —N(Me)—CH₂—C₆H₄—COOH | 279–280 (decomp.) | 91 | 477(MH⁺) | δ(DMSO-d₆); 3.07(2H, s), 4.50(2H, brs), 4.81(2H, s) 5.89(2H, s), 6.51–6.88(3H, m) 7.22(2H, d, J=8.0Hz), 7.26(1H, d, J=9.2Hz) 7.48(1H, dd, J=9.2Hz, 2.4Hz) 7.80(2H, d, J=8.0Hz), 8.15(1H, d, J=2.4Hz) 8.58(1H, brs), 12.77(1H, brs) | |

We claim:

1. A compound represented by the formula or a pharmacologically acceptable salt thereof

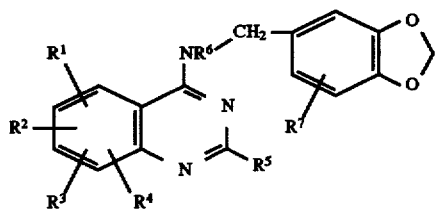

wherein R¹, R², R³ and R⁴, each of which may be the same or different from one another, each represent a hydrogen atom, a halogen atom or a lower alkoxy group;

R⁵ represents a hydrogen atom, a lower alkoxy, formyl, or imidazolyl group;

R⁶ is hydrogen or a $C_{1-4}$ alkyl group; and

R⁷ is a halogen atom or a hydrogen atom, provided that at least one of R¹, R², R³ and R⁴ is a lower alkoxy group.

2. The compound of claim 1 wherein at least three of R¹, R², R³ and R⁴ are lower alkoxy and the other is hydrogen.

3. The compound of claim 1 wherein R⁶ is methyl or ethyl.

4. The compound of claim 1 wherein one of R¹, R², R³ or R⁴ is lower alkoxy and the others are hydrogen, and R⁵, R⁶ and R⁷ are hydrogen.

5. A compound selected from the group consisting of:
4-[N-ethyl-(3,4-dimethylenedioxybenzyl)amino]-6,7,8-trimethoxyquinazoline and 4-(3,4-methylenedioxybenzyl)amino-6-methoxyquinazoline.

6. A pharmaceutical composition comprising a therapeutically effective amount of the compound of claim 1.

7. A method of treating ischemic heart disease which comprises administering to a person in need of same a therapeutically effective amount of the compound of claim 1.

* * * * *